United States Patent
Nishimura et al.

(10) Patent No.: US 9,711,732 B2
(45) Date of Patent: Jul. 18, 2017

(54) ORGANIC ELECTROLUMINESCENT ELEMENT AND MATERIAL FOR ORGANIC ELECTROLUMINESCENT ELEMENTS

(71) Applicant: IDEMITSU KOSAN CO., LTD., Chiyoda-ku (JP)

(72) Inventors: Kazuki Nishimura, Sodegaura (JP); Toshinari Ogiwara, Sodegaura (JP); Kumiko Hibino, Sodegaura (JP); Tetsuya Inoue, Sodegaura (JP); Mitsunori Ito, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 312 days.

(21) Appl. No.: 14/389,079

(22) PCT Filed: Mar. 29, 2013

(86) PCT No.: PCT/JP2013/059638
§ 371 (c)(1),
(2) Date: Sep. 29, 2014

(87) PCT Pub. No.: WO2013/147205
PCT Pub. Date: Oct. 3, 2013

(65) Prior Publication Data
US 2015/0060801 A1   Mar. 5, 2015

(30) Foreign Application Priority Data

Mar. 29, 2012 (JP) .................................. 2012-078284

(51) Int. Cl.
*H01L 51/50* (2006.01)
*H01L 51/00* (2006.01)
(Continued)

(52) U.S. Cl.
CPC ........ *H01L 51/0067* (2013.01); *C07D 403/14* (2013.01); *C09K 11/06* (2013.01);
(Continued)

(58) Field of Classification Search
None
See application file for complete search history.

(56) References Cited

U.S. PATENT DOCUMENTS

| | | | |
|---|---|---|---|
| 7,358,661 B2 | 4/2008 | Kuma | |
| 2011/0278555 A1 | 11/2011 | Inoue et al. | |

(Continued)

FOREIGN PATENT DOCUMENTS

| | | |
|---|---|---|
| JP | 9-3448 | 1/1997 |
| JP | 2000-173774 | 6/2000 |

(Continued)

OTHER PUBLICATIONS

International Search Report issued May 28, 2013, in PCT/JP13/59638 filed Mar. 29, 2013.

(Continued)

*Primary Examiner* — Gregory Clark
(74) *Attorney, Agent, or Firm* — Oblon, McClelland, Maier & Neustadt, L.L.P.

(57) ABSTRACT

An organic electroluminescence device includes: a cathode; an anode; and an organic thin-film layer having one or more layers and provided between the anode and the cathode, in which the organic layer includes an emitting layer. The emitting layer includes a first host material, a second host material and a phosphorescent dopant material. The first host material is a compound represented by a formula (1A). The second host material is a compound represented by a formula (2A).

(Continued)

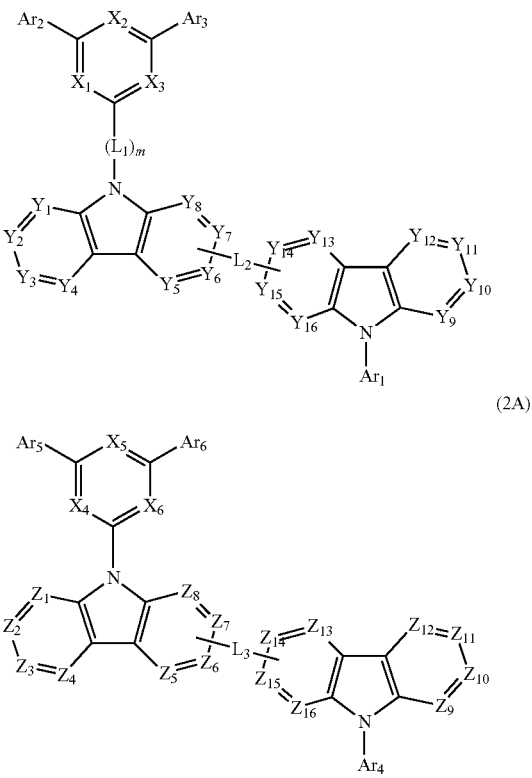

(51) Int. Cl.
*C07D 403/14* (2006.01)
*C09K 11/06* (2006.01)
*H05B 33/10* (2006.01)

(52) U.S. Cl.
CPC ...... *H01L 51/0072* (2013.01); *H01L 51/5016* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/0085* (2013.01); *H01L 2251/5384* (2013.01)

(56) References Cited

U.S. PATENT DOCUMENTS

| | | | |
|---|---|---|---|
| 2011/0279020 | A1* | 11/2011 | Inoue ................ C07D 209/82 313/504 |
| 2012/0119197 | A1 | 5/2012 | Nishimura et al. |
| 2012/0138911 | A1 | 6/2012 | Inoue et al. |
| 2012/0138912 | A1 | 6/2012 | Inoue et al. |
| 2012/0138915 | A1 | 6/2012 | Nishimura et al. |
| 2012/0181518 | A1 | 7/2012 | Ogiwara et al. |
| 2013/0306963 | A1* | 11/2013 | Yamamoto ........ H01L 51/0085 257/40 |

FOREIGN PATENT DOCUMENTS

| | | |
|---|---|---|
| JP | 2012-28634 | 2/2012 |
| JP | 2012-156499 | 8/2012 |
| JP | 2012-216801 | 11/2012 |
| WO | WO 03/080760 A1 | 10/2003 |
| WO | WO 2010/134352 A1 | 11/2010 |
| WO | WO 2011/132683 A1 | 10/2011 |
| WO | WO 2011/148909 A1 | 12/2011 |
| WO | WO 2011/162162 A1 | 12/2011 |

OTHER PUBLICATIONS

Chang, et al., "A dicarbazole-triazine hybrid bipolar host material for highly efficient green phosphorescent OLEDs", Journal of Materials Chemistry, vol. 22, No. 9, Mar. 7, 2012, 8 pages.

* cited by examiner

12 Claims, 5 Drawing Sheets

ORGANIC ELECTROLUMINESCENT ELEMENT AND MATERIAL FOR ORGANIC ELECTROLUMINESCENT ELEMENTS

TECHNICAL FIELD

The present invention relates to an organic electroluminescence device and a material for the organic electroluminescence device.

BACKGROUND ART

There has been known an organic electroluminescence device (hereinafter, occasionally referred to as an "organic EL device") that includes an emitting unit (in which an emitting layer is included) between an anode and a cathode and emits light using exciton energy generated by a recombination of holes and electrons that have been injected into the emitting layer.

A phosphorescent organic EL device using a phosphorescent dopant material as a luminescent material has been known as the organic EL device. The phosphorescent organic EL device can achieve a high luminous efficiency by using a singlet state and a triplet state of excited states of the phosphorescent dopant material. The reason is presumed as follows. When holes and electrons are recombined in the emitting layer, it is presumed that singlet excitons and triplet excitons are produced at a rate of 1:3 due to difference in spin multiplicity. Accordingly, luminous efficiency of the device using a phosphorescent material can reach three to four times as much as that of the device using only a fluorescent material.

Patent Literature 1 describes that a compound in which a nitrogen-containing heterocyclic group is bonded to an arylcarbazoyl group or a carbazoyl alkylene group is suitable to a phosphorescent host material usable in combination with a phosphorescent dopant material. An organic EL device driven at a low voltage and having a high color purity is obtainable by using the phosphorescent dopant material and this compound in the emitting layer.

CITATION LIST

Patent Literature(s)

Patent Literature 1: International Publication No. WO2003/080760

SUMMARY OF THE INVENTION

Problems to be Solved by the Invention

However, since the phosphorescent host material described in Patent Literature 1 has a large HOMO, hole injection into the emitting layer is difficult. Accordingly, emission occurs at an interface of a hole transporting layer, resulting in a short lifetime.

An object of the invention is to provide a long-life organic electroluminescence device exhibiting a high luminous efficiency and a material for the organic electroluminescence device.

Means for Solving the Problems

After conducting concentrated studies in order to achieve the object, the inventors have found that a long-life organic electroluminescence device exhibiting a high luminous efficiency is obtainable in a combined use of a specific first host material and a specific second host material in an emitting layer. The invention has been achieved based on these findings.

According to an aspect of the invention, an organic electroluminescence device includes: a cathode; an anode; and an organic thin-film layer disposed between the cathode and the anode, the organic thin-film layer having one or more layers including an emitting layer, the emitting layer including a first host material, a second host material and a phosphorescent dopant material, in which the first host material is a compound represented by a formula (1A) below, and the second host material is represented by a formula (2A) below.

[Formula 1]

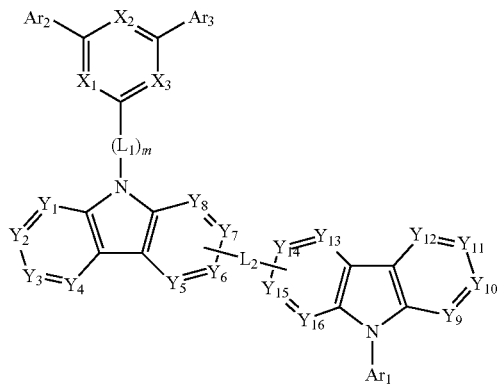

(1A)

In the formula (1A), $Ar_1$ to $Ar_3$ each independently represent a substituted or unsubstituted aryl group having 6 to 30 carbon atoms for forming a ring (hereinafter, referred to as "ring carbon atoms"), or substituted or unsubstituted heterocyclic group having 5 to 30 atoms for forming a ring (hereinafter, referred to as "ring atoms"), with a proviso that $Ar_1$ is not a nitrogen-containing six-membered heterocyclic group.

$L_1$ is a substituted or unsubstituted arylene group having 6 to 30 ring carbon atoms.

$L_2$ represents a single bond, a substituted or unsubstituted arylene group having 6 to 30 ring carbon atoms, or substituted or unsubstituted divalent heterocyclic group having 5 to 30 ring atoms.

$X_1$ to $X_3$ each independently represent CR or a nitrogen atom and at least one of $X_1$ to $X_3$ is a nitrogen atom.

$Y_1$ to $Y_{16}$ each independently represent CR or a nitrogen atom, but one of $Y_5$ to $Y_8$ is a carbon atom to be bonded to $L_2$ and one of $Y_{13}$ to $Y_{16}$ is a carbon atom to be bonded to $L_2$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

m is an integer of 1 to 4. When m is 2 or more, $L_1$ is optionally the same or different.

[Formula 2]

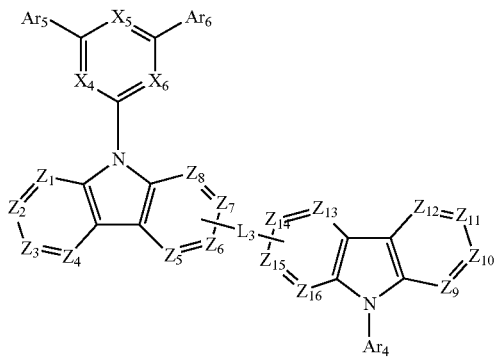

(2A)

In the formula (2A), $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$L_3$ represents a single bond, a substituted or unsubstituted arylene group having 6 to 30 ring carbon atoms, or substituted or unsubstituted divalent heterocyclic group having to 30 ring atoms.

$X_4$ to $X_6$ each independently represent CR or a nitrogen atom and at least one of $X_4$ to $X_6$ is a nitrogen atom.

$Z_1$ to $Z_{16}$ represent CR or a nitrogen atom, but one of $Z_5$ to $Z_8$ is a carbon atom to be bonded to $L_3$ and one of $Z_{13}$ to $Z_{16}$ is a carbon atom to be bonded to $L_3$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

When $Y_6$ is directly bonded to $Y_{14}$ in the compound represented by the formula (1A) and $Z_6$ is bonded to $Z_{14}$ through $L_3$ in the compound represented by the formula (2A), $L_3$ is a substituted or unsubstituted arylene group having 6 to 30 ring carbon atoms, or a substituted or unsubstituted divalent heterocyclic group having 5 to 30 ring atoms.

In the organic electroluminescence device according to the above aspect of the invention, $L_2$ in the formula (1A) is preferably a single bond.

Moreover, in the organic electroluminescence device according to the above aspect of the invention, $L_3$ in the formula (2A) is preferably a single bond.

In the organic electroluminescence device according to the above aspect of the invention, $L_2$ in the formula (1A) is preferably a substituted or unsubstituted arylene group having 6 to 30 ring carbon atoms, or a substituted or unsubstituted divalent heterocyclic group having 5 to 30 ring atoms.

Moreover, in the organic electroluminescence device according to the above aspect of the invention, $L_3$ in the formula (2A) is preferably a substituted or unsubstituted arylene group having 6 to 30 ring carbon atoms, or a substituted or unsubstituted divalent heterocyclic group having 5 to 30 ring atoms.

In the organic electroluminescence device according to the above aspect of the invention, when $Y_6$ is directly bonded to $Y_{14}$ in the compound represented by the formula (1A) and $Z_7$ is bonded to $Z_{14}$ through $L_3$ in the compound represented by the formula (2A), $L_3$ is preferably a substituted or unsubstituted arylene group having 6 to 30 ring carbon atoms, or a substituted or unsubstituted divalent heterocyclic group having 5 to 30 ring atoms.

In the organic electroluminescence device according to the above aspect of the invention, the first host material is a compound represented by a formula (1) below, and the second host material is represented by a formula (2) below.

[Formula 3]

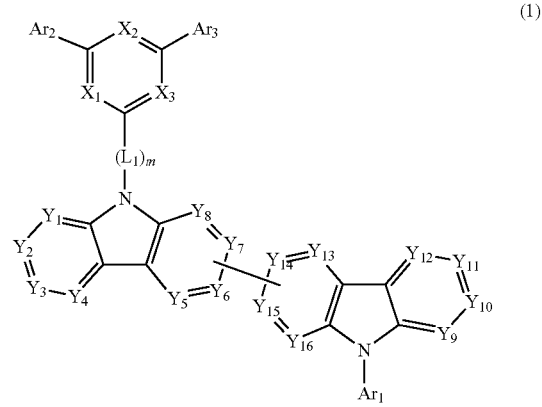

(1)

In the formula (1), $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group.

$L_1$ is a substituted or unsubstituted arylene group having 6 to 30 ring carbon atoms.

$X_1$ to $X_3$ each independently represent CR or a nitrogen atom and at least one of $X_1$ to $X_3$ is a nitrogen atom.

$Y_1$ to $Y_{16}$ each independently represent CR, but one of $Y_6$ and $Y_7$ is a carbon atom to be bonded to $Y_{14}$ or $Y_{15}$ and one of $Y_{14}$ and $Y_{15}$ is a carbon atom to be bonded to $Y_6$ or $Y_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

m is an integer of 1 to 4. When m is 2 or more, $L_1$ is optionally the same or different.

[Formula 4]

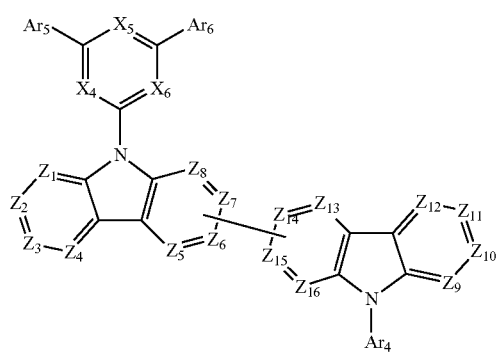

(2)

In the formula (2), $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$X_4$ to $X_6$ each independently represent CR or a nitrogen atom and at least one of $X_4$ to $X_6$ is a nitrogen atom.

$Z_1$ to $Z_{16}$ each independently represent CR, but one of $Z_6$ and $Z_7$ is a carbon atom to be bonded to $Z_{14}$ or $Z_{15}$ and one of $Z_{14}$ and $Z_{15}$ is a carbon atom to be bonded to $Z_6$ or $Z_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

When $Y_6$ is directly bonded to $Y_{14}$ in the compound represented by the formula (1), $Z_6$ is a carbon atom to be bonded to $Z_{15}$ and $Z_{15}$ is a carbon atom to be bonded to $Z_7$ in the compound represented by the formula (2).

In the organic electroluminescence device according to the above aspect of the invention, it is preferable that, in the formula (1), $Y_7$ is bonded to $Y_{14}$ or $Y_6$ is bonded to $Y_{15}$.

In the organic electroluminescence device according to the above aspect of the invention, it is preferable that, in the formula (2), $Y_7$ is bonded to $Y_{14}$ or $Y_6$ is bonded to $Y_{15}$.

Moreover, in the organic electroluminescence device according to the above aspect of the invention, it is preferable that two or more of $X_1$ to $X_3$ are nitrogen atoms and two or more of $X_4$ to $X_6$ are nitrogen atoms.

Further, in the organic electroluminescence device according to the above aspect of the invention, the number of nitrogen atoms of $X_1$ to $X_3$ is preferably different from the number of nitrogen atoms of $X_4$ to $X_6$.

In the organic electroluminescence device according to the above aspect of the invention, $L_1$ is preferably a substituted or unsubstituted phenylene group, substituted or unsubstituted naphthylene group, substituted or unsubstituted fluorenylene group, substituted or unsubstituted phenanthrenediyl group, or substituted or unsubstituted triphenylenediyl group.

According to another aspect of the invention, a material for an organic electroluminescence device includes a compound represented by a formula (1A) and a compound represented by a formula (2A).

[Formula 5]

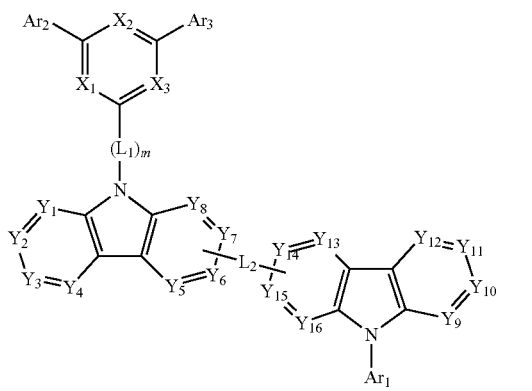

(1A)

In the formula (1A), $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group.

$L_1$ is a substituted or unsubstituted arylene group having 6 to 30 ring carbon atoms.

$L_2$ represents a single bond, a substituted or unsubstituted arylene group having 6 to 30 ring carbon atoms, or substituted or unsubstituted divalent heterocyclic group having 5 to 30 ring atoms.

$X_1$ to $X_3$ each independently represent CR or a nitrogen atom and at least one of $X_1$ to $X_3$ is a nitrogen atom.

$Y_1$ to $Y_{16}$ each independently represent CR or a nitrogen atom, but one of $Y_5$ to $Y_8$ is a carbon atom to be bonded to $L_2$ and one of $Y_{13}$ to $Y_{16}$ is a carbon atom to be bonded to $L_2$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

When a plurality of R are present, the plurality of R are optionally mutually the same or different and adjacent ones of the plurality of R are optionally mutually bonded to form a ring structure.

m is an integer of 1 to 4. When m is 2 or more, $L_1$ is optionally the same or different.

[Formula 6]

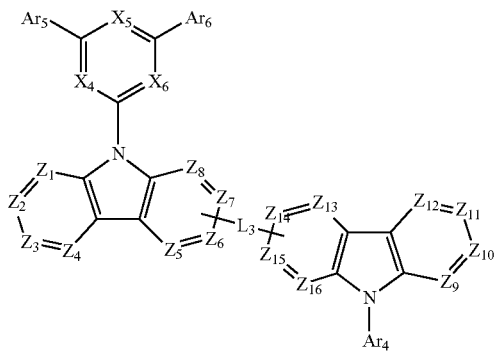

(2A)

In the formula (2A), $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$L_3$ represents a single bond, a substituted or unsubstituted arylene group having 6 to 30 ring carbon atoms, or substituted or unsubstituted divalent heterocyclic group having 5 to 30 ring atoms.

$X_4$ to $X_6$ each independently represent CR or a nitrogen atom and at least one of $X_4$ to $X_6$ is a nitrogen atom.

$Z_1$ to $Z_{16}$ represent CR or a nitrogen atom, but one of $Z_5$ to $Z_8$ is a carbon atom to be bonded to $L_3$ and one of $Z_{13}$ to $Z_{16}$ is a carbon atom to be bonded to $L_3$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

When a plurality of R are present, the plurality of R are optionally mutually the same or different and adjacent ones of the plurality of R are optionally mutually bonded to form a ring structure.

When $Y_6$ is directly bonded to $Y_{14}$ in the compound represented by the formula (1A) and $Z_6$ is bonded to $Z_{14}$ through $L_3$ in the compound represented by the formula (2A), $L_3$ is a substituted or unsubstituted arylene group having 6 to 30 ring carbon atoms, or a substituted or unsubstituted divalent heterocyclic group having 5 to 30 ring atoms.

In the material for the organic electroluminescence device according to the above aspect of the invention, it is preferable that $L_2$ in the formula (1A) is a single bond and $L_3$ in the formula (2A) is a single bond.

In the material for the organic electroluminescence device according to the above aspect of the invention, it is preferable that the compound represented by the formula (1A) is a compound represented by a formula (1) below and the compound represented by the formula (2A) is a compound represented by a formula (2) below.

[Formula 7]

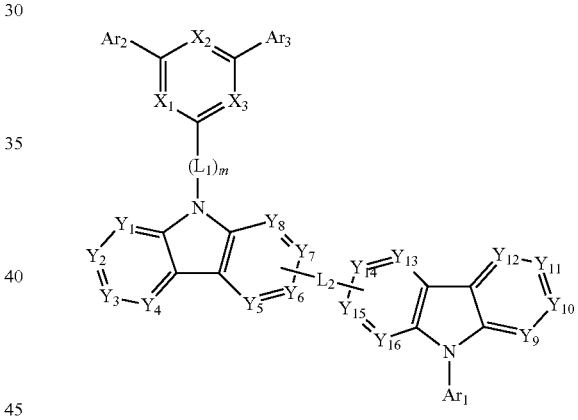

(1)

In the formula (1), $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group.

$L_1$ represents a substituted or unsubstituted arylene group having 6 to 30 ring carbon atoms.

$X_1$ to $X_3$ each independently represent CR or a nitrogen atom and at least one of $X_1$ to $X_3$ is a nitrogen atom.

$Y_1$ to $Y_{16}$ represent CR, but one of $Y_6$ and $Y_7$ is a carbon atom to be bonded to $Y_{14}$ or $Y_{15}$ and one of $Y_{14}$ and $Y_{15}$ is a carbon atom to be bonded to $Y_6$ or $Y_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

m is an integer of 1 to 4. When m is 2 or more, $L_1$ is optionally the same or different.

[Formula 8]

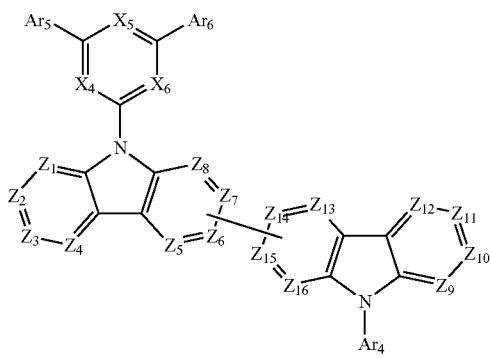

(2)

In the formula (2), $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$X_4$ to $X_6$ each independently represent CR or a nitrogen atom and at least one of $X_4$ to $X_6$ is a nitrogen atom. $Z_1$ to $Z_{16}$ are CR, but one of $Z_6$ and $Z_7$ is a carbon atom to be bonded to $Z_{14}$ or $Z_{15}$ and one of $Z_{14}$ and $Z_{15}$ is a carbon atom to be bonded to $Z_6$ or $Z_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R are optionally mutually the same or different and adjacent ones of the plurality of R are optionally mutually bonded to form a ring structure.

When $Y_6$ is directly bonded to $Y_{14}$ in the compound represented by the formula (1), $Z_6$ is a carbon atom to be bonded to $Z_{15}$ and $Z_{15}$ is a carbon atom to be bonded to $Z_7$ in the compound represented by the formula (2).)

Moreover, in the material for the organic electroluminescence device according to the above aspect of the invention, it is preferable that two or more of $X_1$ to $X_3$ are nitrogen atoms and two or more of $X_4$ to $X_6$ are nitrogen atoms.

Further, in the material for the organic electroluminescence device according to the above aspect of the invention, the number of nitrogen atoms of $X_1$ to $X_3$ is preferably different from the number of nitrogen atoms of $X_4$ to $X_6$.

Moreover, in the material for the organic electroluminescence device according to the above aspect of the invention, $L_1$ is preferably a substituted or unsubstituted phenylene group, substituted or unsubstituted naphthylene group, substituted or unsubstituted fluorenylene group, substituted or unsubstituted phenanthrenediyl group, or substituted or unsubstituted triphenylenediyl group.

According to the invention, a long-life organic electroluminescence device exhibiting a high luminous efficiency and a material for the organic electroluminescence device can be provided.

DESCRIPTION OF EMBODIMENT(S)

First Exemplary Embodiment
Arrangement of Organic EL Device
Arrangement(s) of an organic electroluminescence device (hereinafter referred to as an organic EL device) of the invention will be described below.

The following are representative arrangement examples of an organic EL device:
(1) anode/emitting layer/cathode;
(2) anode/hole injecting layer/emitting layer/cathode;
(3) anode/emitting layer/electron injecting transporting layer/cathode;
(4) anode/hole injecting layer/emitting layer/electron injecting•transporting layer/cathode; and
(5) anode/hole injecting•transporting layer/emitting layer/electron injecting transporting layer/cathode.

While the arrangement (5) is preferably used among the above, the arrangement of the invention is not limited to the above arrangements.

Note that the aforementioned "emitting layer" is an organic layer including a host material and a dopant material typically through a doping system. The host material generally promotes recombination of electrons and holes and transmits exciton energy generated by the recombination to the dopant material. The dopant material is preferably a compound having a high quantum efficiency. The dopant material receiving the exciton energy from the host material exhibits a high emitting performance.

The "hole injecting/transporting layer (or hole injecting transporting layer) means "at least one of a hole injecting layer and a hole transporting layer while the "electron injecting/transporting layer (or electron injecting transporting layer) means "at least one of an electron injecting layer and an electron transporting layer. Herein, when the hole injecting layer and the hole transporting layer are provided, the hole injecting layer is preferably closer to the anode. When the electron injecting layer and the electron transporting layer are provided, the electron injecting layer is preferably closer to the cathode.

Figure 1:
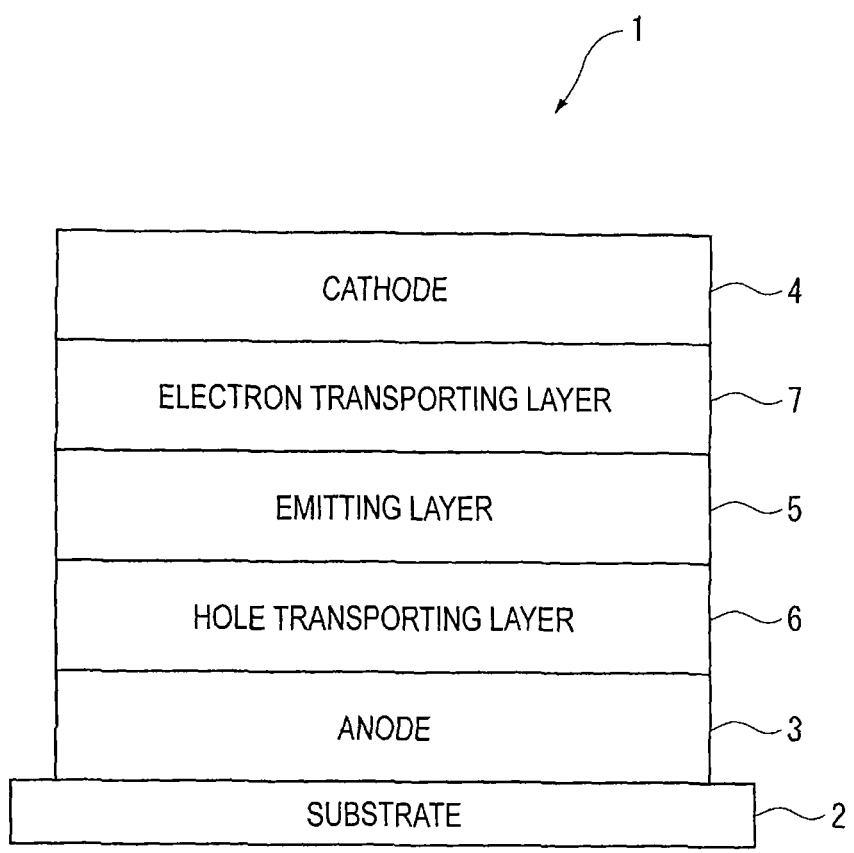
FIG. 1 schematically shows an exemplary arrangement of an organic EL device according to a first exemplary embodiment of the invention.

Next, an organic EL device 1 according to a first exemplary embodiment will be shown in FIG. 1.

The organic EL device 1 includes a transparent substrate 2, an anode 3, a cathode 4, a hole transporting layer 6, an emitting layer 5 and an electron transporting layer 7.

The hole transporting layer 6, the emitting layer 5, the electron transporting layer 7 and the cathode 4 are sequentially laminated on the anode 3.

Emitting Layer

The emitting layer 5 contains a first host material, a second host material and a phosphorescent dopant material.

It is preferable that the first host material is set in a range of 10 mass % to 90 mass %, the second host material is set in a range of 10 mass % to 90 mass %, and the phosphorescent dopant material is set in a range of 0.1 mass % to 30 mass % so that a total mass percentage of the materials contained in the emitting layer 5 becomes 100 mass %. More preferably, the first host material is set in a range of 40 mass % to 60 mass %.

First Host Material

As the first host material used in the organic EL device of this exemplary embodiment, a compound represented by the above formula (1A) is usable.

[Formula 9]

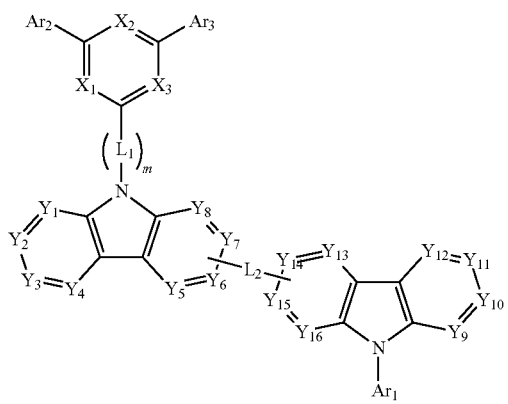

(1A)

In the formula (1A): $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group.

$L_1$ represents a substituted or unsubstituted arylene group having 6 to 30 ring carbon atoms.

$L_2$ represents a single bond, a substituted or unsubstituted arylene group having 6 to 30 ring carbon atoms, or a substituted or unsubstituted divalent heterocyclic group having 5 to 30 ring atoms.

$X_1$ to $X_3$ each independently represent CR or a nitrogen atom and at least one of $X_1$ to $X_3$ is a nitrogen atom.

$Y_1$ to $Y_{16}$ each independently represent CR or a nitrogen atom. However, one of $Y_5$ to $Y_8$ is a carbon atom to be bonded to $L_2$ and one of $Y_{13}$ to $Y_{16}$ is a carbon atom to be bonded to $L_2$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R may be mutually the same or different and adjacent ones of the plurality of R may be mutually bonded to form a ring structure.

m is an integer of 1 to 4. When m is 2 or more, $L_1$ may be the same or different.

In the formula (1A), $L_2$ is preferably a single bond. $L_2$ in the formula (1A) is also preferably a substituted or unsubstituted arylene group having 6 to 30 ring carbon atoms, or a substituted or unsubstituted divalent heterocyclic group having 5 to 30 ring atoms.

Further preferably, the compound represented by the formula (1A) is represented by a formula (1) below.

[Formula 10]

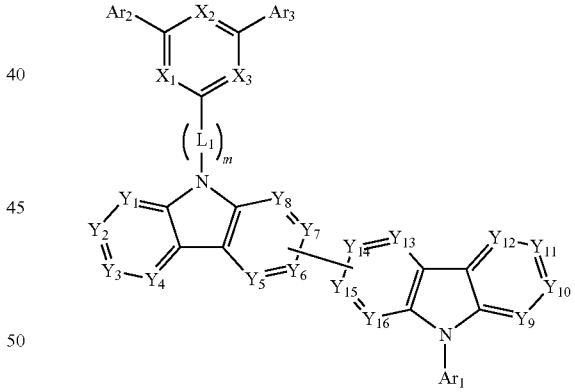

(1)

In the formula (1), $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group.

$L_1$ represents a substituted or unsubstituted arylene group having 6 to 30 ring carbon atoms.

$X_1$ to $X_3$ each independently represent CR or a nitrogen atom and at least one of $X_1$ to $X_3$ is a nitrogen atom.

$Y_1$ to $Y_{16}$ represent CR.

However, one of $Y_6$ and $Y_7$ is a carbon atom to be bonded to $Y_{14}$ or $Y_{15}$ and one of $Y_{14}$ and $Y_{15}$ is a carbon atom to be bonded to $Y_6$ or $Y_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R may be mutually the same or different and adjacent ones of the plurality of R may be mutually bonded to form a ring structure.

m is an integer of 1 to 4. When m is 2 or more, $L_1$ may be the same or different.

Groups respectively represented by $Ar_1$ to $Ar_3$ in the formulae (1A) and (1) will be described.

Examples of the aryl group having 6 to 30 ring carbon atoms are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, naphthacenyl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 3-triphenylenyl group, 4-triphenylenyl group, 1-fluorenyl group, 2-fluorenyl group, 3-fluorenyl group, 4-fluorenyl group, 9-fluorenyl group, benzofluorenyl group, dibenzofluorenyl group, 2-biphenylyl group, 3-biphenylyl group, 4-biphenylyl group, o-terphenyl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarterphenyl group, 3-fluoranthenyl group, 4-fluoranthenyl group, 8-fluoranthenyl group, 9-fluoranthenyl group, benzofluoranthenyl group, o-tolyl group, m-tolyl group, p-tolyl group, 2,3-xylyl group, 3,4-xylyl group, 2,5-xylyl group, mesityl group, o-cumenyl group, m-cumenyl group, p-cumenyl group, p-t-butylphenyl group, p-(2-phenylpropyl)phenyl group, 4'-methylbiphenylyl group, and 4"-t-butyl-p-terphenyl-4-yl group.

The aryl group preferably has 6 to 20 ring carbon atoms, more preferably 6 to 12 ring carbon atoms. Among the aryl group, a phenyl group, biphenyl group, naphthyl group, phenanthryl group, terphenyl group and fluorenyl group are particularly preferable. In a 1-fluorenyl group, 2-fluorenyl group, 3-fluorenyl group and 4-fluorenyl group, a carbon atom at a position 9 is preferably substituted by a substituted or unsubstituted alkyl group having 1 to 30 carbon atoms.

Examples of the heterocyclic group having 5 to 30 ring atoms are a pyroryl group, a pyrazinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenantridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiopheyl group, and a group derived from a pyridine ring, a pyrazine ring, a pyrimidine ring, a pyridazine ring, a triazine ring, an indol ring, a quinoline ring, an acridine ring, a pirrolidine ring, a dioxane ring, a piperidine ring, a morpholine ring, a piperadine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyrane ring and a dibenzofuran ring.

More specifically, the examples of the heterocyclic group having 5 to 30 ring atoms in the formulae (1) to (6) are a 1-pyrrolyl group, 2-pyrrolyl group, 3-pyrrolyl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolizinyl group, 2-indolizinyl group, 3-indolizinyl group, 5-indolizinyl group, 6-indolizinyl group, 7-indolizinyl group, 8-indolizinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl, 4-pyridinyl, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl, 6-quinoxalinyl, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl, 5-oxadiazolyl, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. In 1-carbazolyl group, 2-carbazolyl group, 3-carbazolyl group and 4-carbazolyl group, a nitrogen atom at the ninth position is preferably substituted by a substituted or unsubstituted aryl group having 6 to 30 ring carbon atoms or a substituted or unsubstituted heterocyclic group having 5 to 30 ring atoms.

However, $Ar_1$ is not a pyridine ring, pyrazine ring, pyrimidine ring, pyridazine or triazine ring among the above heterocyclic group having 5 to 30 ring atoms.

In the formulae (1A) and (1), $Ar_t$ to $Ar_3$ are more preferably a substituted or unsubstituted aryl group having 6 to 30 ring carbon atoms, further preferably a substituted or unsubstituted phenyl group.

In the formulae (1A) and (1), CR represents R bonded to a carbon atom (C). A group represented by R in the formulae (1A) and (1) will be described.

The aryl group having 6 to 30 ring carbon atoms and the heterocyclic group having 5 to 30 ring atoms are exemplified by the aforementioned groups.

The alkyl group having 1 to 30 carbon atoms may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Examples of the cyclic alkyl group (cycloalkyl group) are a cyclopropyl group, cyclobutyl group, cyclopentyl group, cyclohexyl group, 4-methylcyclohexyl group, 3,5-tetramethylcyclohexyl group, cycloheptyl group, cyclooctyl group, 1-adamantyl group, 2-adamantyl group, 1-norbornyl group and 2-norbornyl group.

The linear or branched alkyl group preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group preferably has 3 to 10 ring carbon atoms, more preferably 5 to 8 ring carbon atoms. Among the cycloalkyl group, a cyclopentyl group and a cyclohexyl group are preferable.

A halogenated alkyl group provided by substituting an alkyl group with a halogen atom is exemplified by one provided by substituting an alkyl group having 1 to 30 carbon atoms with one or more halogen groups. Specific examples of the halogenated alkyl group are a fluoromethyl group, difluoromethyl group, trifluoromethyl group, fluoroethyl group and trifluoromethylmethyl group.

The alkenyl group having 2 to 30 carbon atoms may be linear, branched or cyclic. Examples of alkenyl group having 2 to 30 carbon atoms are a vinyl group, a propenyl group, a butenyl group, an oleyl group, an eicosapentaenyl group, a docosahexaenyl group, a styryl group, a 2,2-diphenylvinyl group, a 1,2,2-triphenylvinyl group and a 2-phenyl-2-propenyl group, among which a vinyl group is preferable.

The alkynyl group having 2 to 30 carbon atoms may be linear, branched or cyclic. Examples of the alkynyl group having 2 to 30 carbon atoms are an ethynyl group, a propynyl group and a 2-phenylethynyl group, among which an ethynyl group is preferable.

The alkylsilyl group having 3 to 30 carbon atomsis exemplified by a trialkylsilyl group having the above examples of the alkyl group having 1 to 30 carbon atoms.

Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms. The two alkyl groups may be mutually the same or different.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms. The two aryl groups may be mutually the same or different.

The triarylsilyl group is exemplified by a triarylsilyl group including three of the aryl group listed as the examples of the aryl group having 6 to 30 ring carbon atoms. The triarylsilyl group preferably has 18 to 30 carbon atoms. The three aryl groups may be mutually the same or different.

Examples of the above arylsilyl group are a phenyldimethylsilyl group, a diphenylmethylsilyl group, a diphenyl-t-butylsilyl group and a triphenylsilyl group.

The alkoxy group having 1 to 30 carbon atoms is represented by $-OR_x$. $R_x$ is exemplified by the alkyl group having 1 to 30 carbon atoms. The alkoxy group is preferably an alkoxy group having 1 to 6 carbon atoms, examples of which are a methoxy group, an ethoxy group, a propoxy group, a butoxy group, a pentyloxy group, and a hexyloxy group.

A halogenated alkoxy group provided by substituting an alkoxy group with a halogen atom is exemplified by one provided by substituting an alkoxy group having 1 to 30 carbon atoms with one or more halogen groups.

The aralkyl group having 6 to 30 ring carbon atoms is represented by $-Ry-Rz$. Ry is exemplified by an alkylene group corresponding to the alkyl group having 1 to 30 carbon atoms. Rz is exemplified by the above aryl group having 6 to 30 ring carbon atoms. The aralkyl group is preferably an aralkyl group having 7 to 30 carbon atoms, in which an aryl portion has 6 to 30 carbon atoms, preferably 6 to 20 carbon atoms, more preferably 6 to 12 carbon atoms, and an alkyl portion has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group having 6 to 30 ring carbon atoms is represented by $-ORv$. Rv is exemplified by the aryl group having 6 to 30 ring carbon atoms or a monocyclic group and a fused cyclic group described below. The aryloxy group is exemplified by a phenoxy group.

Examples of the halogen atom are a fluorine atom, a chlorine atom, a bromine atom and a iodine atom, among which the fluorine atom is preferable.

The arylene group having 6 to 30 ring carbon atoms represented by $L^1$ and $L^2$ in the formulae (1A) and (1) is exemplified by a divalent group derived from the above aryl groups. Among the above group, $L_1$ is preferably a substituted or unsubstituted phenylene group, substituted or unsubstituted naphthylene group, substituted or unsubstituted fluorenylene group, substituted or unsubstituted phenanthrenediyl group, or substituted or unsubstituted triphenylenediyl group. The substituted or unsubstituted divalent heterocyclic group having 5 to 30 ring atoms, which is represented by $L_2$ in the formula (1A), is exemplified by a divalent group derived from the above heterocyclic group.

In the formulae (1A) and (1), at least one of $X_1$ to $X_3$ is a nitrogen atom. More preferably, two or more of $X_1$ to $X_3$ are nitrogen atoms in terms of long lifetime of the organic EL device. Particularly preferably, all of $X_1$ to $X_3$ are nitrogen atoms.

In the invention, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, unsaturated ring, or aromatic ring.

In the invention, a "hydrogen atom" encompasses isotopes having different numbers of neutrons, specifically, protium, deuterium and tritium.

Examples of a substituent which may be used in a case of being "substituted or unsubstituted" are an hydroxyl group, a nitro group and a carboxy group in addition to an aryl group, a heterocyclic group, an alkyl group (a linear or branched alkyl group, a cycloalkyl group and a halogenated alkyl group), an alkenyl group, an alkynyl group, an alkylsilyl group, an arylsilyl group, an alkoxy group, a halogenated alkoxy group, an aralkyl group, an aryloxy group, a halogen atom, and a cyano group as described above. In the above-described substituents, the aryl group, heterocyclic group, alkyl group, halogen atom, alkylsilyl group, arylsilyl group, cyano group and deuterium atom are preferable. The preferable ones of the specific examples of each substituent are further preferable. Herein, "unsubstituted" used in a case of being "substituted or unsubstituted" means that a group is not substituted by the above substituents but bonded with a hydrogen atom.

In a later-described compound or a partial structure thereof, the same applies to a substituent when being "substituted or unsubstituted."

In the compound represented by the formulae (1A) and (1), it is preferable that one of $Y_6$ and $Y_7$ is a carbon atom to be bonded to $Y_{14}$ or $Y_{15}$ and one of $Y_{14}$ and $Y_{15}$ is a carbon atom to be bonded to $Y_6$ or $Y_7$. The compound represented by the formulae (1A) and (1) is preferably represented by one of formulae (11A) to (11C) below. More preferably, the compound represented by the formulae (1A) and (1) is preferably represented by one of formulae (12A) to (12C) below.

[Formula 11]

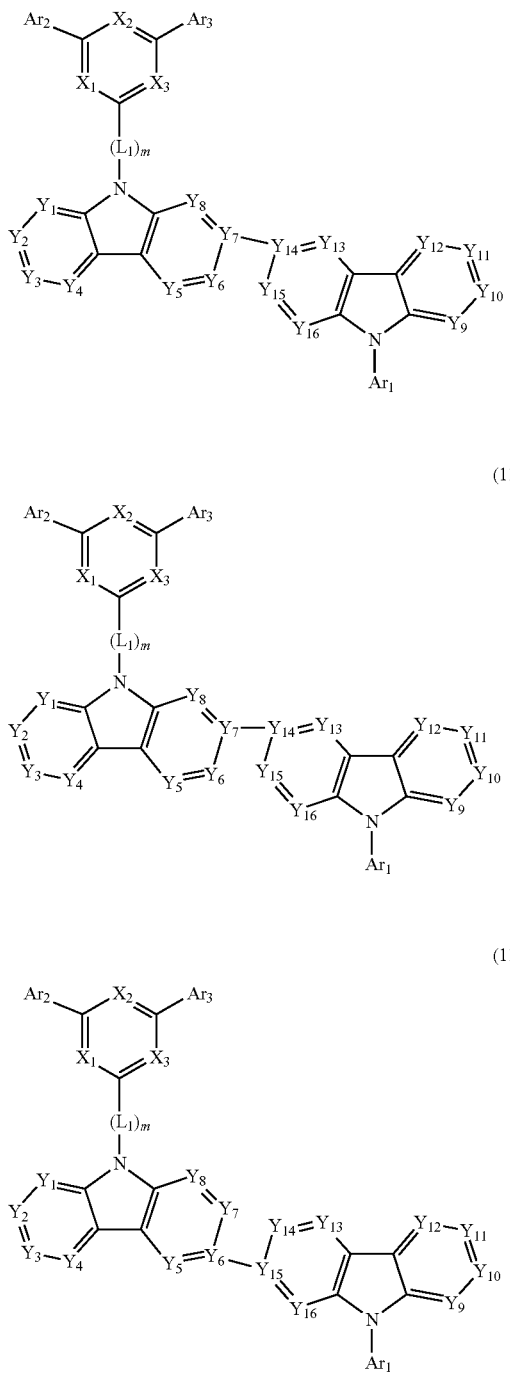

[Formula 12]

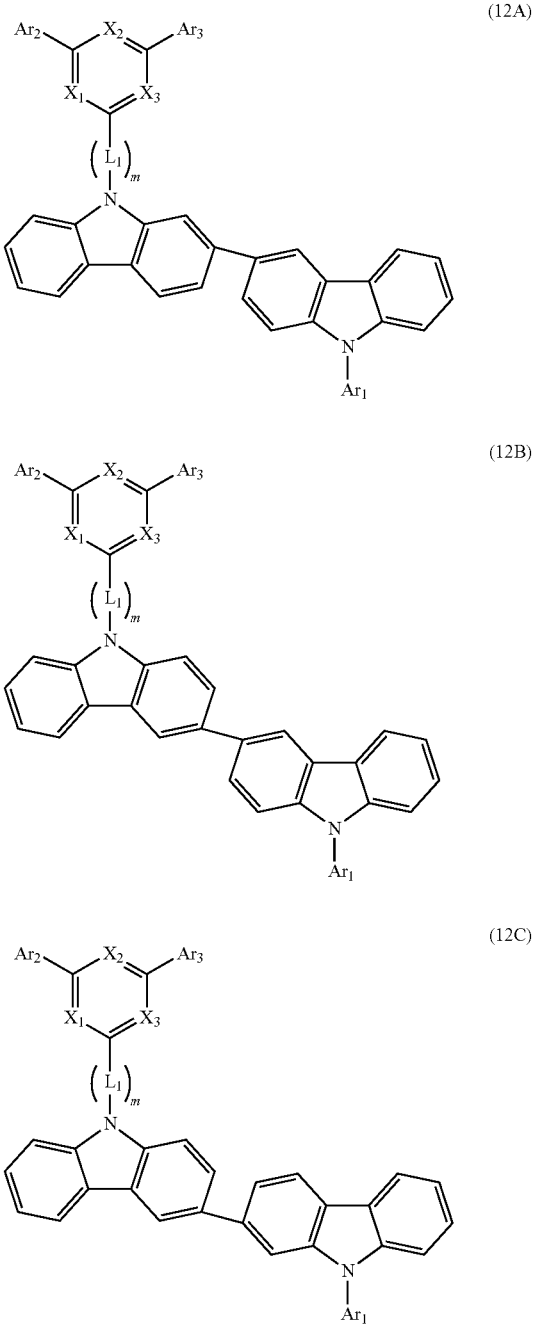

In the formulae (11A) to (11C), $Ar_1$ to $Ar_3$, $X_1$ to $X_3$, $L_1$, $Y_1$ to $Y_{16}$ and m respectively represent the same as $Ar_1$ to $Ar_3$, $X_1$ to $X_3$, $L_1$, $Y_1$ to $Y_{16}$ and m in the formula (1A) or (1).

In the formulae (12A) to (12C), $Ar_1$ to $Ar_3$, $X_1$ to $X_3$, $L_1$ and m respectively represent the same as $Ar_1$ to $Ar_3$, $X_1$ to $X_3$, $L_1$ and m in the formula (1A) or (1).

In the formulae (11A) to (11C) and (12A) to (12C), more preferably, two or more of $X_1$ to $X_3$ are nitrogen atoms. Particularly preferably, all of $X_1$ to $X_3$ are nitrogen atoms.

Examples of the compounds represented by any one of the formulae (1A), (1), (11A) to (11C) and (12A) to (12C) are as follows. Note that a bond without a formula (e.g., Ph, CN and a benzene ring) at an end represents a methyl group in the following structures.

[Formula 13]
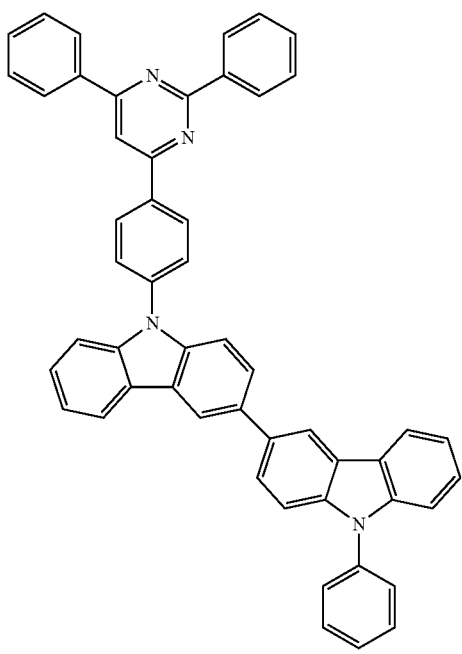
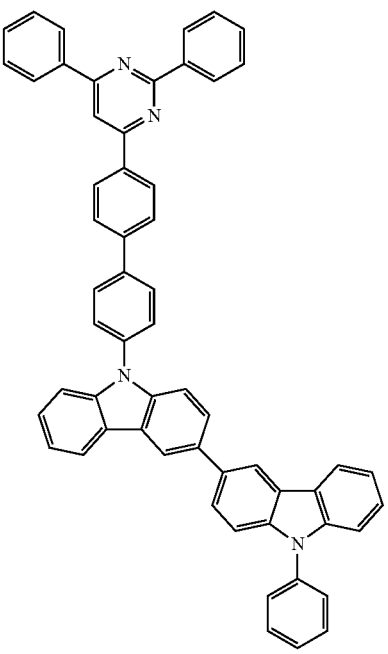
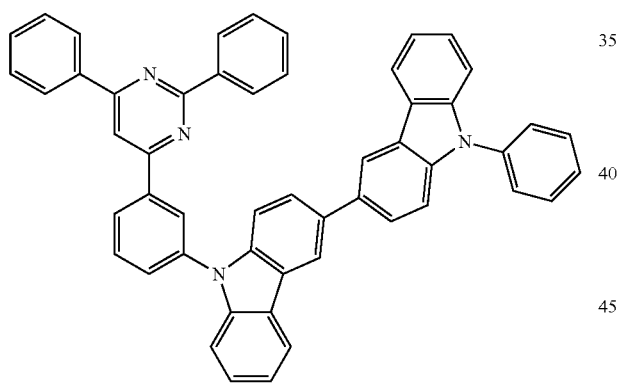
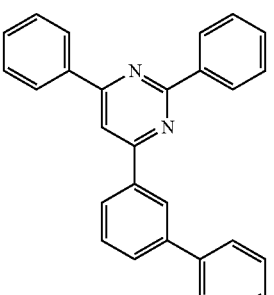
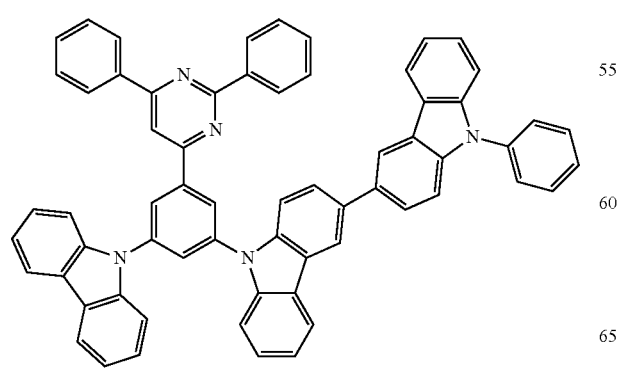

23
-continued
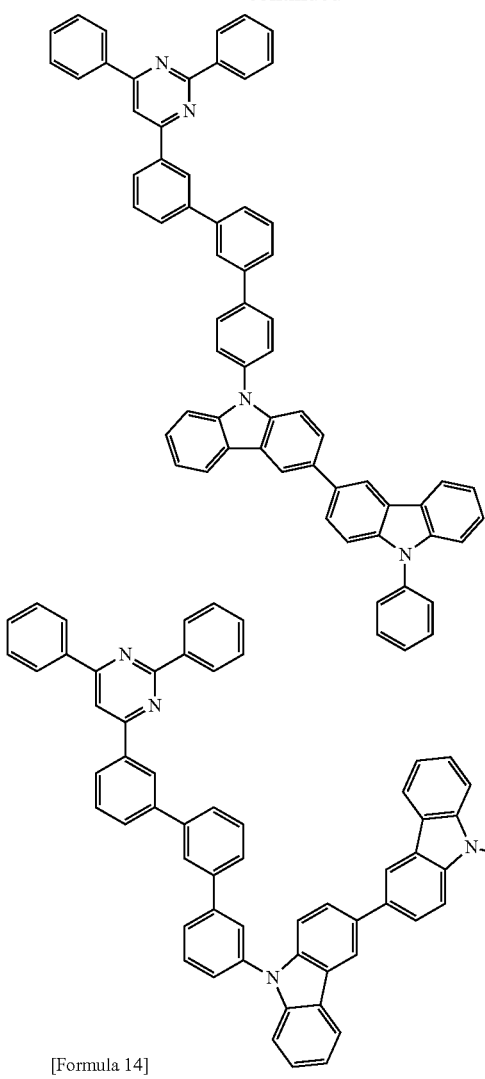
[Formula 14]
24
-continued
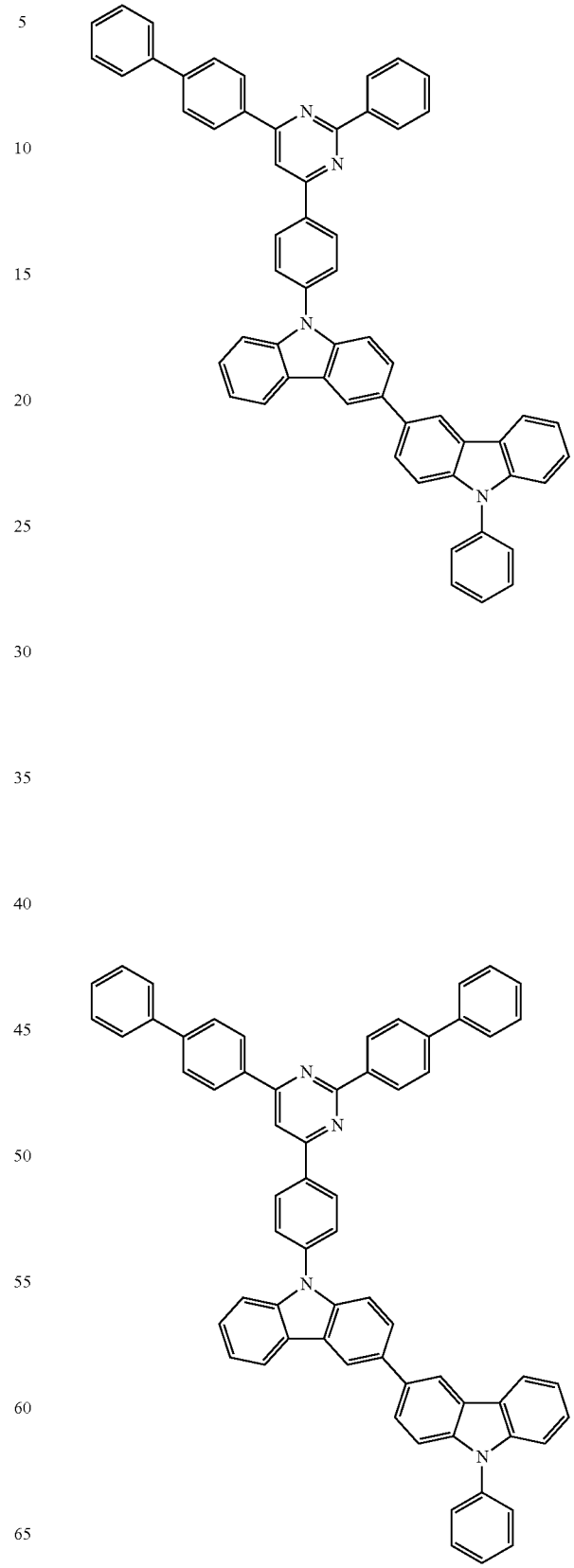

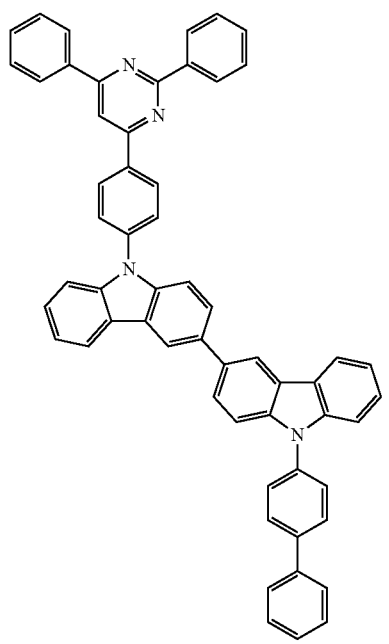
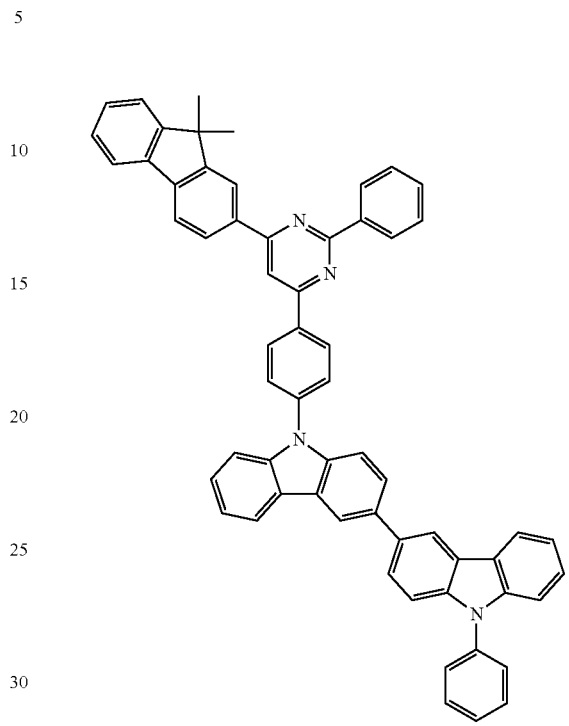
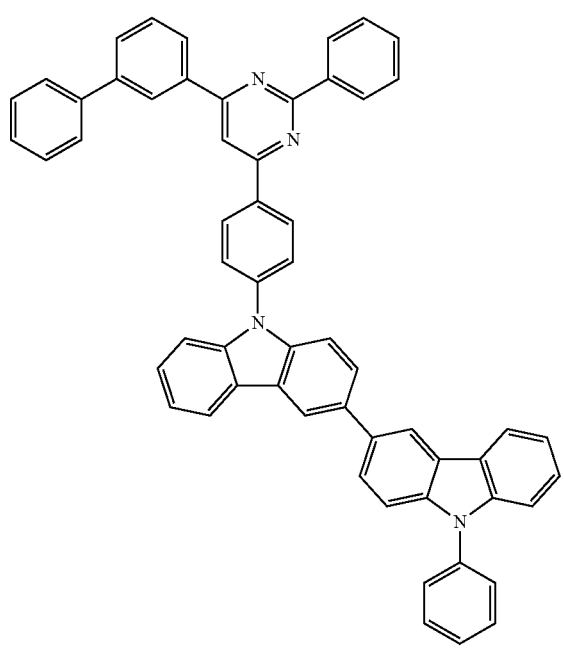
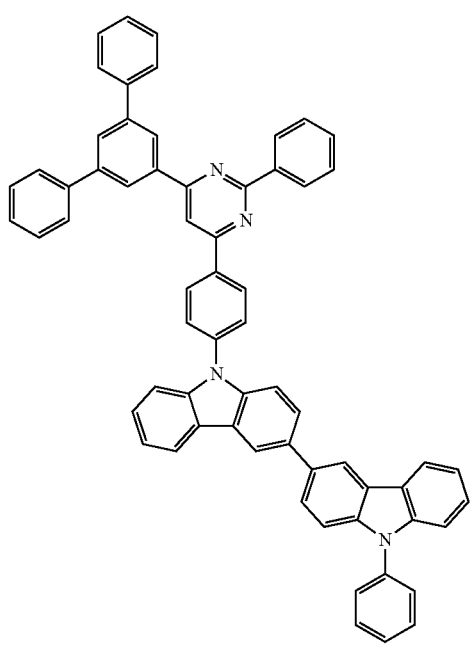

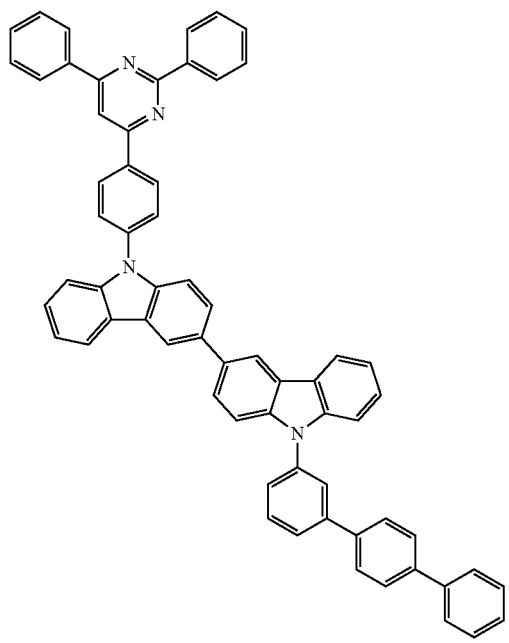
[Formula 15]
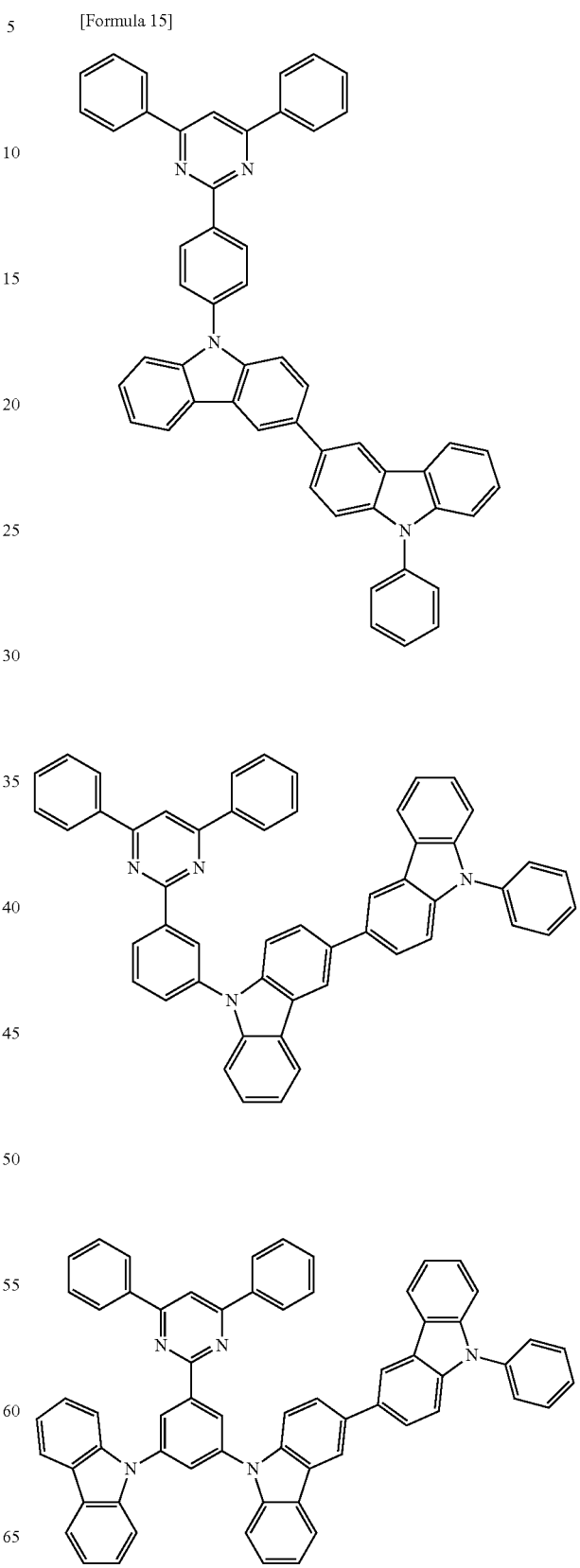

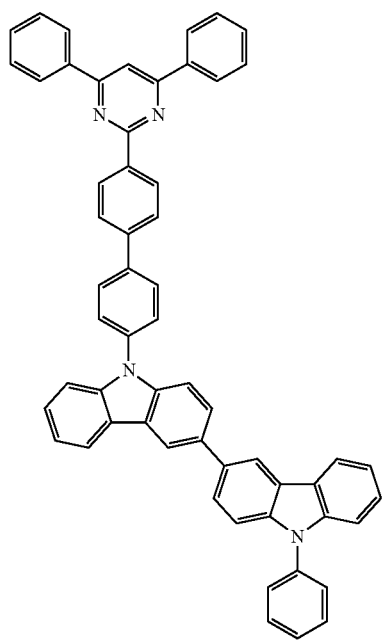
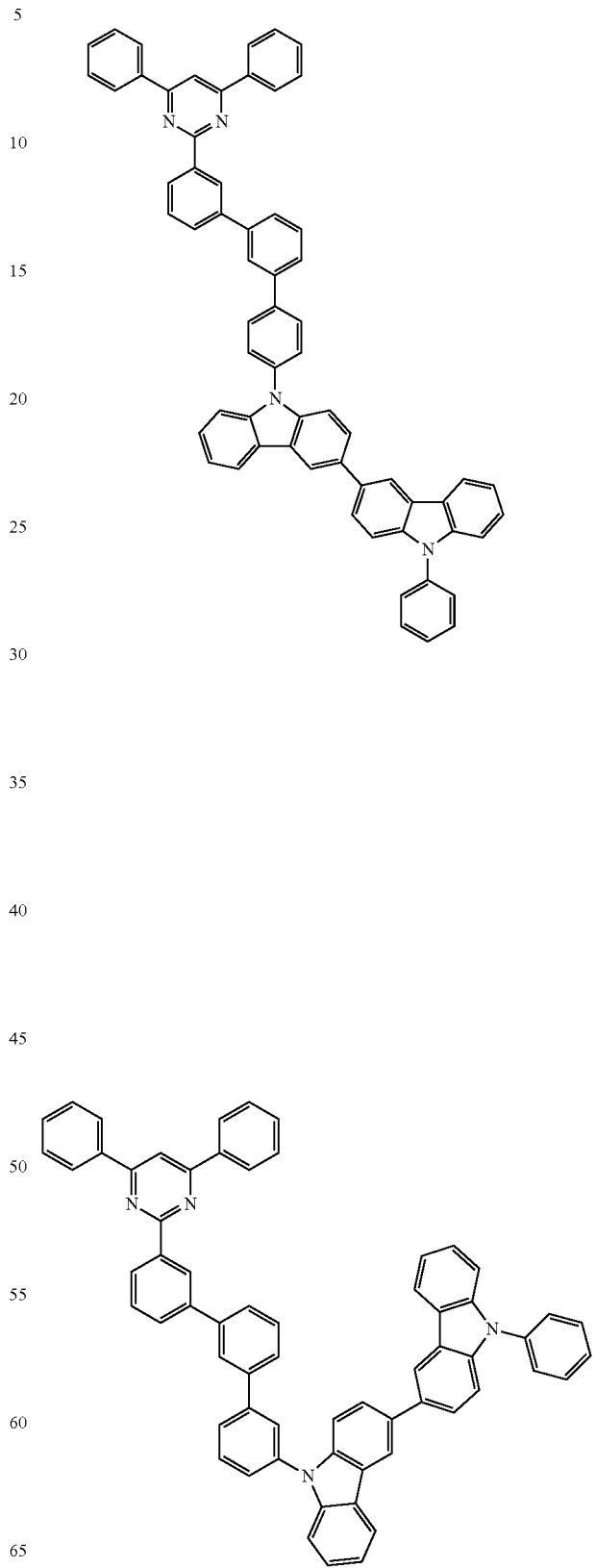

31
-continued
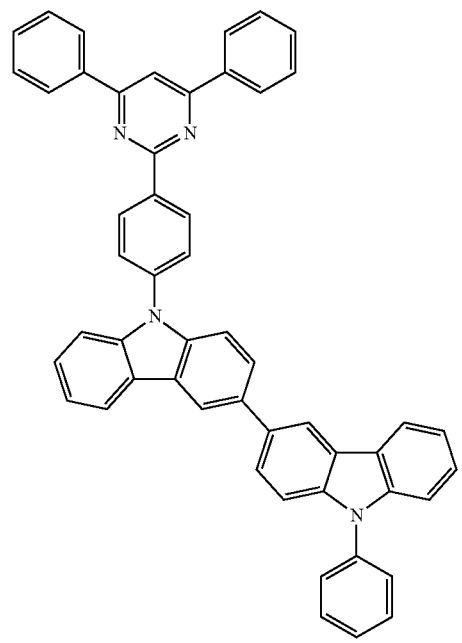
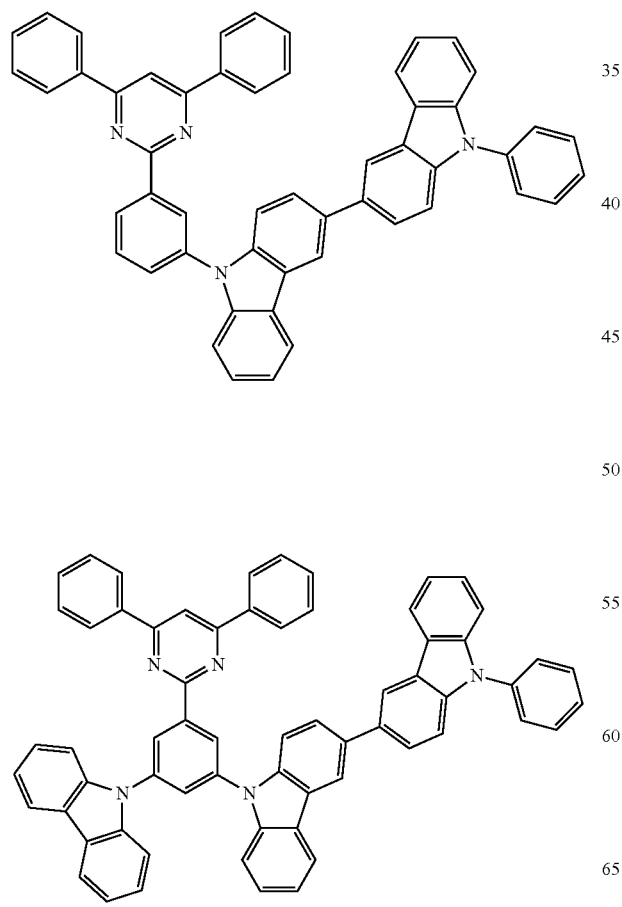
32
-continued
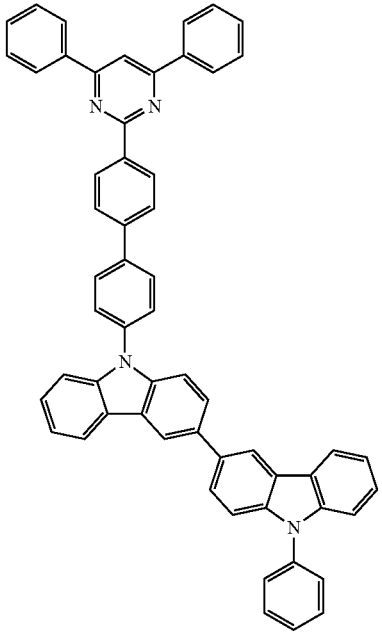
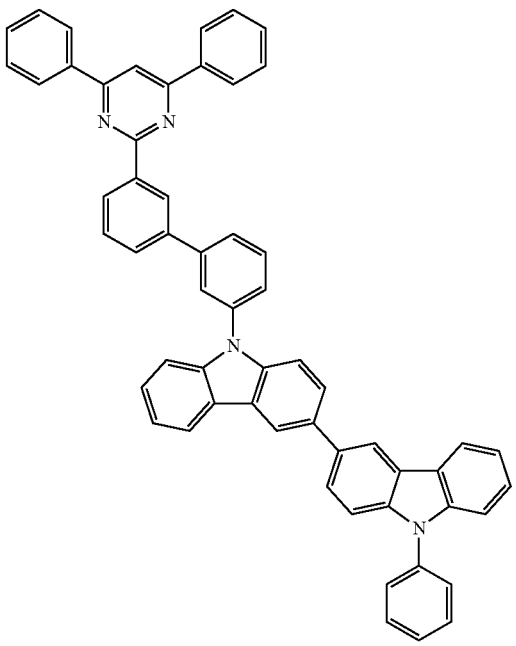

33
-continued
34
-continued
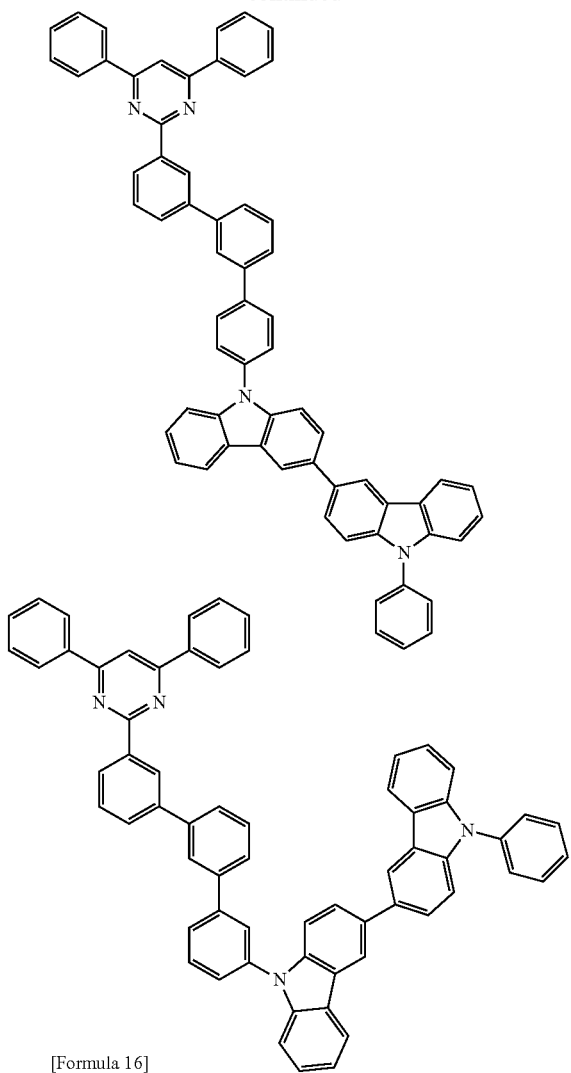
[Formula 16]
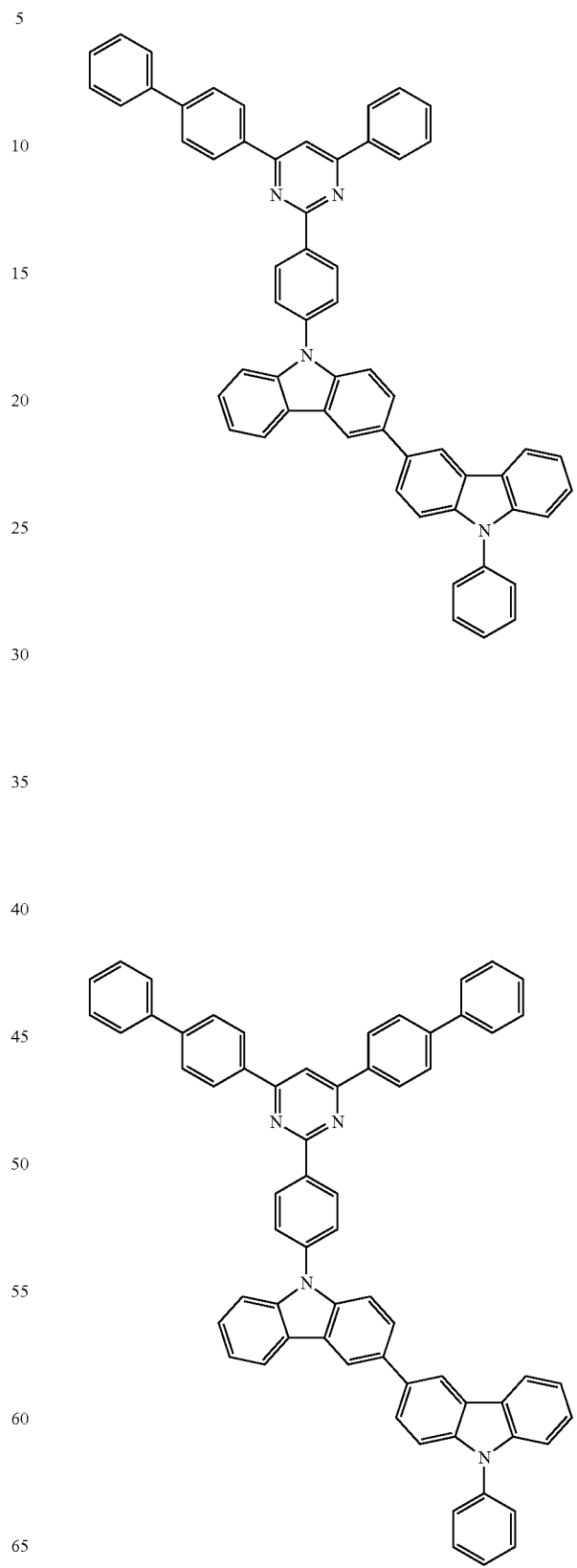

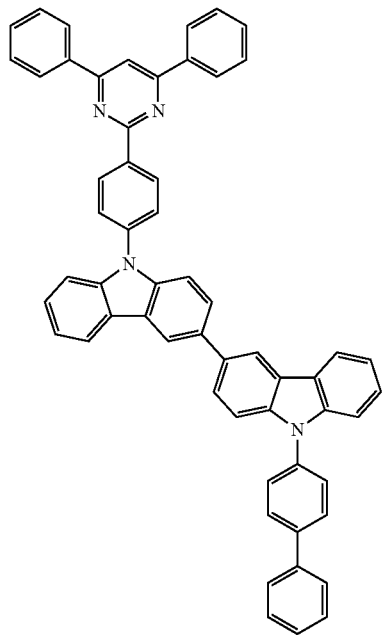
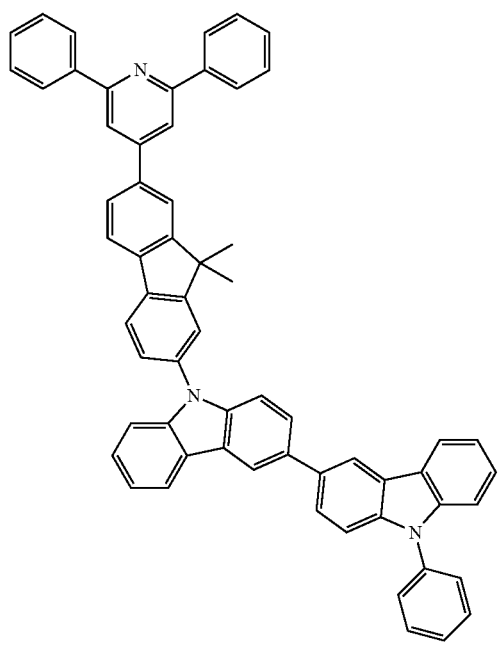
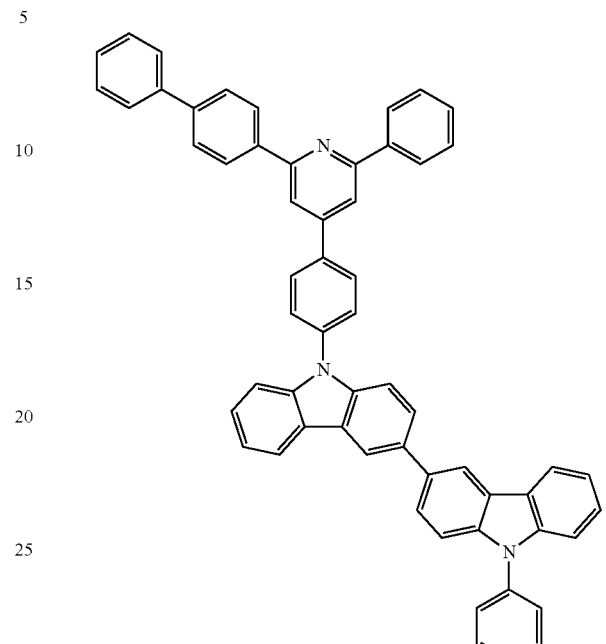
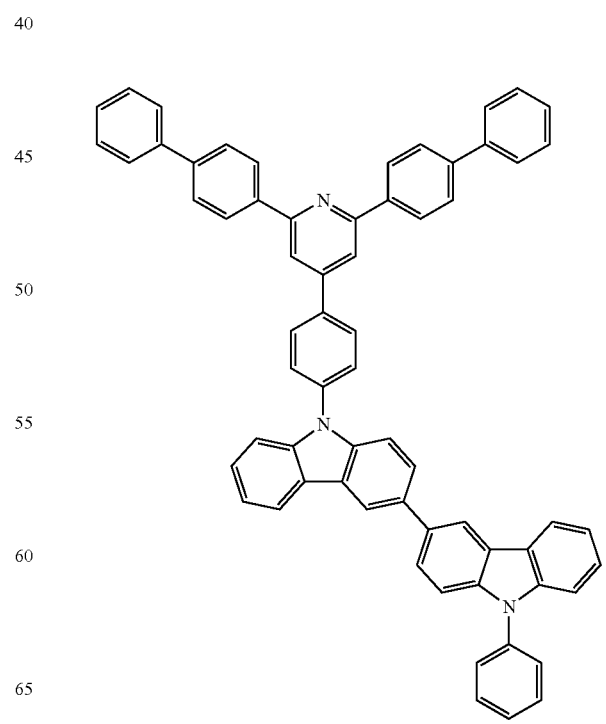

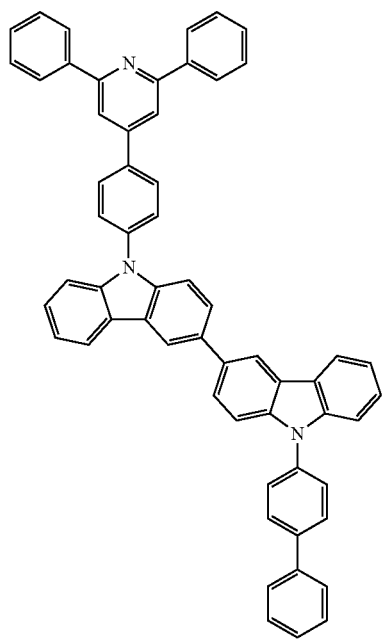
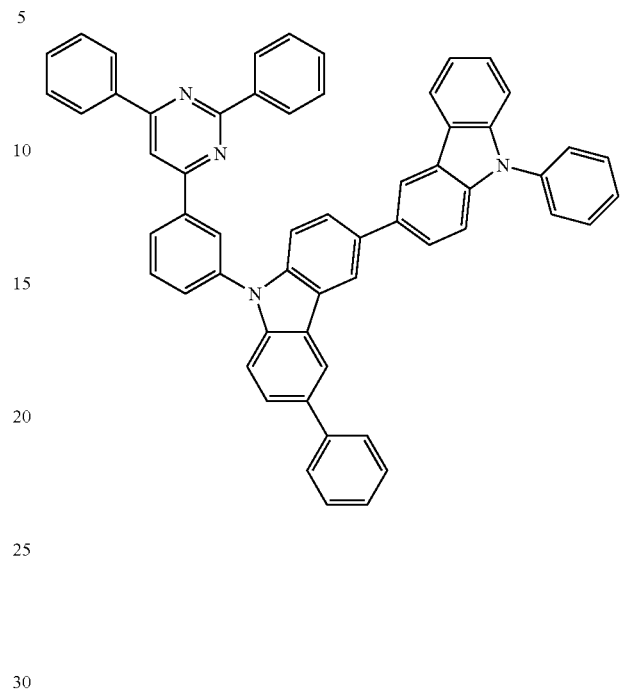
[Formula 17]
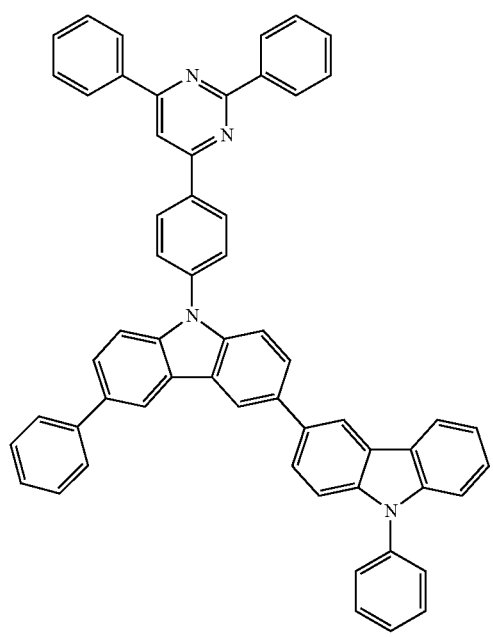
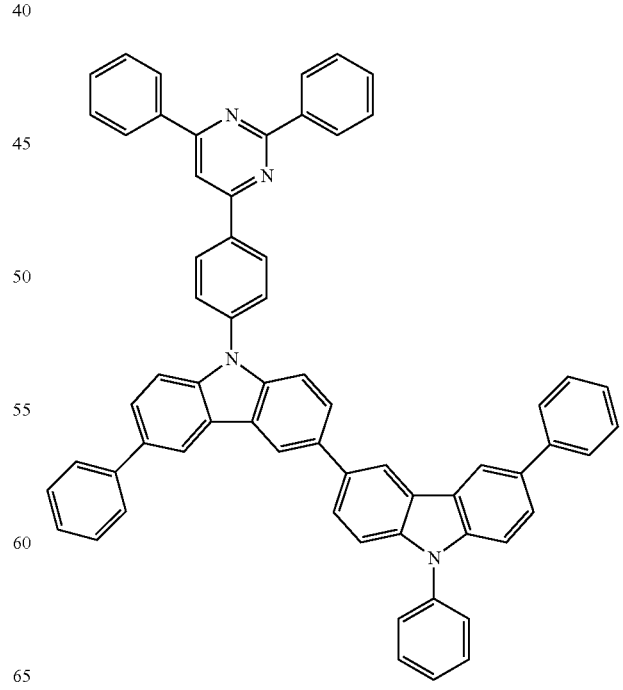

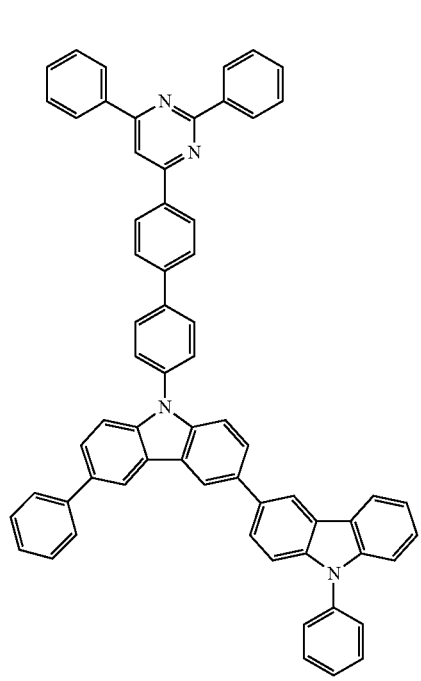
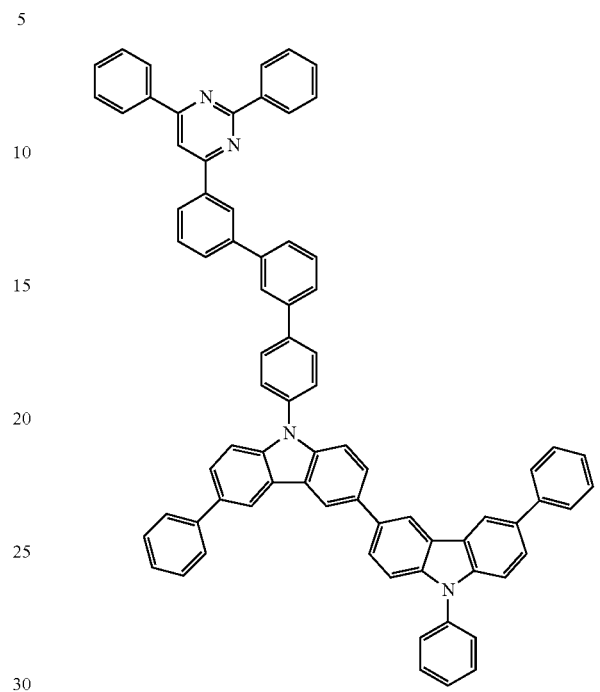
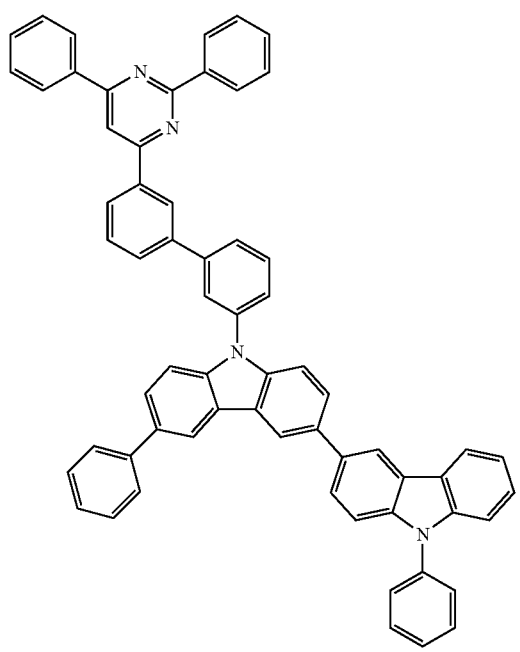
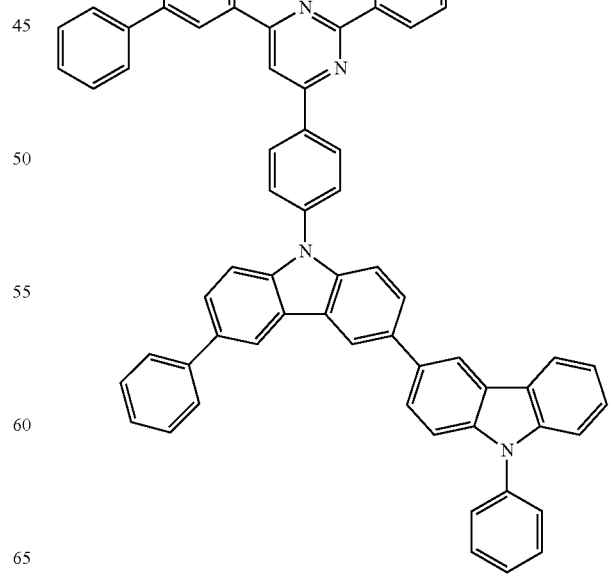

-continued
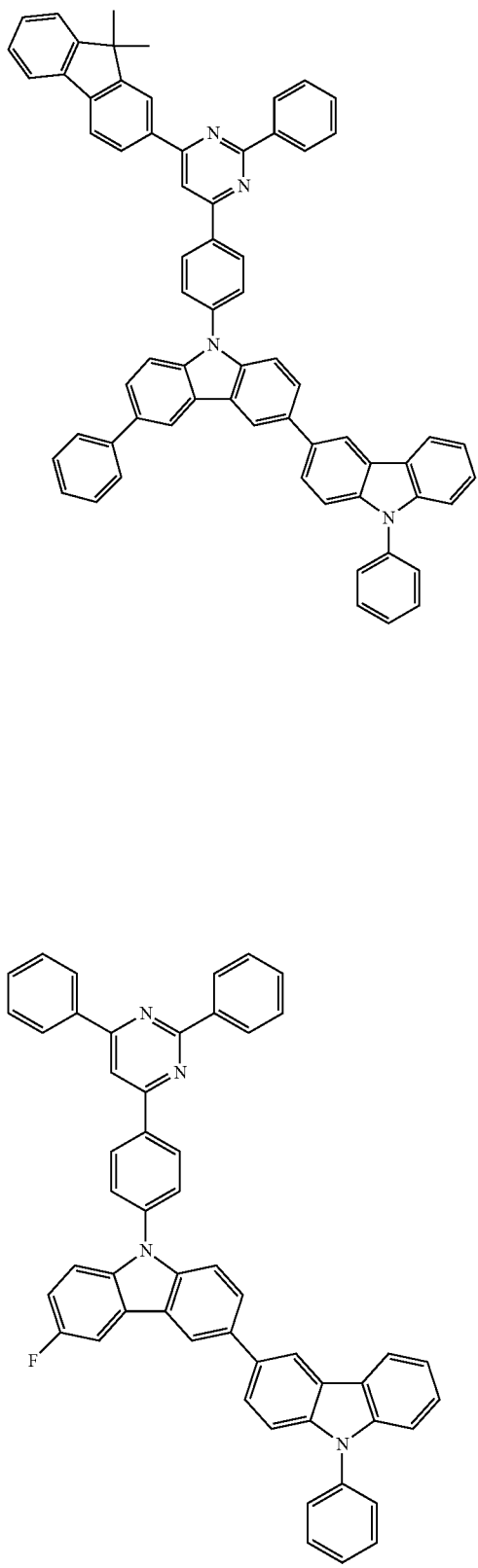
-continued
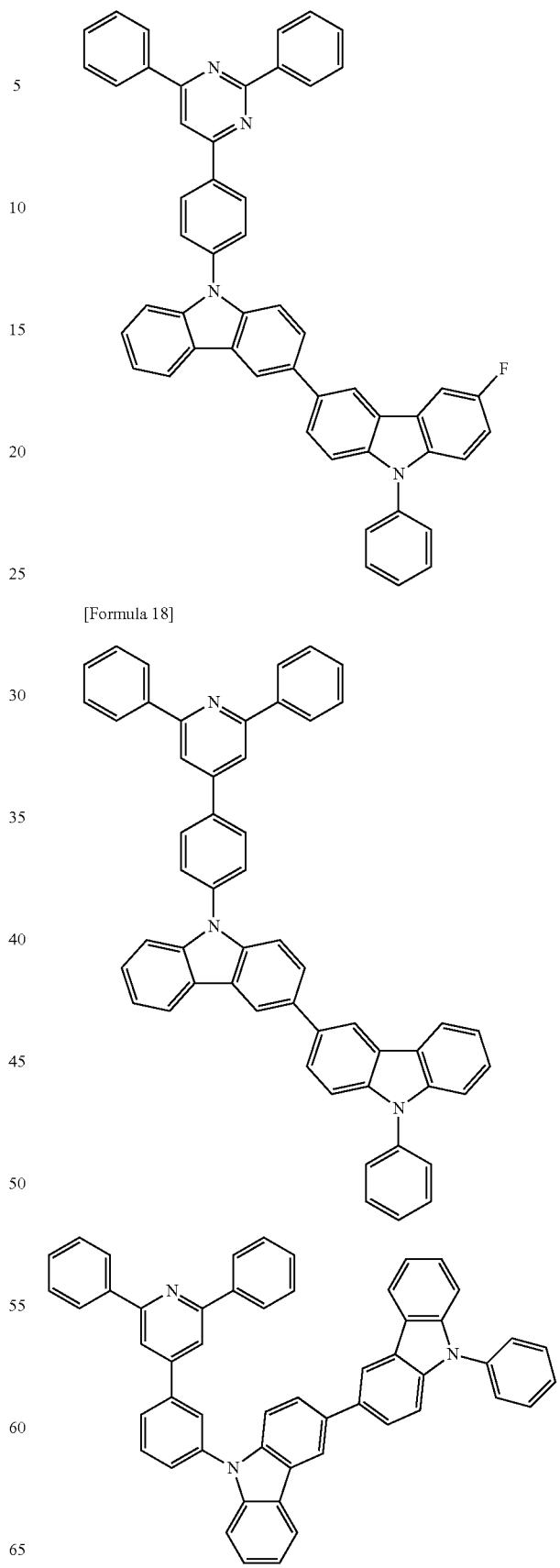
[Formula 18]

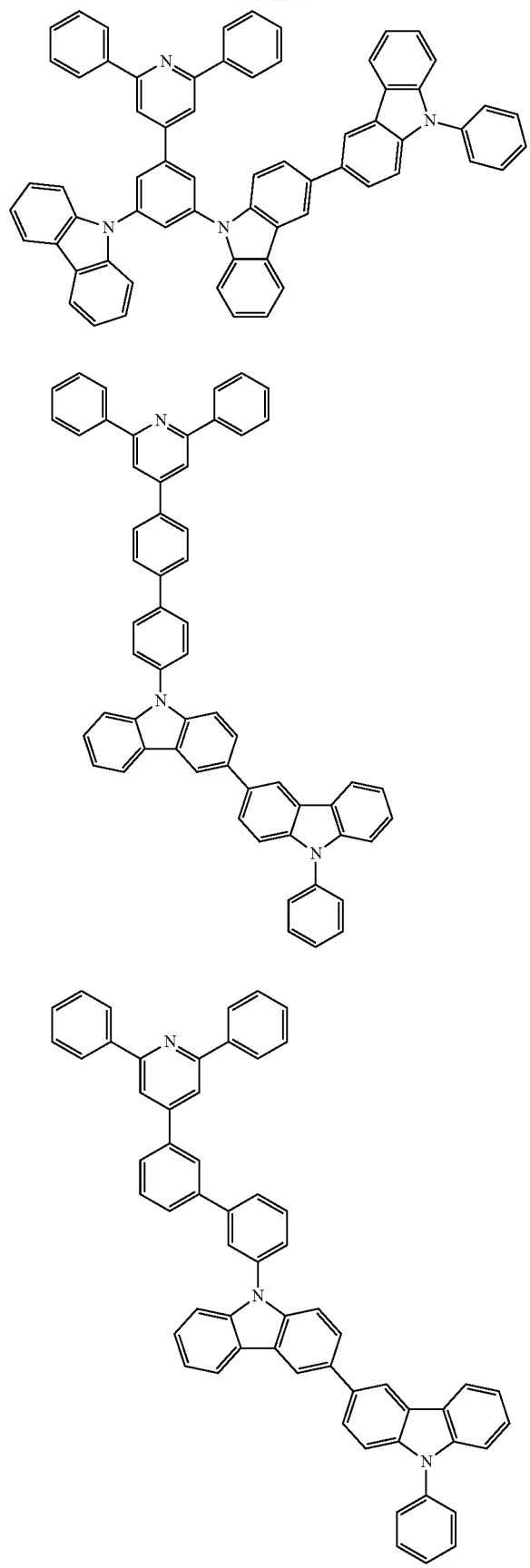
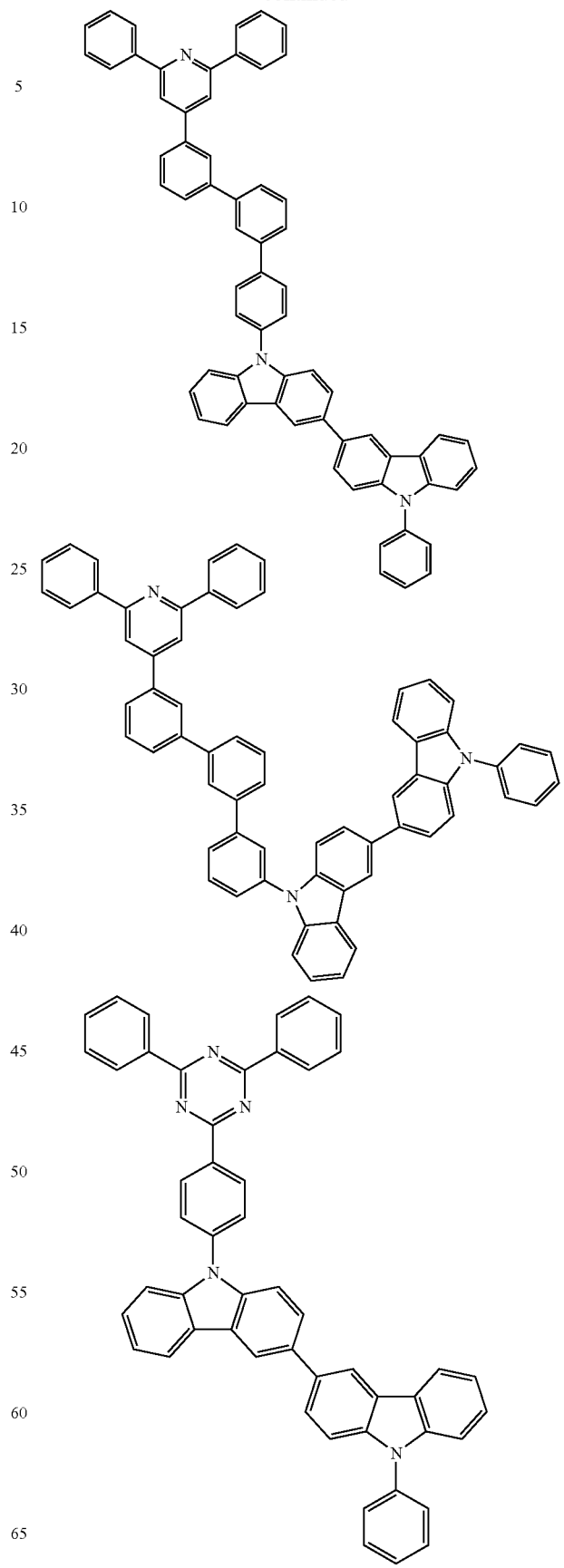

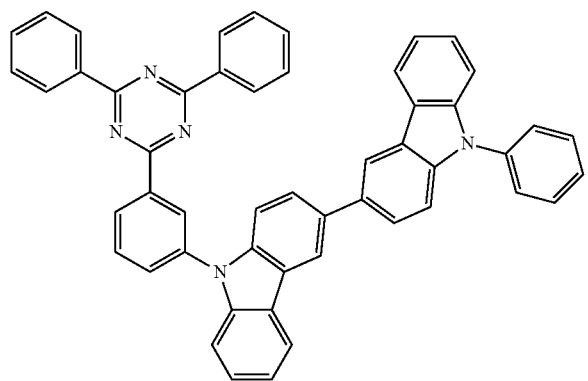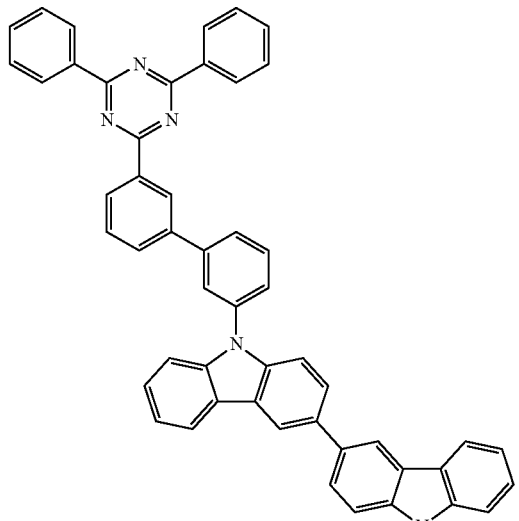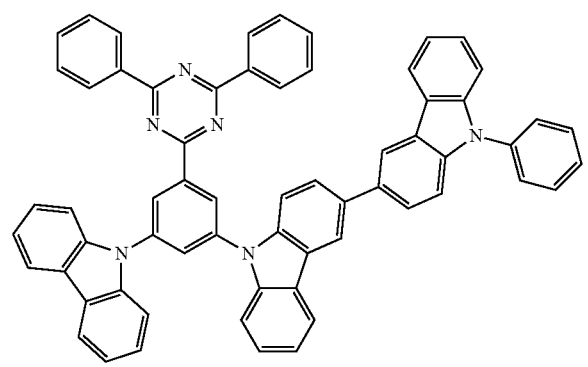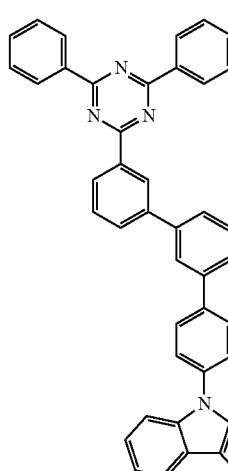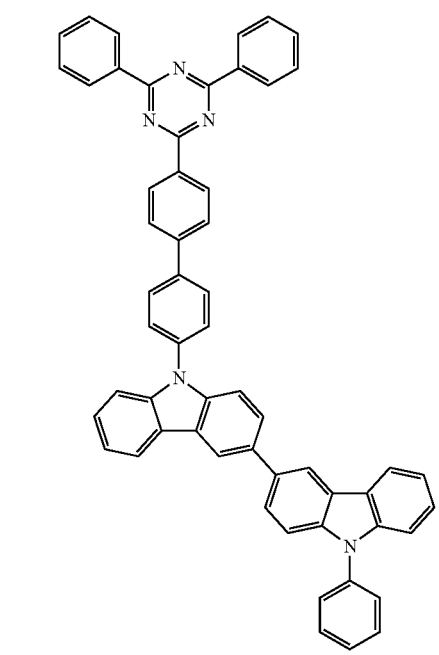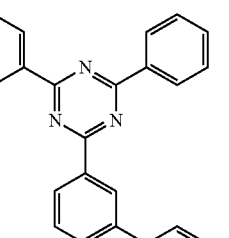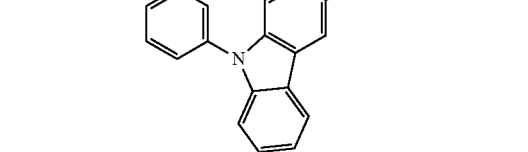

[Formula 19]
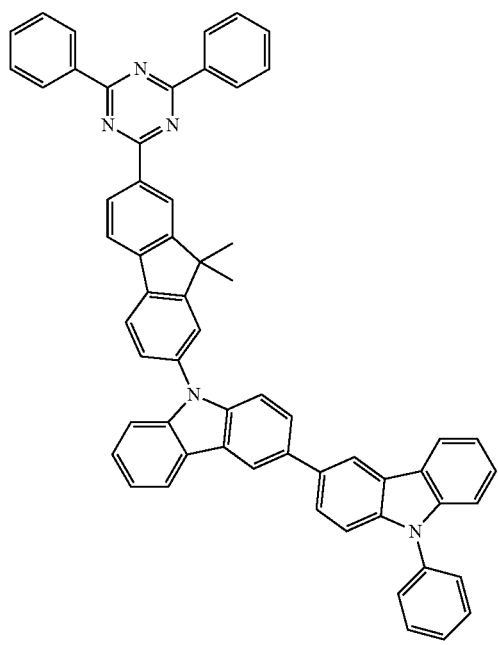
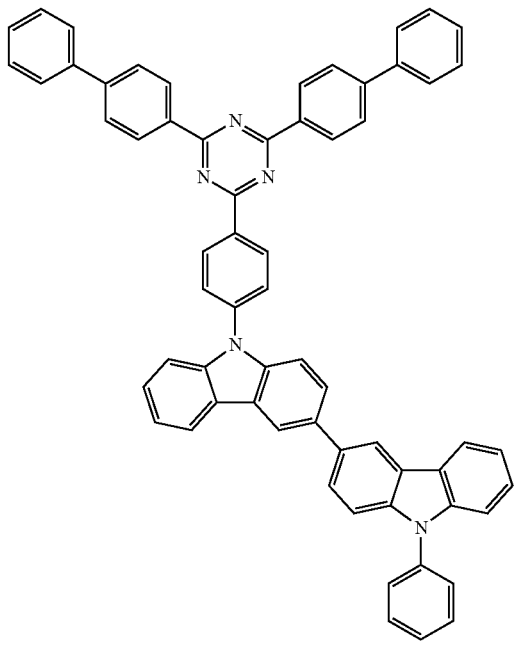
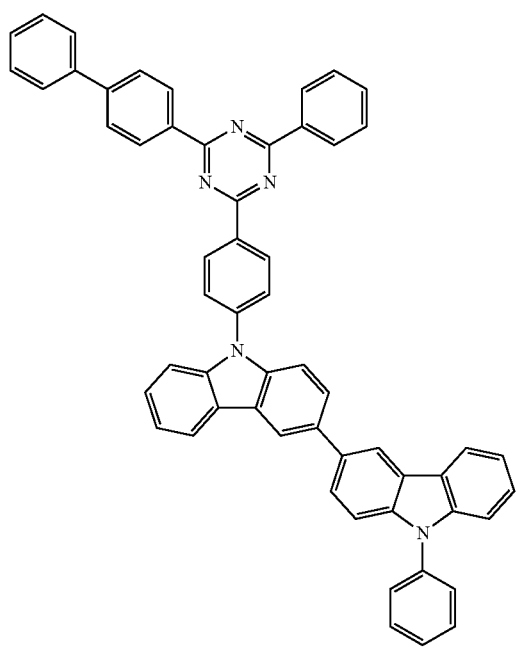

[Formula 20]
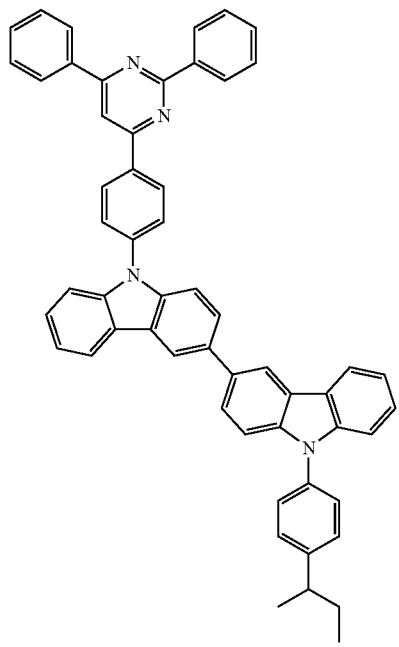
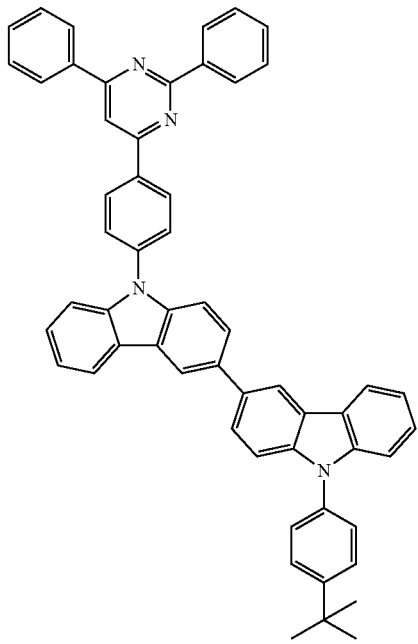
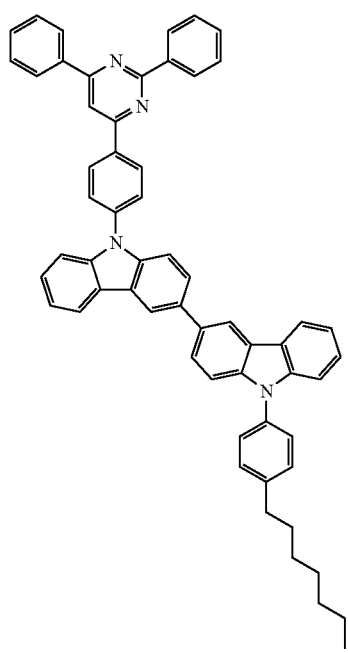
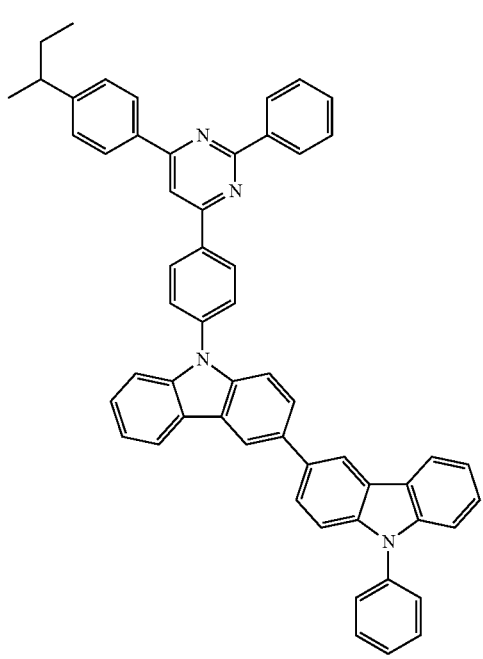

51
-continued
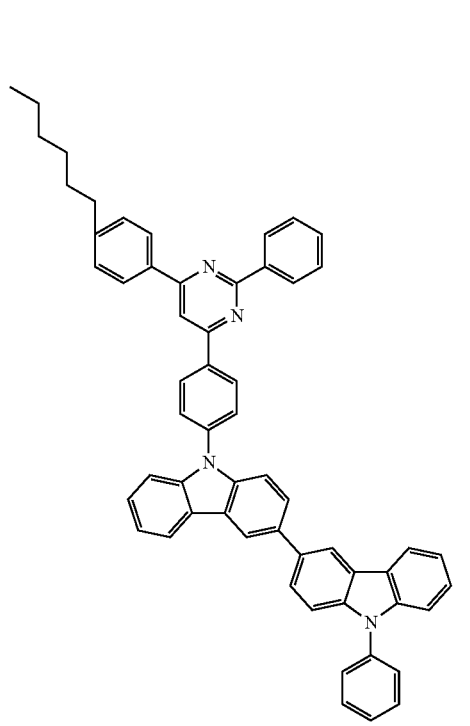
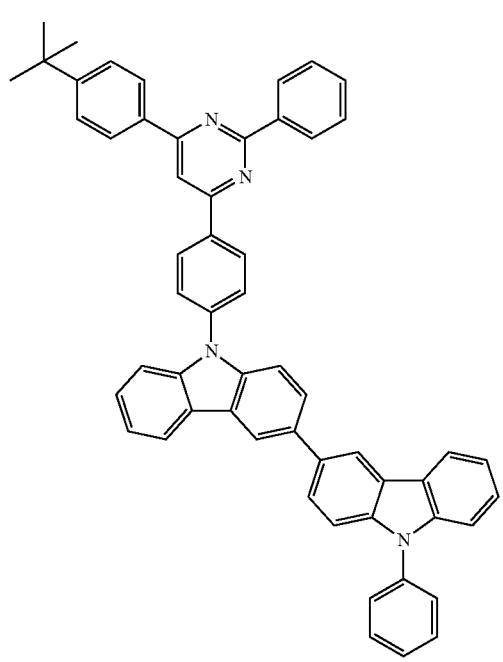
52
-continued
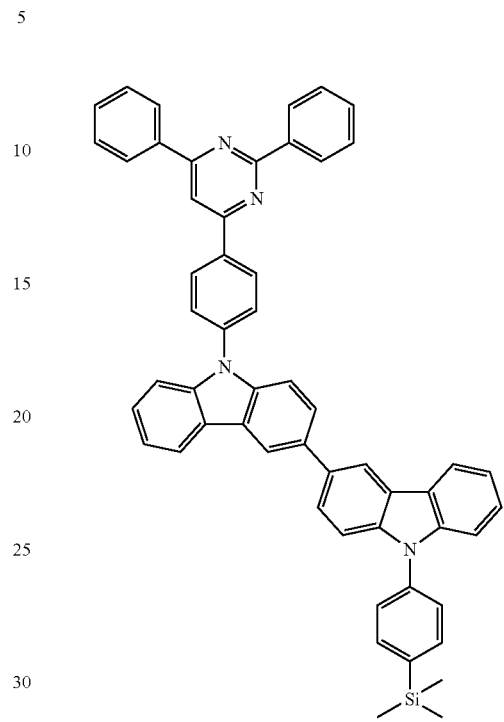
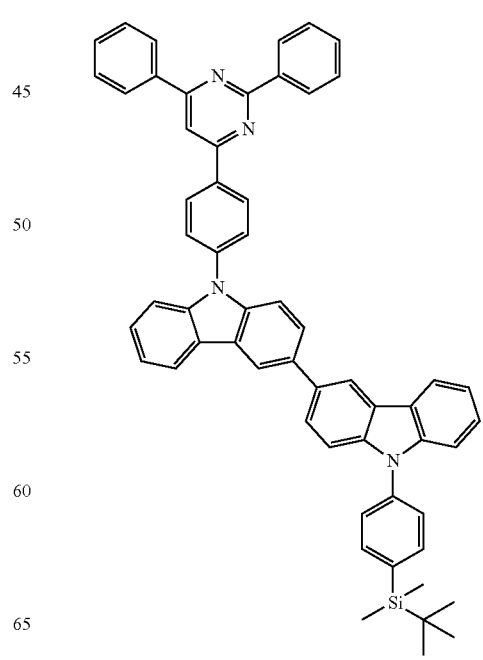

[Formula 21]
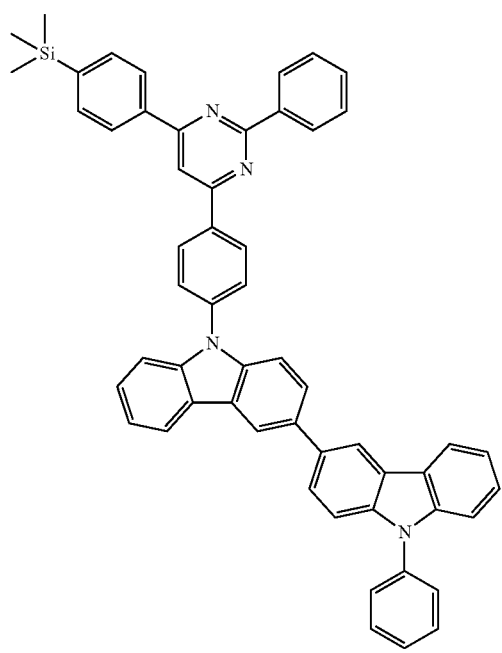
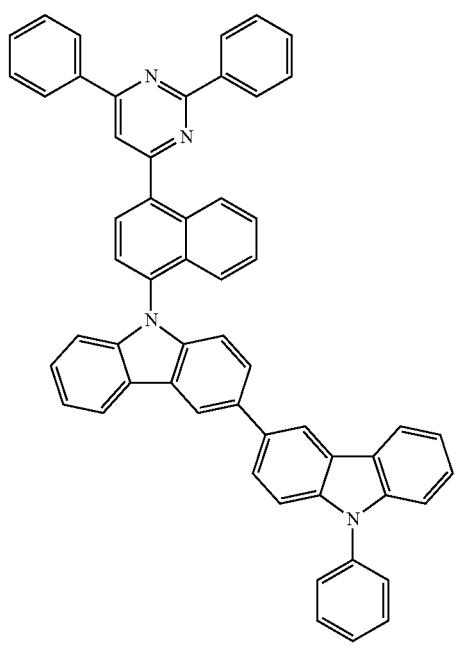
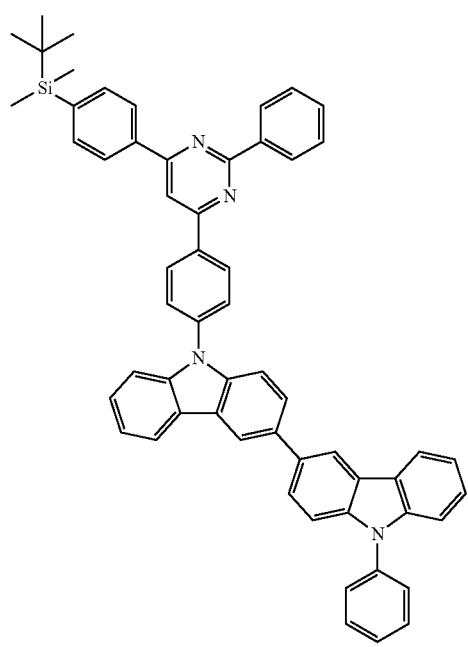
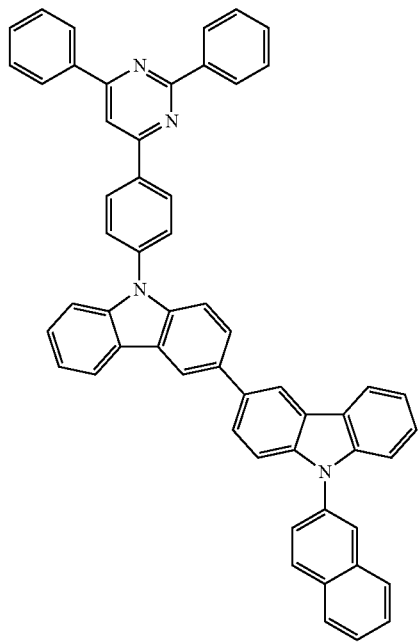

55
-continued
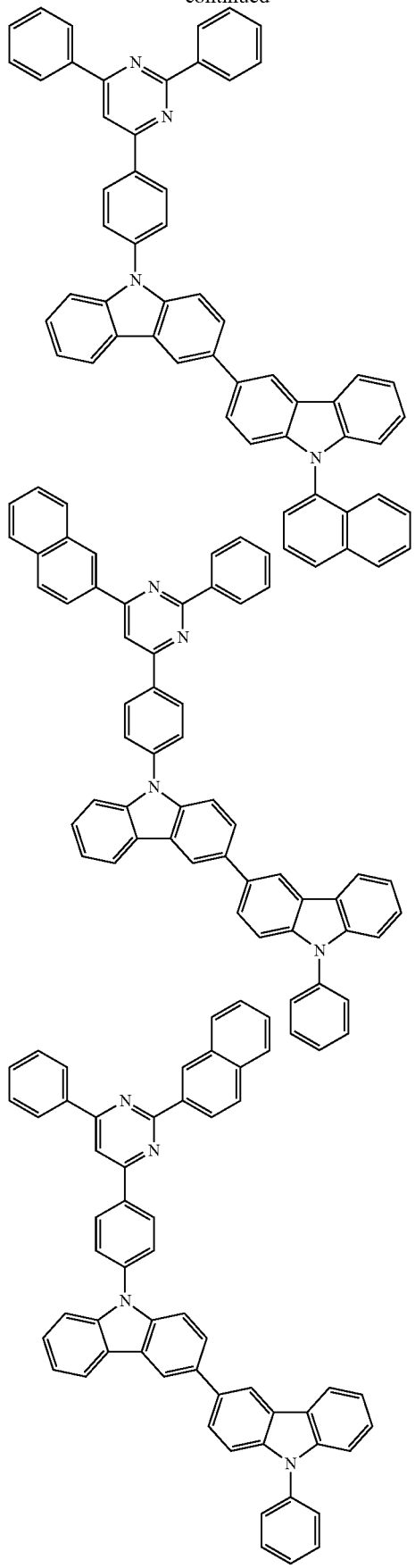
56
-continued
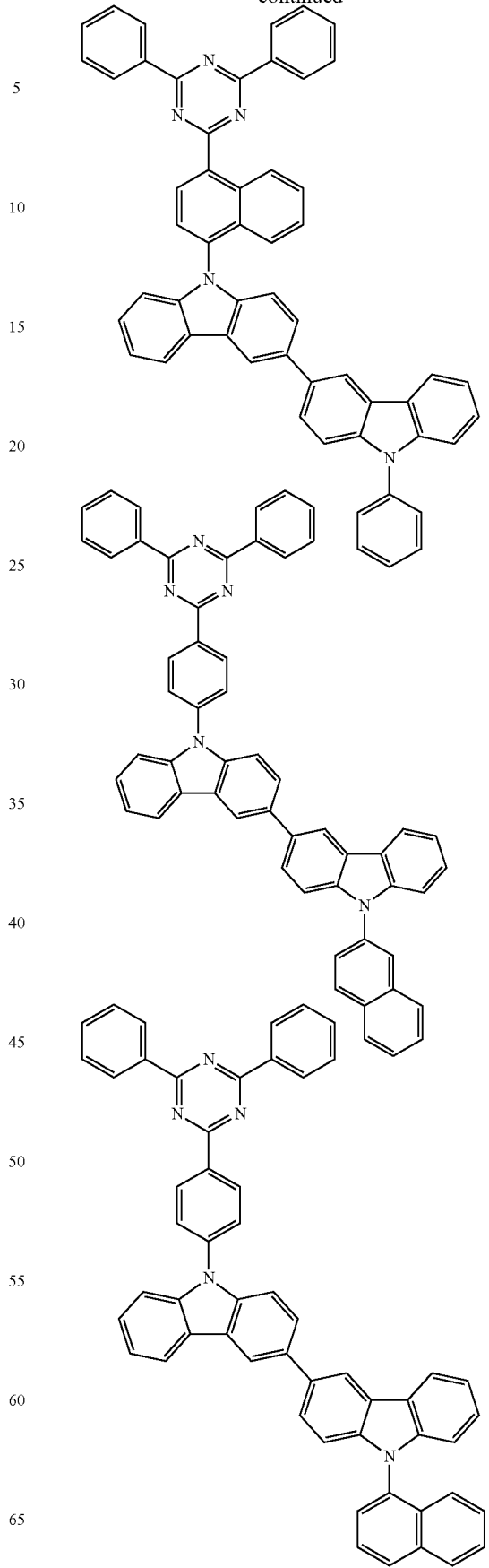

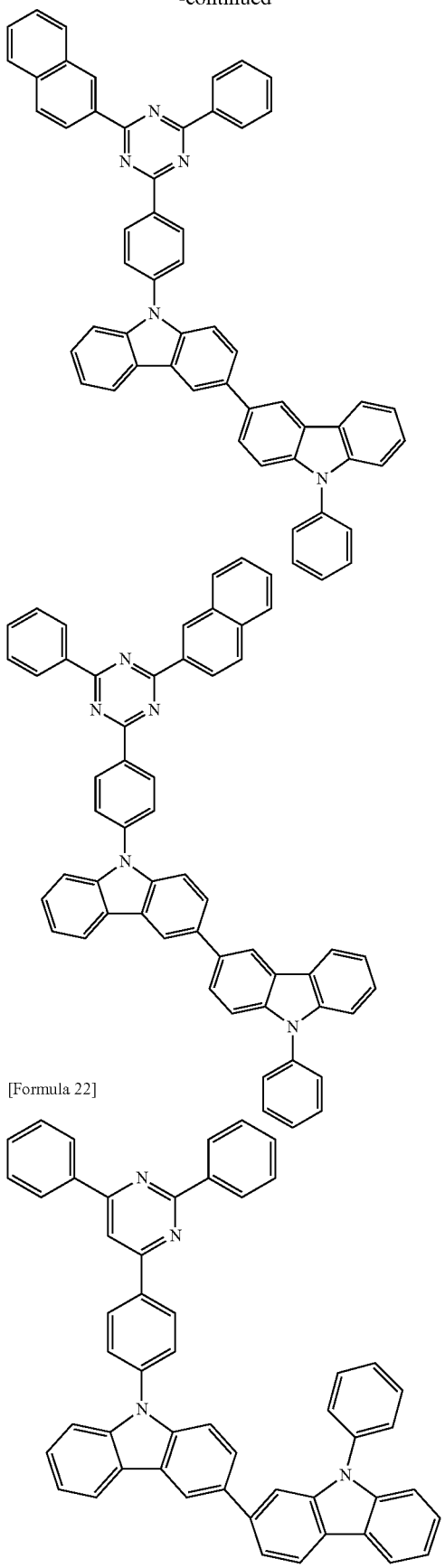
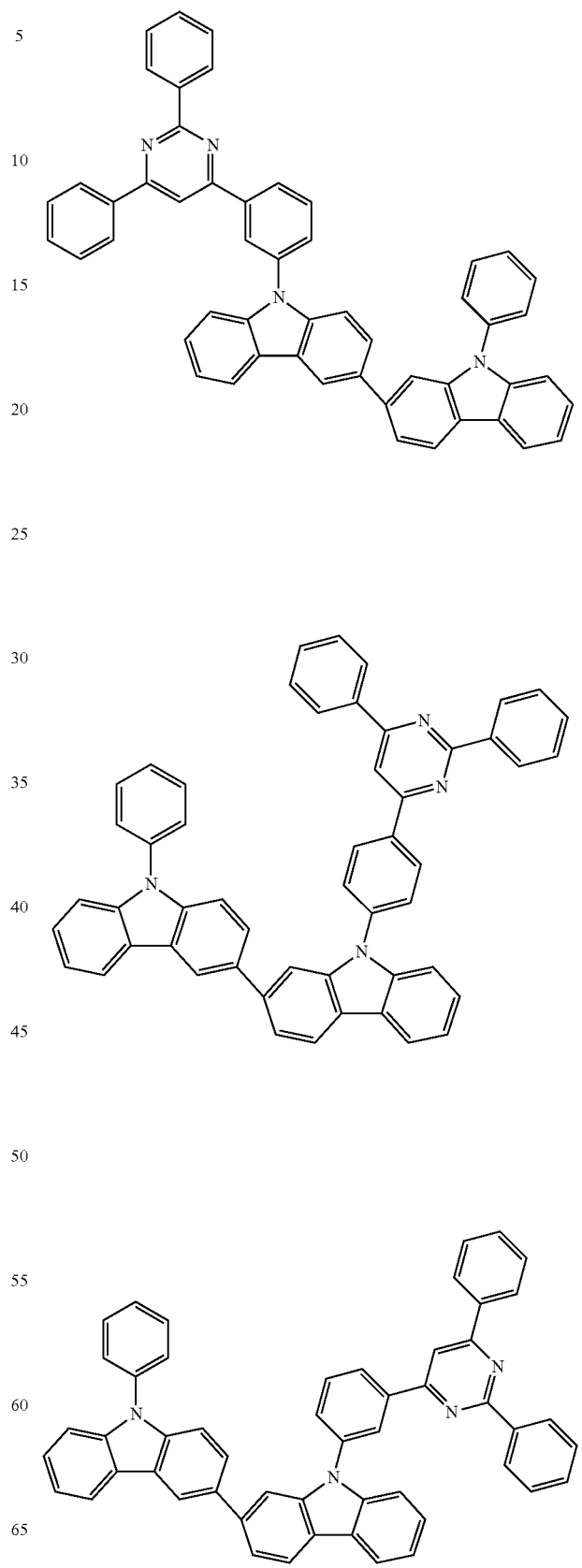
[Formula 22]

-continued
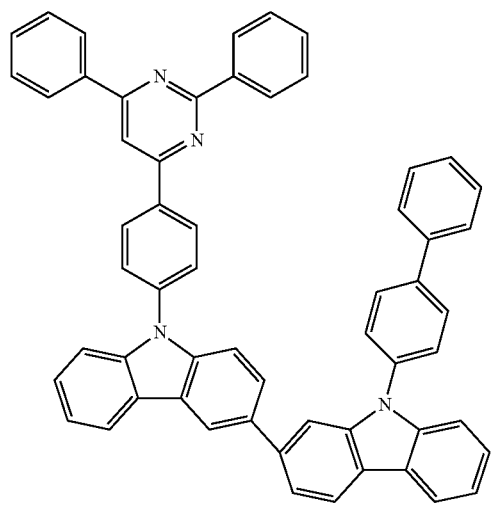
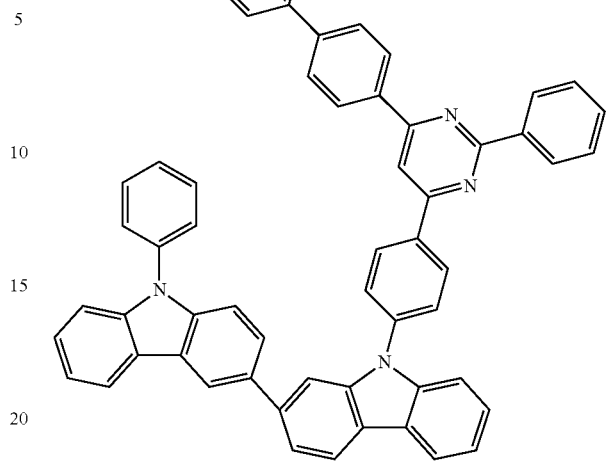
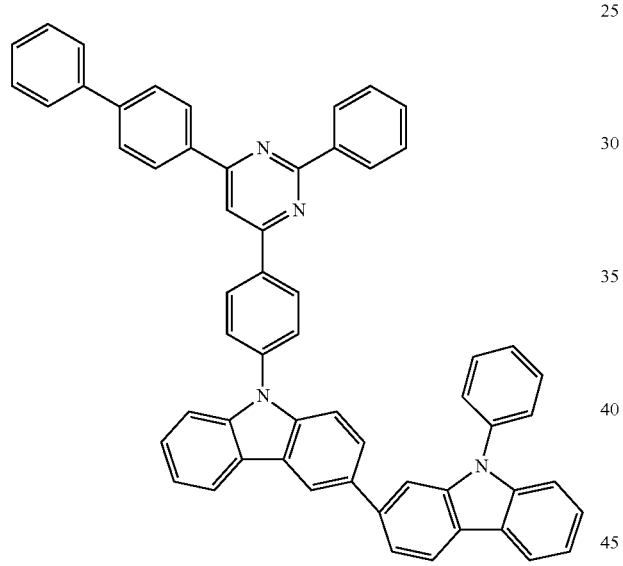
[Formula 23]
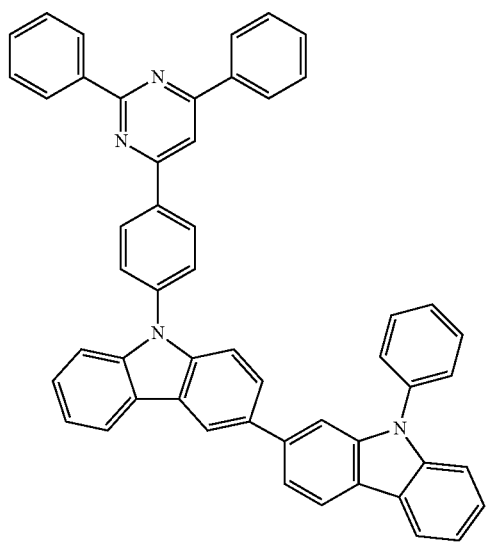
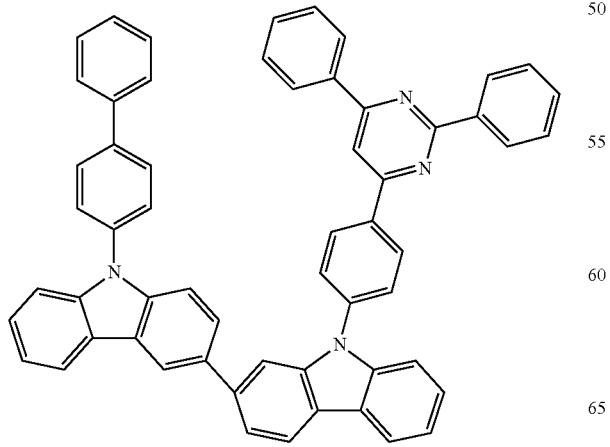
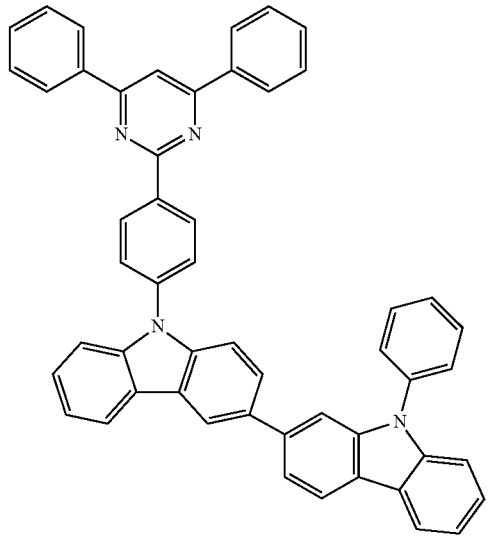

-continued
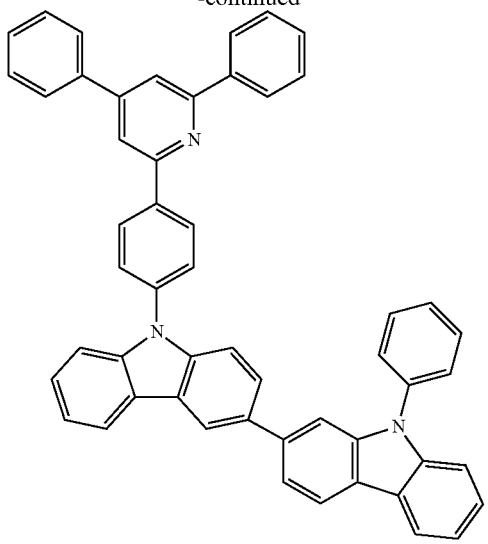
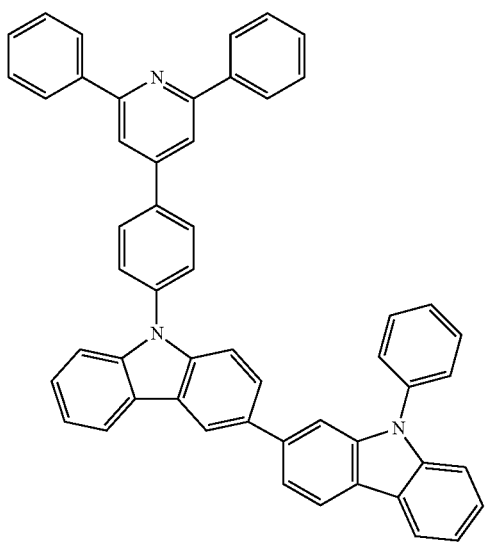
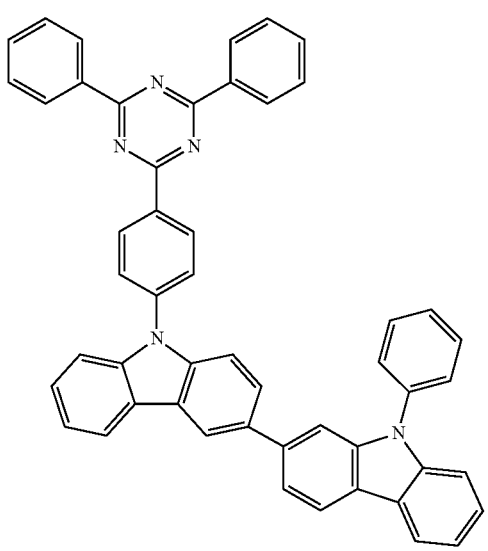
-continued
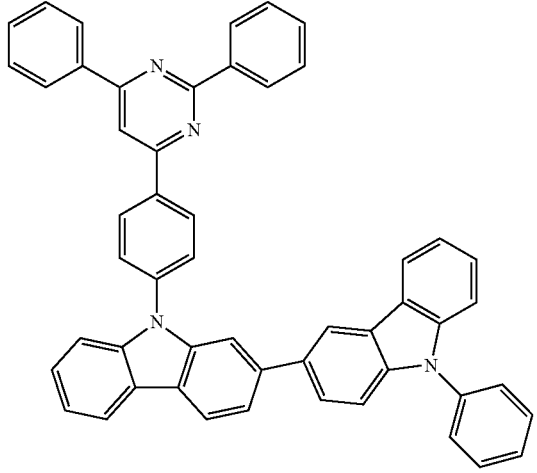
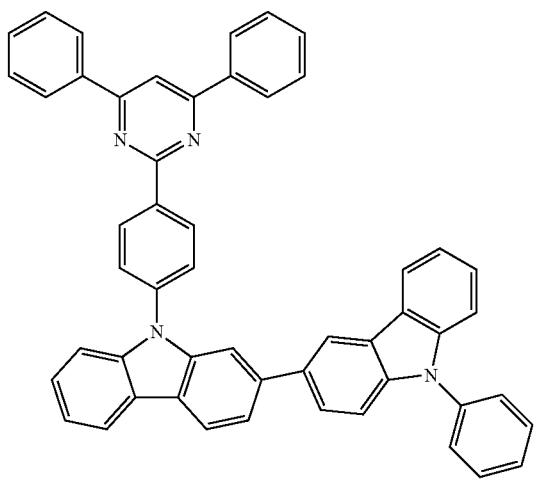
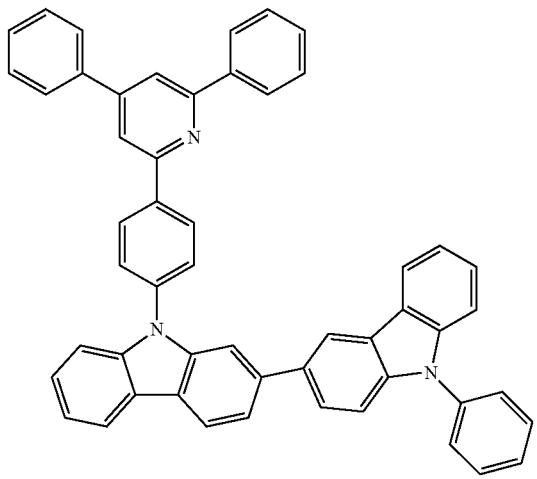

63
-continued
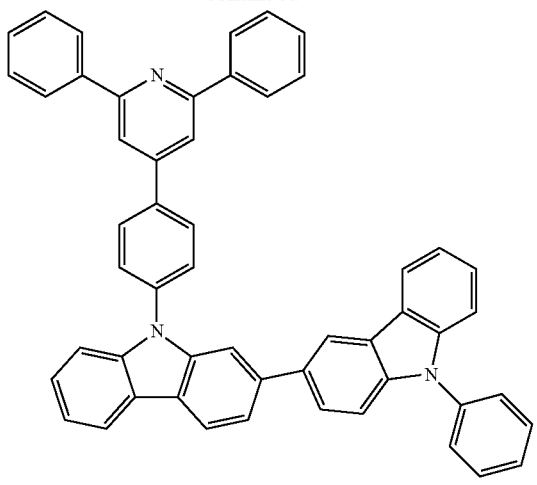
64
-continued
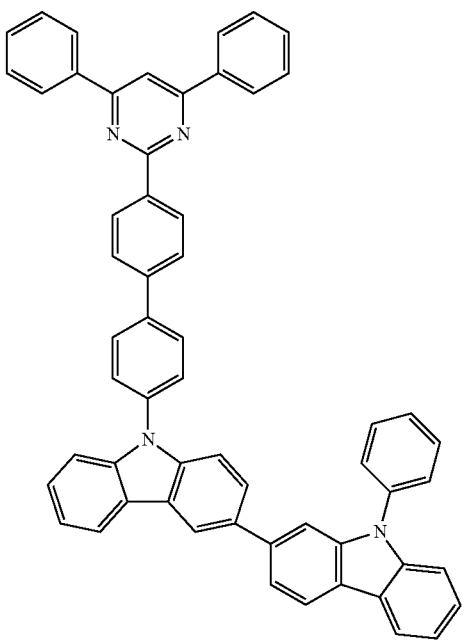
[Formula 24]
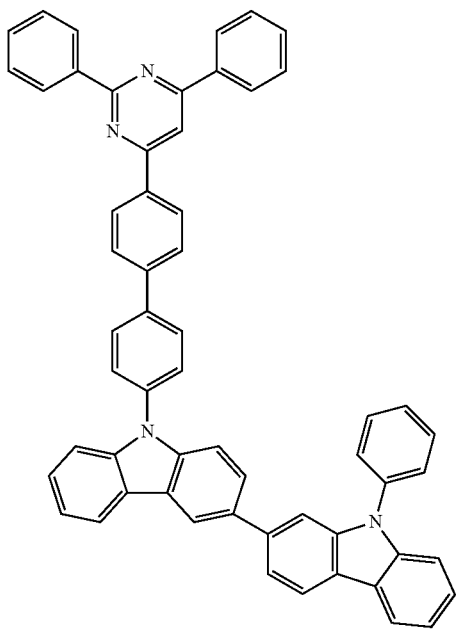
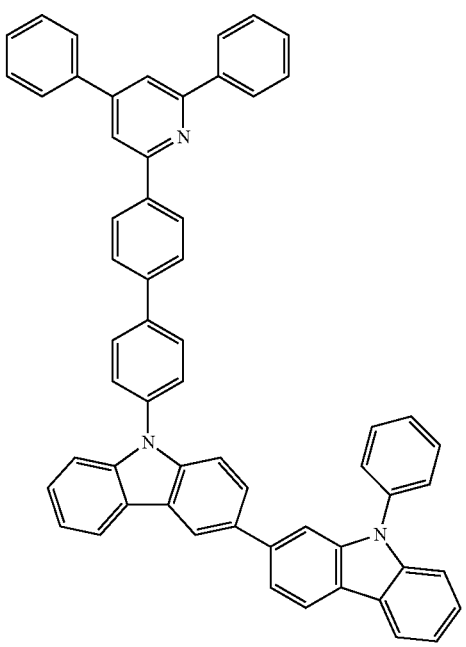

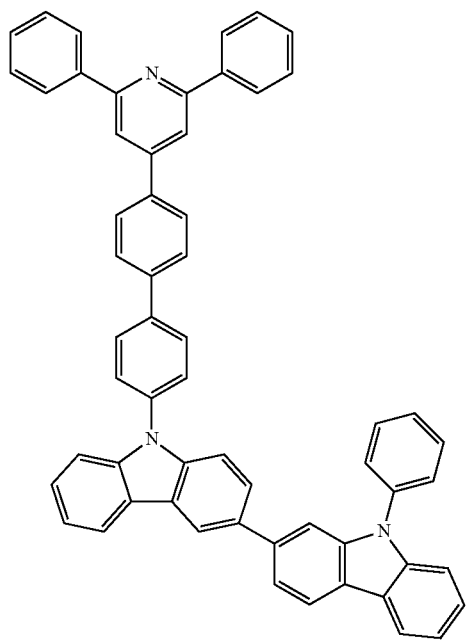
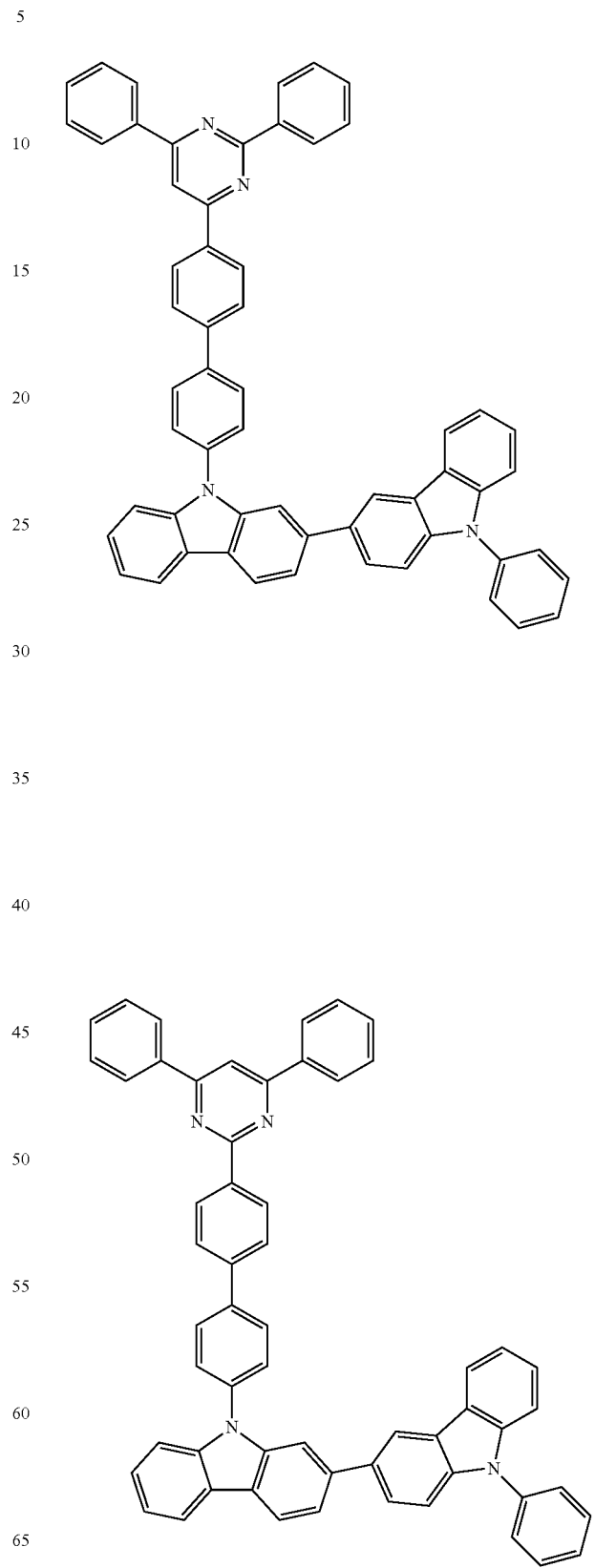

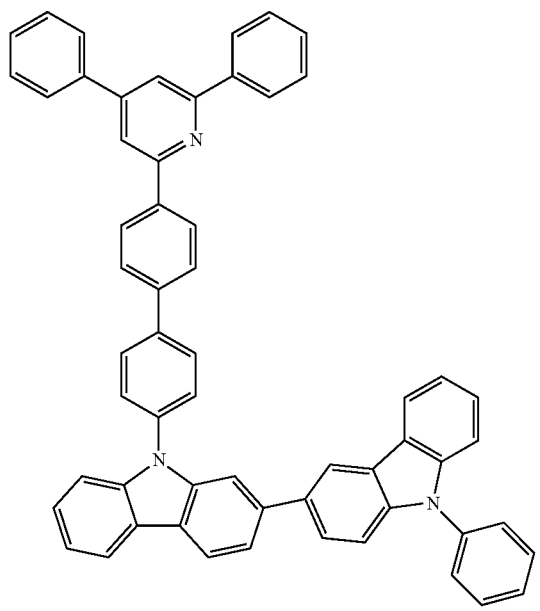
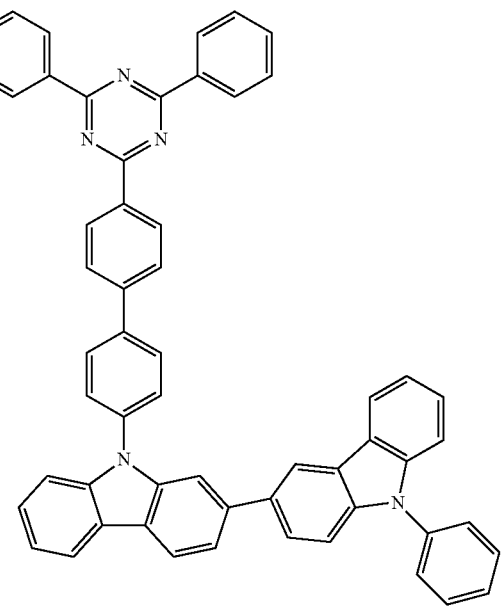
[Formula 25]
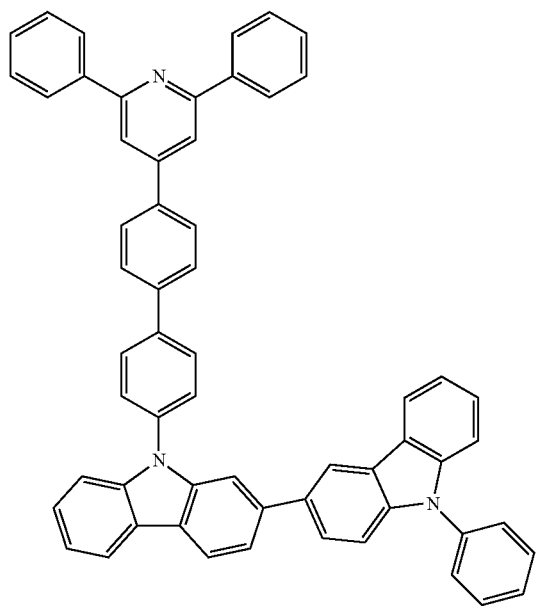
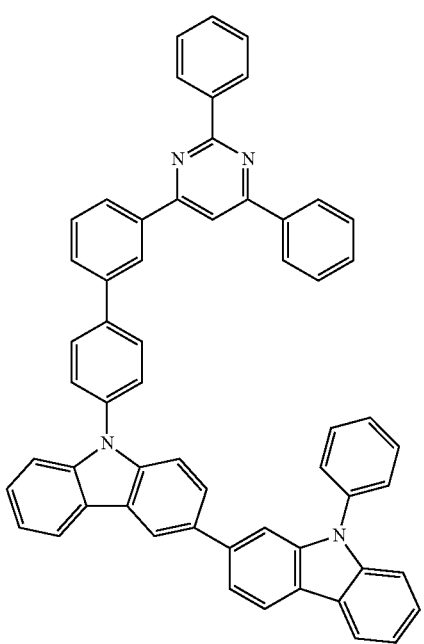

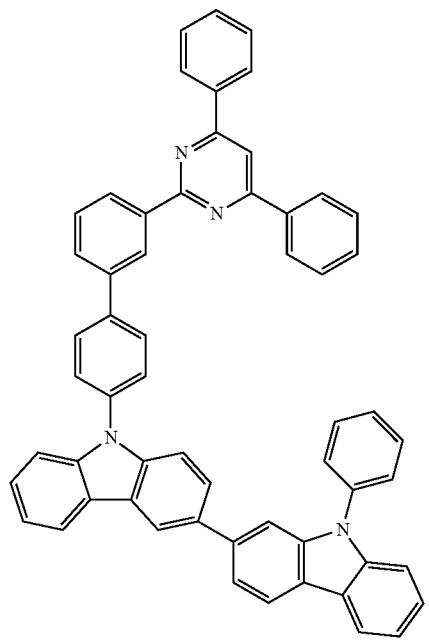
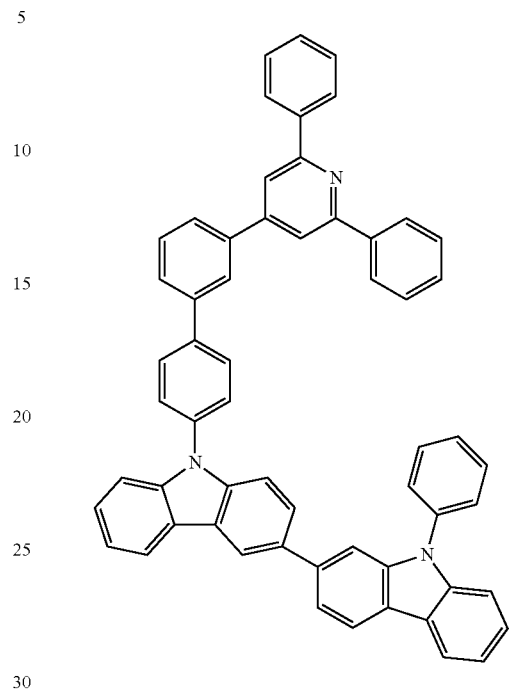
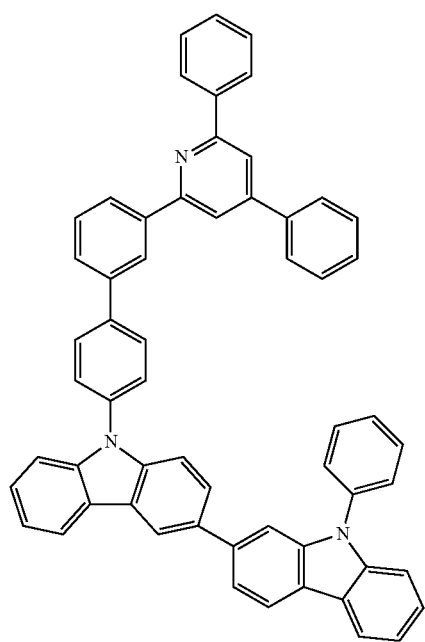
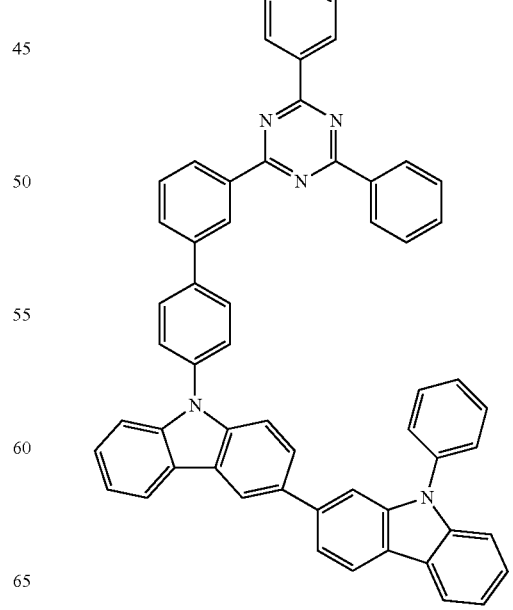

[Formula 26]
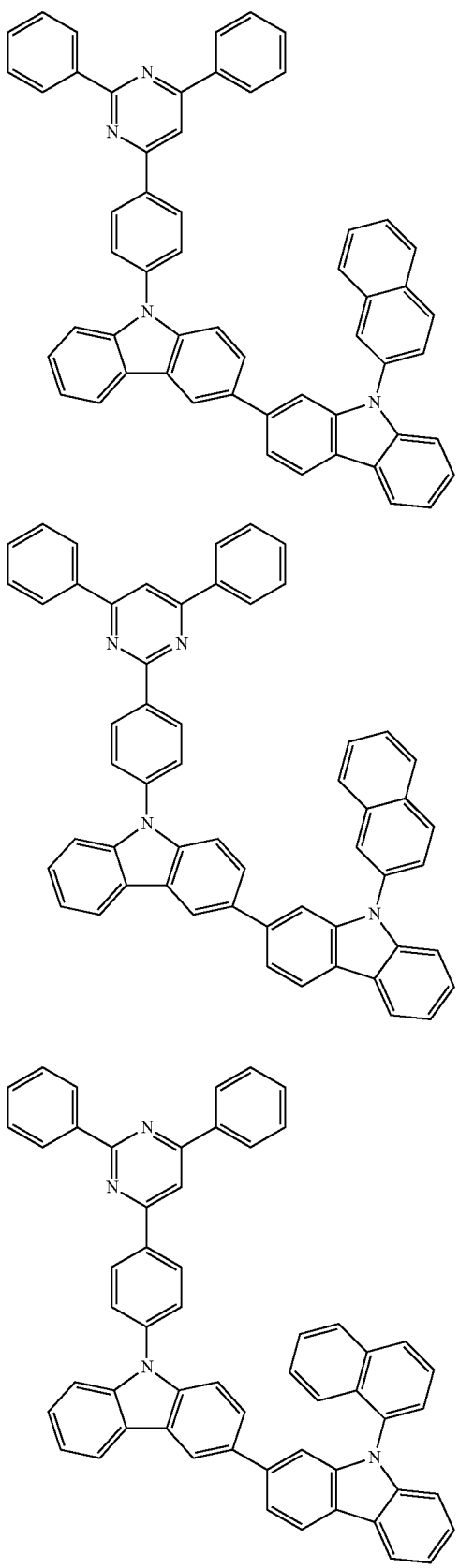
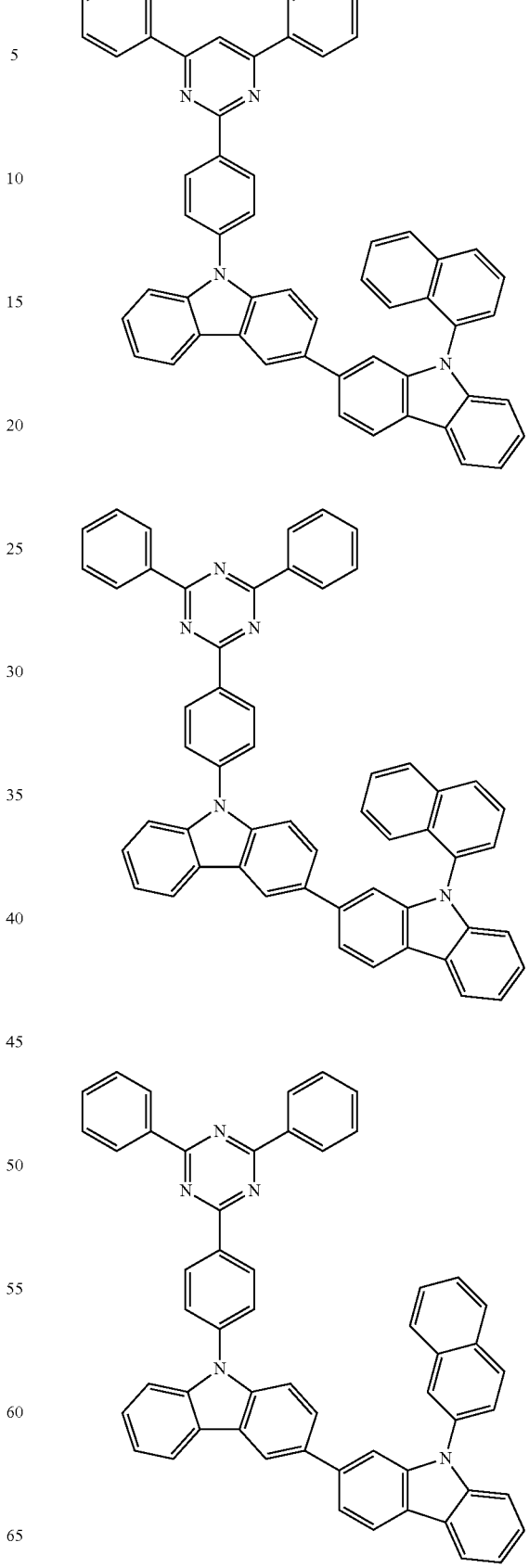

73
-continued
[Formula 27]
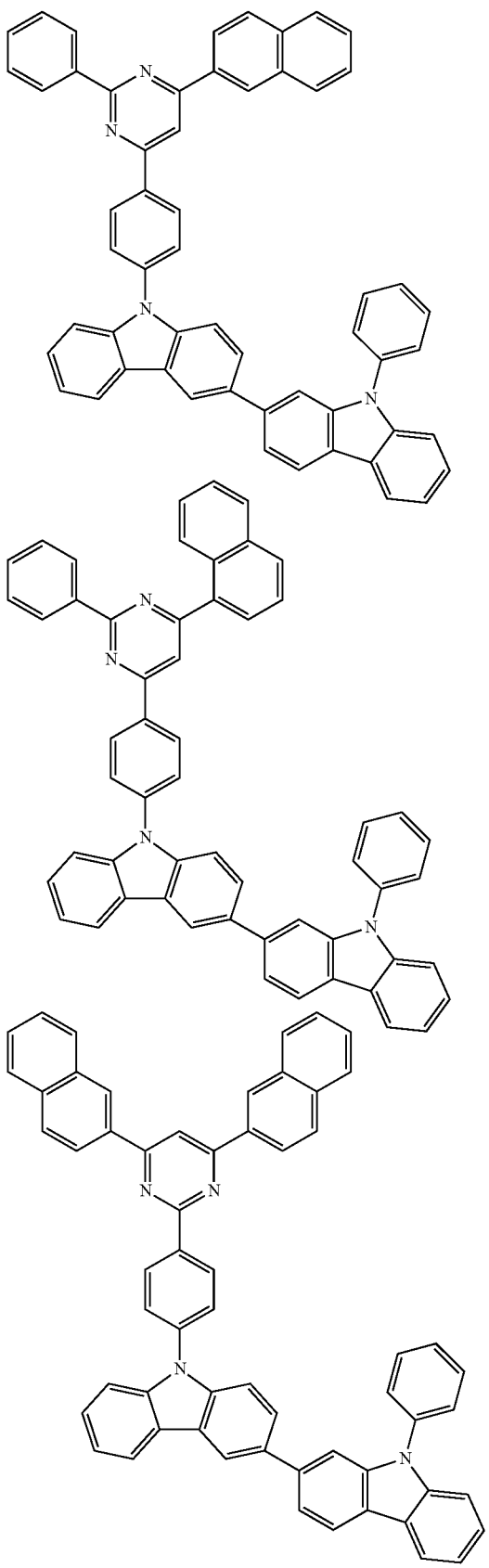
74
-continued
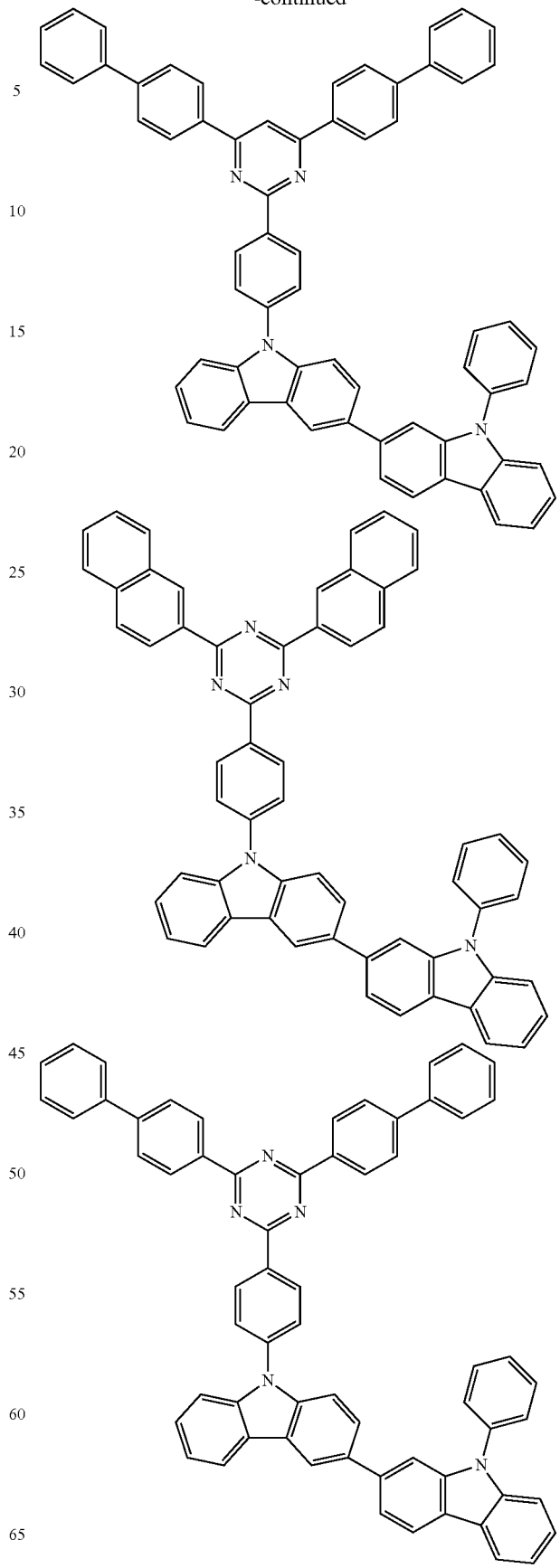

[Formula 28]
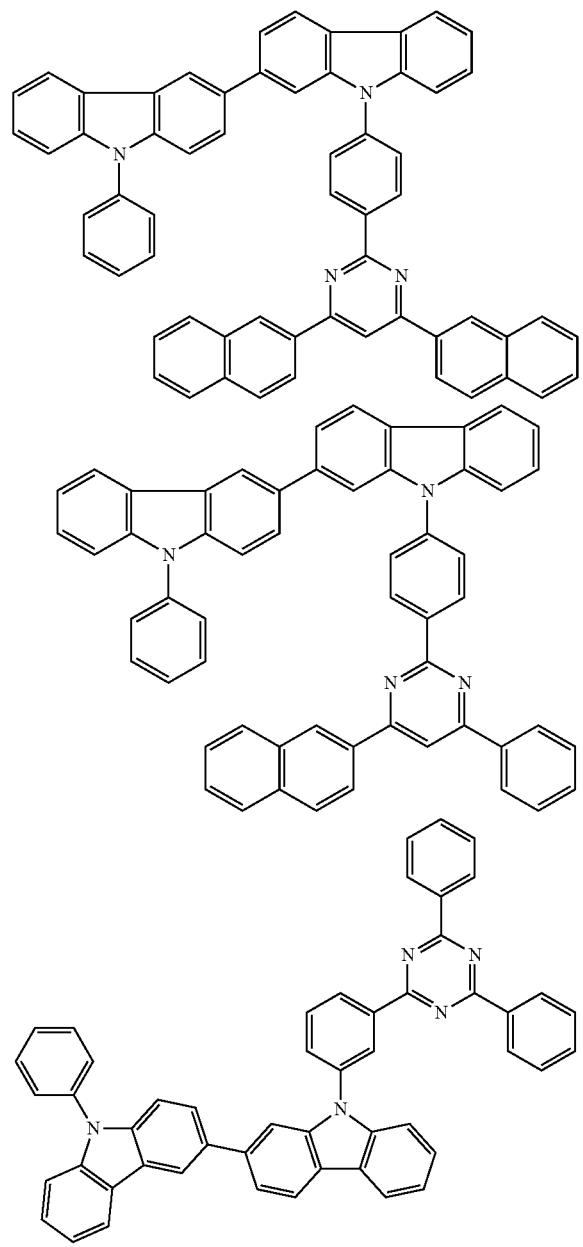
[Formula 29]
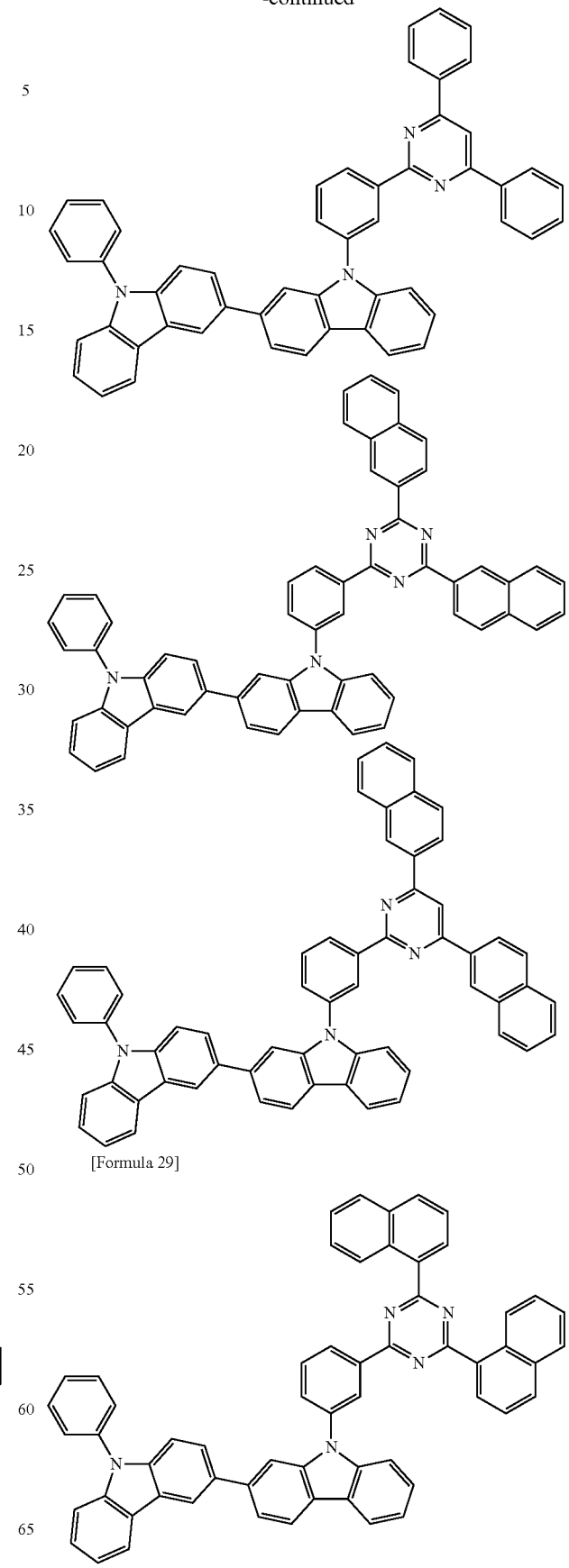

-continued
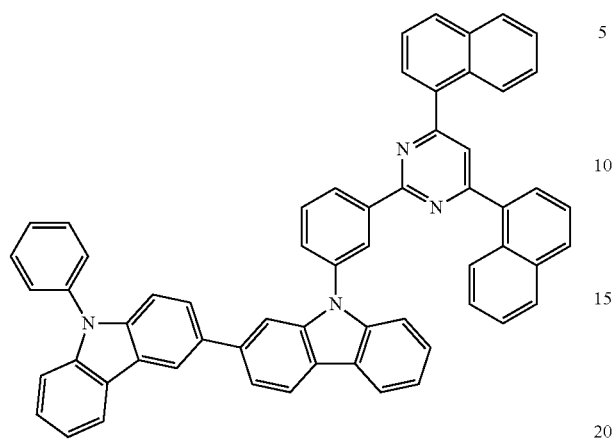
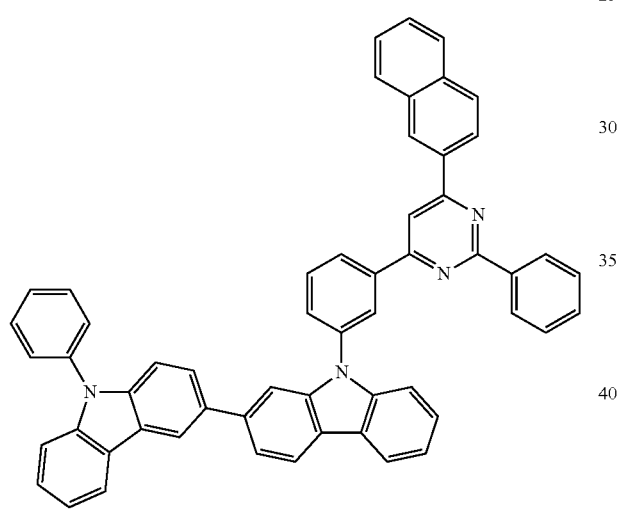
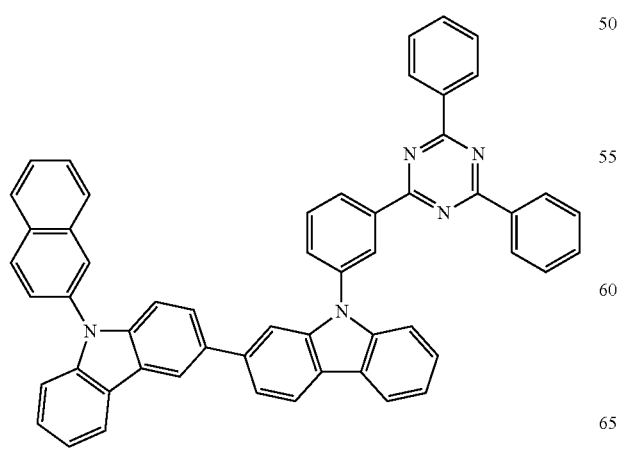
-continued
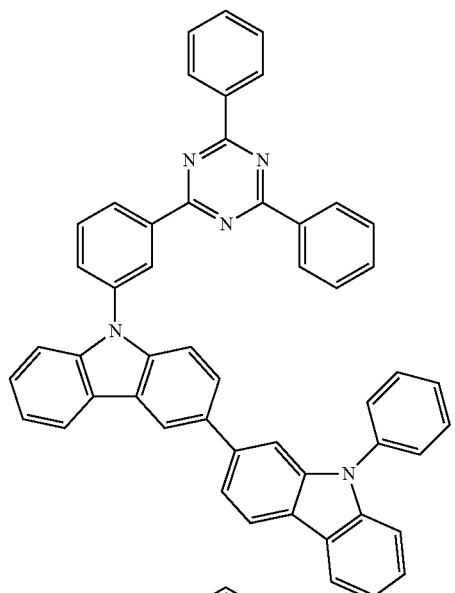
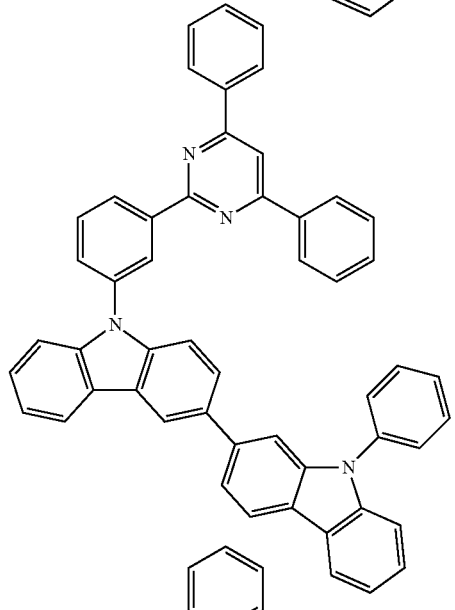
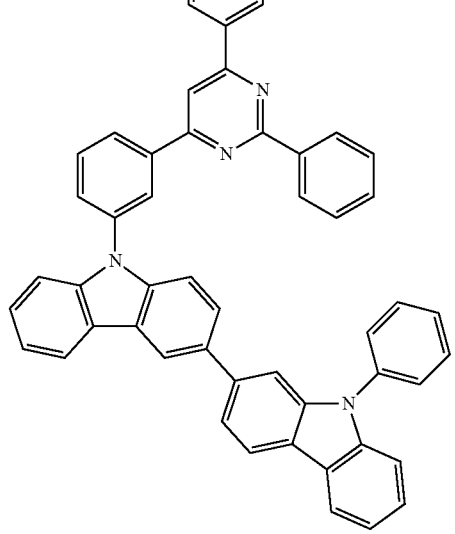

[Formula 30]
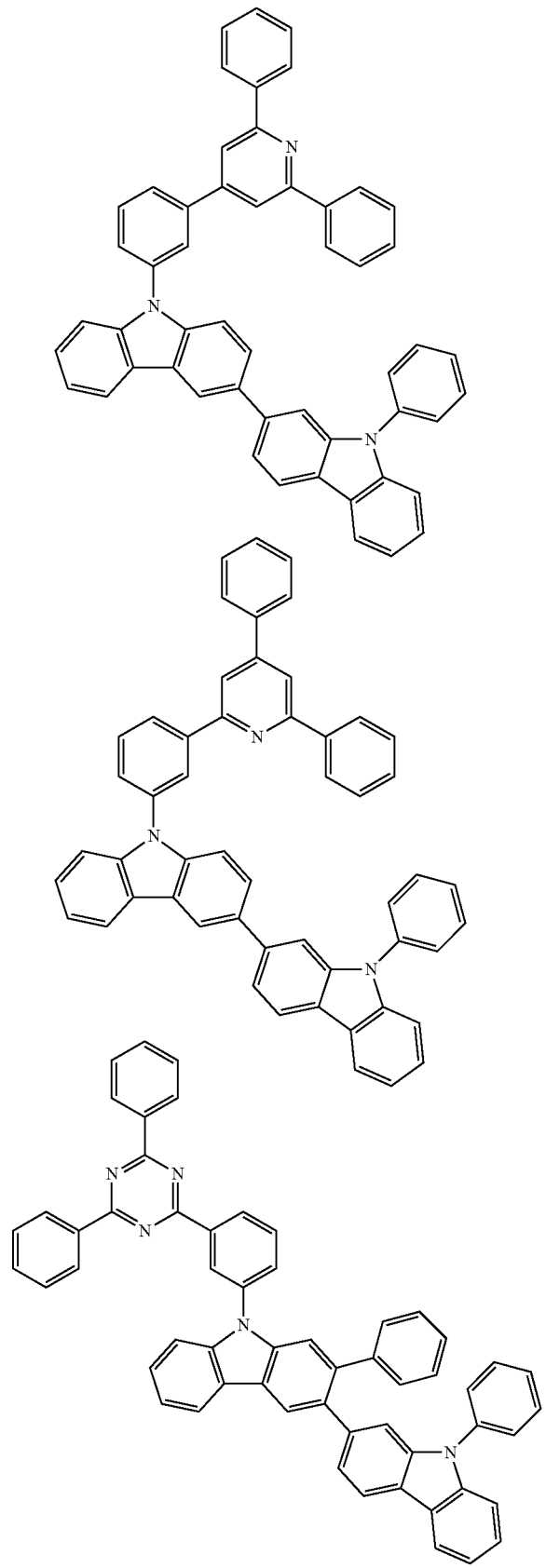
[Formula 31]
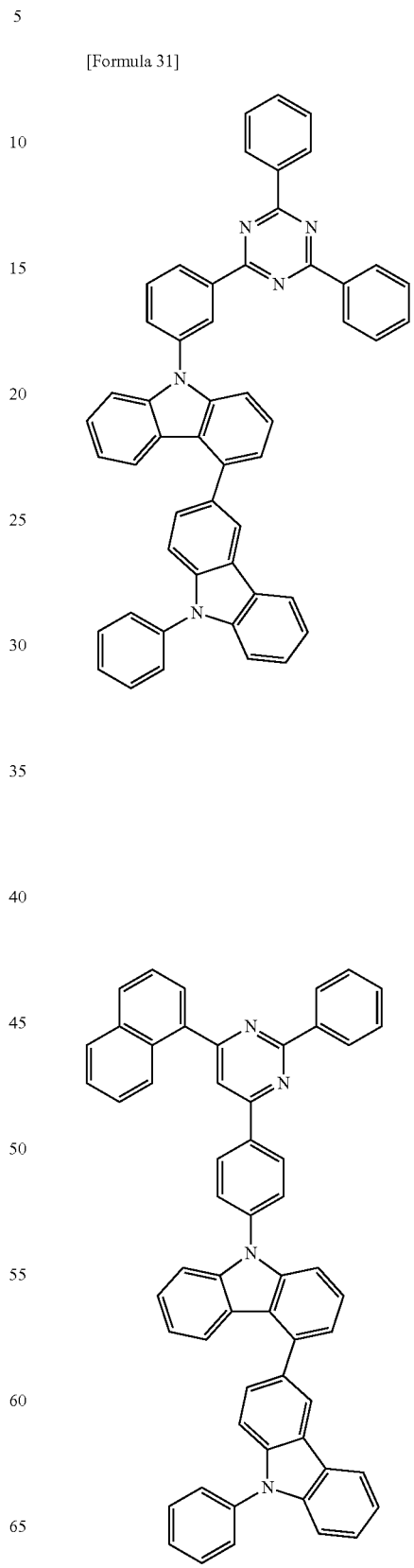

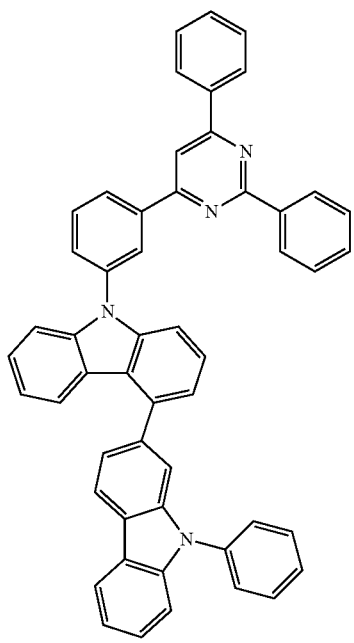
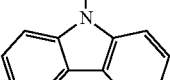
[Formula 32]
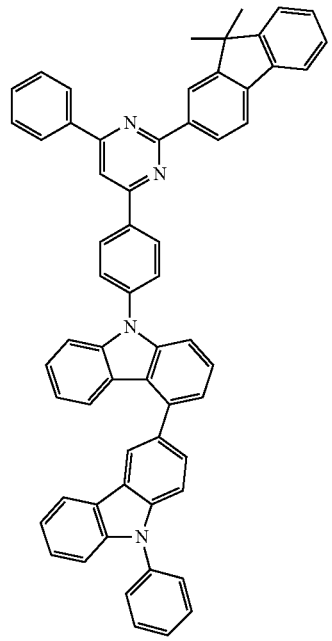
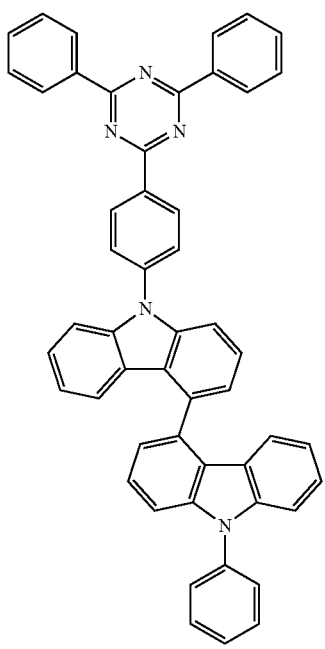
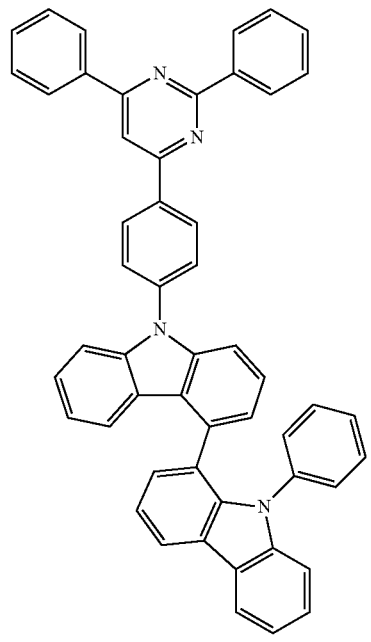

-continued
[Formula 33]
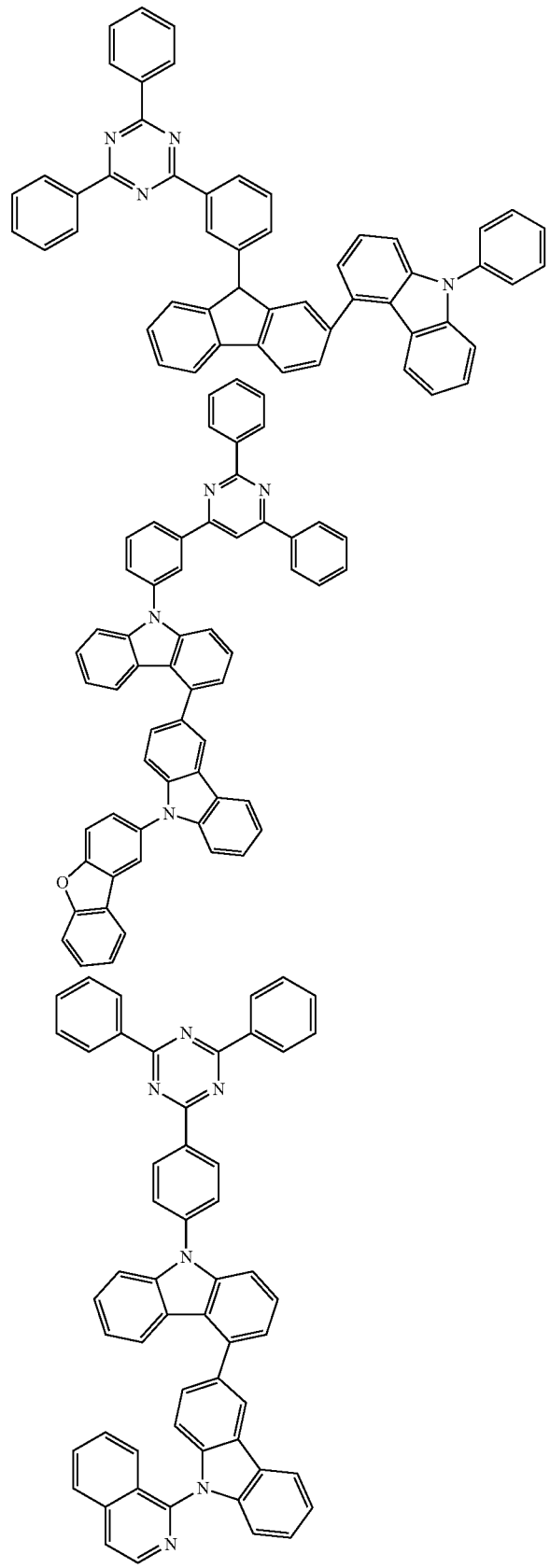
-continued
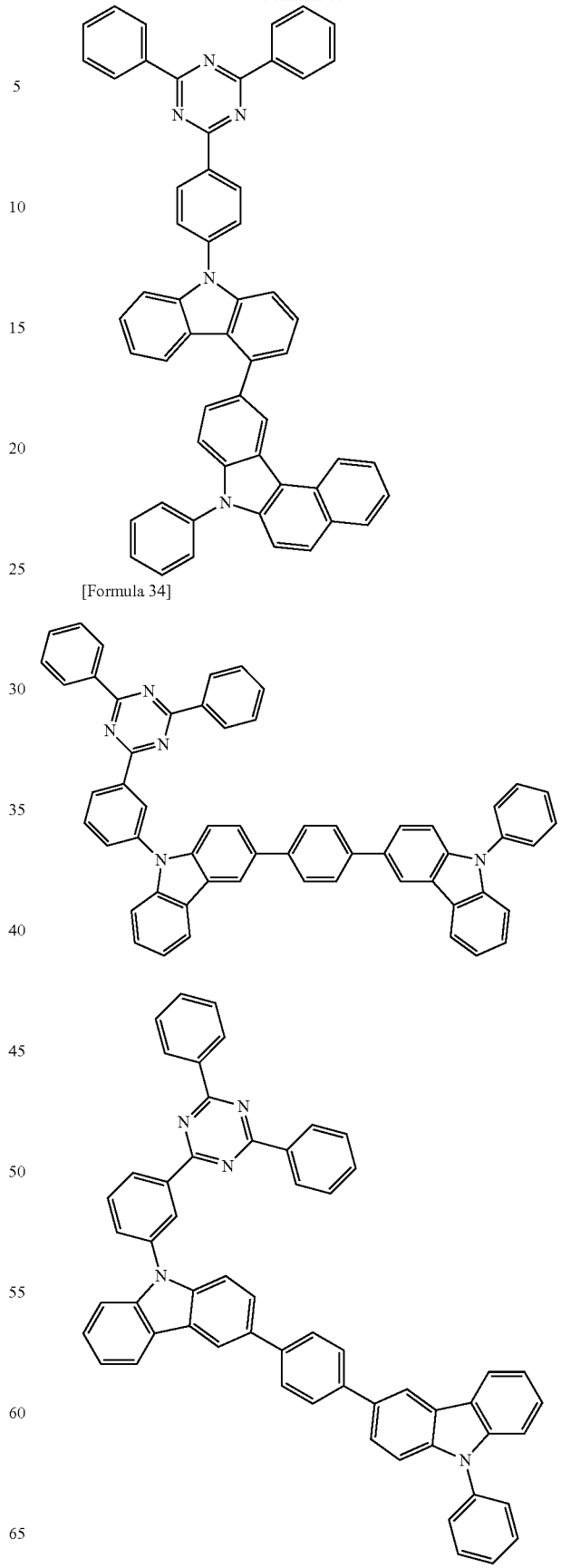
[Formula 34]

-continued

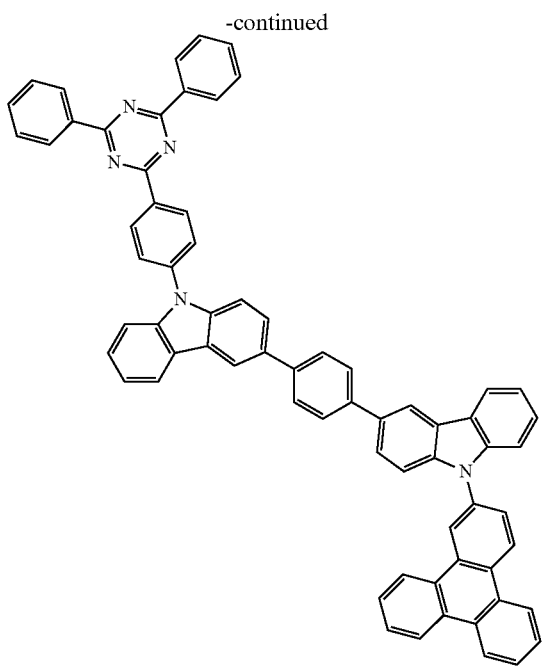

Second Host Material

As the second host material used in the organic EL device of this exemplary embodiment, a compound represented by the above formula (2A) is preferable.

[Formula 35]

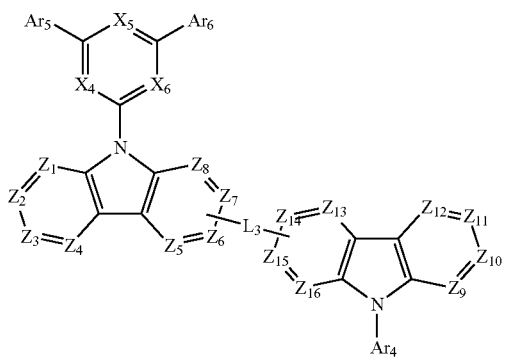

(2A)

In the formula (2A): $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$L_3$ represents a single bond, a substituted or unsubstituted arylene group having 6 to 30 ring carbon atoms, or substituted or unsubstituted divalent heterocyclic group having 5 to 30 ring atoms.

$X_4$ to $X_6$ each independently represent CR or a nitrogen atom and at least one of $X_4$ to $X_6$ is a nitrogen atom.

$Z_1$ to $Z_{16}$ represent CR or a nitrogen atom. However, one of $Z_5$ to $Z_8$ is a carbon atom to be bonded to $L_3$ and one of $Z_{13}$ to $Z_{16}$ is a carbon atom to be bonded to $L_3$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms.

A plurality of R may be mutually the same or different and adjacent ones of the plurality of R may be mutually bonded to form a ring structure.

However, when $Y_6$ is directly bonded to $Y_{14}$ in the compound represented by the formula (1A) and $Z_6$ is bonded to $Z_{14}$ through $L_3$ in the compound represented by the formula (2A), $L_3$ is a substituted or unsubstituted arylene group having 6 to 30 ring carbon atoms, or a substituted or unsubstituted divalent heterocyclic group having 5 to 30 ring atoms.

In the formula (2A), $L_3$ is preferably a single bond. $L_3$ in the formula (2A) is also preferably a substituted or unsubstituted arylene group having 6 to 30 ring carbon atoms, or a substituted or unsubstituted divalent heterocyclic group having 5 to 30 ring atoms.

The compound represented by the formula (2A) is preferably a compound represented by a formula (2) below.

[Formula 36]

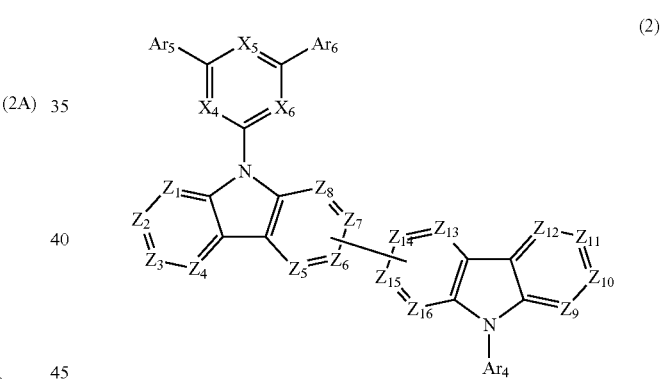

(2)

In the formula (2), $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group.

$X_4$ to $X_6$ each independently represent CR or a nitrogen atom and at least one of $X_4$ to $X_6$ is a nitrogen atom.

$Z_1$ to $Z_{16}$ each independently represent CR.

However, one of $Z_6$ and $Z_7$ is a carbon atom to be bonded to $Z_{14}$ or $Z_{15}$ and one of $Z_{14}$ and $Z_{15}$ is a carbon atom to be bonded to $Z_6$ or $Z_7$.

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

A plurality of R may be mutually the same or different and adjacent ones of the plurality of R may be mutually bonded to form a ring structure.

However, when $Y_6$ is directly bonded to $Y_{14}$ in the compound represented by the formula (1), $Z_6$ is a carbon atom to be bonded to $Z_{15}$ and $Z_{15}$ is a carbon atom to be bonded to $Z_7$ in the compound represented by the formula (2).

In the formulae (2A) and (2), $Ar_4$ to $Ar_6$ represent the same as the examples described in relation to $Ar_1$ to $Ar_3$. However, similar to $Ar_1$, when $Ar_4$ is a substituted or unsubstituted heterocyclic ring having 5 to 30 ring atoms, $Ar_4$ is not a pyridine ring, pyrazine ring, pyrimidine ring, pyridazine or triazine ring among the above heterocyclic group having 5 to 30 ring atoms.

In the formulae (2A) and (2), at least one of $X_4$ to $X_6$ is a nitrogen atom. In terms of a long lifetime of the organic EL device, it is more preferable that two of $X_4$ to $X_6$ are nitrogen atoms than an instance where all of $X_4$ to $X_6$ are nitrogen atoms.

Groups for R in the formulae (2A) and (2) are the same as the examples described in relation to the formulae (2A) and (2).

In the formulae (2A) and (2), when $Ar_4$ to $Ar_6$ and R have one or more substituents, the substituent(s) is the same as those of the formulae (1A) and (1).

The arylene group having 6 to 30 ring carbon atoms, which is represented by $L_3$ in the formulae (1A) and (1), is exemplified by a divalent group derived from the aryl groups described in the formulae (1A) and (1). The substituted or unsubstituted divalent heterocyclic group having 5 to 30 ring atoms, which is represented by $L_3$ in the formulae (2A) and (2), is exemplified by a divalent group derived from the above heterocyclic group described in the formulae (1A) and (1).

In the compound represented by the formulae (2A) and (2), it is preferable that $Z_7$ is bonded to $Z_{14}$ or $Z_6$ is bonded to $Z_{15}$. The compound represented by the formulae (2A) and (2) is preferably represented by one of formulae (21A) to (21C) below. More preferably, the compound represented by the formulae (2A) and (2) is preferably represented by one of formulae (22A) to (22C) below.

[Formula 37]

(21A)

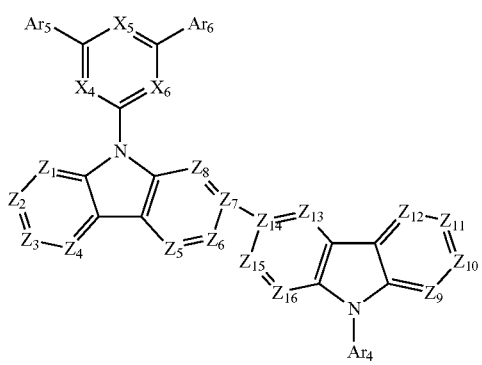

(21B)

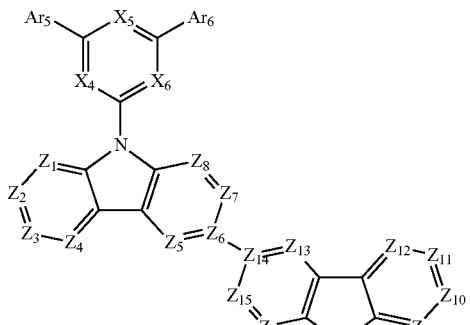

(21C)

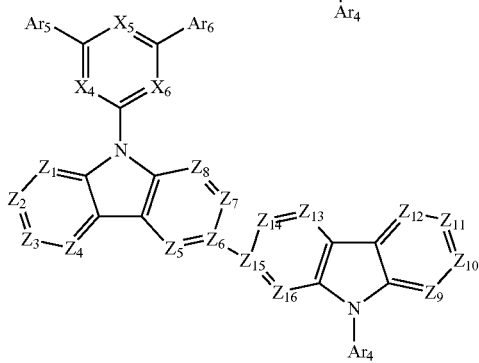

In the formula (21A) to (21C), $Ar_4$ to $Ar_6$, $X_4$ to $X_6$, and $Z_1$ to $Z_{16}$ respectively represent the same as $Ar_4$ to $Ar_6$, $X_4$ to $X_6$, and $Z_1$ to $Z_{16}$ in the formula (2A) or (2).

[Formula 38]

(22A)

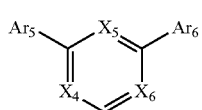

(22B)

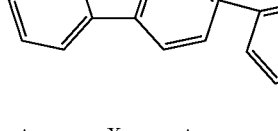

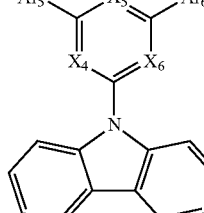

-continued

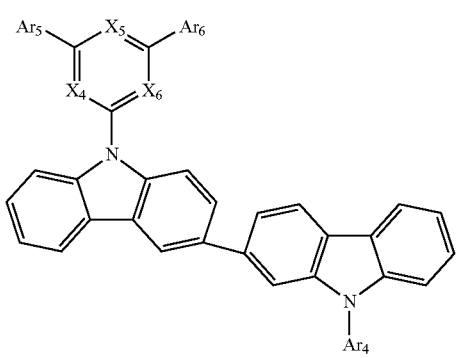
(22C)

In the formulae (22A) to (22C), $Ar_4$ to $Ar_6$ and $X_4$ to $X_6$ respectively represent the same as $Ar_4$ to $Ar_6$ and $X_4$ to $X_6$ in the formula (2A) or (2).

In the formulae (21A) to (21C) and (22A) to (22C), more preferably, two or more of $X_1$ to $X_3$ are nitrogen atoms.

Examples of the compounds represented by the formulae (2A), (2), (21A) to (21C) and (22A) to (22C) are as follows. Note that a bond without a formula (e.g., Ph, CN and a benzene ring) at an end represents a methyl group in the following structures.

[Formula 39]

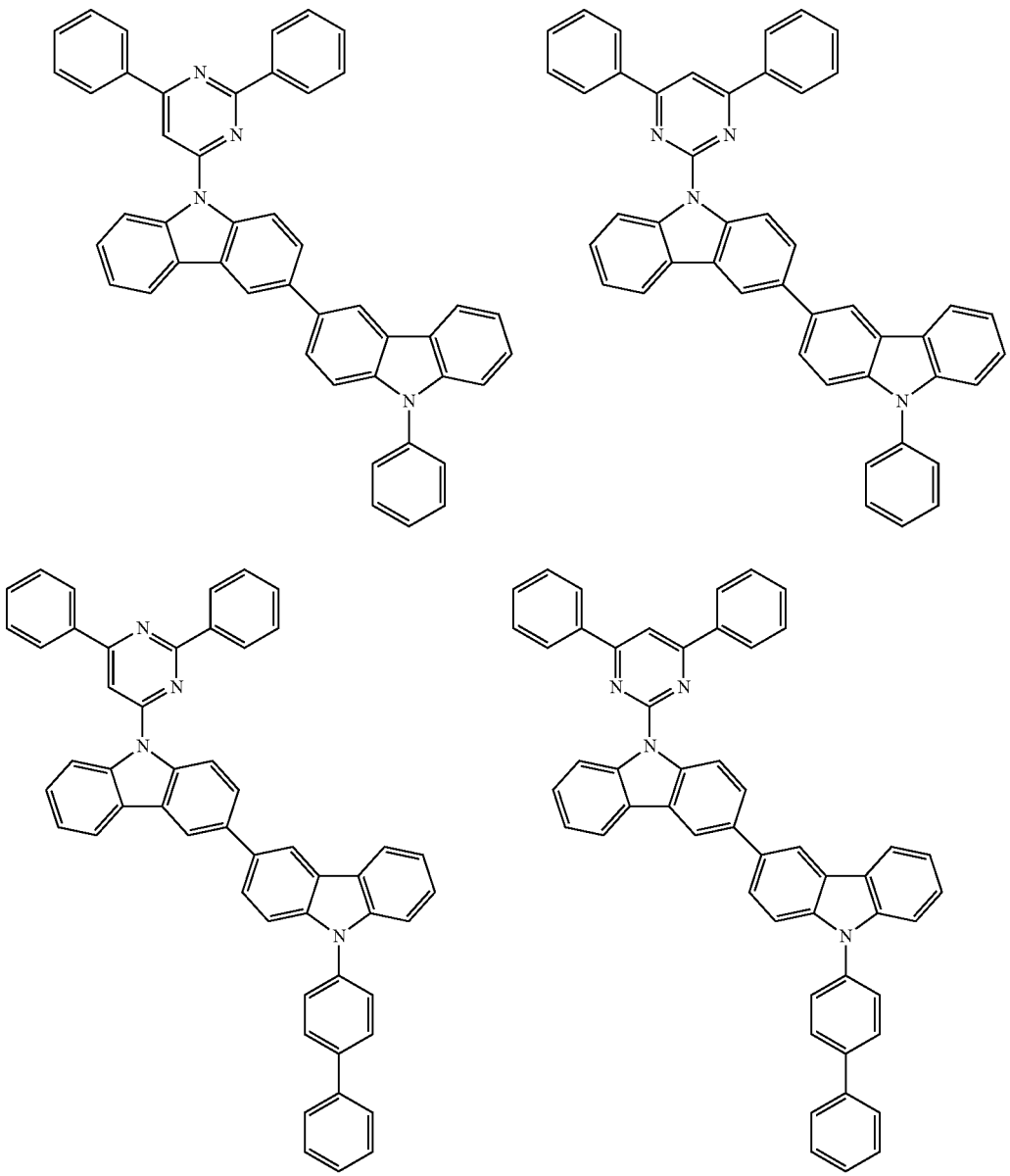

91
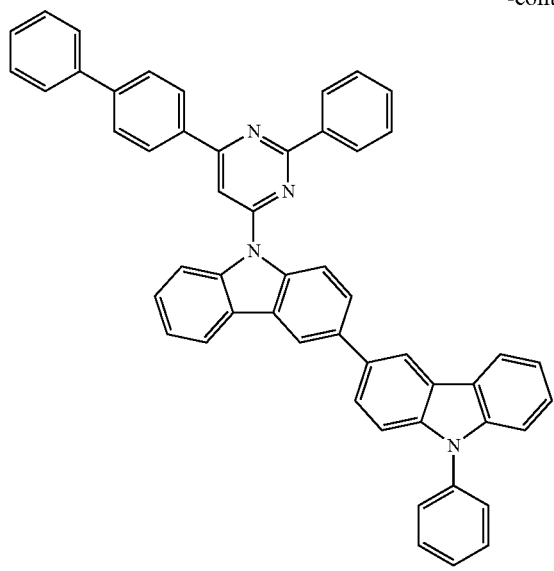
92
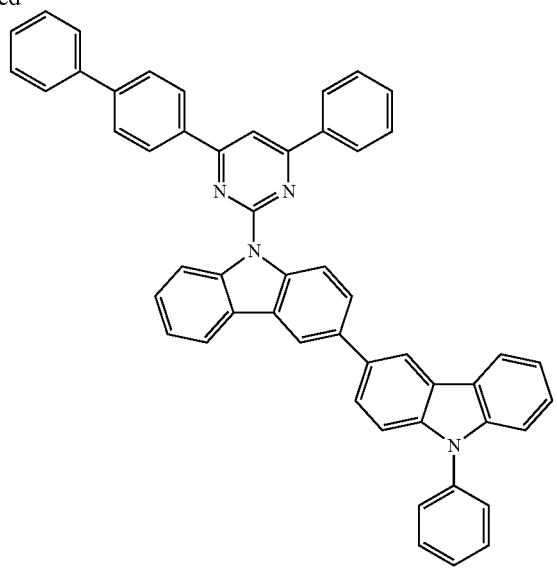
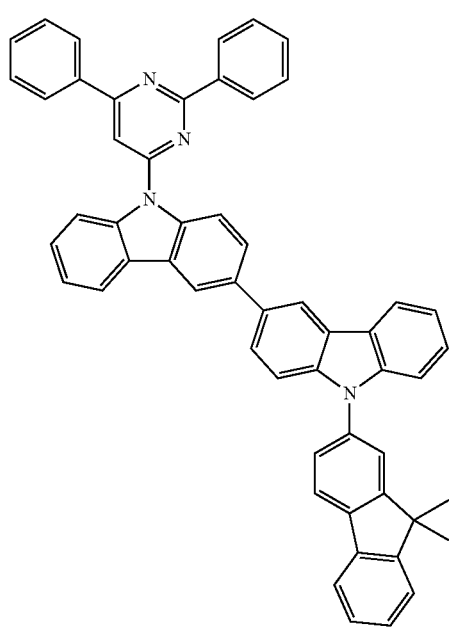
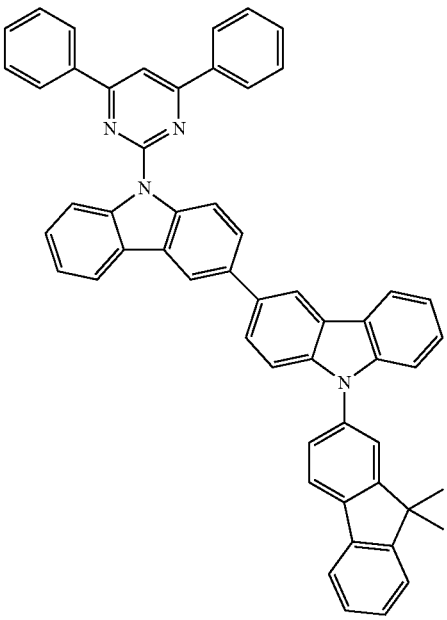
[Formula 40]
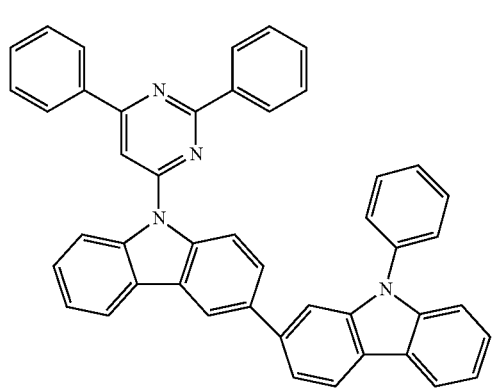
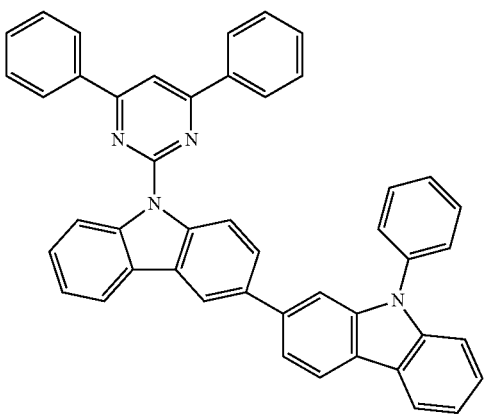

-continued
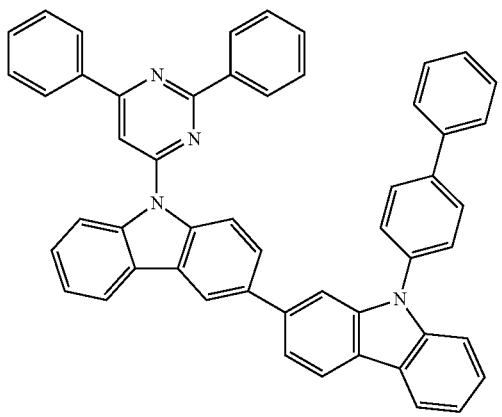
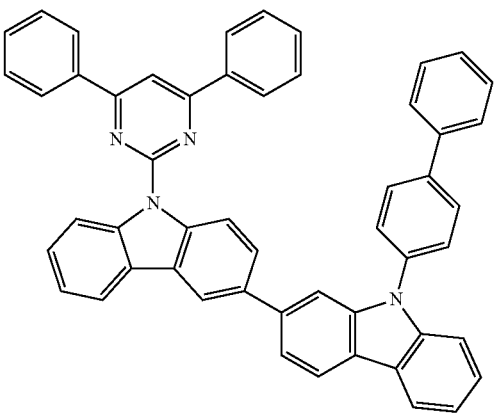
[Formula 41]
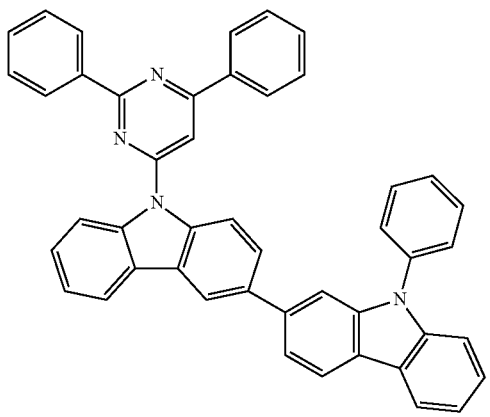
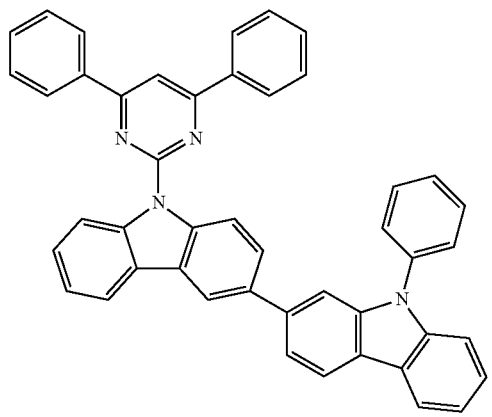
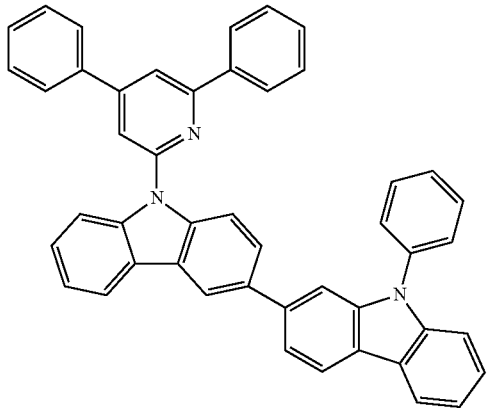
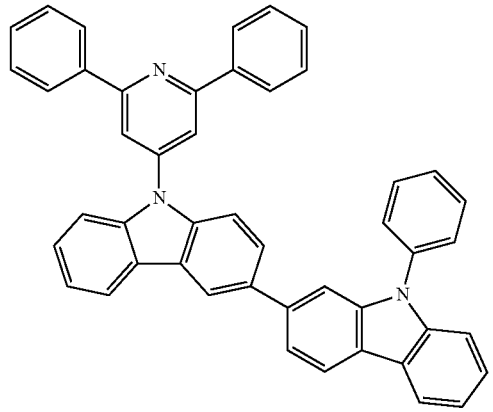
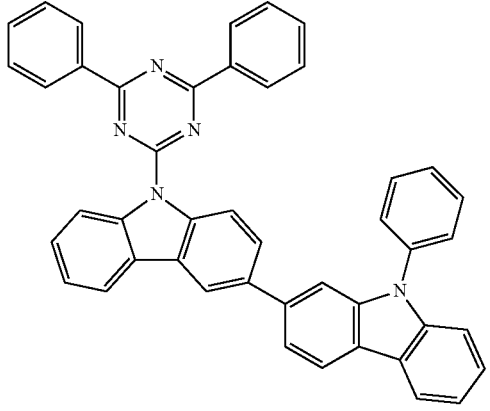
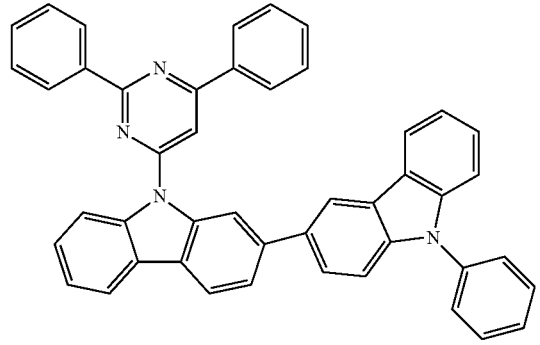

95
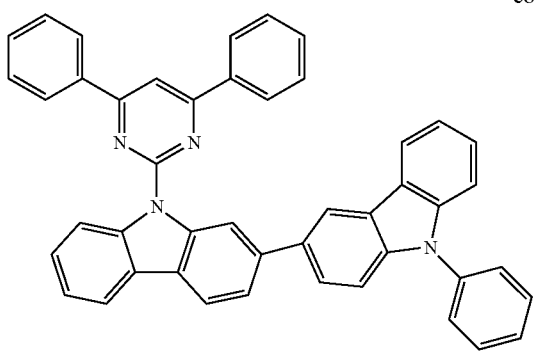
96
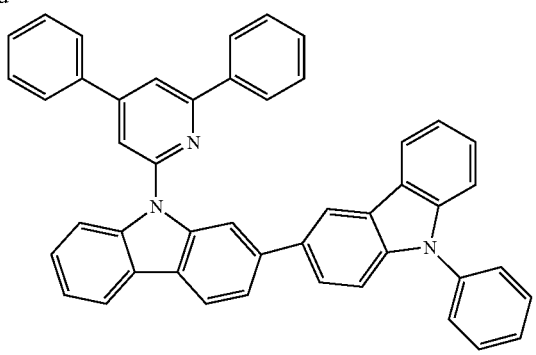
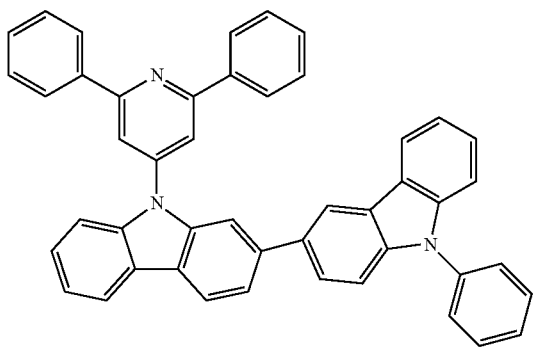
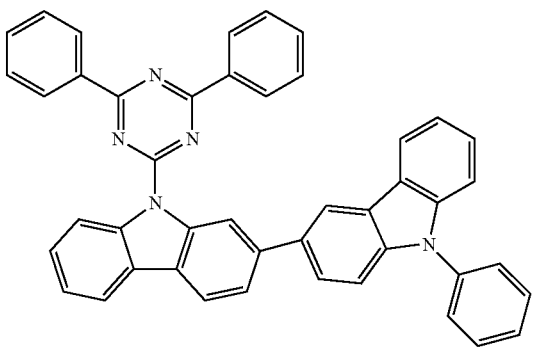
[Formula 42]
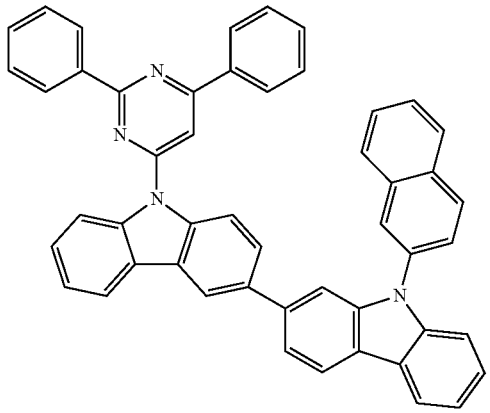
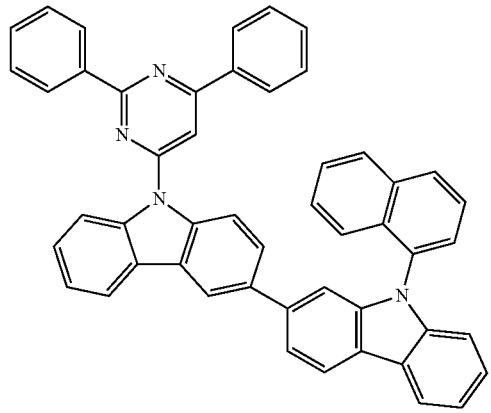
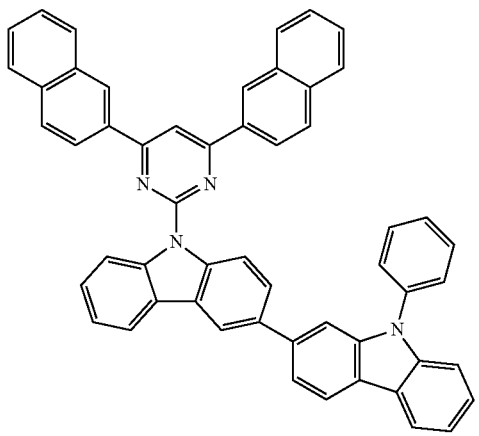
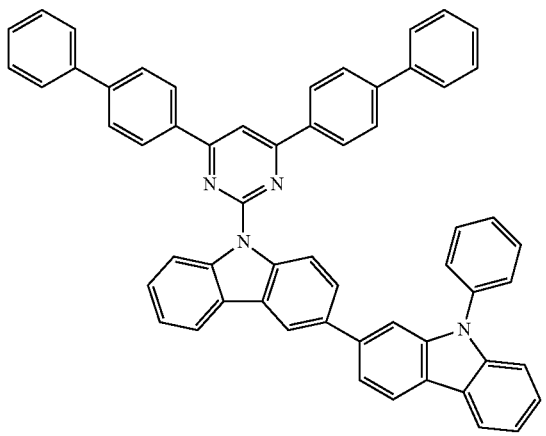

-continued
[Formula 43]
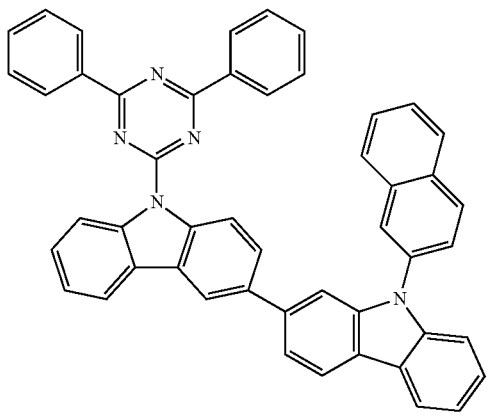
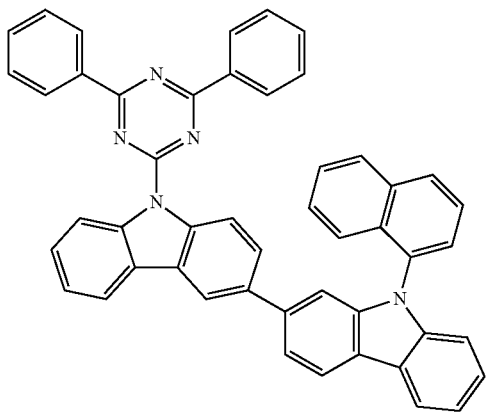
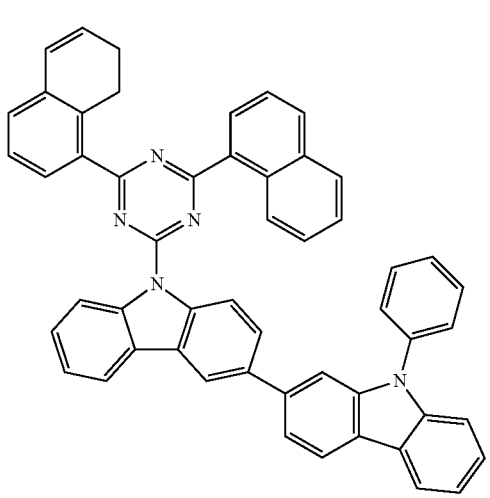
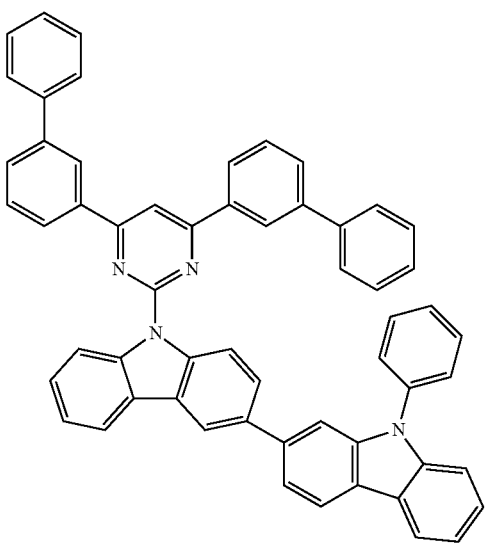
[Formula 44]
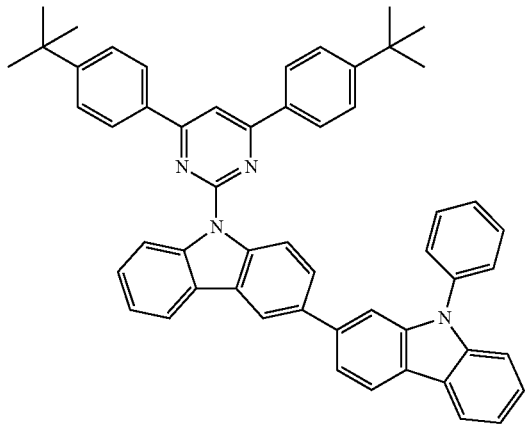
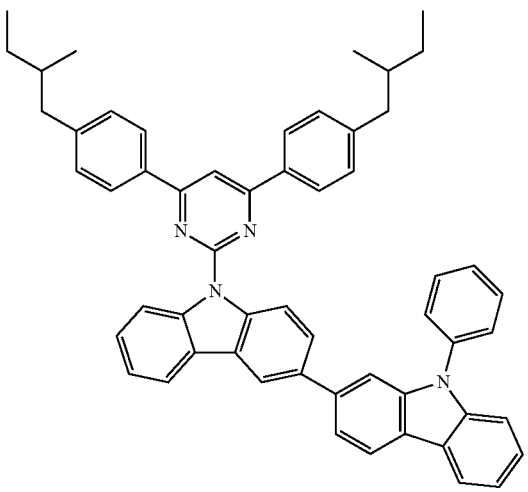

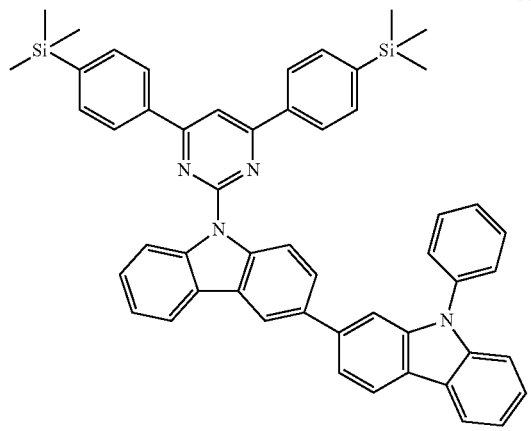
[Formula 45]
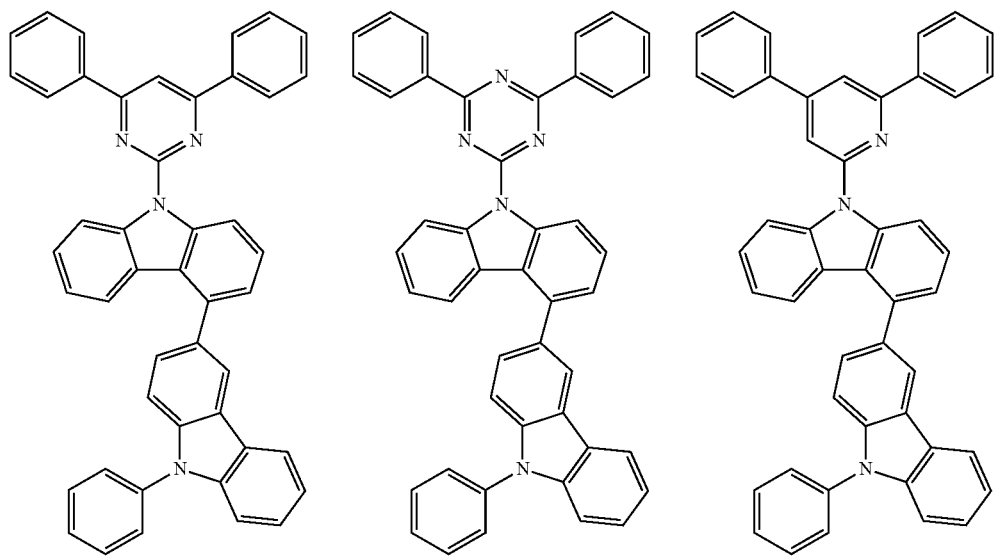
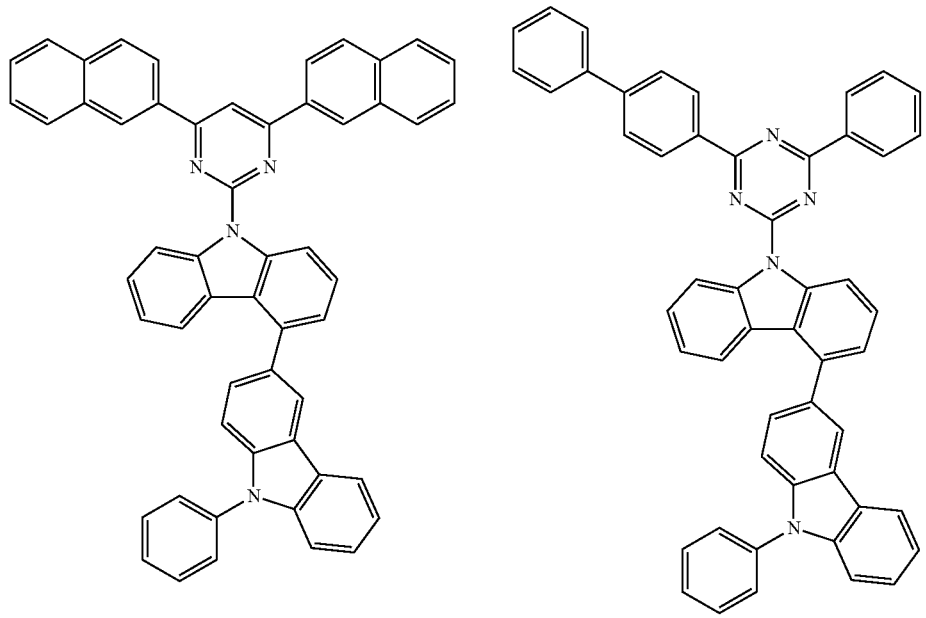

[Formula 46]
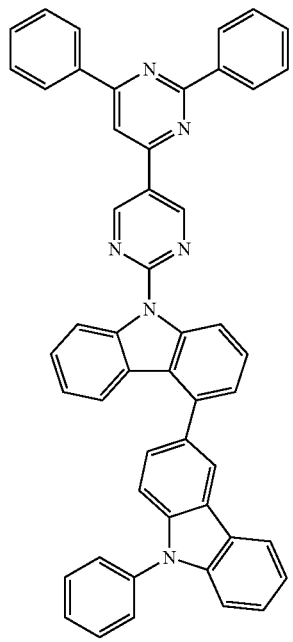
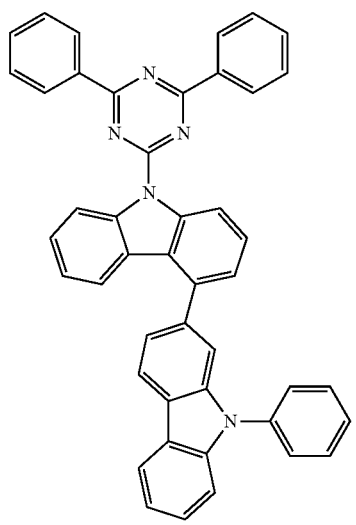
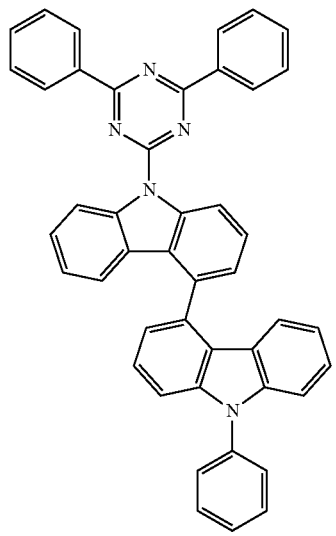
[Formula 47]
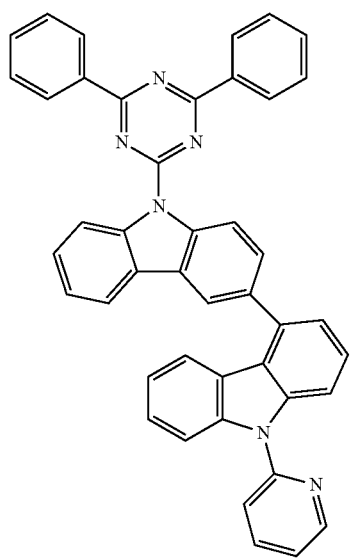
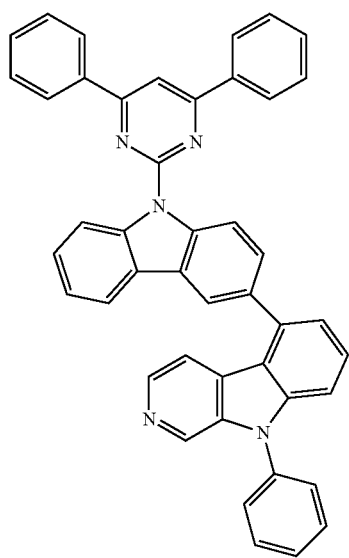
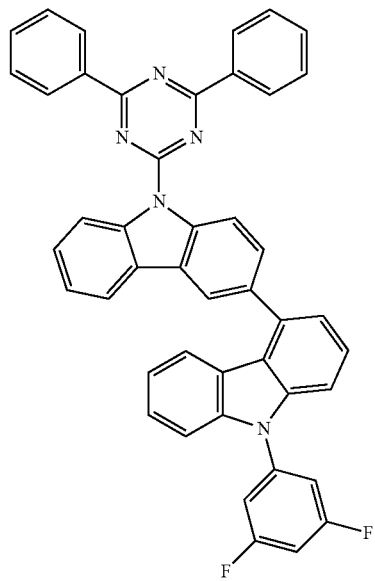

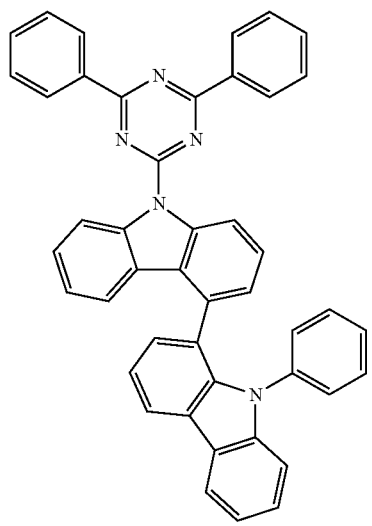
[Formula 48]
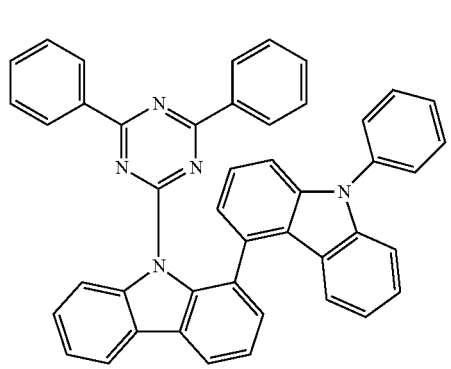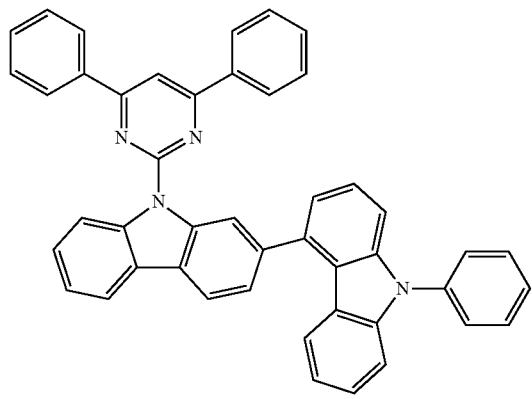
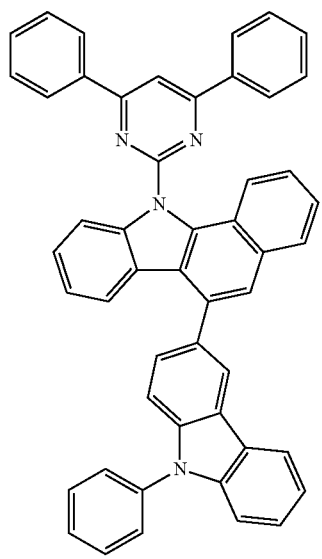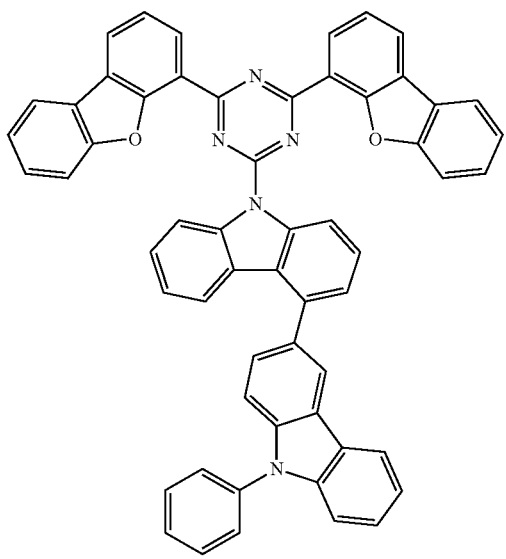

[Formula 49]
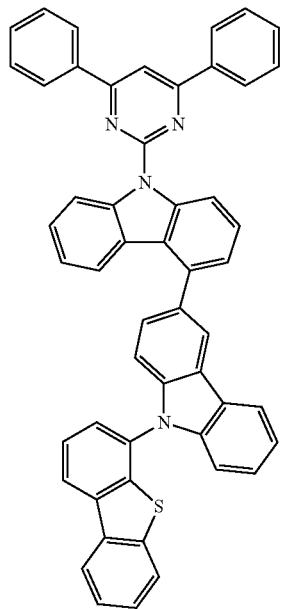
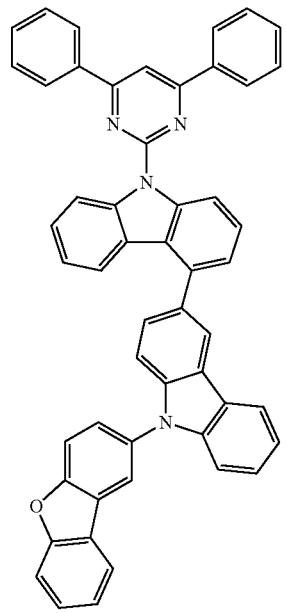
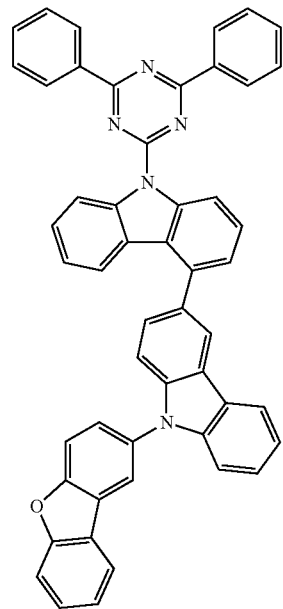
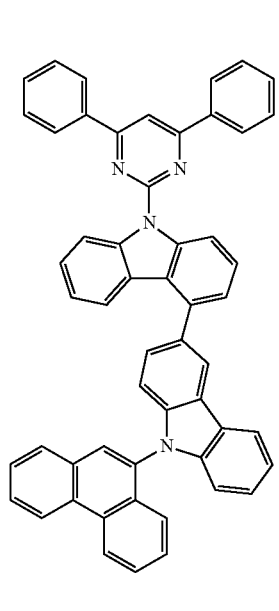
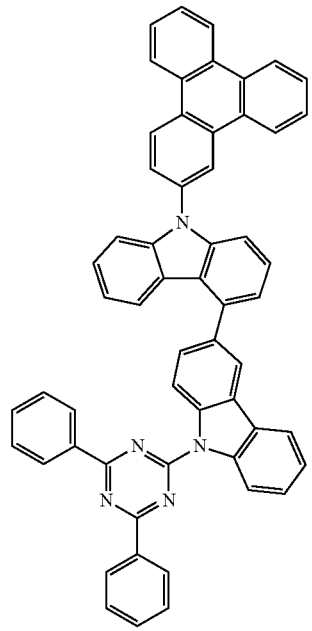
[Formula 50]
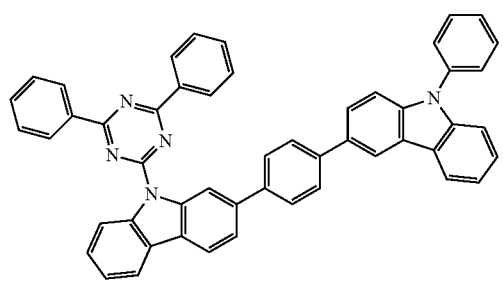
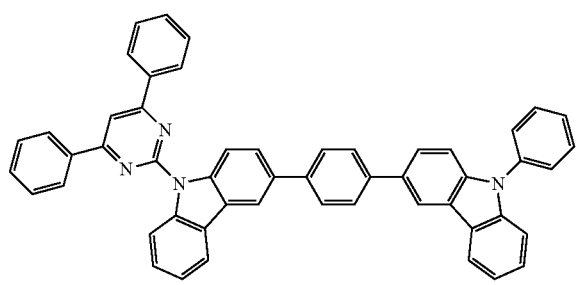

-continued
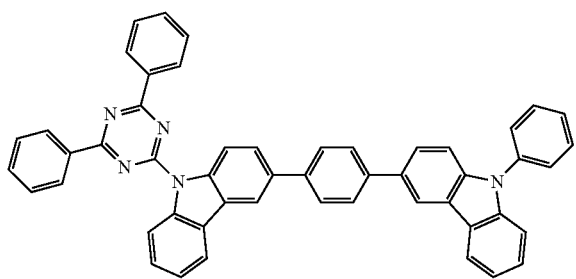
[Formula 51]
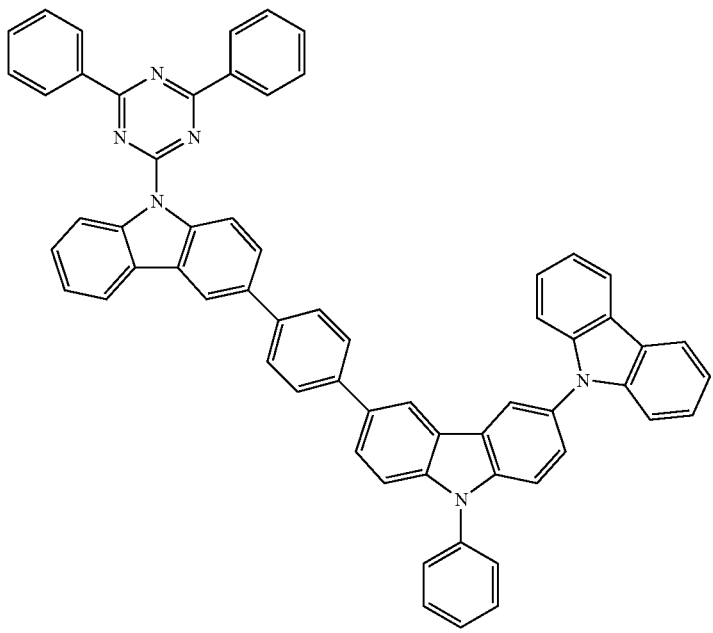
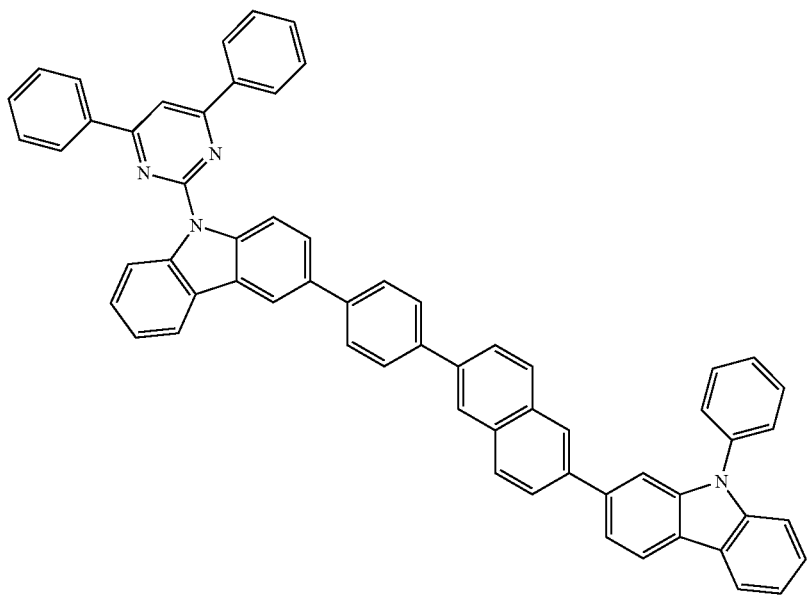

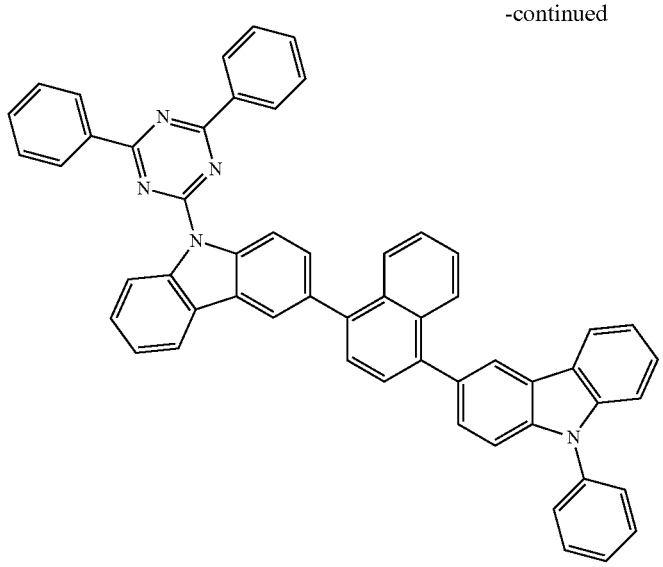

Combination of First Host Material and Second Host Material

Herein, a combination of the first host material and the second host material will be described.

In the first host material represented by the formula (1A) or (1), a bonding position of two carbazole rings or two azacarbazole rings (hereinafter, inclusively referred to as a carbazole skeleton) is not particularly limited, but one of $Y_5$ to $Y_8$ is bonded to one of $Y_{13}$ to $Y_{16}$ directly or through the linking group $L_2$.

In the second host material represented by the formula (2A) or (2), the bonding position of two carbazole skeletons is not particularly limited, but one of $Z_5$ to $Z_8$ is bonded to one of $Z_{13}$ to $Z_{16}$ directly or through the linking group $L_3$.

However, when $Y_6$ is directly bonded to $Y_{14}$ in the compound represented by the formula (1A) and $Z_6$ is bonded to $Z_{14}$ through $L_3$ in the compound represented by the formula (2A), $L_3$ is a substituted or unsubstituted arylene group having 6 to 30 ring carbon atoms, or a substituted or unsubstituted divalent heterocyclic group having 5 to 30 ring atoms. Moreover, when $Y_6$ is directly bonded to $Y_{14}$ in the compound represented by the formula (1), $Z_6$ is a carbon atom to be bonded to $Z_{15}$ and $Z_{15}$ is a carbon atom to be bonded to $Z_7$ in the compound represented by the formula (2). Moreover, when $Y_6$ is directly bonded to $Y_{14}$ in the compound represented by the formula (1), $Z_6$ is a carbon atom to be bonded to $Z_{15}$ and $Z_{15}$ is a carbon atom to be bonded to $Z_7$ in the compound represented by the formula (2).

When the carbon atom of $Y_6$ is bonded to the carbon atom of $Y_{14}$ in the first host material represented by the formula (1), it is preferable that the carbon atom of $Z_6$ is bonded to the carbon atom of $Z_{15}$ or the carbon atom of $Z_7$ is bonded to the carbon atom of $Z_{14}$ in the second host material represented by the formula (2).

When the carbon atom of $Z_6$ is bonded to the carbon atom of $Z_{14}$ in the second host material represented by the formula (2), it is preferable that the carbon atom of $Y_6$ is bonded to the carbon atom of $Y_{15}$ or the carbon atom of $Y_7$ is bonded to the carbon atom of $Y_{14}$ in the first host material represented by the formula (1).

In other words, as the combination of the first and second host materials in the exemplary embodiment, the first host material in which the carbon atom of $Y_6$ is bonded to the carbon atom of $Y_{14}$ in the formula (1) is not combined with the second host material in which the carbon atom of $Z_6$ is bonded to the carbon atom of $Z_{14}$ in the formula (2).

When $Y_6$ is directly bonded to $Y_{14}$ in the compound represented by the formula (1A) and $Z_7$ is bonded to $Z_{14}$ through $L_3$ in the compound represented by the formula (2A), $L_3$ is a substituted or unsubstituted arylene group having 6 to 30 ring carbon atoms, or a substituted or unsubstituted divalent heterocyclic group having 5 to 30 ring atoms.

As the combination of the first and second host materials, the number of nitrogen atoms of $X_1$ to $X_3$ in the formulae (1A), (1), (11A) to (11C) and (12A) to (12C) is preferably different from the number of nitrogen atoms of $X_4$ to $X_6$ in the formulae (2A), (2), (21A) to (21C) and (22A) to (22C). Particularly preferably, the number of the nitrogen atoms of $X_1$ to $X_3$ are three and the number of the nitrogen atoms of $X_4$ to $X_6$ are two.

The compounds represented by the formulae (1A), (1), (2A) and (2) have a relatively high electron mobility and a relatively high hole mobility. Since both of the compounds for the first and second host materials adjust carrier balance within the emitting layer of the organic EL device, a central position of recombination can be set within the emitting layer. Damage to the electron transporting material caused by holes transferred over the emitting layer and damage to the hole transporting material caused by electrons transferred over the emitting layer can be decreased by setting the central position of recombination within the emitting layer. Consequently, the lifetime of the organic EL device is prolonged.

The compound represented by the formulae (1A) and (1) having more nitrogen atoms in $X_1$ to $X_3$ can exhibit a higher electron transporting performance. Accordingly, the compound having more nitrogen atoms can express a performance more suitable for the electron transporting performance, thereby achieving a favorable carrier balance in the emitting layer of the organic EL device to prolong the lifetime of the organic EL device.

Note that the first host material is more effective for increasing the electron transporting performance than a compound for the later-described second host material.

On the other hand, the compound represented by the formulae (2A) and (2) having less nitrogen atoms can reduce the electron transporting performance and express a performance more suitable for the hole transporting performance, thereby achieving a favorable carrier balance in the emitting layer of the organic EL device to prolong the lifetime of the organic EL device.

As the combination of the first and second host materials in the bonding position of the carbazole rings, the first host material represented by the formulae (1A), (1), (11A) to (11C) and (12A) to (12C) may be combined with the second host material represented by the formulae (2A), (2), (21A) to (21C) and (22A) to (22C). Preferably, the first host material represented by the formula (11A) is combined with the second host material represented by the formula (21A). More preferably, the first host material represented by the formula (12A) is combined with the second host material represented by the formula (22A).

Phosphorescent Dopant Material

The phosphorescent material preferably contains a metal complex, and the metal complex preferably has a metal atom selected from Ir (iridium), Pt (platinum), Os (osmium), Au (gold), Cu (copper), Re (rhenium) and Ru (ruthenium), and a ligand. Particularly, the ligand preferably has an ortho-metal bond.

The phosphorescent material is preferably a compound containing a metal selected from Ir, Os and Pt because such a compound, which exhibits high phosphorescence quantum yield, can further enhance external quantum efficiency of the organic EL device. The phosphorescent material is more preferably a metal complex such as an iridium complex, osmium complex or platinum complex, among which an iridium complex and platinum complex are more preferable and ortho metalation of an iridium complex is the most preferable. The organic metal complex formed of the ligand selected from the group consisting of phenyl quinoline, phenyl isoquinoline, phenyl pyridine, phenyl pyrimidine, phenyl pyrazine, phenyl imidazole and benzoquinoline is preferable in terms of luminous efficiency and the like.

Examples of such a preferable metal complex are shown below.

[Formula 52]

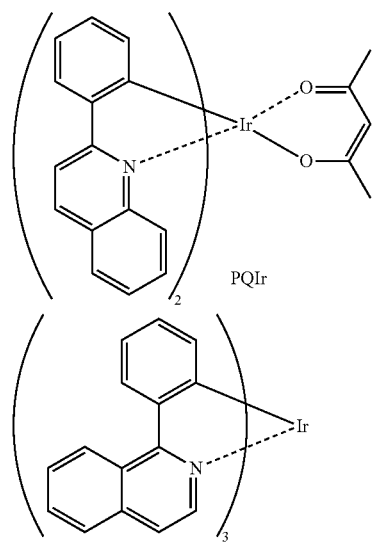

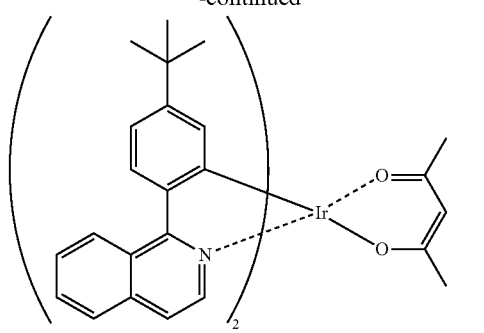

-continued

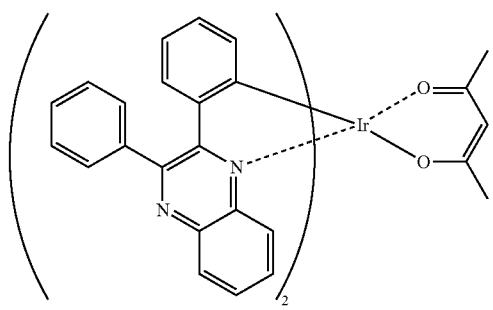

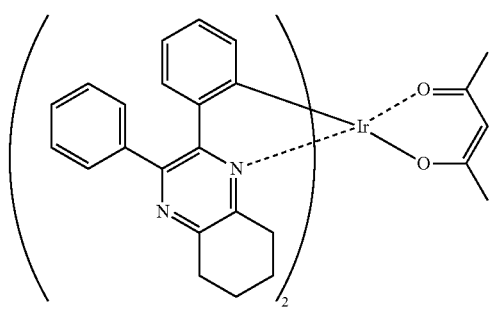

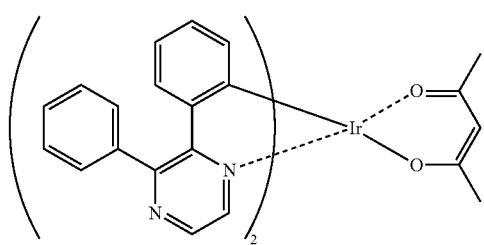

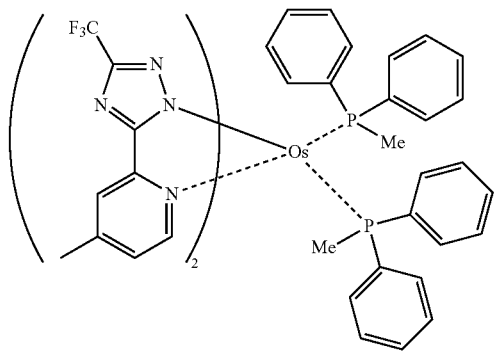

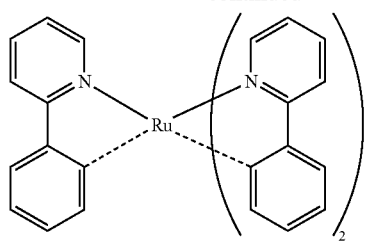
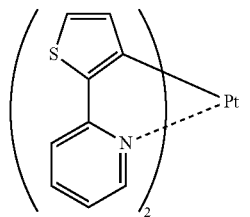
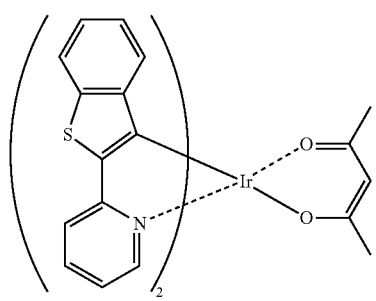
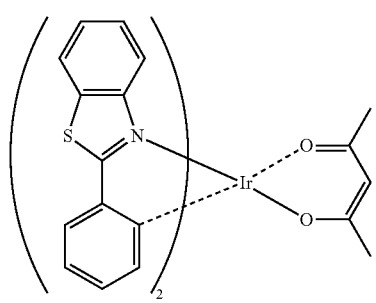
[Formula 53]
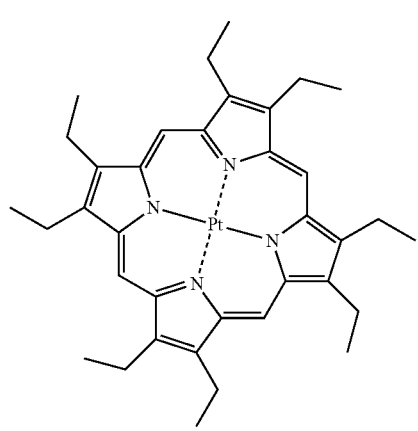
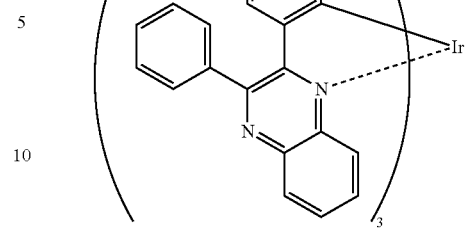
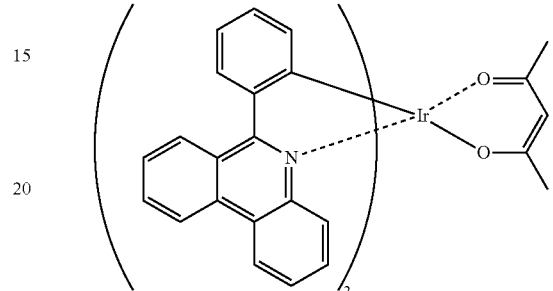
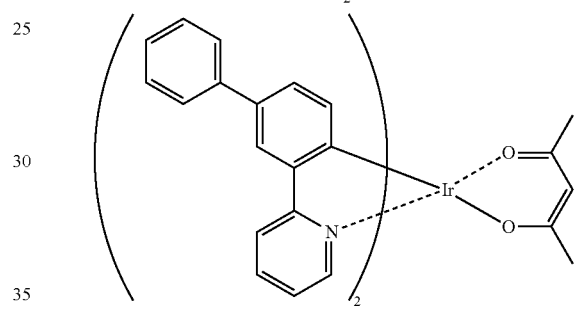
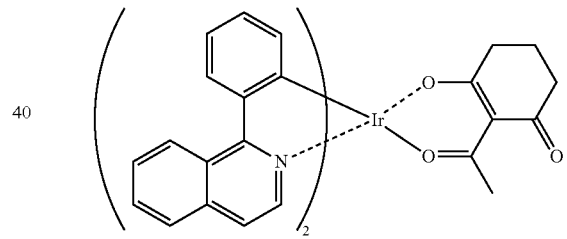
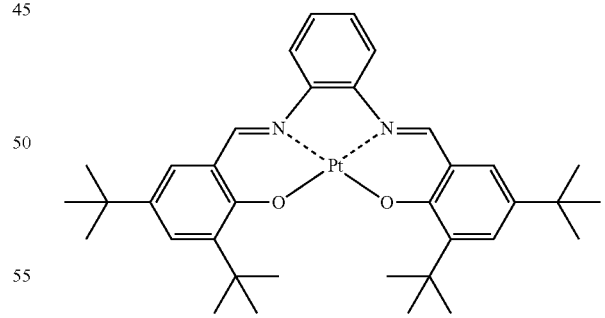
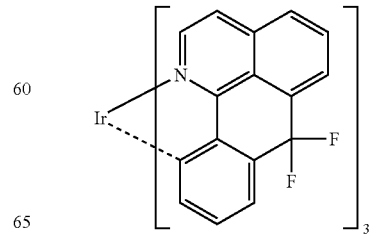

[Formula 54]
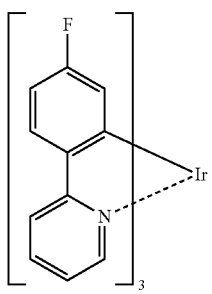
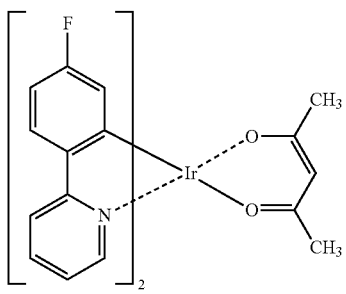
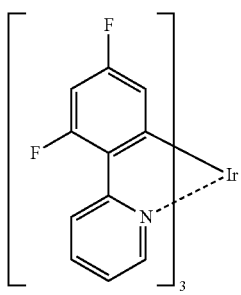
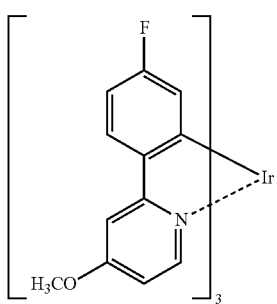
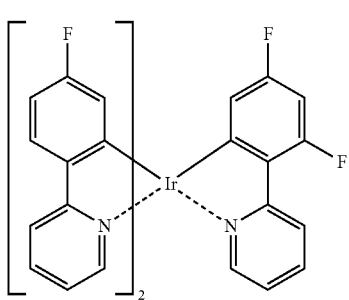
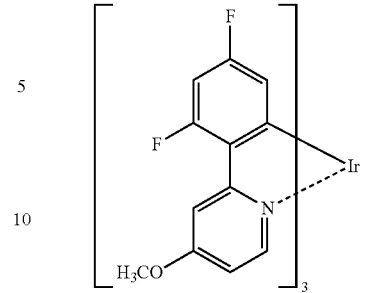
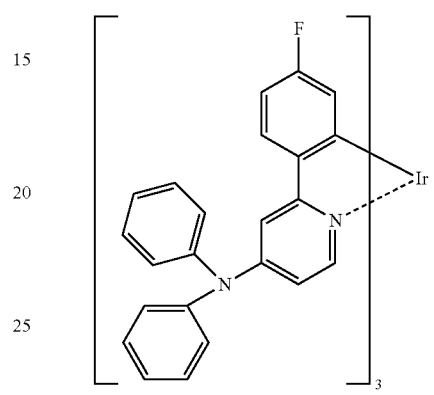
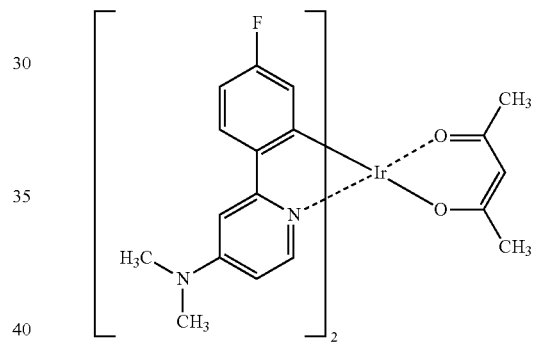
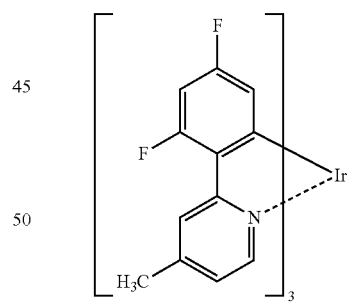
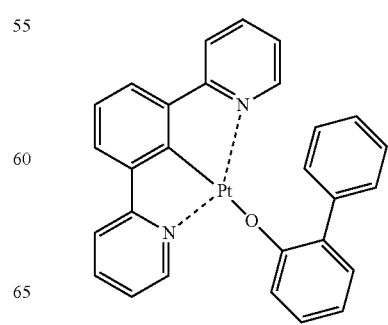

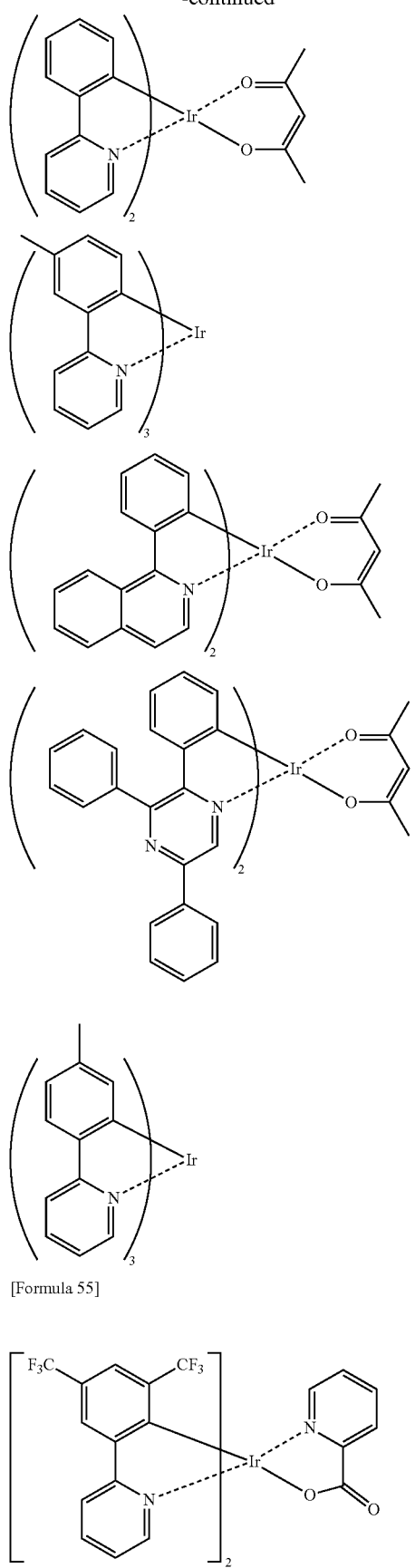
[Formula 55]
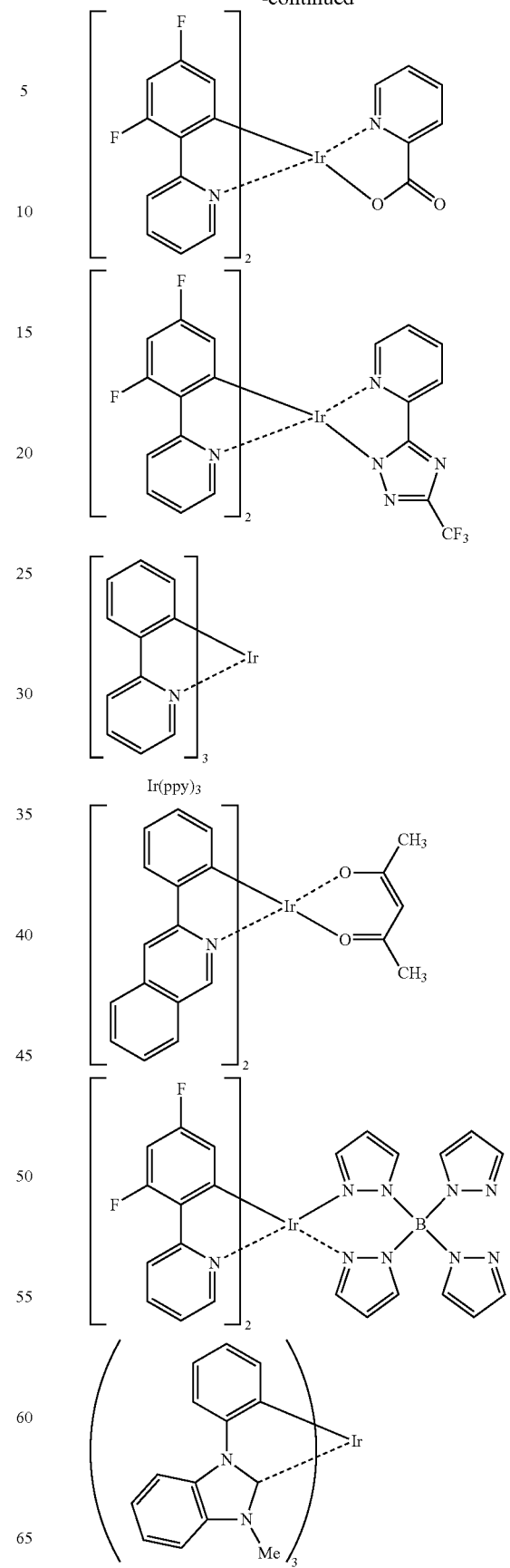
Ir(ppy)₃

-continued

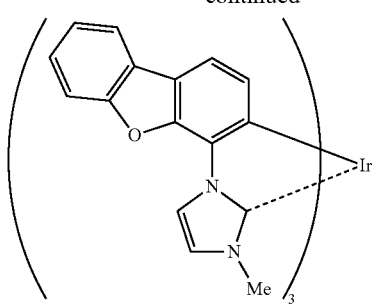

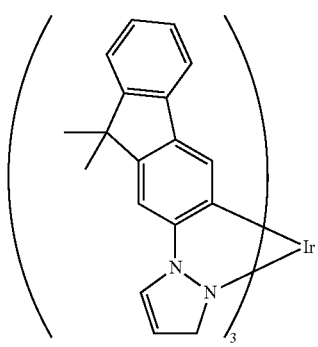

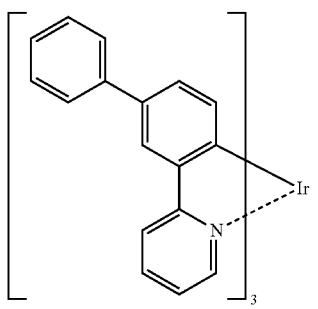

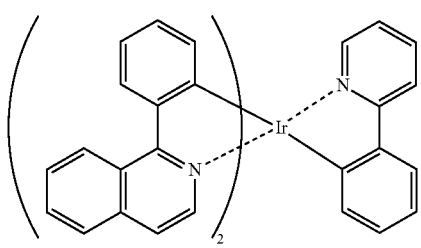

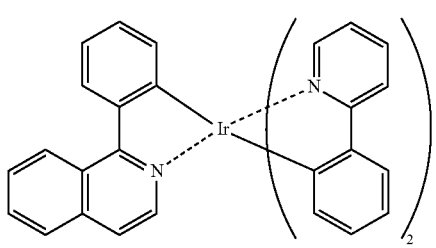

-continued

[Formula 56]

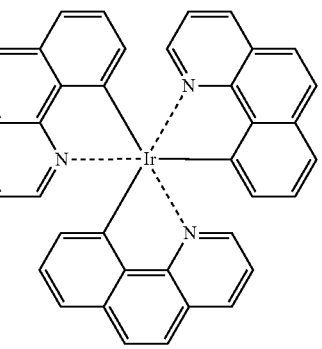

Ir(bzq)₃

One of the phosphorescent dopant materials may be used alone, or two or more thereof may be used in combination.

At least one phosphorescent material contained in the emitting layer 5 preferably has an emission wavelength peak in a range of 490 nm to 700 nm, more preferably in a range of 490 nm to 650 nm, further preferably in a range of 490 nm to 600 nm. An emission color of the emitting layer 5 in the exemplary embodiment is preferably yellow or green. Though an emission wavelength peak of yellow is typically in a range of 530 nm to 620 nm, the emission wavelength is particularly preferably in a range of 540 nm to 580 nm in the exemplary embodiment.

By doping the phosphorescent dopant material having such an emission wavelength to the aforementioned specific first and second host materials so as to form the emitting layer 5, the organic EL device can exhibit high efficiency.

Substrate

The organic EL device 1 is configured to include the anode 3, the emitting layer 5 and the cathode 4 laminated on the light-transmissive substrate. The substrate 2, which supports the anode 3 and the like, is preferably a flat and smooth substrate that transmits 50% or more of light in a visible region of 400 nm to 700 nm.

The light-transmissive plate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

Anode and Cathode

The anode 3 of the organic EL device 1 is used for injecting holes into the hole injecting layer, the hole transporting layer 6 or the emitting layer 5. It is effective that the anode 3 has a work function of 4.5 eV or more.

Specific examples of a material for the anode are alloys of indium-tin oxide (ITO), tin oxide (NESA), indium zinc oxide, gold, silver, platinum and copper.

The anode 3 can be manufactured by forming a thin film from these anode materials, for instance, on the substrate 2 through methods such as vapor deposition and sputtering.

When light from the emitting layer 5 is to be emitted through the anode 3, the anode 3 preferably transmits more than 10% of the light in the visible region. Sheet resistance of the anode is preferably several hundreds Ω/square or lower. Although depending on the material of the anode 3, a thickness of the anode 3 is typically in a range of 10 nm to 1 μm, and preferably in a range of 10 nm to 200 nm.

The cathode is preferably formed of a material with smaller work function in order to inject electrons into the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode 3, the cathode 4 may also be made by forming a thin film, for instance, on the electron transporting layer 7 from the above materials through a method such as vapor deposition or sputtering. In addition, light from the emitting layer 5 may be adapted to be emitted through the cathode 4. When light from the emitting layer 5 is to be emitted through the cathode 4, the cathode 4 preferably transmits more than 10% of the light in the visible region.

Sheet resistance of the cathode is preferably several hundreds Ω/square or lower.

Although depending on the material of the cathode, a thickness of the cathode is typically in a range from 10 nm to 1 μm, preferably in a range from 50 to 200 nm.

Other Layers

In order to improve current (luminous) efficiency, a hole injecting layer, a hole transporting layer, an electron injecting layer and the like may be provided. The organic El device 1 includes the hole transporting layer 6 and the electron transporting layer 7.

Hole Transporting Layer

The hole transporting layer 6 helps injection of holes to the emitting layer and transports the holes to an emitting region. The hole transporting layer 6 exhibits a large hole mobility and a small ionization potential.

A hole transporting material for forming the hole transporting layer 6 is preferably a material of transporting the holes to the emitting layer 5 at a lower electric field intensity. For instance, the second host material represented by the formula (2) in the exemplary embodiment is usable. In addition, an aromatic amine derivative represented by the following formula (A1) is preferably used as the material for the hole transporting layer 6.

[Formula 57]

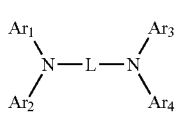

(A1)

In the formula (A1), $Ar^1$ to $Ar^4$ each independently represent an aromatic hydrocarbon group having 6 to 50 ring carbon atoms, an aromatic heterocyclic group having 2 to 40 ring carbon atoms, a group provided by bonding the aromatic hydrocarbon group and the aromatic heterocyclic group, or a group provided by bonding the aromatic hydrocarbon group and the aromatic heterocyclic group.

Note that the aromatic hydrocarbon group and the aromatic heterocyclic group described herein may have a substituent.

In the formula (A1), L is a linking group and represents a divalent aromatic hydrocarbon group having 6 to 50 ring carbon atoms, a divalent aromatic heterocyclic group having 5 to 50 ring carbon atoms, a divalent group provided by bonding at least two of the aromatic heterocyclic groups or the aromatic heterocyclic group through a single bond, an ether bond, a thioether bond, an alkylene group having 1 to 20 carbon atoms, an alkenylene group having 2 to 20 carbon atoms, or an amino group.

Note that the divalent aromatic hydrocarbon group and the divalent aromatic heterocyclic group described herein may have a substituent.

Examples of the compound represented by the formula (A1) are shown below. However, the compound represented by the formula (A1) is not limited thereto.

[Formula 58]

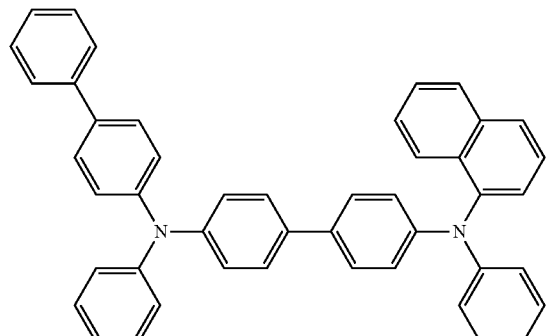

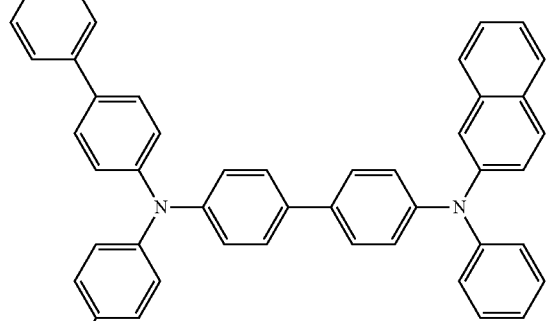

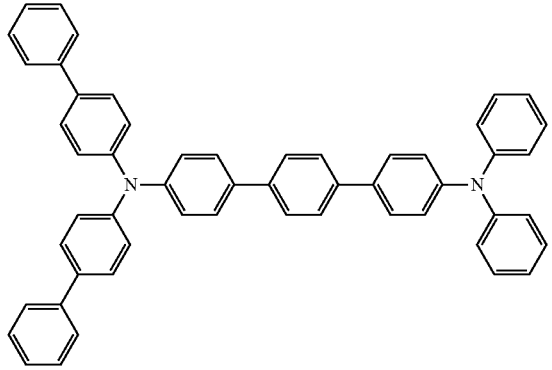

123
-continued
124
-continued
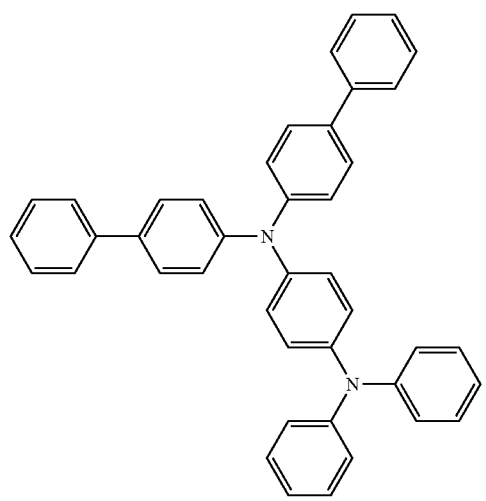
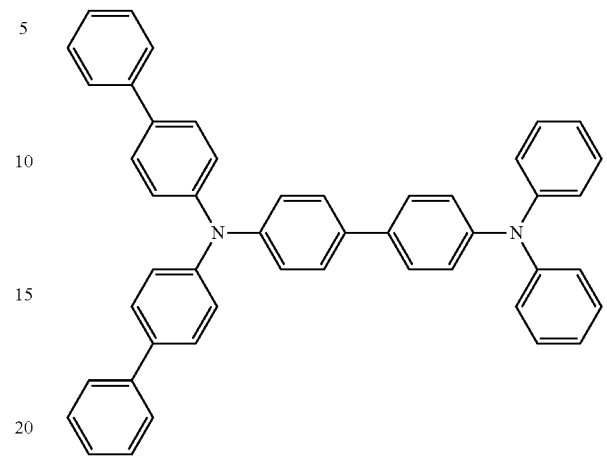
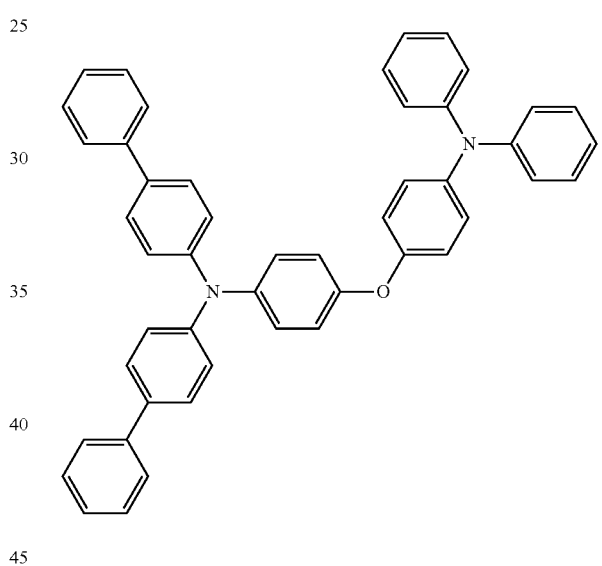
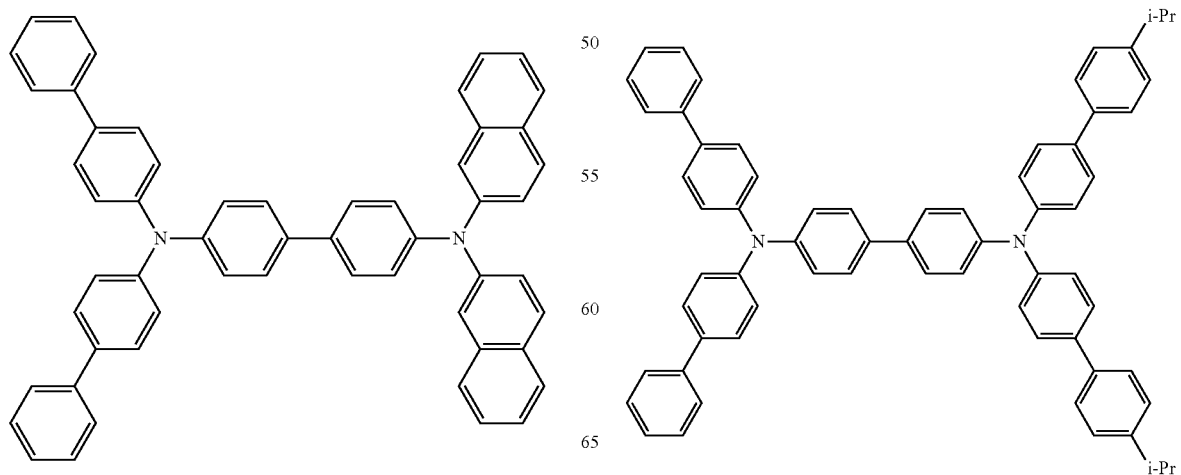

125
-continued
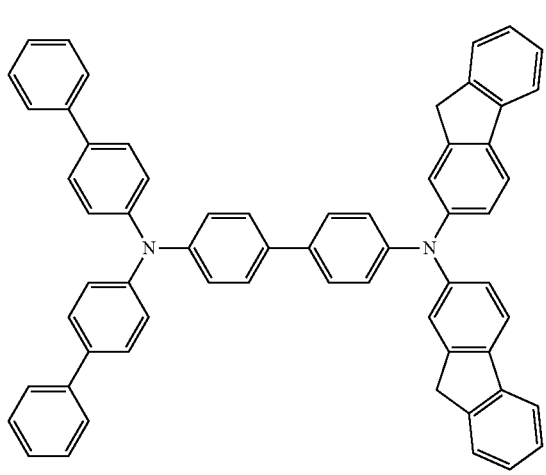
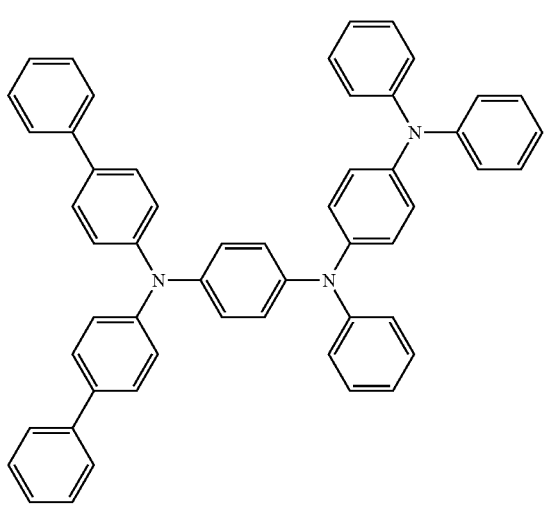
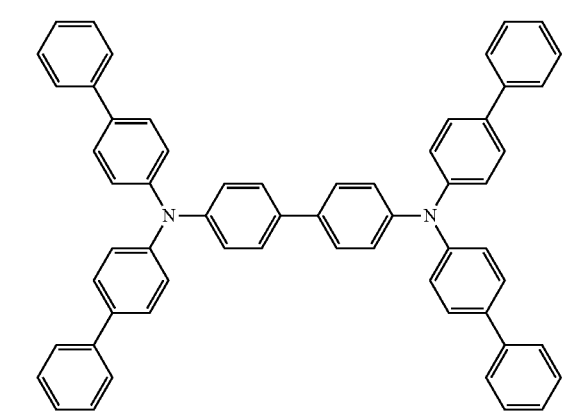
126
-continued
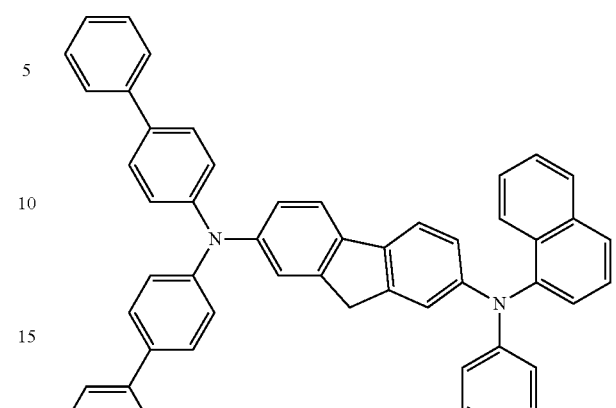
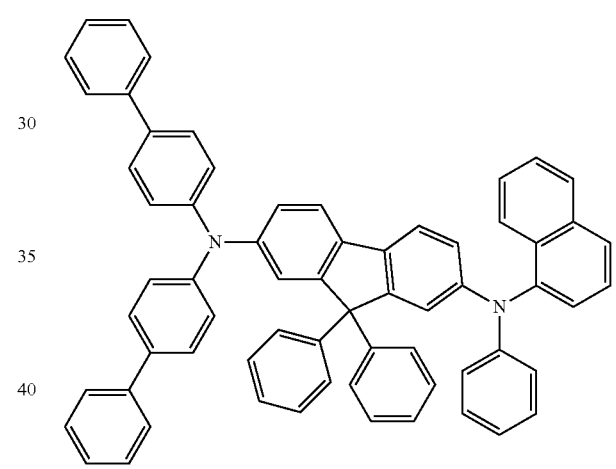
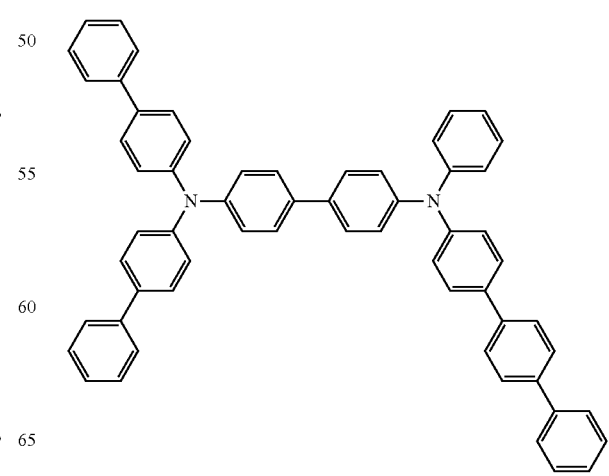

127
-continued
128
-continued
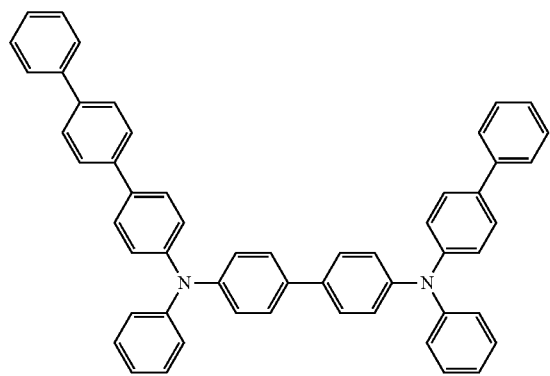
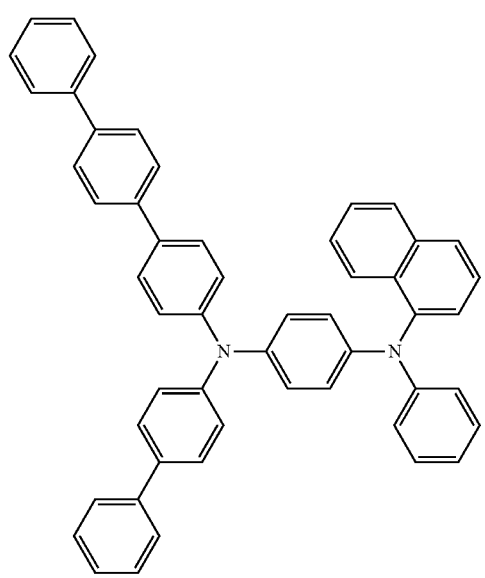
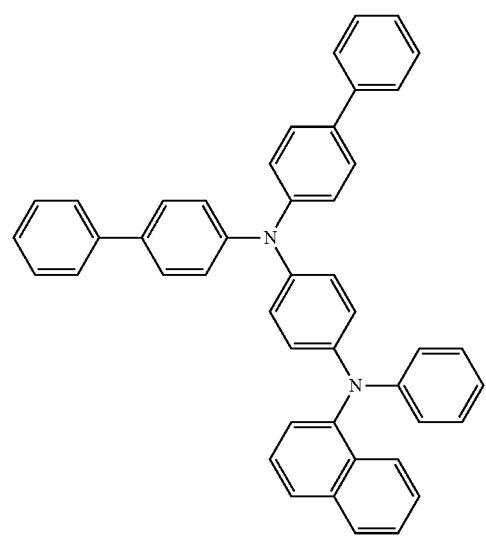
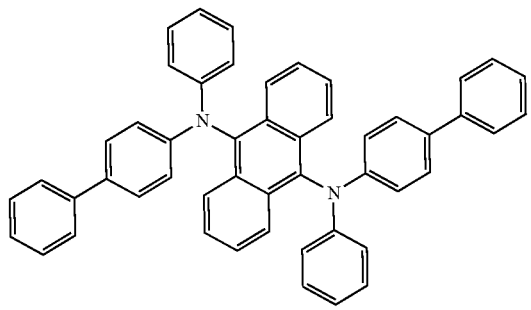
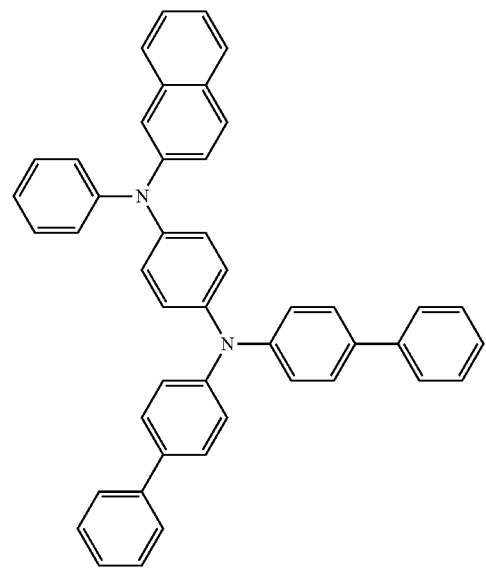

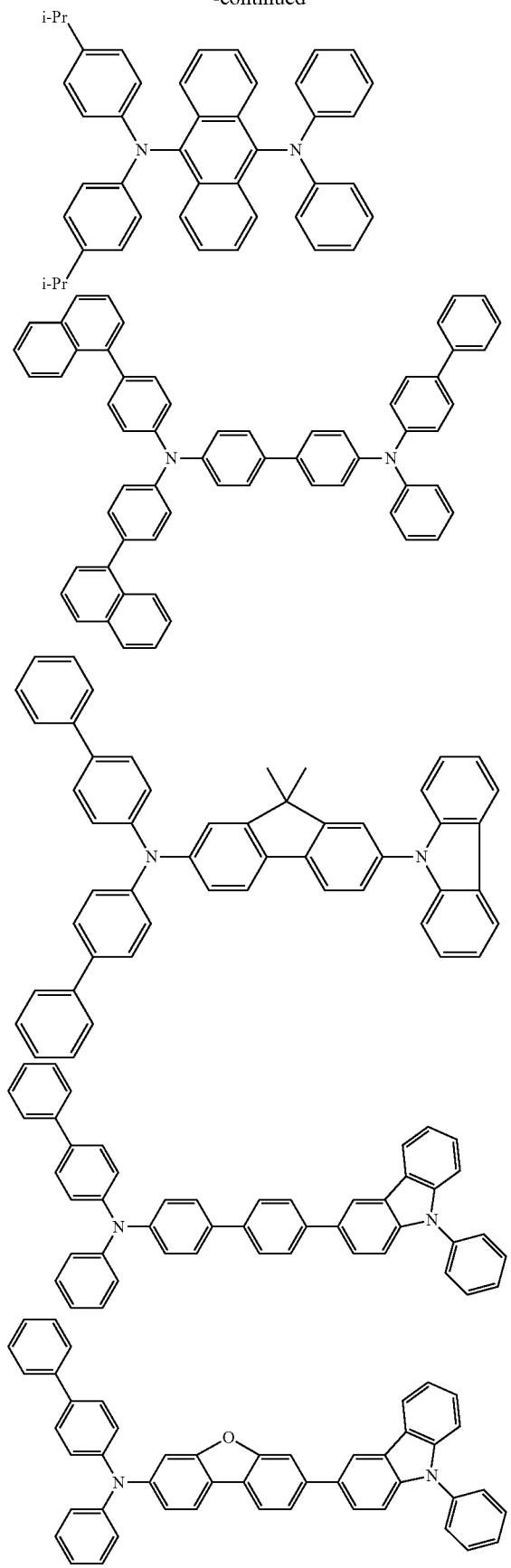
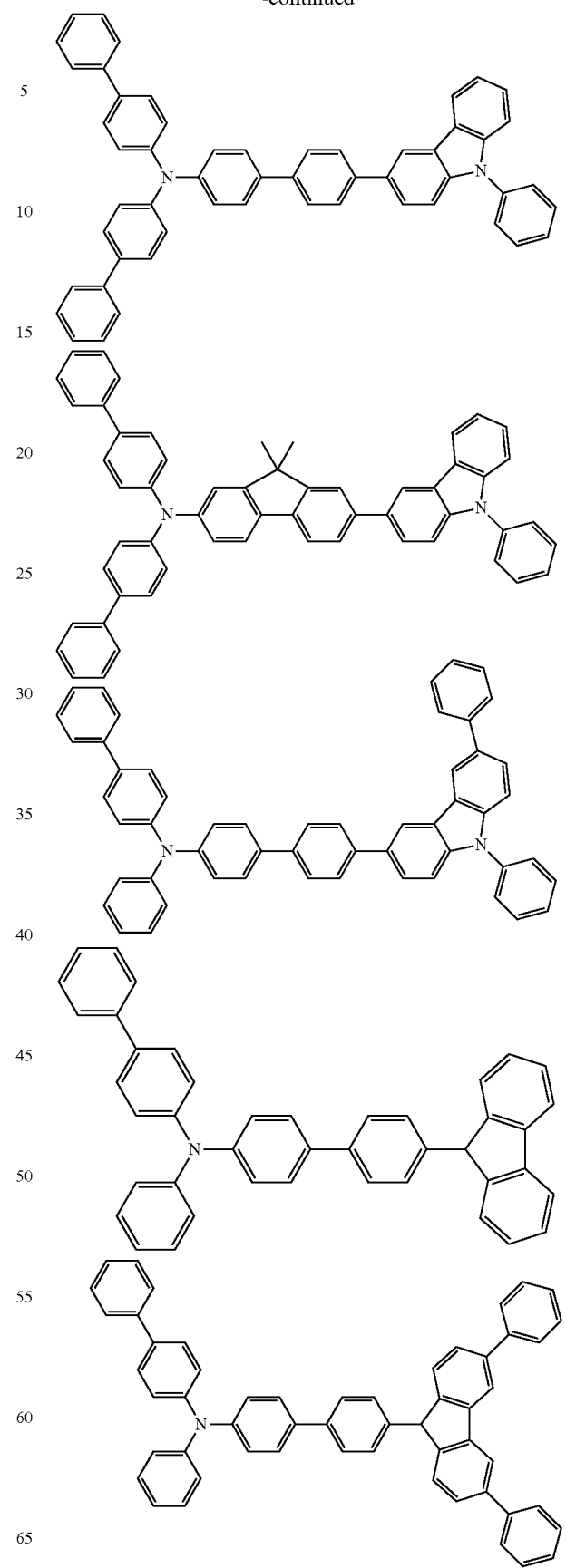

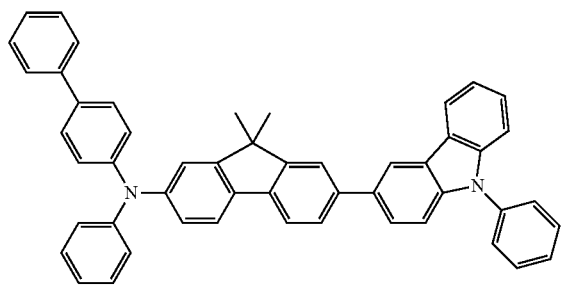

Aromatic amine represented by the following formula (A2) can also be preferably used for forming the hole injecting/transporting layer.

[Formula 59]

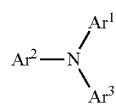
(A2)

In the above formula (A2), $Ar^1$ to $Ar^3$ each represent the same as $Ar^1$ to $Ar^4$ of the above formula (A1). Examples of the compound represented by the formula (A2) are shown below. However, the compound represented by the formula (A2) is not limited thereto.

[Formula 60]

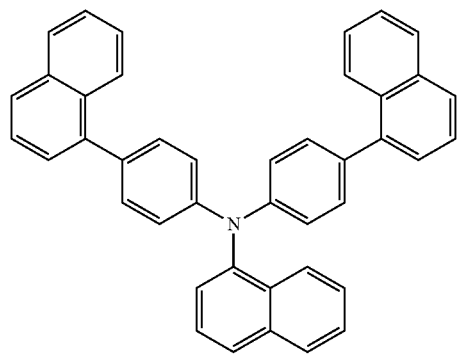

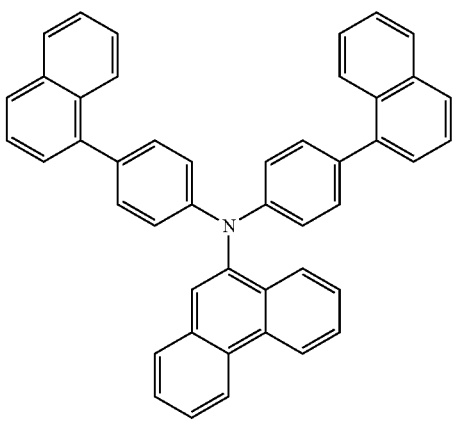

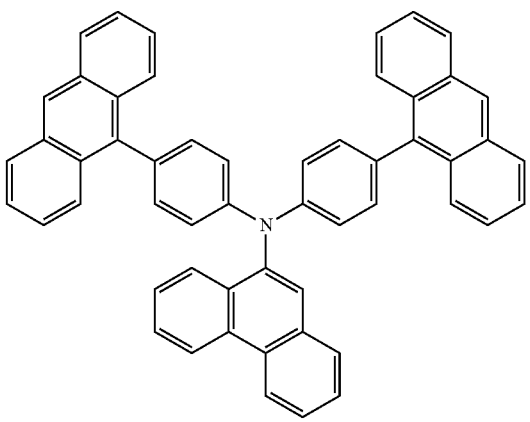

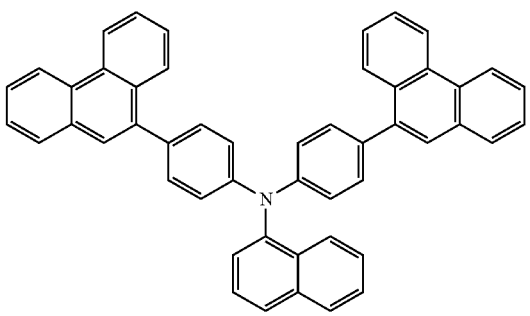

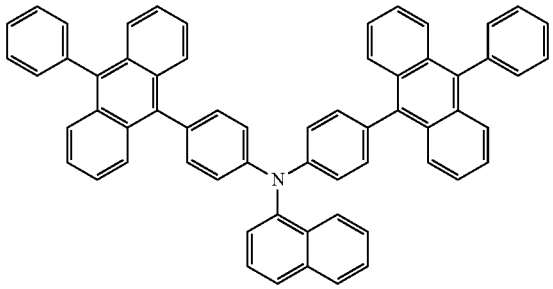

133
-continued
134
-continued
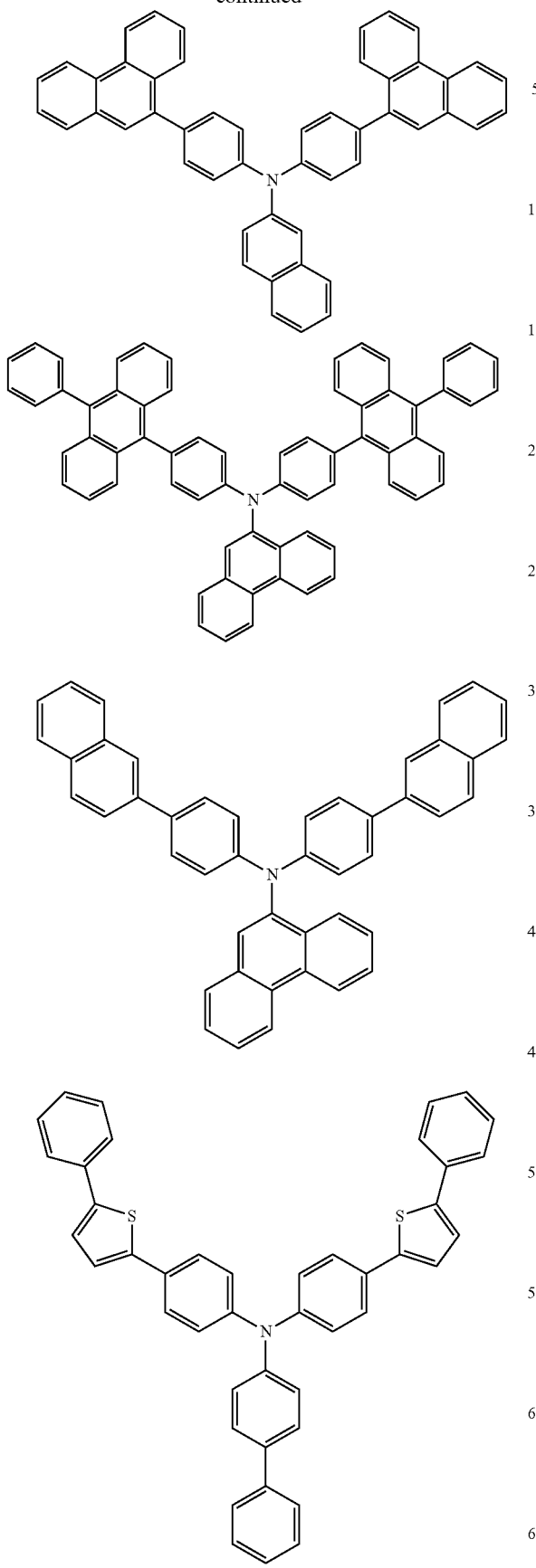
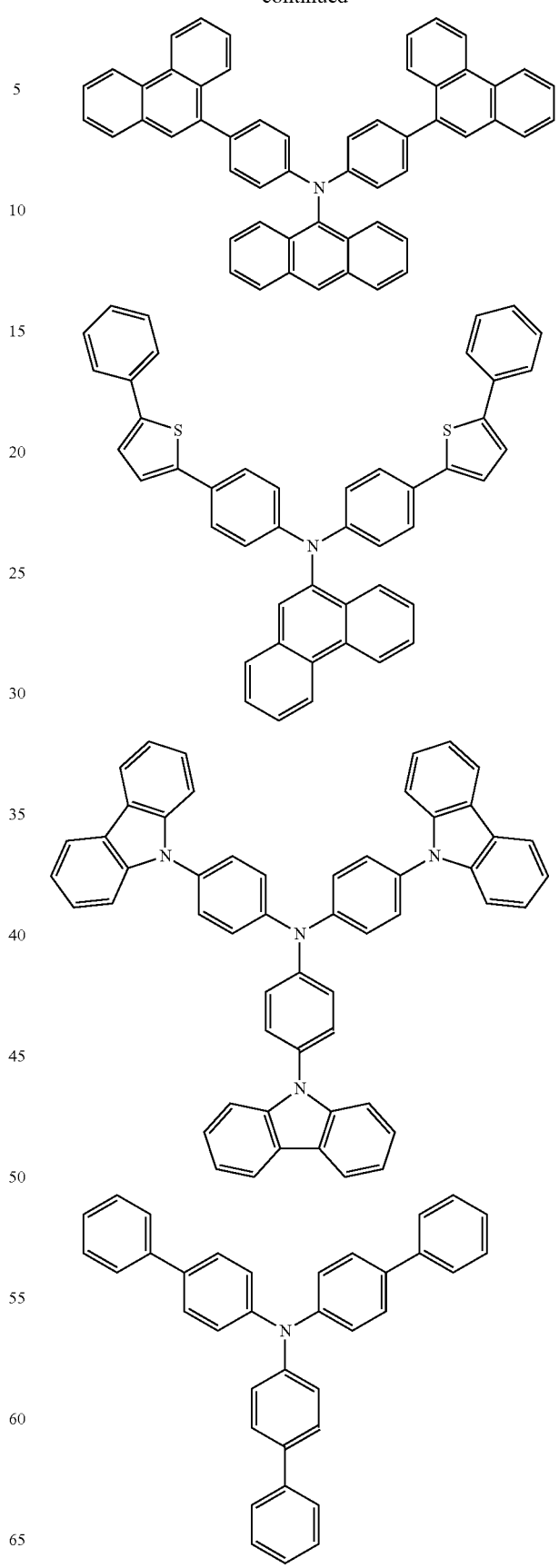

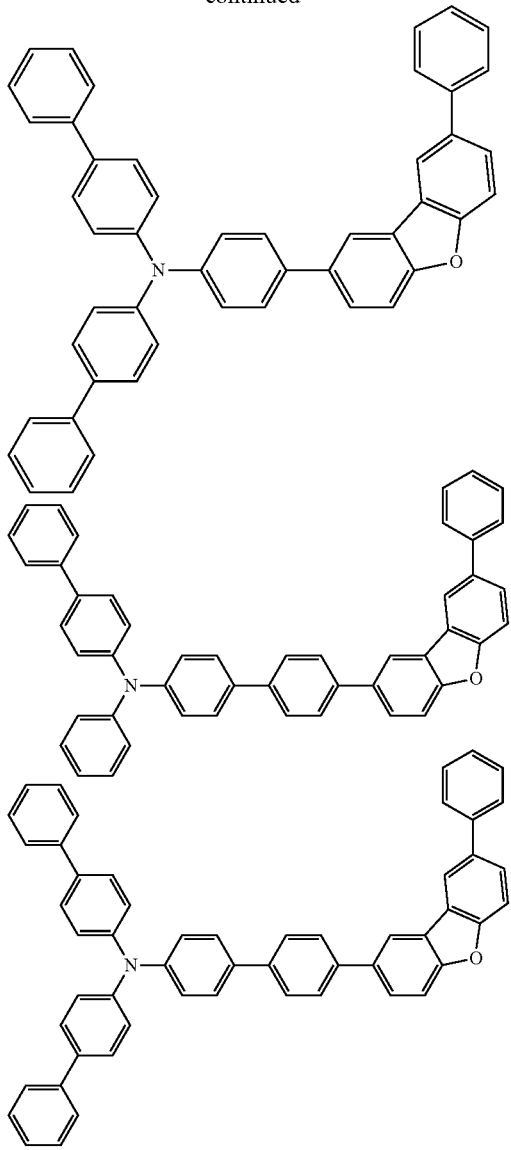

A biscarbazole derivative represented by a formula (A3) below can also be preferably used for forming the hole injecting/transporting layer.

[Formula 61]

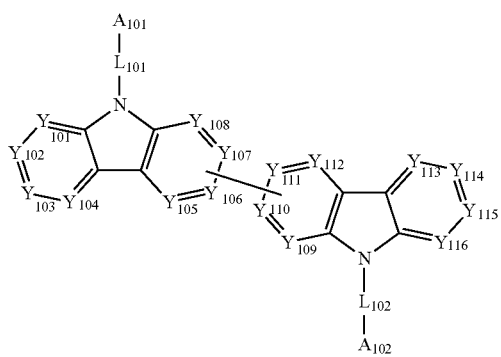

(A3)

In the formula (A3), $A_{101}$ and $A_{102}$ each independently represent a substituted or unsubstituted aromatic hydrocarbon group having 6 to 30 ring carbon atoms, or a substituted or unsubstituted heterocyclic group having 5 to 30 ring atoms.

$Y_{101}$ to $Y_{116}$ each independently represent $C(R_{100})$ or a nitrogen atom, in which $R_{100}$ independently represents a hydrogen atom, a substituent or a bond to the carbazole skeleton.

$L_{101}$ to $L_{102}$ each independently represent a single bond or a divalent linking group.

Examples of the aromatic hydrocarbon group having 6 to 30 ring carbon atoms for $A_{101}$ and $A_{102}$ are the same as the examples of the aryl group having 6 to 30 ring carbon atoms for $Ar_t$ to $Ar_3$ in the formula (1). Examples of the heterocyclic group having 5 to 30 ring atoms for $A_{101}$ and $A_{102}$ are the same as the examples of the heterocyclic group having 5 to 30 ring atoms for $Ar_1$ to $Ar_3$ in the formula (1).

Examples of $R_{100}$ as the substituent are the same as the examples of any substituents being in the case of "substituted or unsubstituted" described above.

Examples of $L_{101}$ and $L_{102}$ as the divalent linking group are a substituted or unsubstituted divalent aromatic hydrocarbon group having 6 to 30 ring carbon atoms, or a substituted or unsubstituted divalent heterocyclic group having 5 to 30 ring atoms.

In the formula (A3), at least one of $A_1$, $A_2$ and R is preferably a substituted or unsubstituted fluoranthenyl group, substituted or unsubstituted triphenylenyl group, substituted or unsubstituted benzophenanthrenyl group, substituted or unsubstituted benzotriphenylenyl group, substituted or unsubstituted dibenzotriphenylenyl group, substituted or unsubstituted chrysenyl group, substituted or unsubstituted benzochrysenyl group, substituted or unsubstituted picenyl group, substituted or unsubstituted benzo[b]fluoranthenyl group, substituted or unsubstituted bnezofuranyl group, substituted or unsubstituted dibenzofuranyl group, substituted or unsubstituted benzothiophenyl group, substituted or unsubstituted dibenzothiophenyl group, substituted or unsubstituted phenanthrenyl group, substituted or unsubstituted fluorenyl group, or substituted or unsubstituted binaphthyl group.

In the formula (A3), at least one of $A_1$ and $A_2$ is preferably a substituted or unsubstituted fluoranthenyl group, substituted or unsubstituted triphenylenyl group, substituted or unsubstituted benzophenanthrenyl group, substituted or unsubstituted benzotriphenylenyl group, substituted or unsubstituted dibenzotriphenylenyl group, substituted or unsubstituted chrysenyl group, substituted or unsubstituted benzochrysenyl group, substituted or unsubstituted picenyl group, substituted or unsubstituted benzo[b]fluoranthenyl group, substituted or unsubstituted bnezofuranyl group, substituted or unsubstituted dibenzofuranyl group, substituted or unsubstituted benzothiophenyl group, substituted or unsubstituted dibenzothiophenyl group, substituted or unsubstituted phenanthrenyl group, substituted or unsubstituted fluorenyl group, or substituted or unsubstituted binaphthyl group.

Examples of the compound represented by the formula (A3) are shown below. However, the compound represented by the formula (A3) is not limited thereto.

[Formula 62]
137
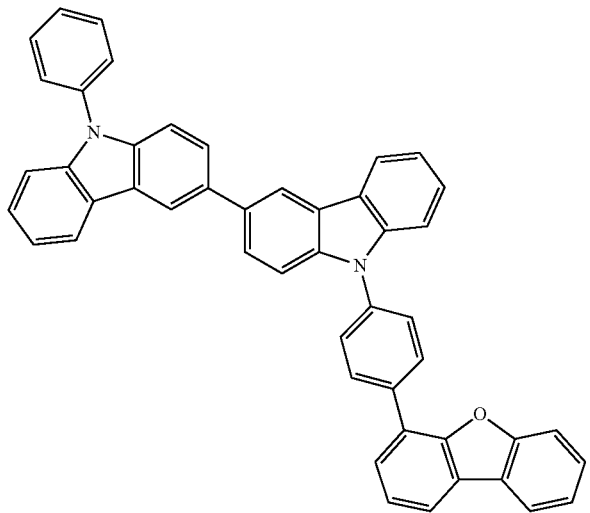
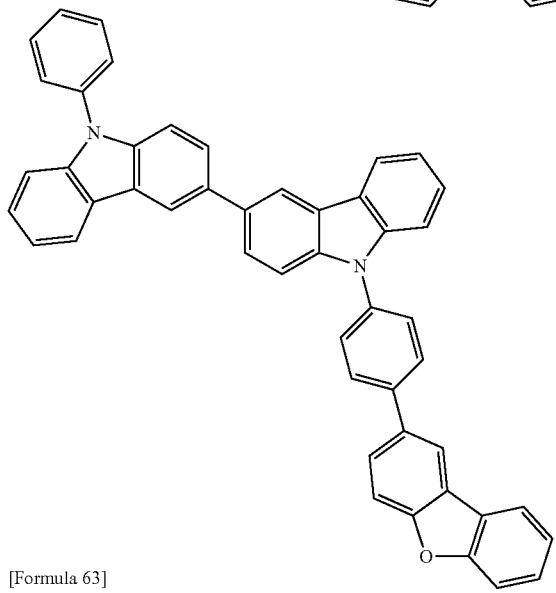
138
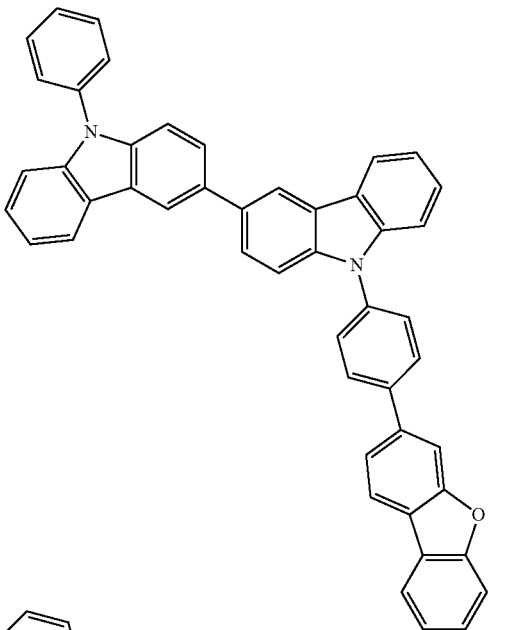
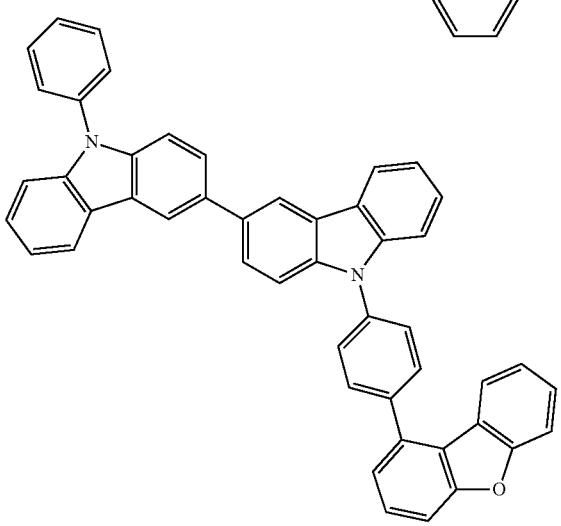
[Formula 63]
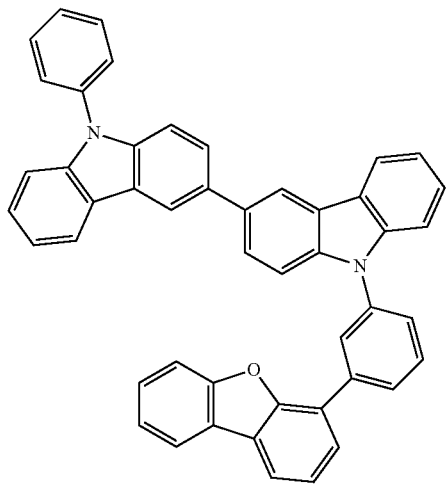
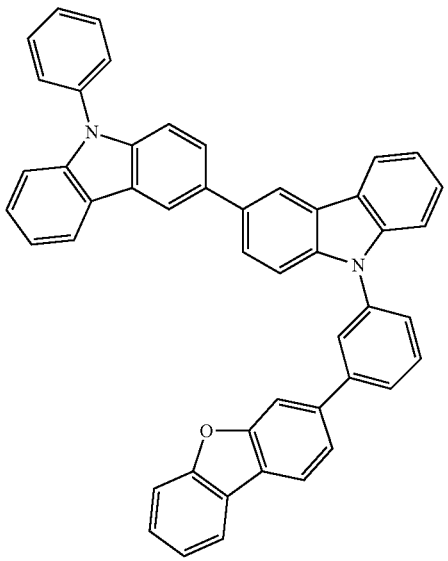

139
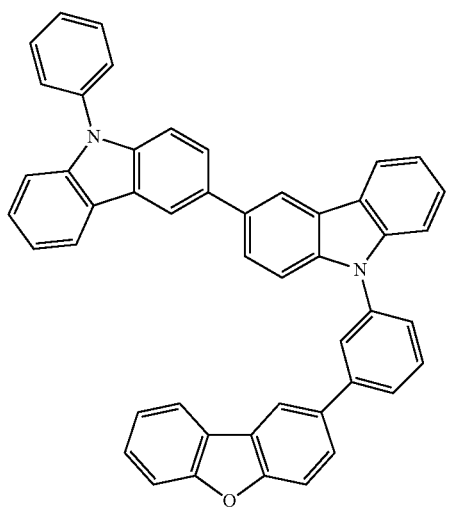
140
-continued
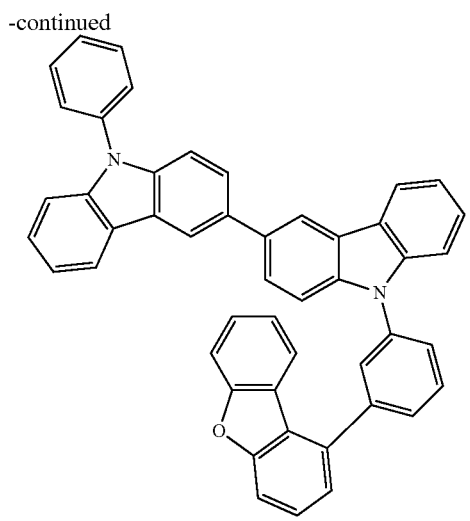
[Formula 64]
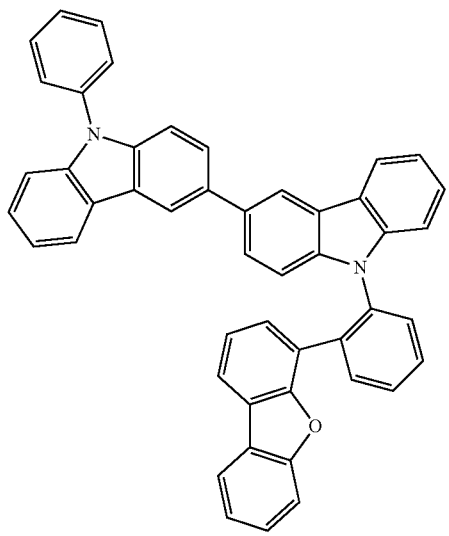
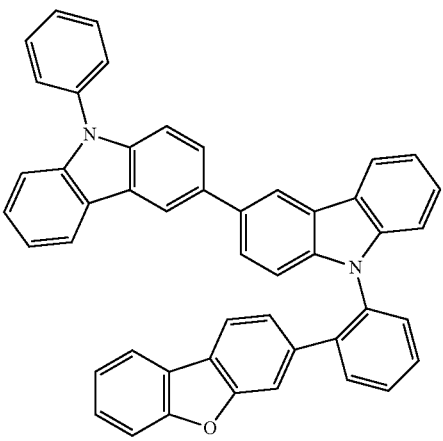
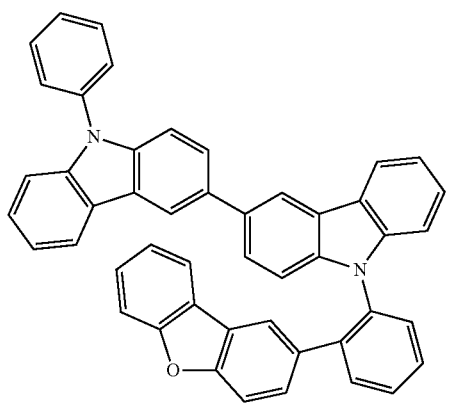
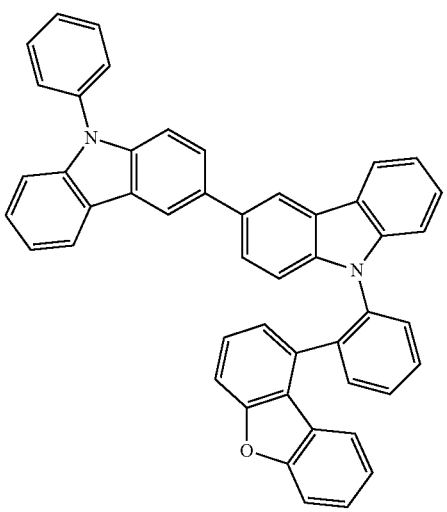

[Formula 65]
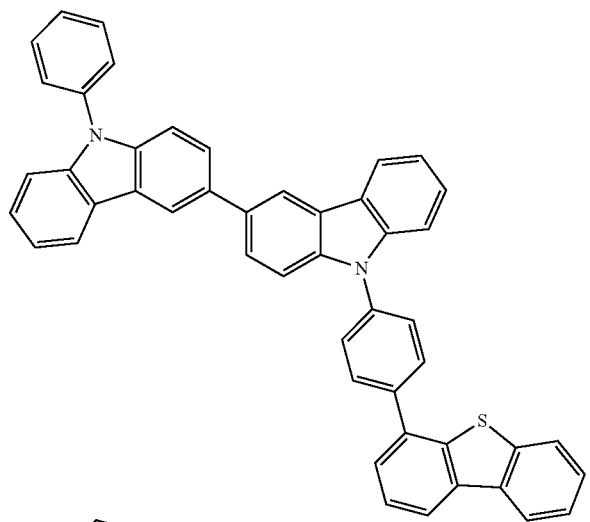
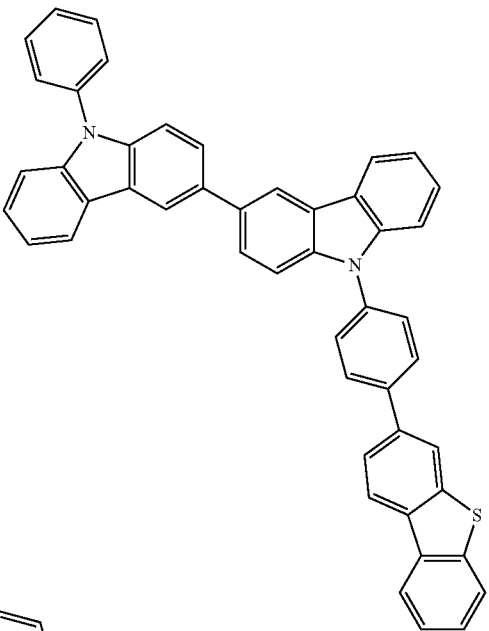
[Formula 66]
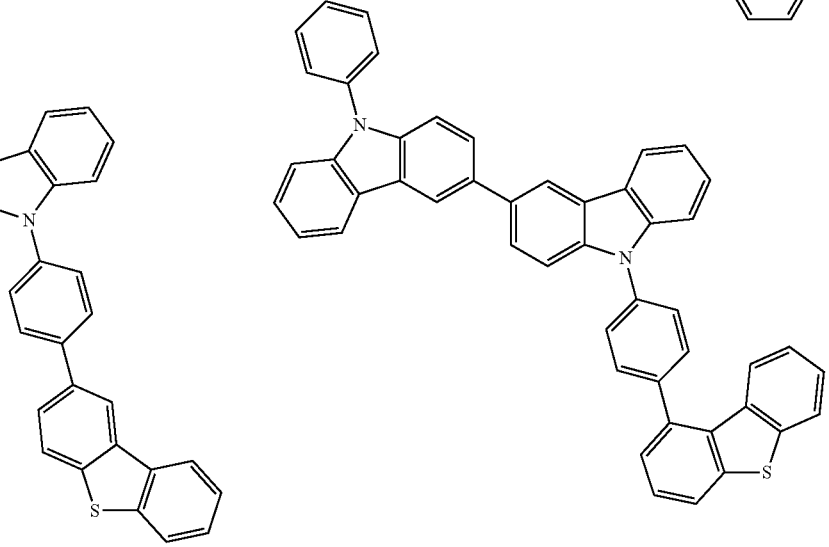
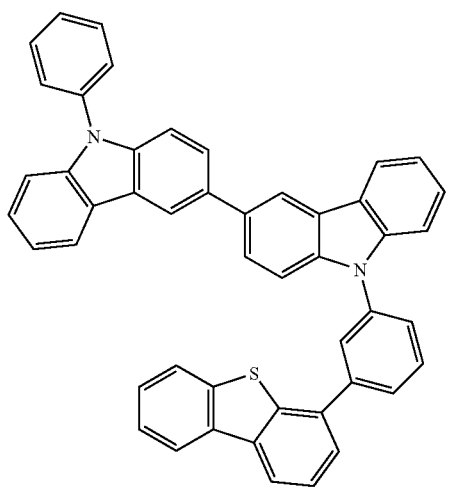
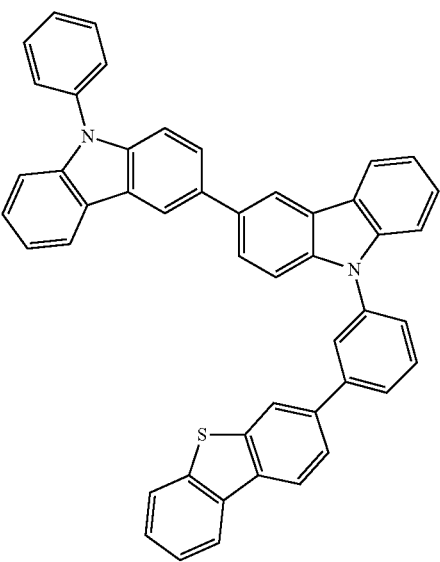

143
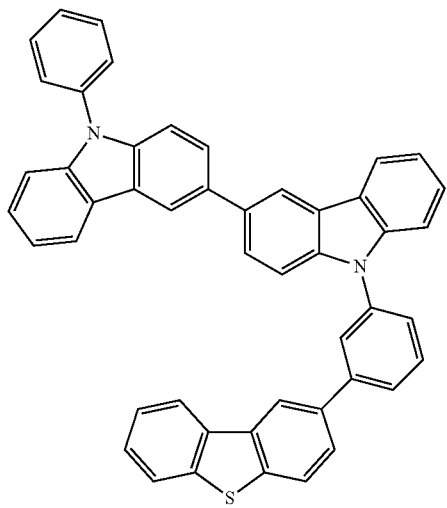
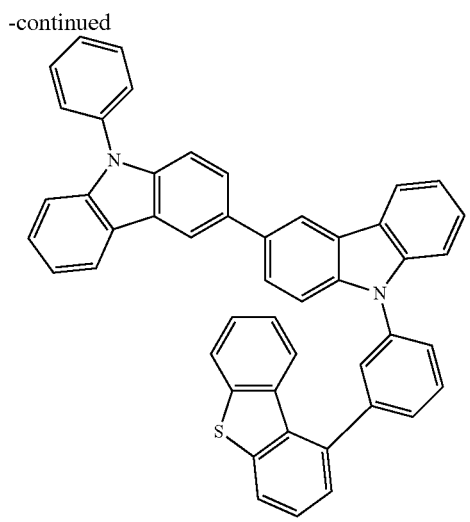
[Formula 67]
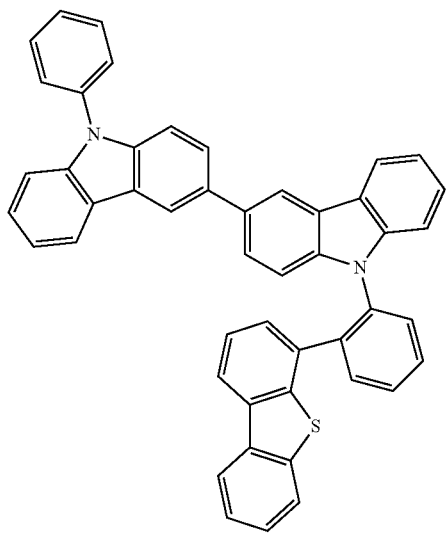
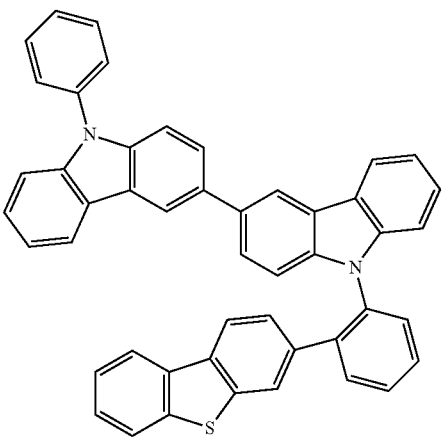
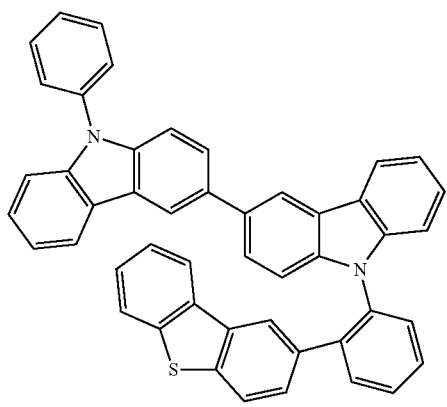
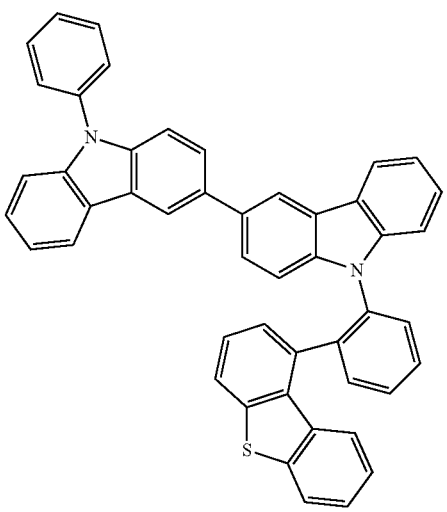

[Formula 68]
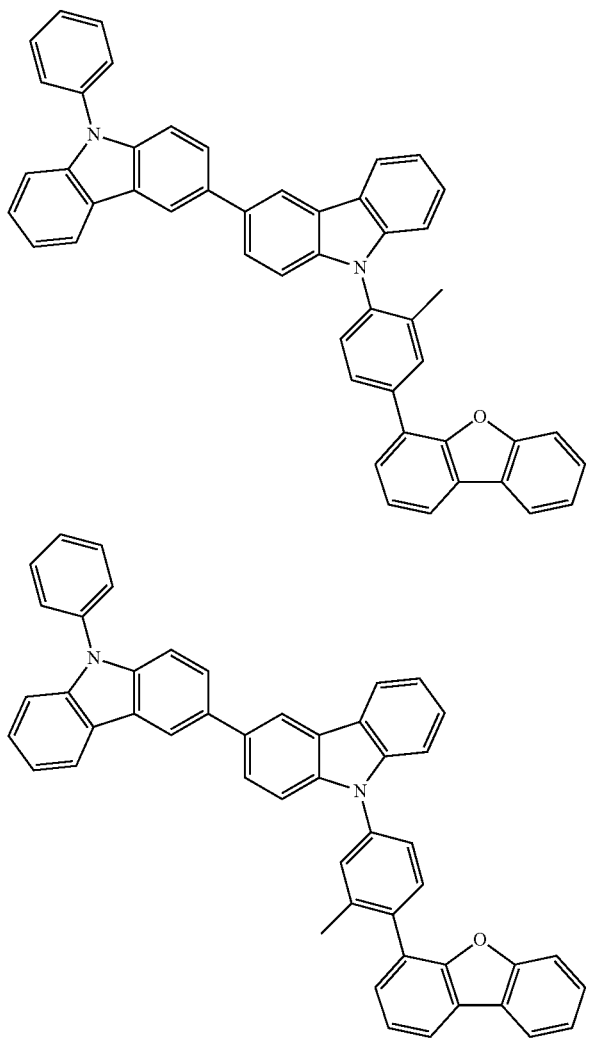
-continued
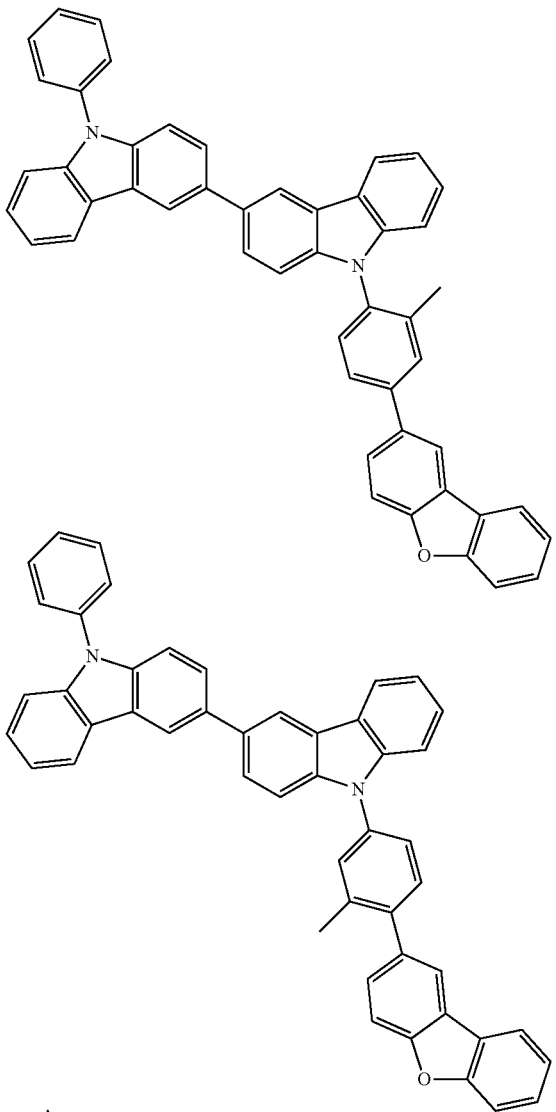
[Formula 69]
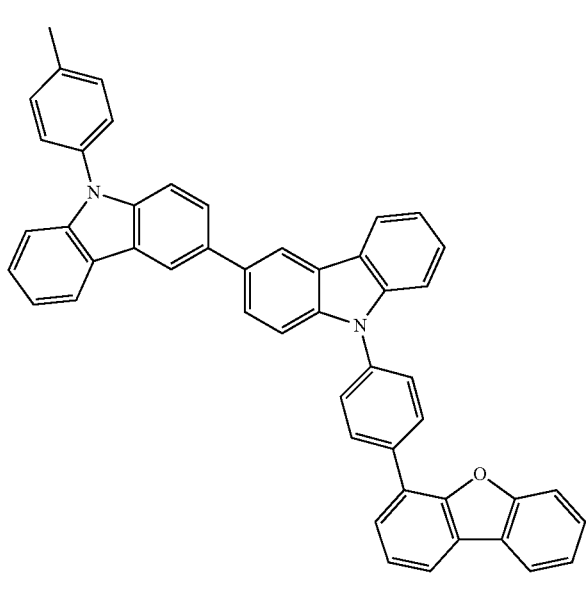
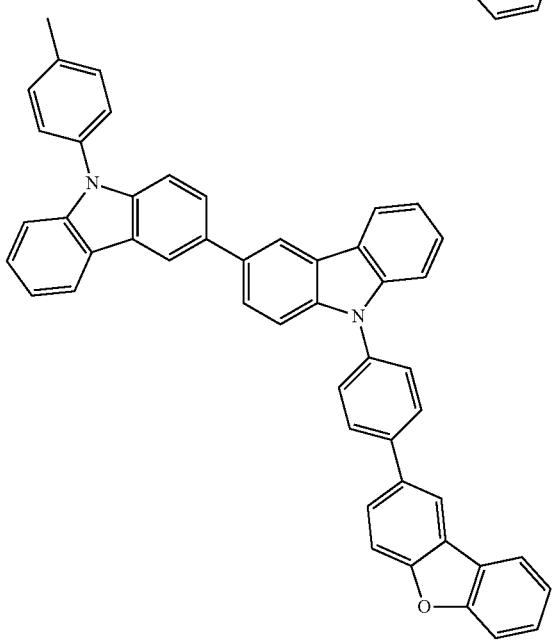

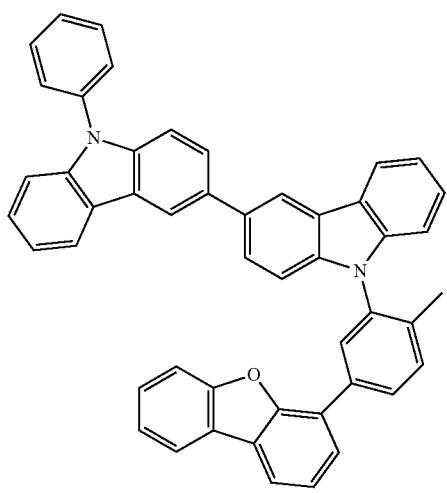
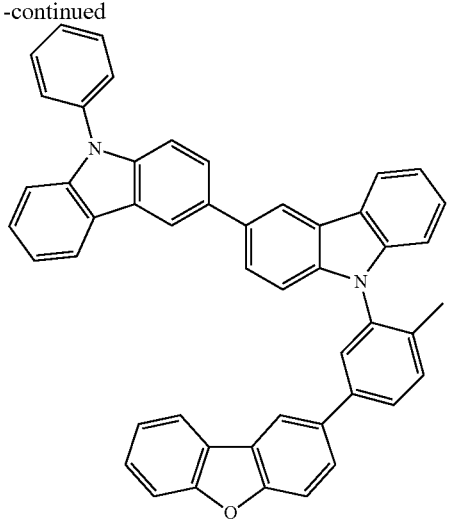
[Formula 70]
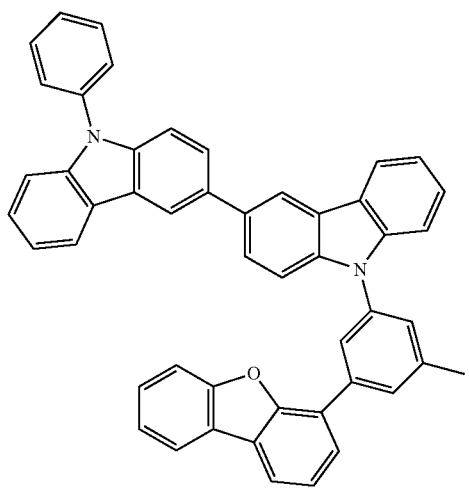
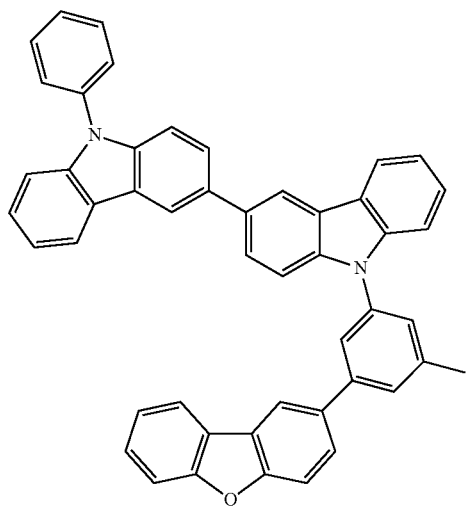
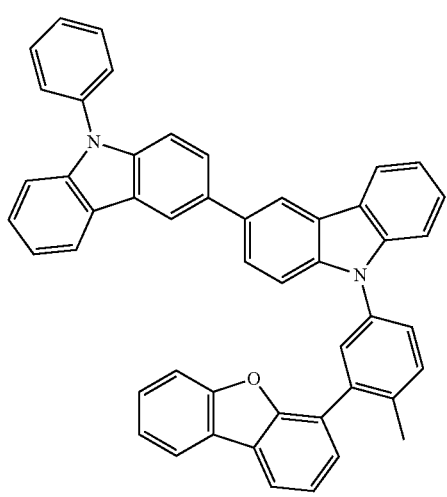
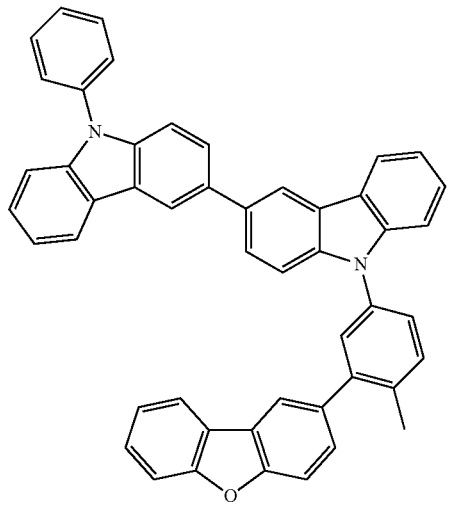

-continued
[Formula 71]
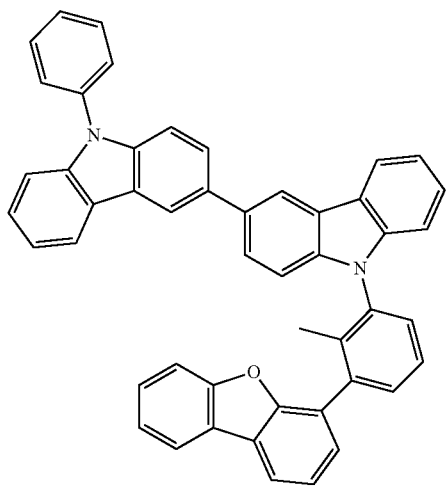
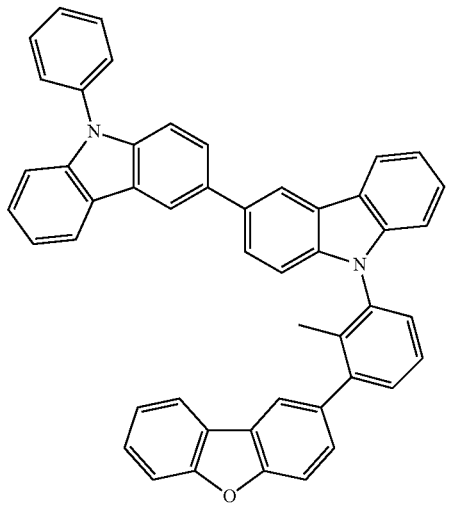
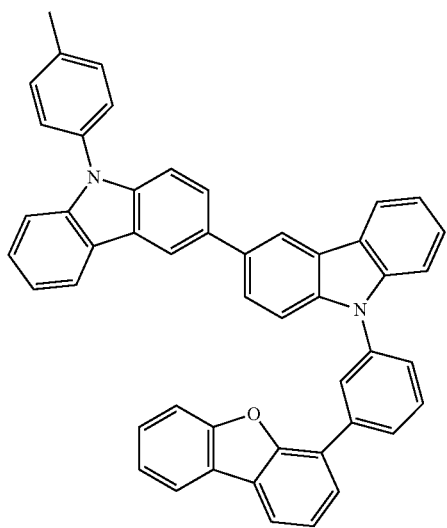
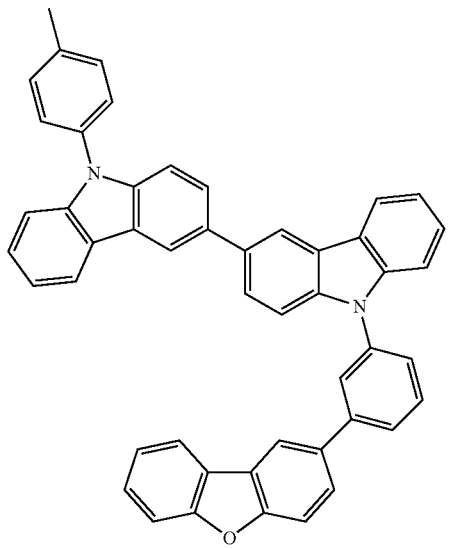
[Formula 72]
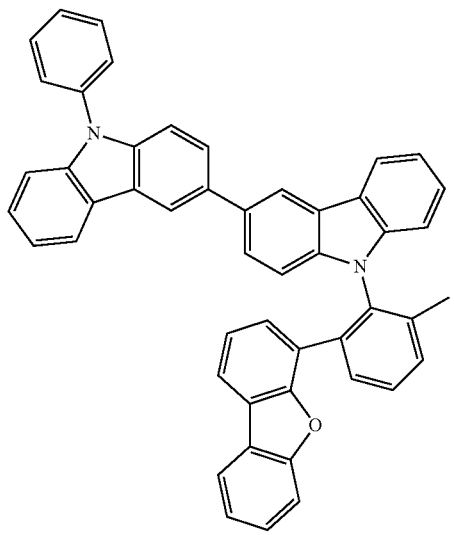
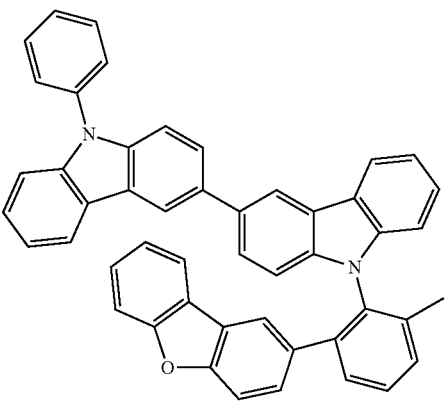

-continued
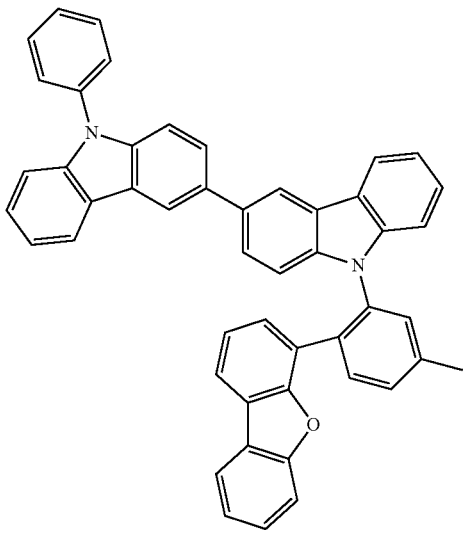
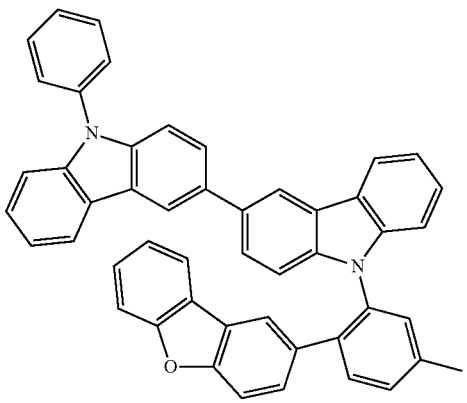
[Formula 73]
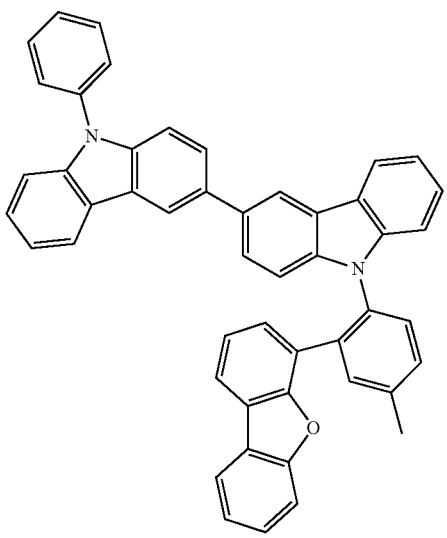
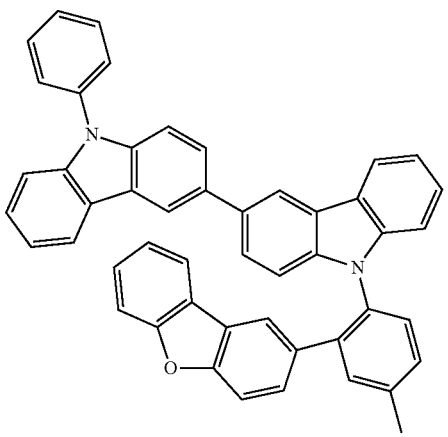
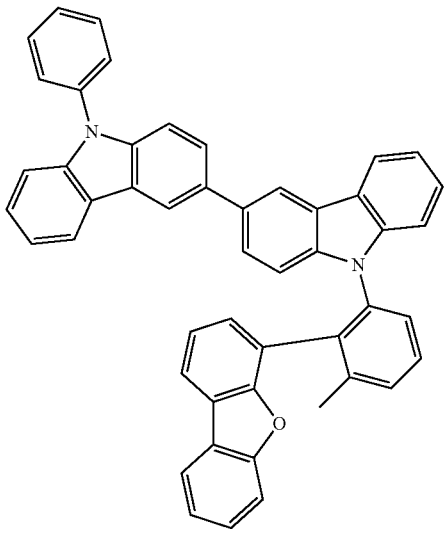
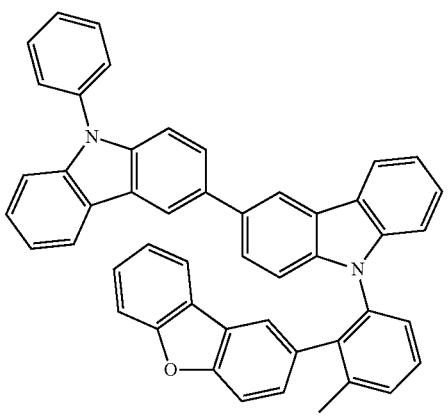

[Formula 74]
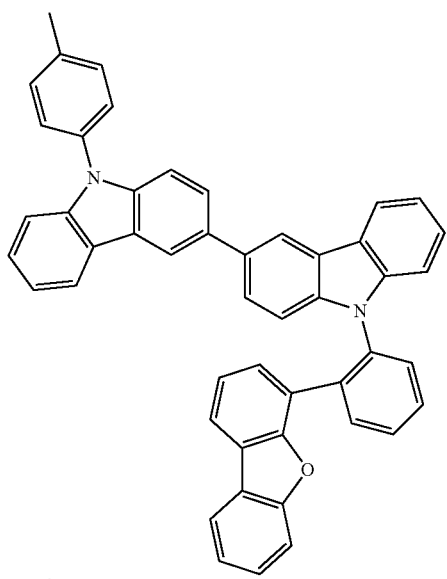
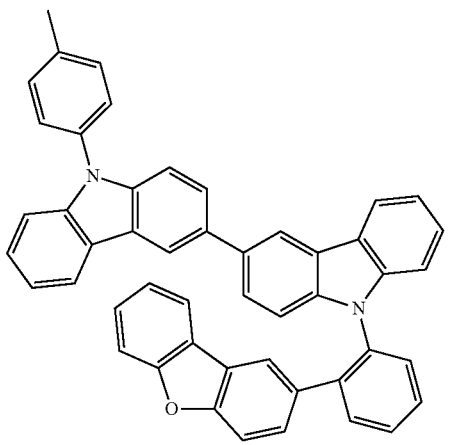
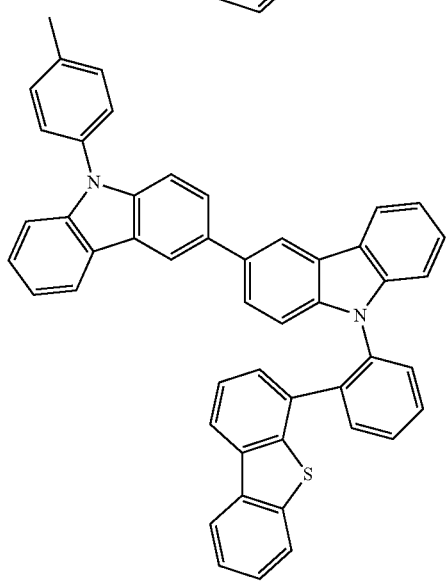
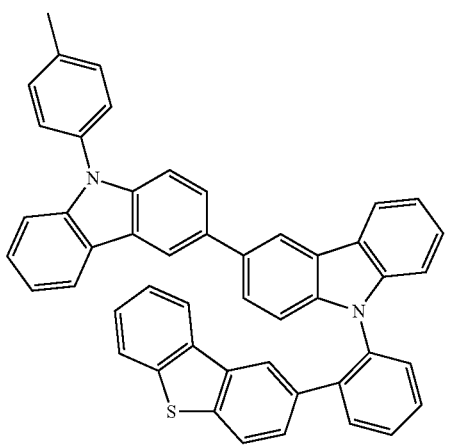
[Formula 75]
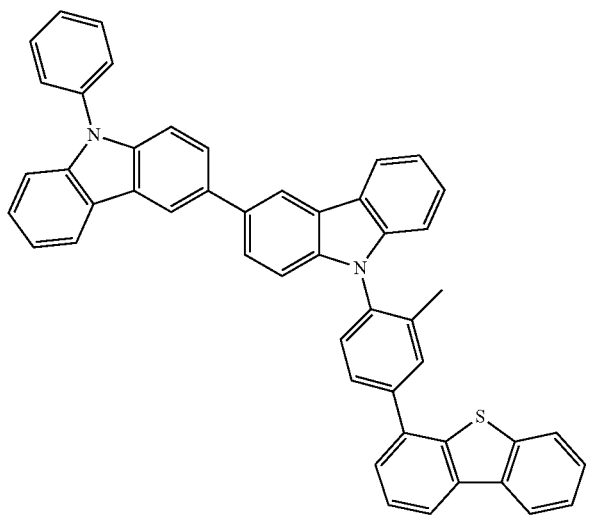

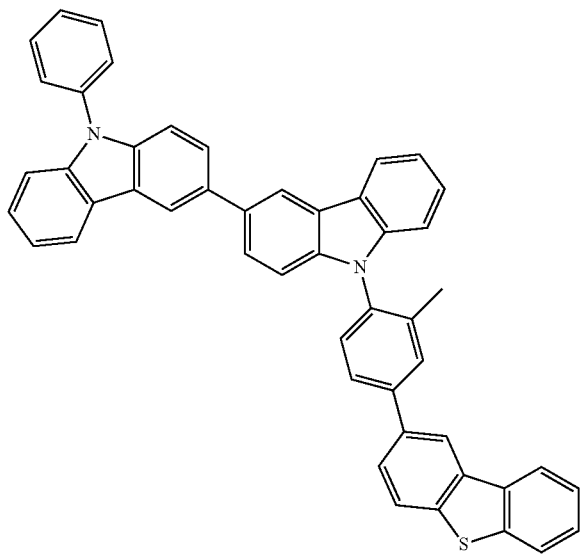
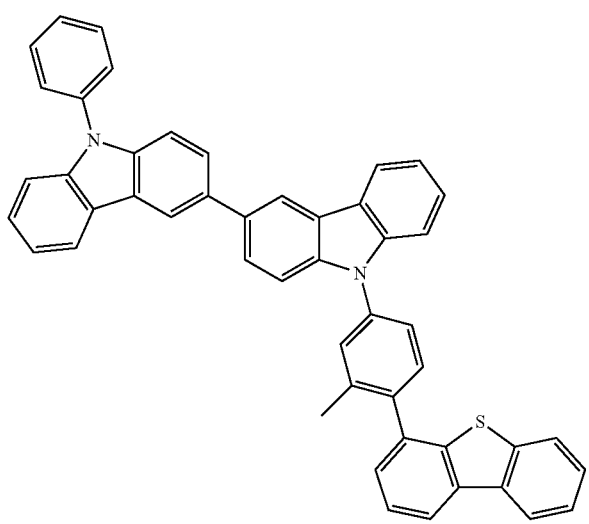
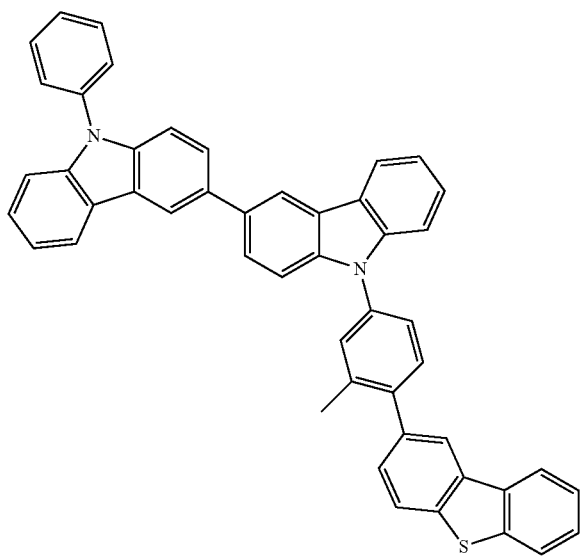

[Formula 76]
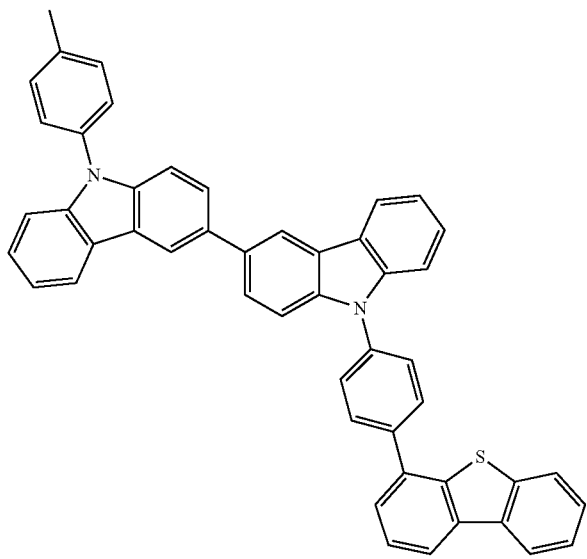
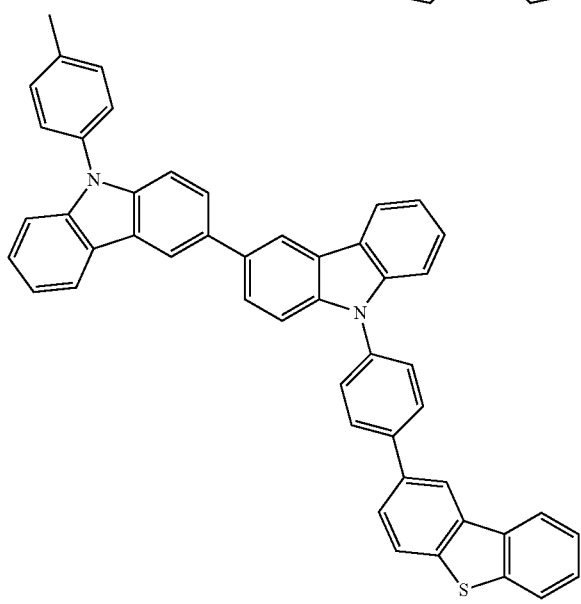
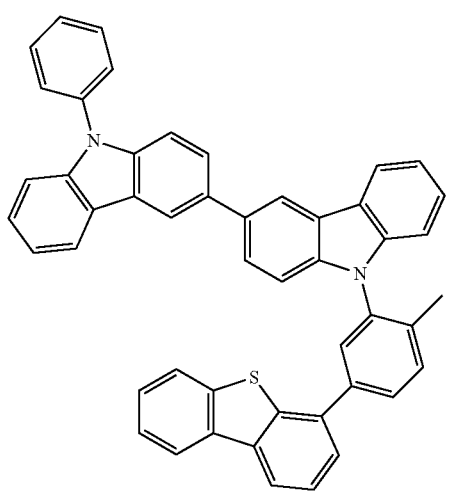
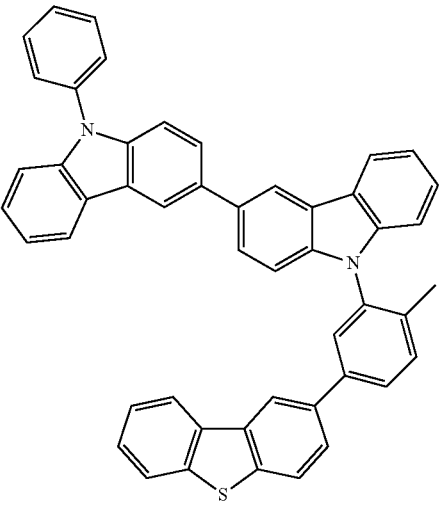

[Formula 77]
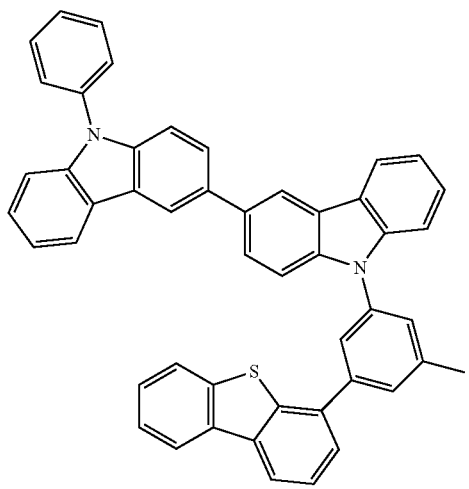
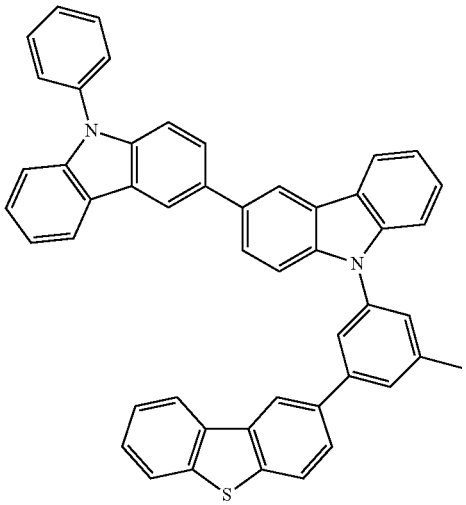
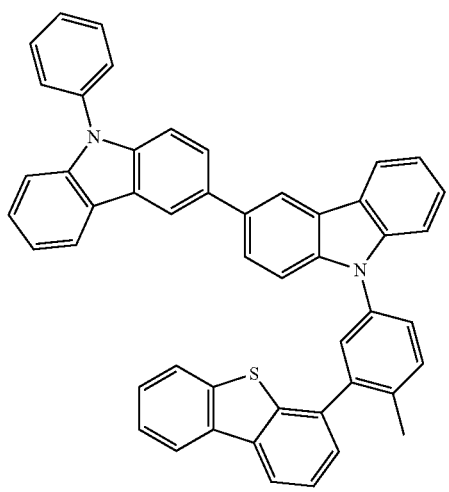
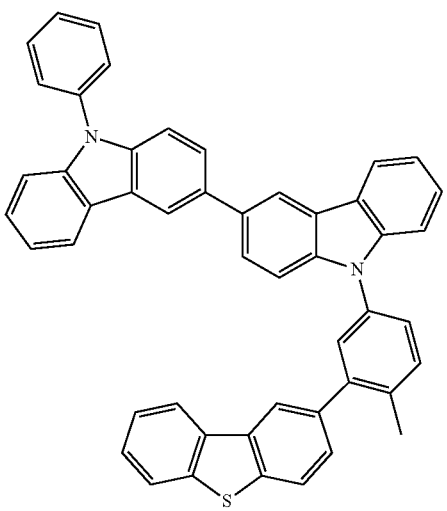
[Formula 78]
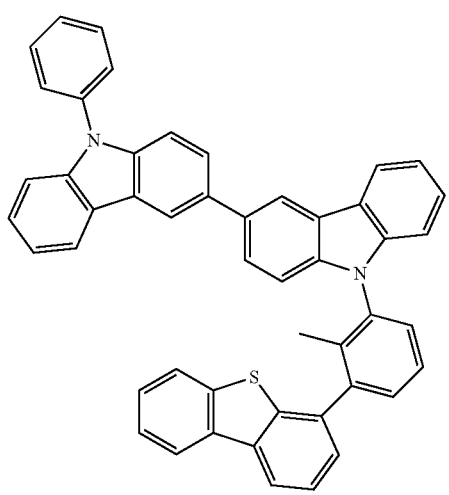
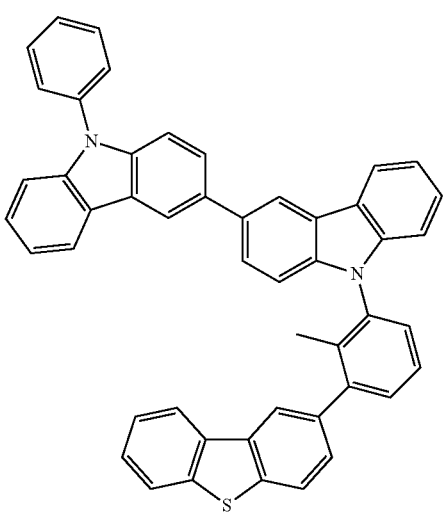

-continued
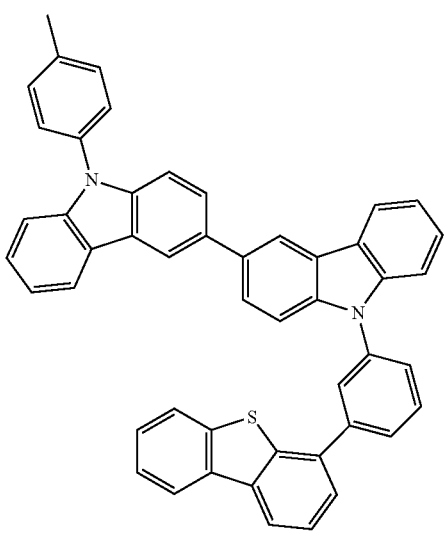
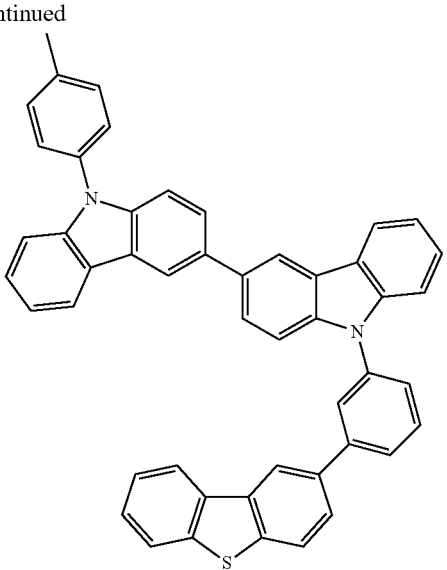
[Formula 79]
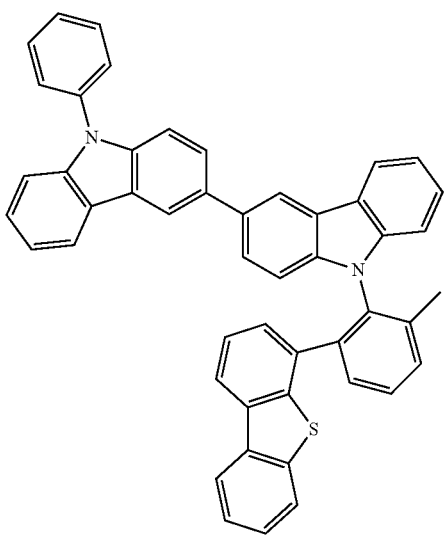
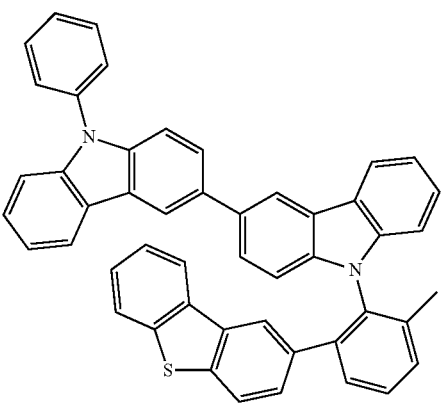
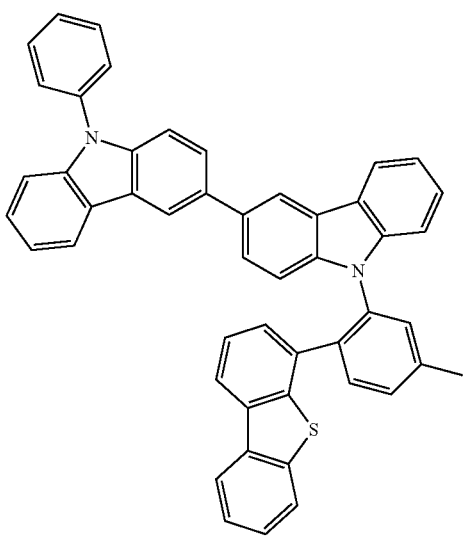
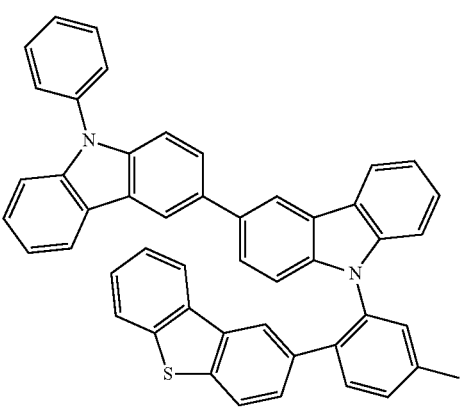

-continued
[Formula 80]
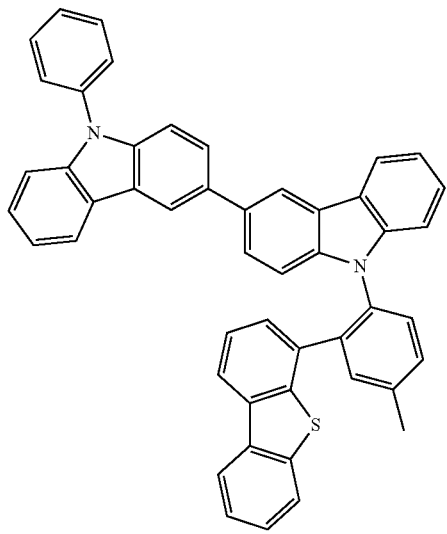
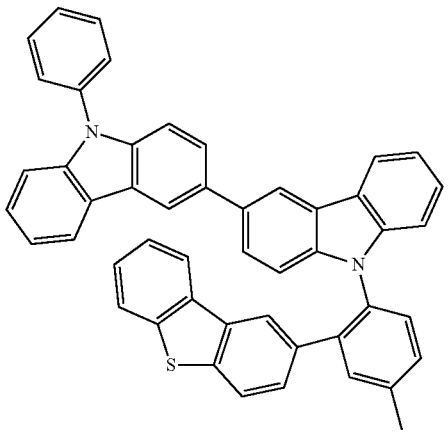
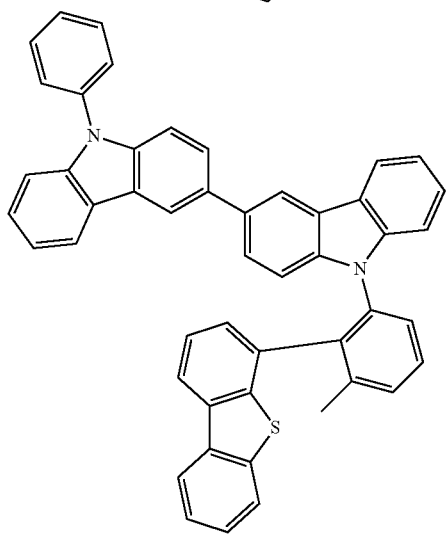
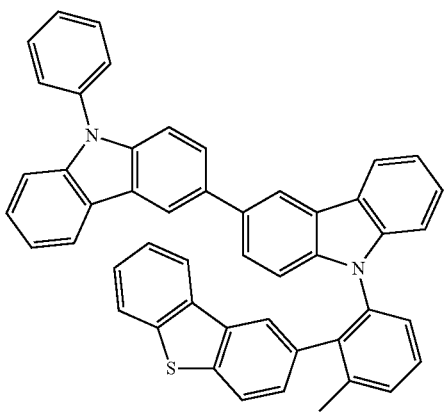
[Formula 81]
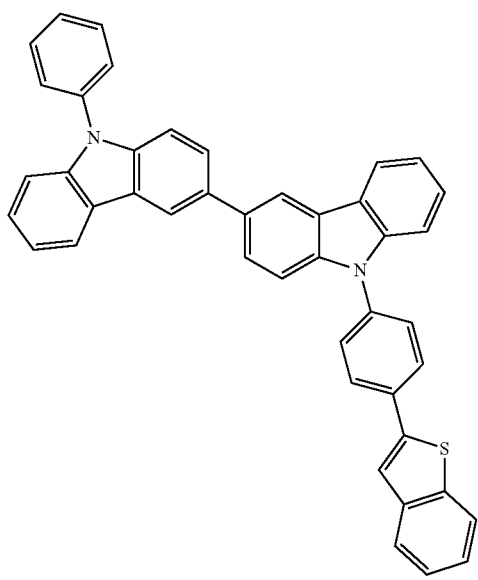
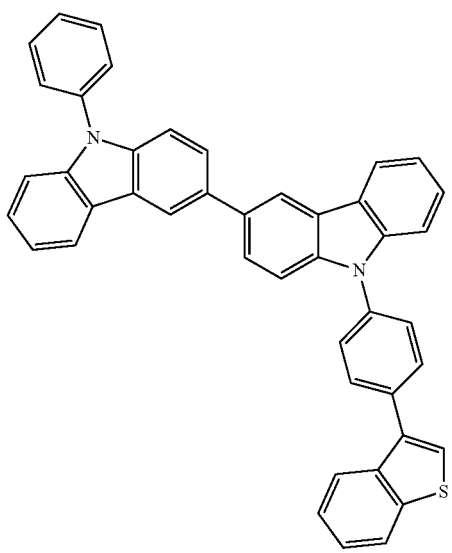

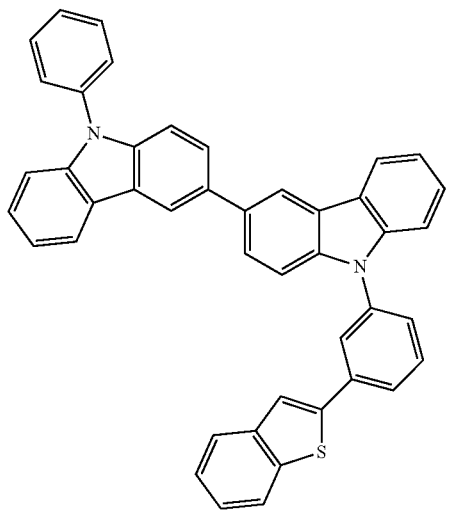
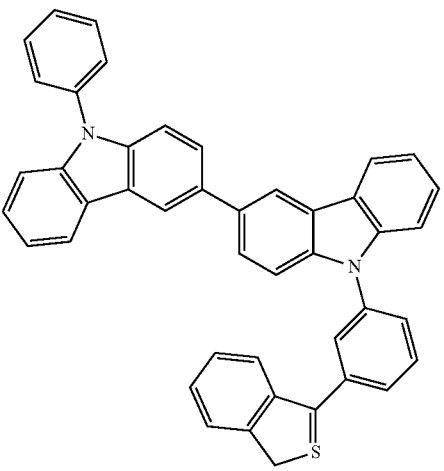
[Formula 82]
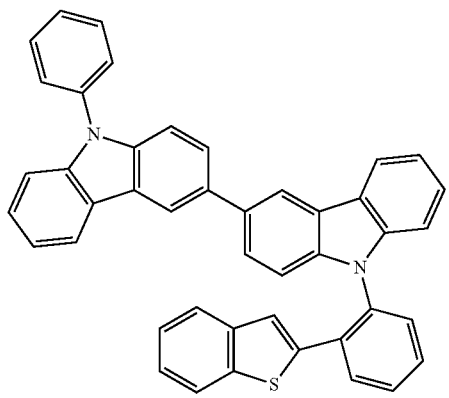
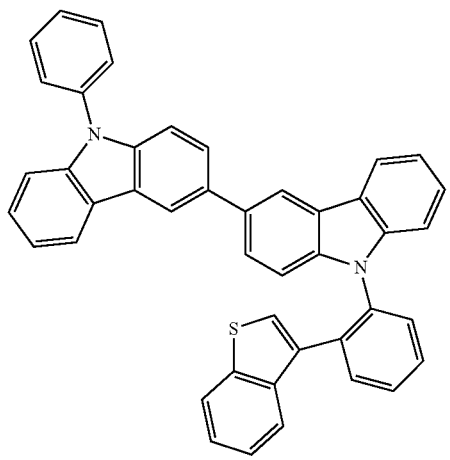
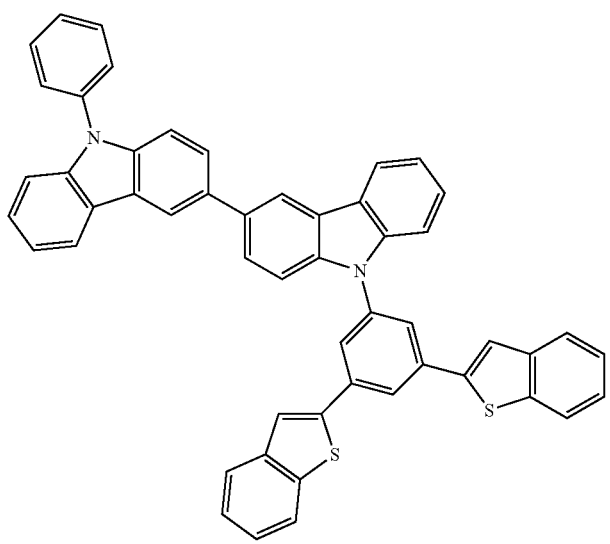

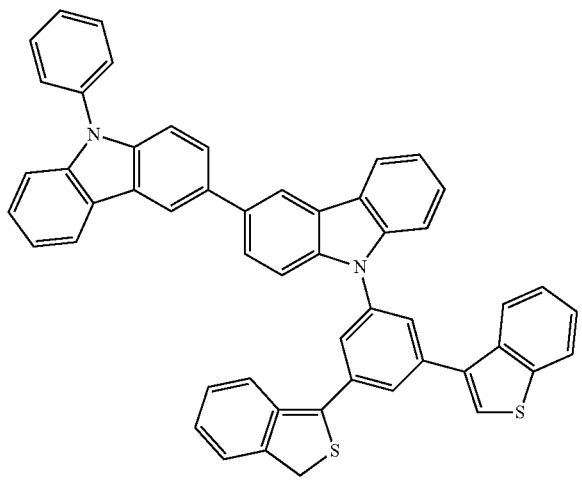
[Formula 83]
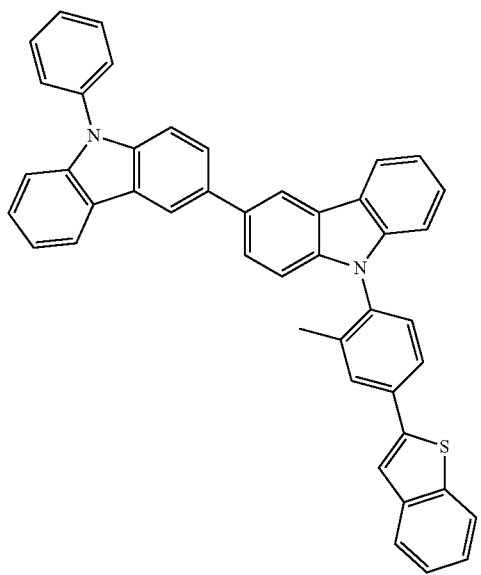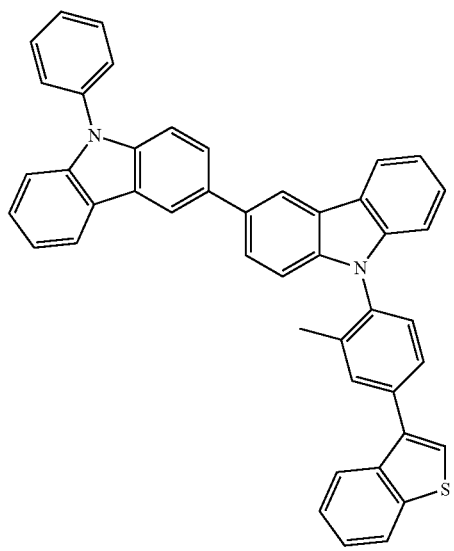
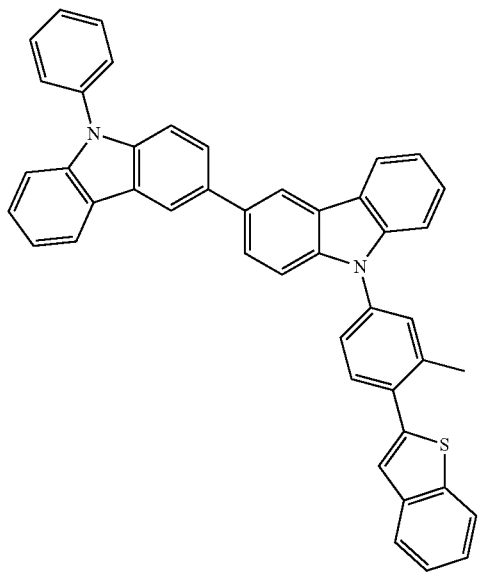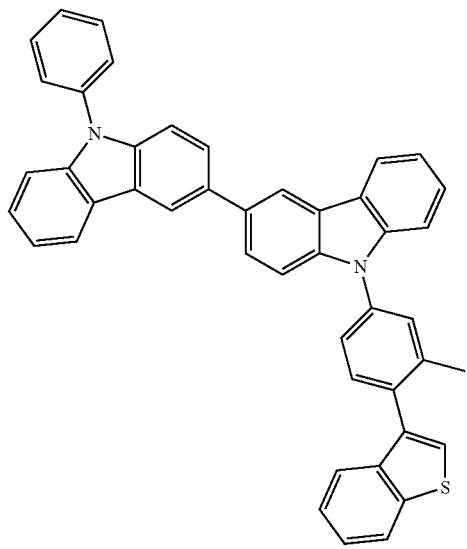

[Formula 84]
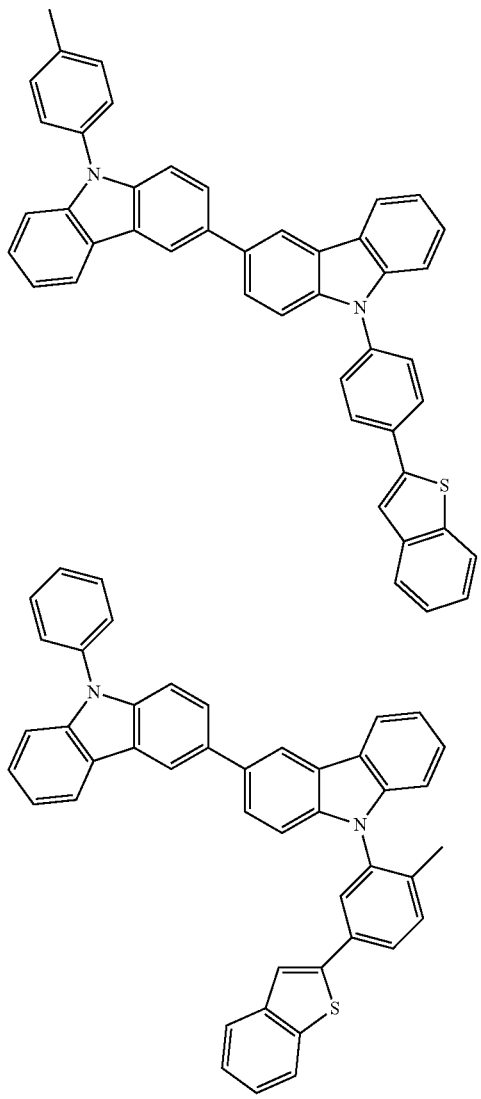
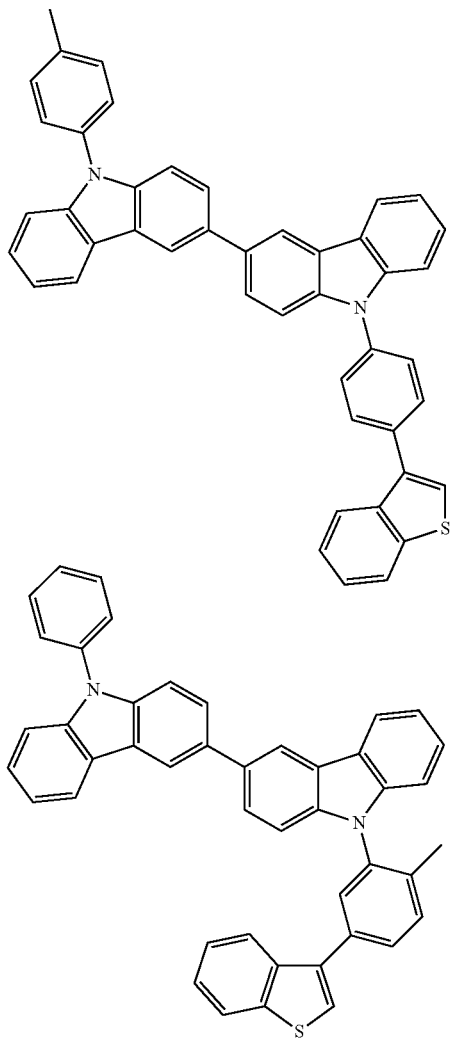
[Formula 85]
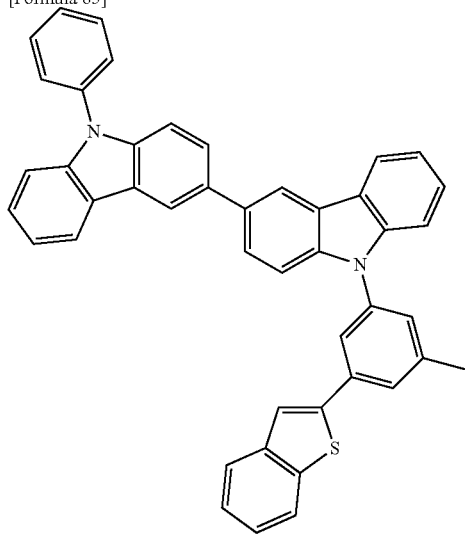
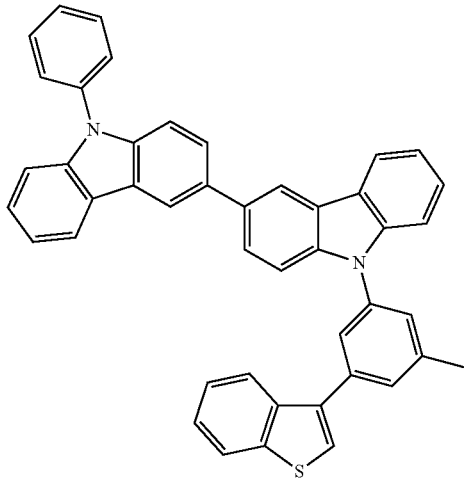

171
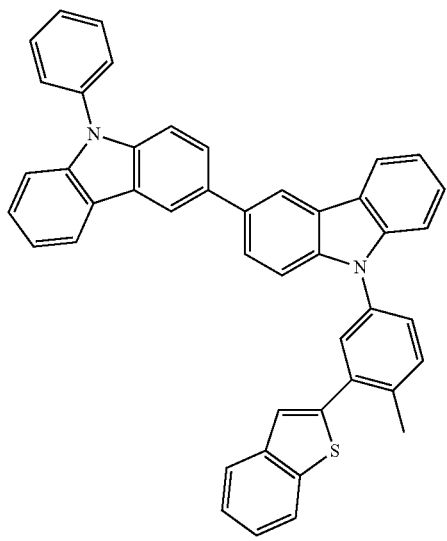
172
-continued
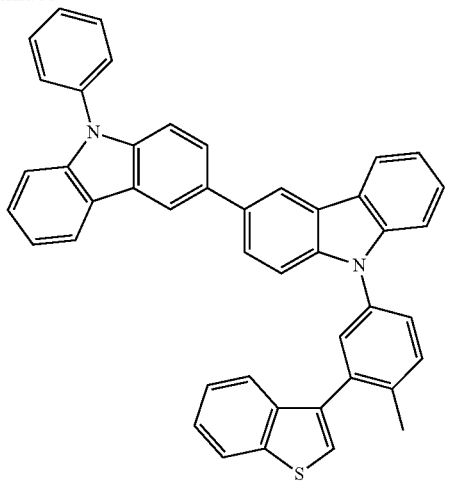
[Formula 86]
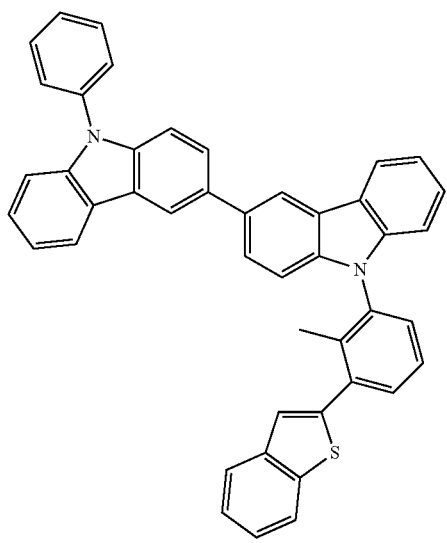
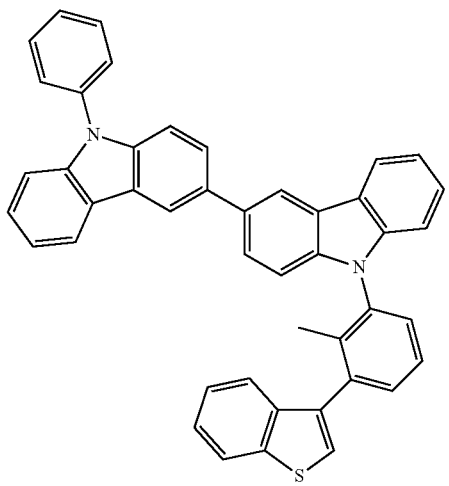
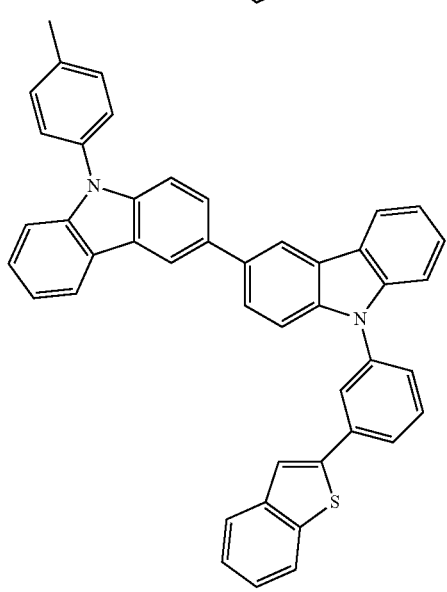
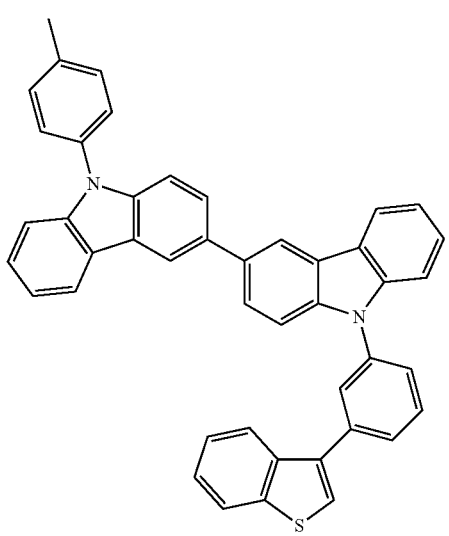

[Formula 87]
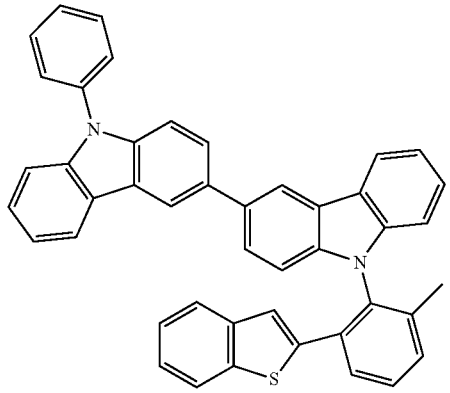
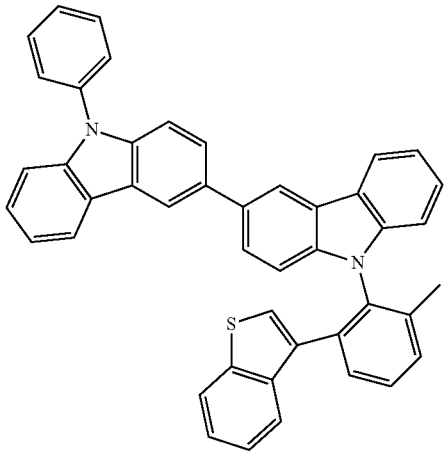
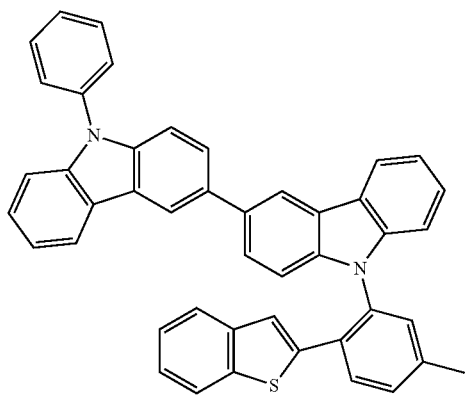
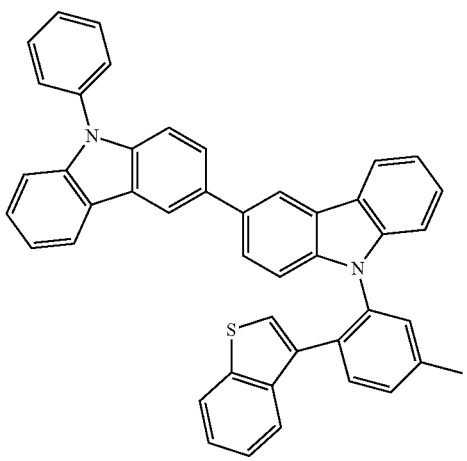
[Formula 88]
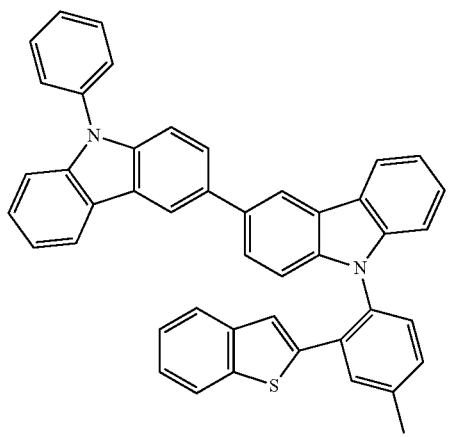
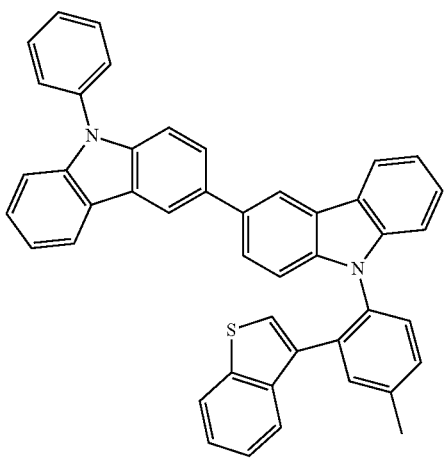

175
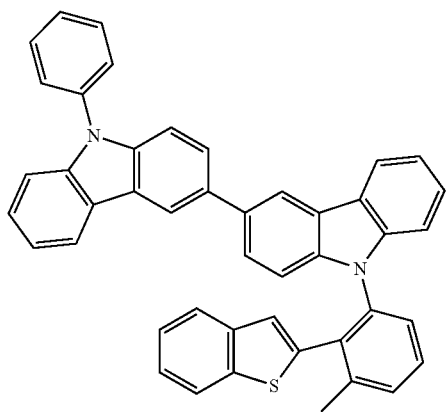
[Formula 89]
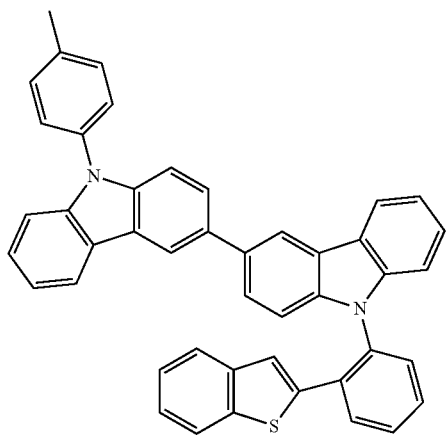
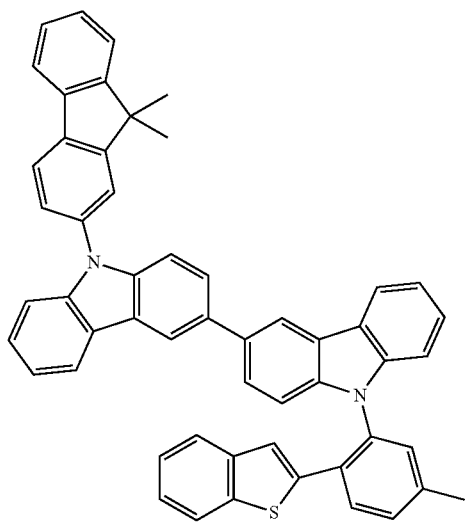
176
-continued
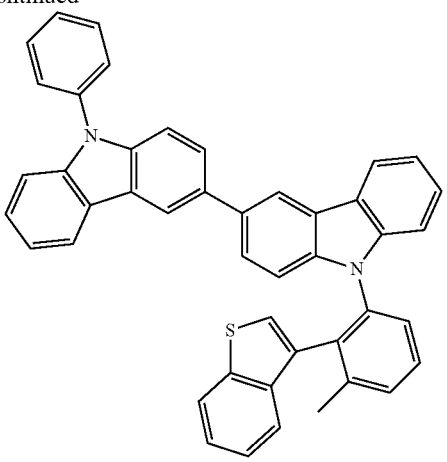
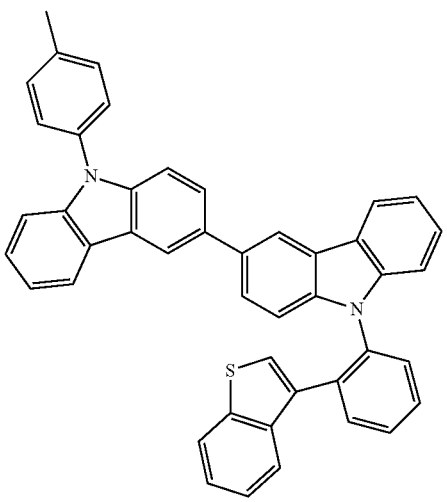
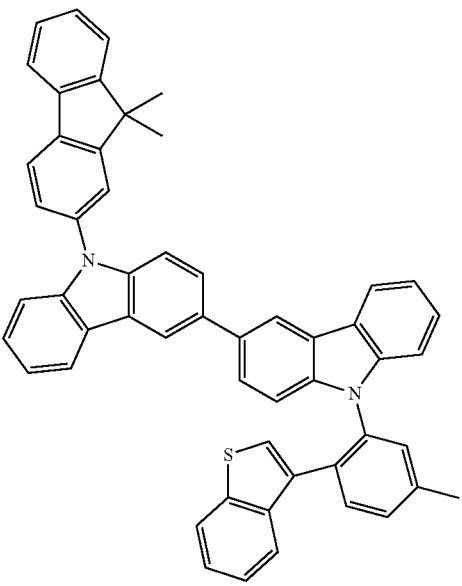

[Formula 90]
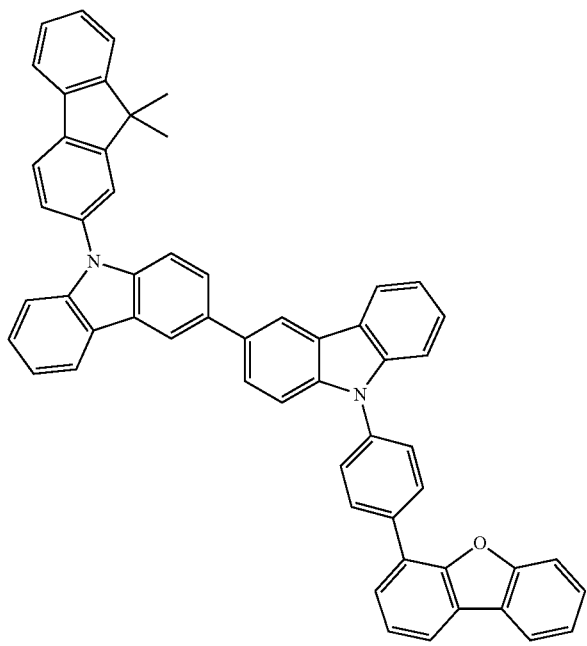
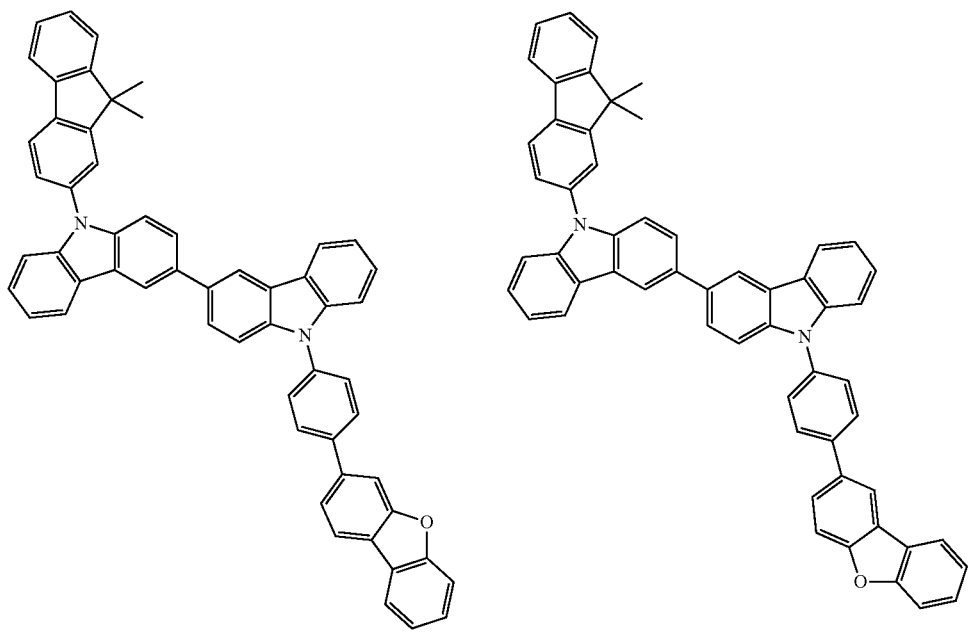

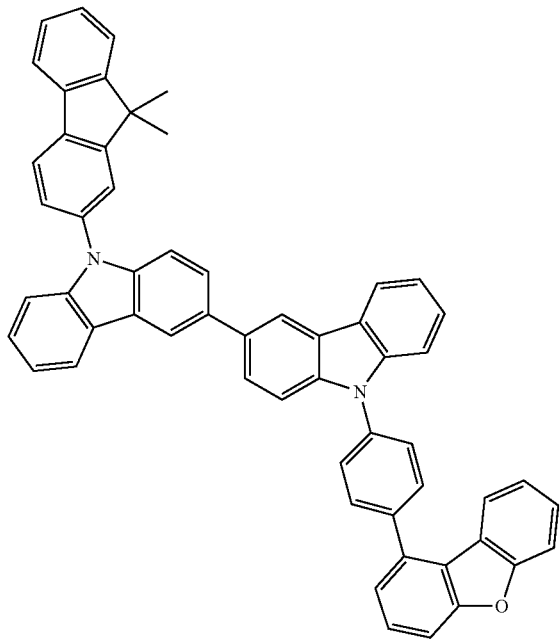
[Formula 91]
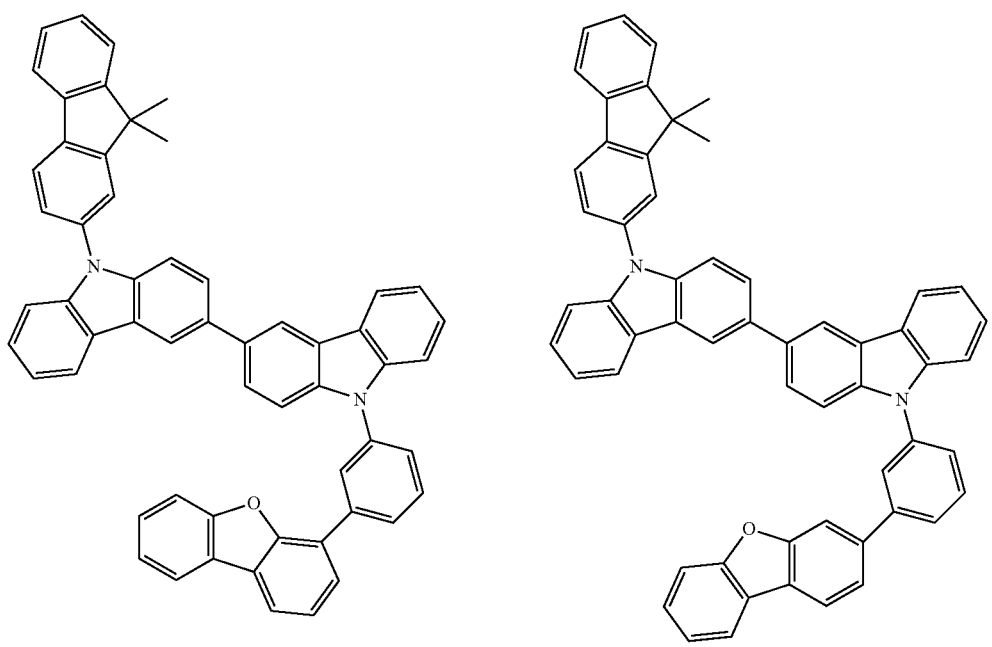

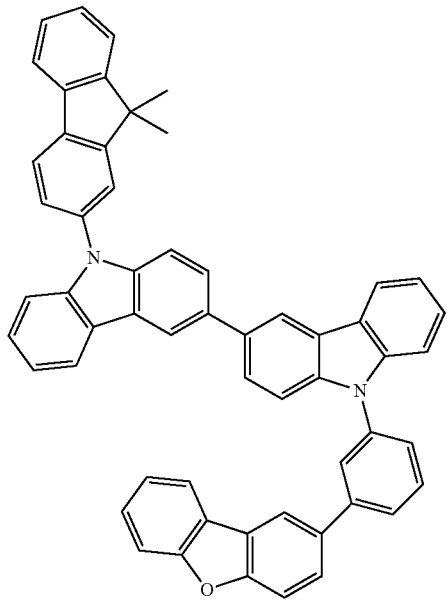
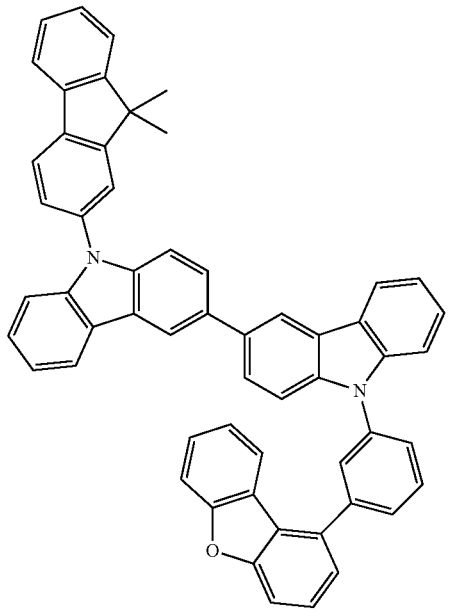
[Formula 92]
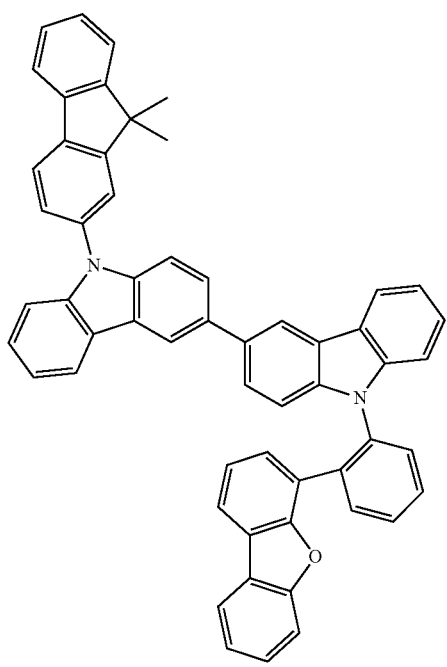
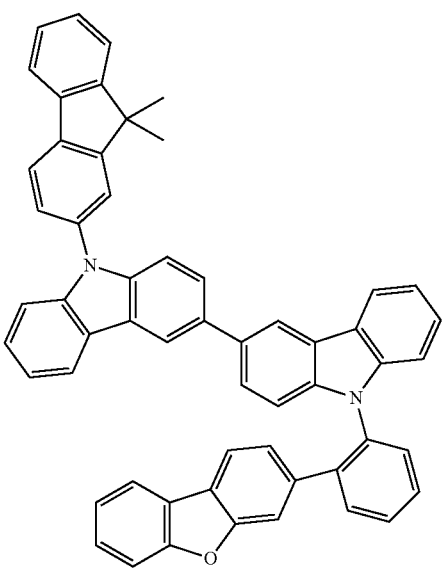

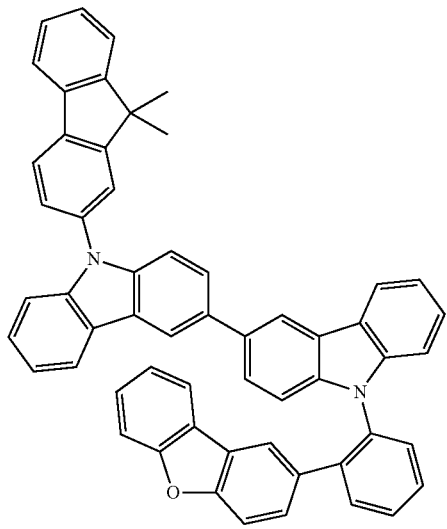
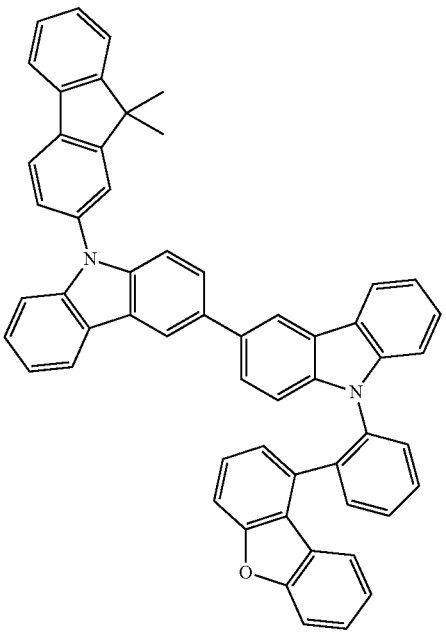
[Formula 93]
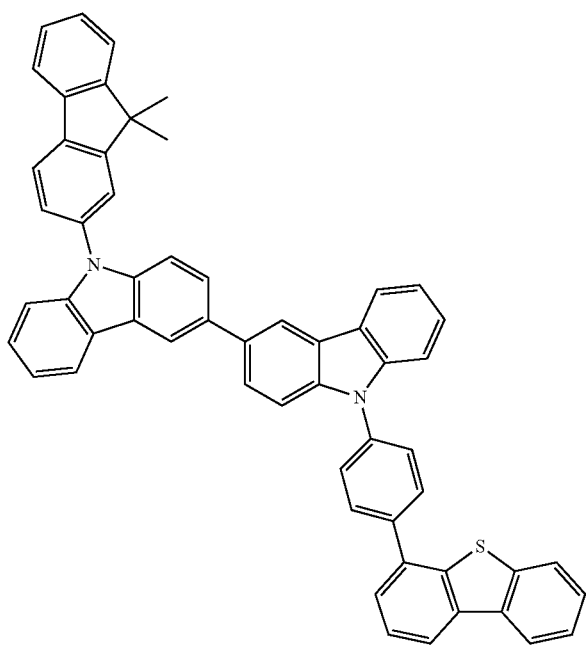

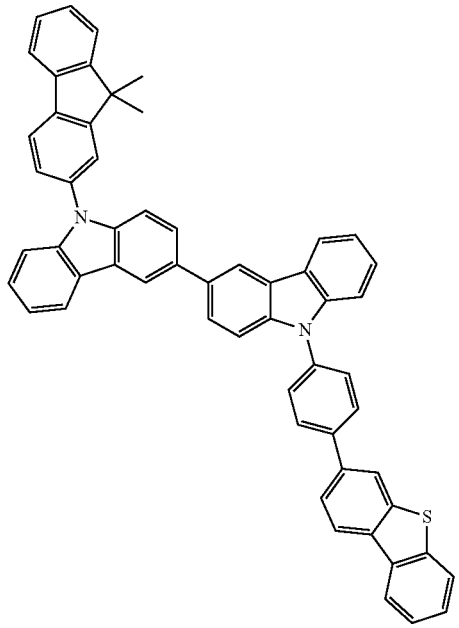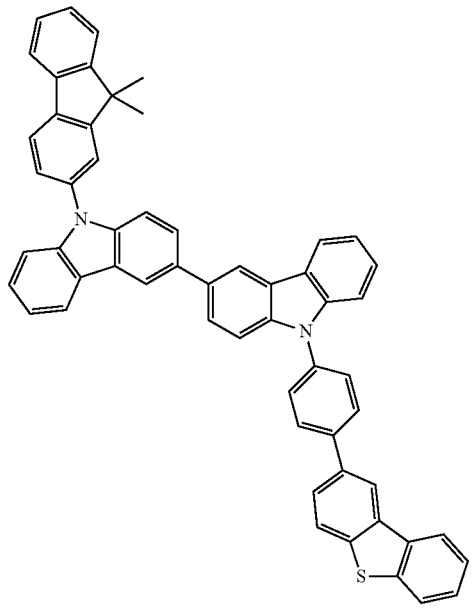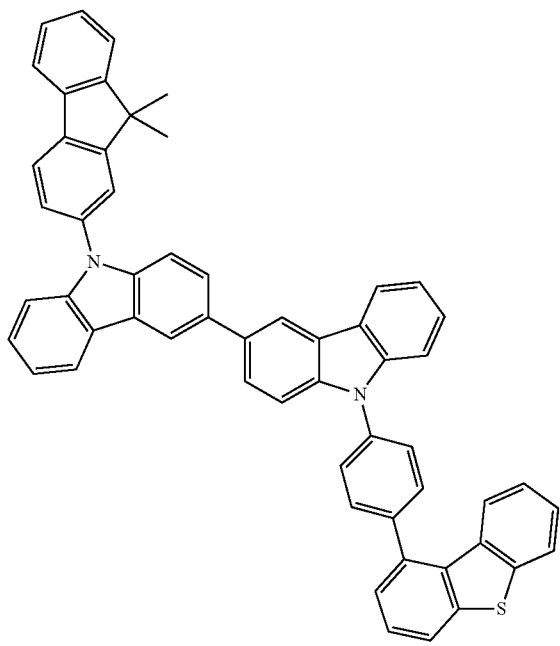

[Formula 94]
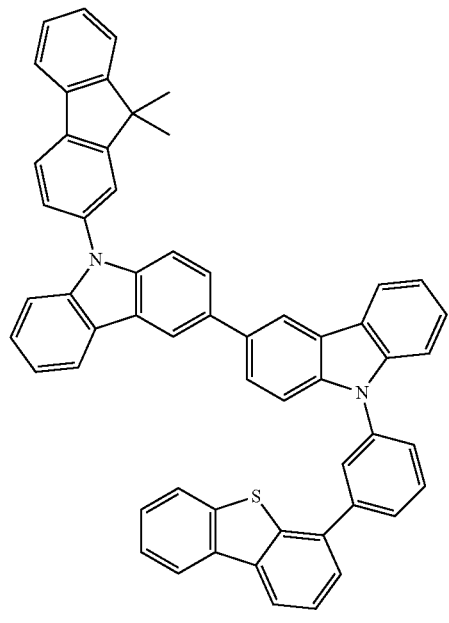
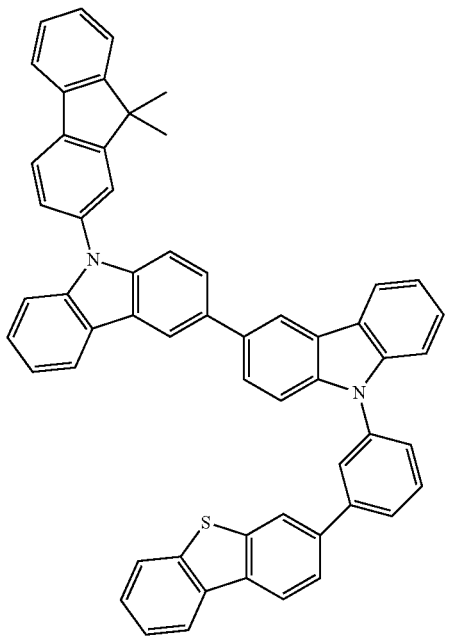
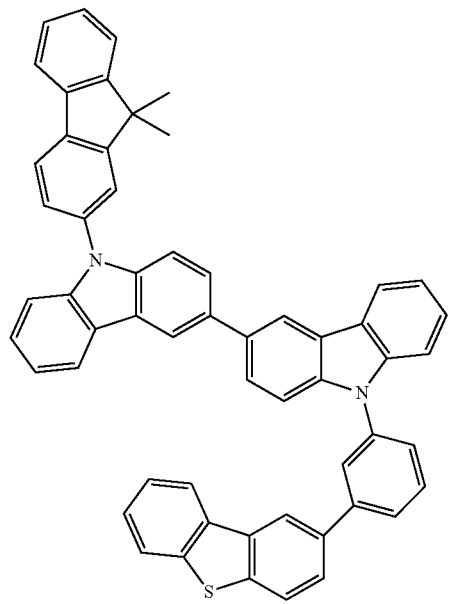
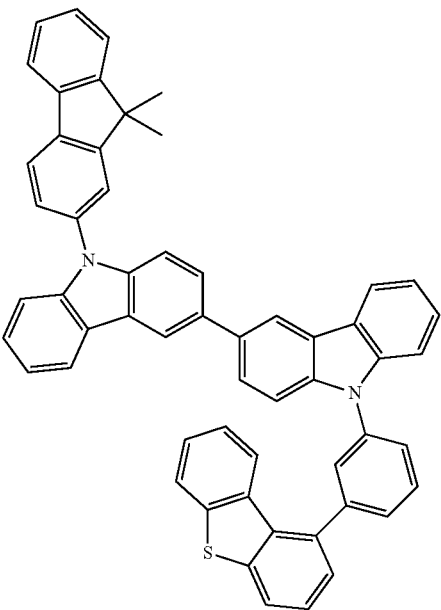

[Formula 95]
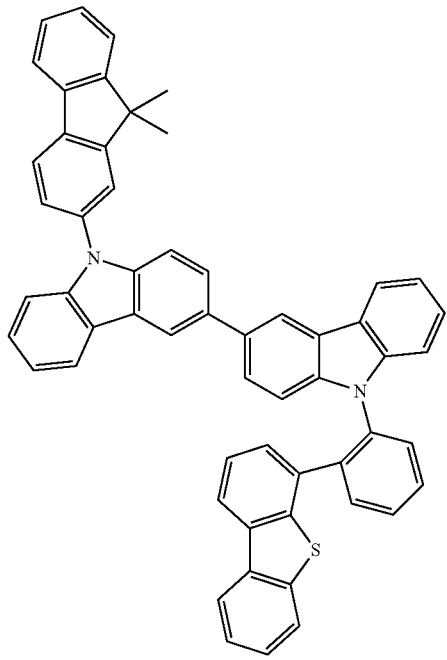
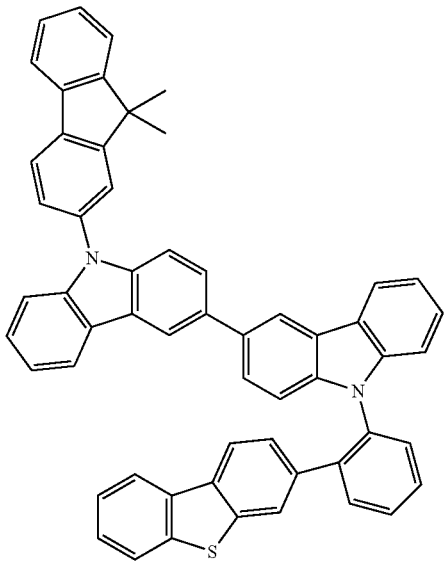
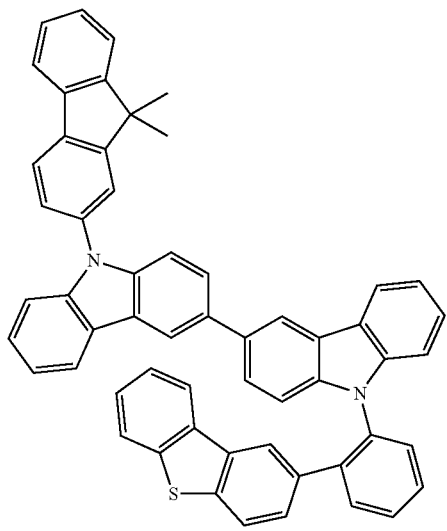
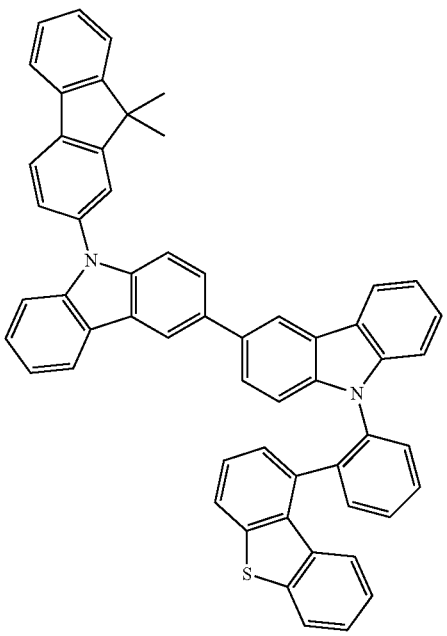

[Formula 96]
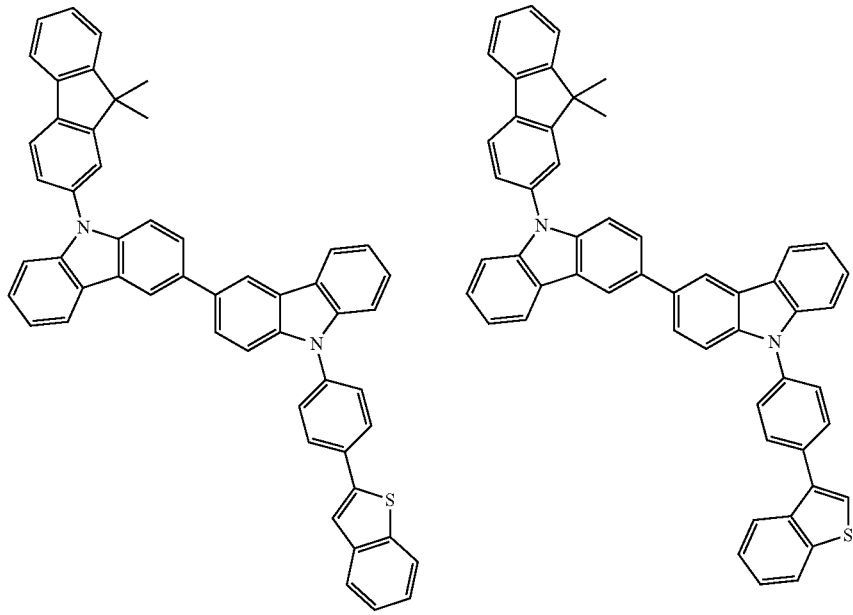
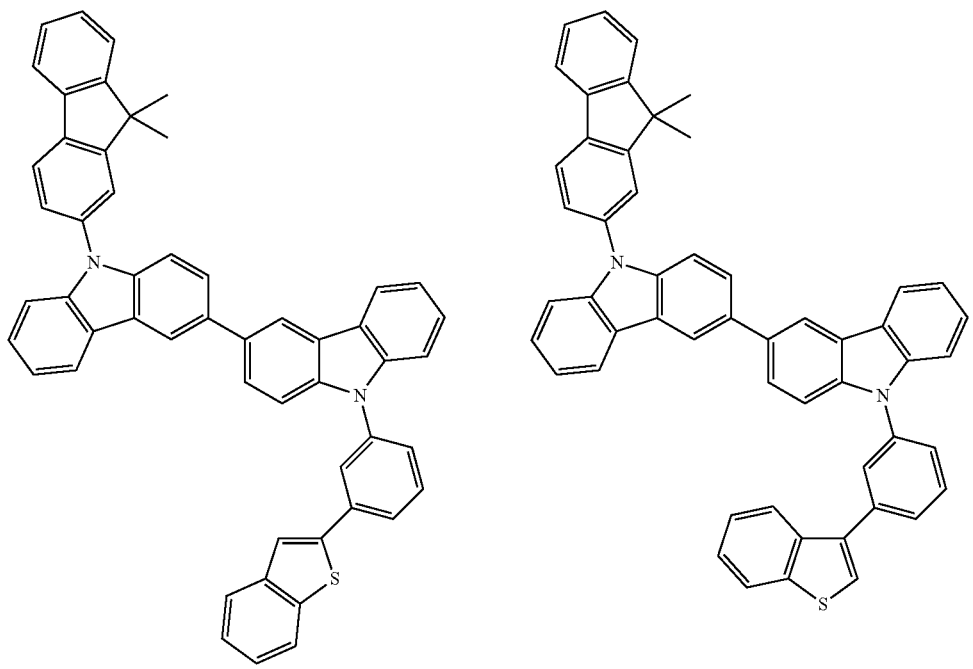
[Formula 97]
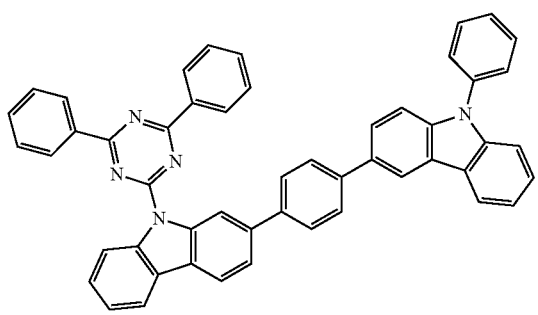

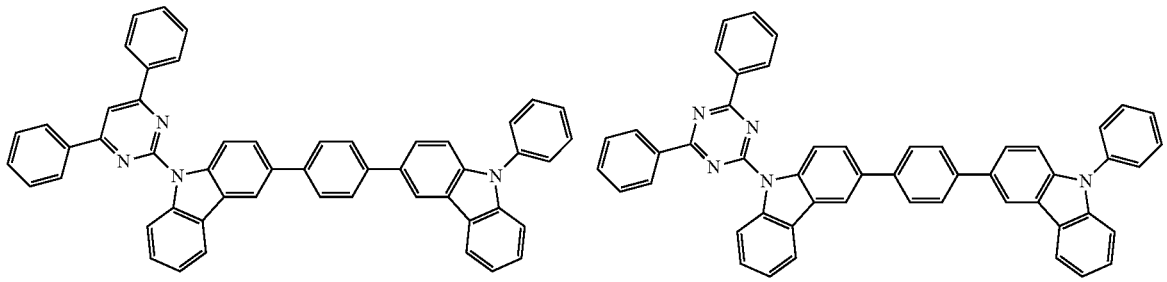
[Formula 98]
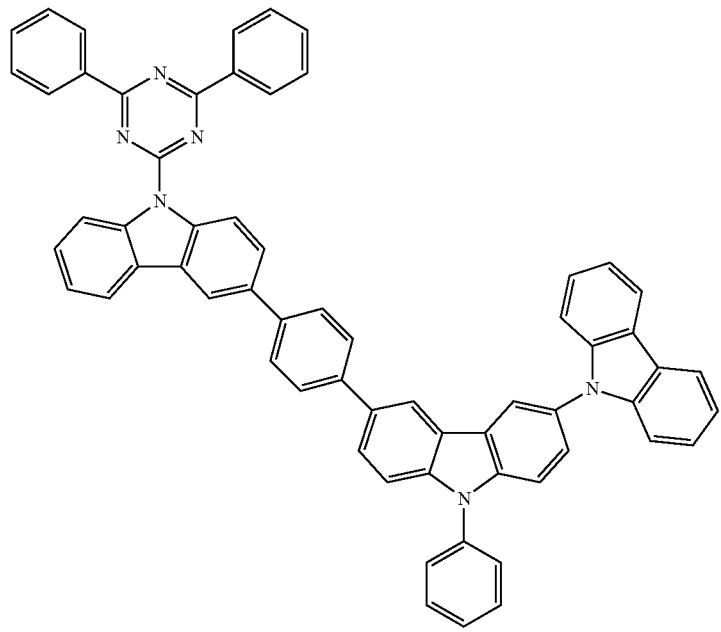
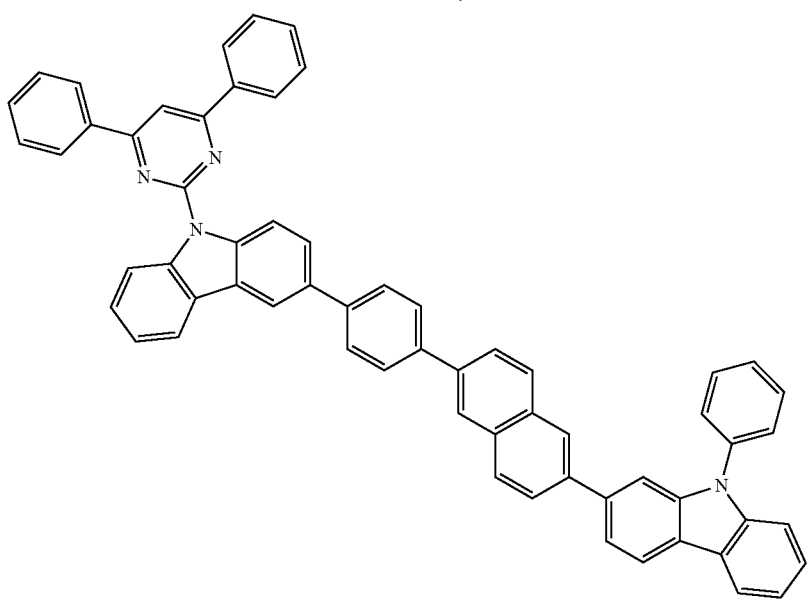

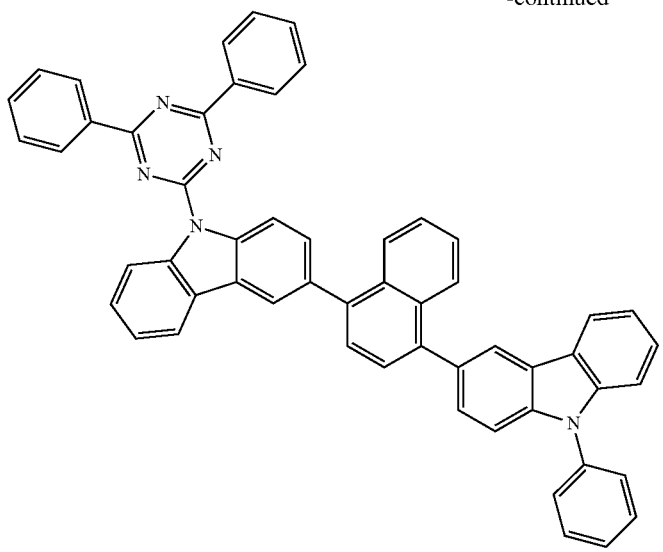

Electron Transporting Layer

The electron transporting layer 7, which helps injection of electrons to the emitting layer 5, has a high electron mobility.

In this exemplary embodiment, the electron transporting layer 7 is provided between the emitting layer 5 and the cathode, and the electron transporting layer 7 preferably contains a nitrogen-containing cyclic derivative as a main component. The electron injecting layer may serve as the electron transporting layer.

Note that "as a main component" means that the nitrogen-containing cyclic derivative is contained in the electron transporting layer 7 at a content of 50 mass % or more.

A preferable example of an electron transporting material for forming the electron transporting layer 7 is an aromatic heterocyclic compound having at least one heteroatom in a molecule. Particularly, a nitrogen-containing cyclic derivative is preferable. The nitrogen-containing cyclic derivative is preferably an aromatic ring having a nitrogen-containing six-membered or five-membered ring skeleton, or a condensed aromatic cyclic compound having a nitrogen-containing six-membered or five-membered ring skeleton.

The nitrogen-containing cyclic derivative is preferably exemplified by a nitrogen-containing cyclic metal chelate complex represented by the following formula (B1).

[Formula 99]

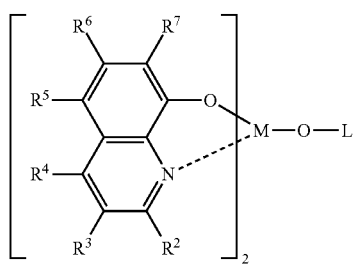

In the formula (B1), $R^2$ to $R^7$ each independently represent a hydrogen atom, a deuterium atom, a halogen atom, an oxy group, an amino group, a hydrocarbon group having 1 to 40 carbon atoms, an alkoxy group, an aryloxy group, an alkoxycarbonyl group, or an aromatic heterocyclic group, all of which may have a substituent.

Examples of the halogen atom are fluorine, chlorine, bromine and iodine. In addition, examples of the substituted or unsubstituted amino group include an alkylamino group, an arylamino group, and an aralkylamino group.

The alkoxycarbonyl group is represented by —COOY'. Examples of Y' are the same as the examples of the alkyl group. The alkylamino group and the aralkylamino group are represented by —$NQ^1Q^2$. Examples for each of $Q^1$ and $Q^2$ are the same as the examples described in relation to the alkyl group and the aralkyl group (i.e., a group obtained by substituting a hydrogen atom of an alkyl group with an aryl group), and preferable examples for each of $Q^1$ and $Q^2$ are also the same as those described in relation to the alkyl group and the aralkyl group. One of $Q^1$ and $Q^2$ may be a hydrogen atom. Note that the aralkyl group is a group obtained by substituting the hydrogen atom of the alkyl group with the aryl group.

The arylamino group is represented by —$NAr^1Ar^2$. Examples for each of $Ar^1$ and $Ar^2$ are the same as the examples described in relation to the non-fused aromatic hydrocarbon group. One of $Ar^1$ and $Ar^2$ may be a hydrogen atom.

M in the formula (B1) represents aluminum (Al), gallium (Ga) or indium (In), among which In is preferable.

L in the formula (B1) represents a group represented by a formula (B2) or (B3) below.

[Formula 100]

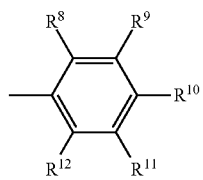

(B3)

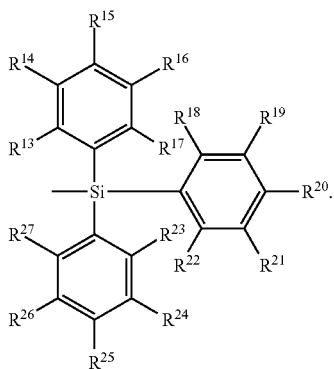

In the formula (B2), $R^8$ to $R^{12}$ each independently represent a hydrogen atom or a hydrocarbon group having 1 to 40 carbon atoms. Adjacent ones of the hydrocarbon groups may form a cyclic structure. The hydrocarbon group may have a substituent.

In the formula (B3), $R^{13}$ to $R^{27}$ independently represent a hydrogen atom or a hydrocarbon group having 1 to 40 carbon atoms.
Adjacent groups may form a cyclic structure. The hydrocarbon group may have a substituent.

Examples of the hydrocarbon group having 1 to 40 carbon atoms represented by each of $R^8$ to $R^{12}$ and $R^{13}$ to $R^{27}$ in the formulae (B2) and (B3) are the same as the examples of $R^2$ to $R^7$ in the formula (B1).

Examples of a divalent group formed when adjacent groups of $R^8$ to $R^{12}$ in the formula (B2) and adjacent groups of $R^{13}$ to $R^{27}$ in the formula (B3) form a cyclic structure are a tetramethylene group, pentamethylene group, hexamethylene group, diphenylmethane-2,2'-diyl group, diphenylethane-3,3'-diyl group and diphenylpropane-4,4'-diyl group.

The electron transporting layer preferably contains at least one of nitrogen-containing heterocyclic derivatives respectively represented by the following formulae (B4) to (B6).

[Formula 101]

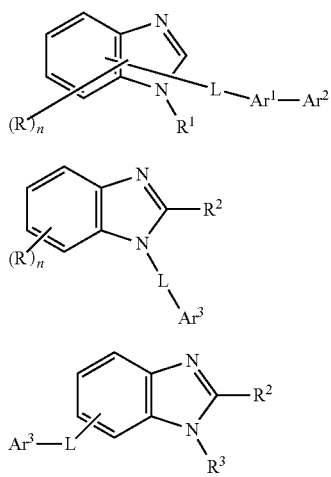

In the formulae (B4) to (B6), R represents a hydrogen atom, an aromatic hydrocarbon group having 6 to 60 ring carbon atoms, a pyridyl group, a quinolyl group, an alkyl group having 1 to 20 carbon atoms, or an alkoxy group having 1 to 20 carbon atoms. n is an integer in a range of 0 to 4.

In the formulae (B4) to (B6), $R^1$ represents an aromatic hydrocarbon group having 6 to 60 ring carbon atoms, a pyridyl group, a quinolyl group, an alkyl group having 1 to 20 carbon atoms, or an alkoxy group having 1 to 20 carbon atoms.

In the formulae (B4) to (B6), $R^2$ and $R^3$ each independently represent a hydrogen atom, an aromatic hydrocarbon group having 6 to 60 ring carbon atoms, a pyridyl group, a quinolyl group, an alkyl group having 1 to 20 carbon atoms, or an alkoxy group having 1 to 20 carbon atoms.

In the formulae (B4) to (B6), L represents an aromatic hydrocarbon group having 6 to 60 ring carbon atoms, a pyridinylene group, a quinolinylene group, or a fluorenylene group.

In the formulae (B4) to (B6), $Ar^1$ represents an aromatic hydrocarbon group having 6 to 60 ring carbon atoms, a pyridinylene group, or a quinolinylene group.

In the formulae (B4) to (B6), $Ar^2$ represents an aromatic hydrocarbon group having 6 to 60 ring carbon atoms, a pyridyl group, a quinolyl group, an alkyl group having 1 to 20 carbon atoms, or an alkoxy group having 1 to 20 carbon atoms.

In the formulae (B4) to (B6), $Ar^3$ represents an aromatic hydrocarbon group having 6 to 60 ring carbon atoms, a pyridyl group, a quinolyl group, an alkyl group having 1 to 20 carbon atoms, an alkoxy group having 1 to 20 carbon atoms, or a group represented by —$Ar^1$—$Ar^2$ in which $Ar^1$ and $Ar^2$ are the same as the above.

The aromatic hydrocarbon group, pyridyl group, quinolyl group, alkyl group, alkoxy group, pyridinylene group, quinolinylene group and fluorenylene group which are described in relation to R, $R^1$, $R^2$, $R^3$, L, $Ar^1$, $Ar^2$ and $Ar^3$ in the formulae (B4) to (B6) may have a substituent.

As an electron transporting compound for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

[Formula 102]

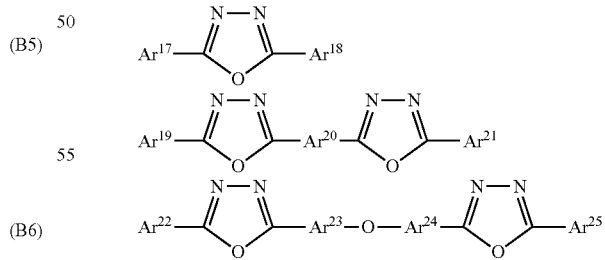

In each of the formulae of the oxadiazole derivatives, $Ar^{17}$, $Ar^{18}$, $Ar^{19}$, $A^{21}$, $Ar^{22}$ and $Ar^{25}$ represent an aromatic hydrocarbon group having 6 to 40 ring carbon atoms.

Note that the aromatic hydrocarbon group described herein may have a substituent. $Ar^{17}$, $Ar^{19}$ and $Ar^{22}$ are respectively the same as or different from $Ar^{18}$, $Ar^{21}$ and $Ar^{25}$.

Examples of the aromatic hydrocarbon group described herein are a phenyl group, naphthyl group, biphenyl group, anthranil group, perylenyl group and pyrenyl group. Examples of the substituent therefor are an alkyl group having 1 to 10 carbon atoms, alkoxy group having 1 to 10 carbon atoms and cyano group.

In the formulae representing the oxadiazole derivatives, $Ar^{20}$, $Ar^{23}$ and $Ar^{24}$ are a divalent aromatic hydrocarbon group having 6 to 40 ring carbon atom.

Note that the aromatic hydrocarbon group described herein may have a substituent.

$Ar^{23}$ and $Ar^{24}$ are mutually the same or different.

Examples of the divalent aromatic hydrocarbon group described herein are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Such an electron transport compound is preferably an electron transport compound that can be favorably formed into a thin film(s). Examples of the electron transporting compounds are as follows.

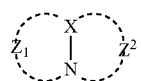

(B8)

In the formula (B8), X represents a carbon atom or a nitrogen atom. $Z_1$ and $Z_2$ each independently represent a group of atoms capable of forming a nitrogen-containing heterocycle.

Preferably, the nitrogen-containing heterocyclic derivative is an organic compound having a nitrogen-containing aromatic polycyclic group having a five-membered ring or six-membered ring. Further, in the organic compound having the nitrogen-containing aromatic polycyclic group having plural nitrogen atoms, a nitrogen-containing aromatic polycyclic organic compound having a skeleton formed by a combination of the skeletons respectively represented by

[Formula 103]

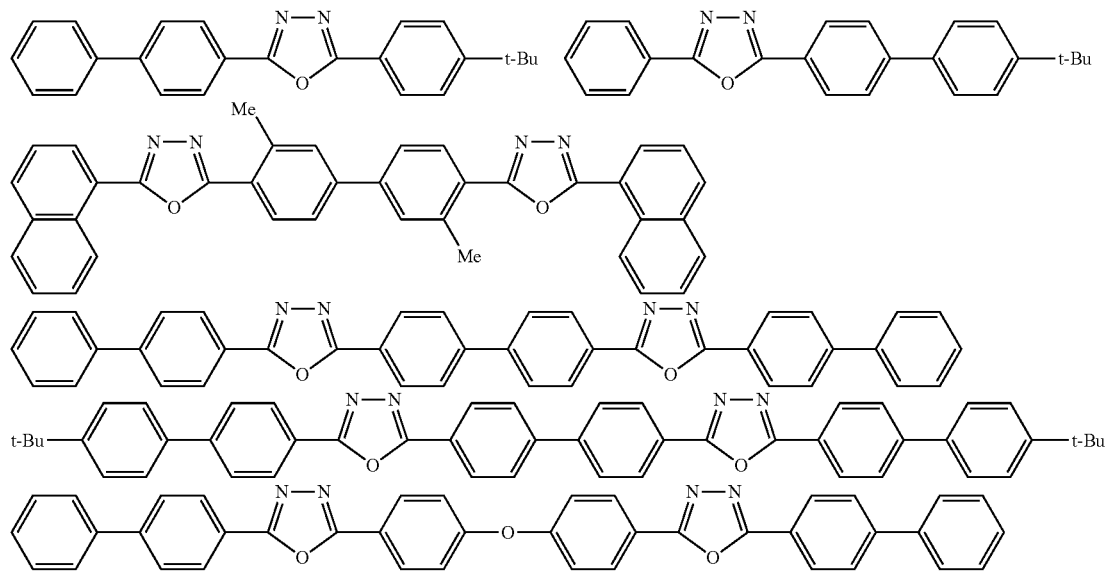

An example of the nitrogen-containing heterocyclic derivative as the electron transporting compound is a nitrogen-containing compound that is not a metal complex, the derivative being formed of an organic compound represented by one of the following formulae. Examples of the nitrogen-containing compound are a nitrogen-containing compound having five-membered ring or six-membered ring with a skeleton represented by the following formula (B7) and a nitrogen-containing compound having a structure represented by the following formula (B8).

the formulae (B7) and (B8), or by a combination of the skeletons respectively represented by the formula (B7) and the following formula (B9) is preferable.

[Formula 105]

(B9)

A nitrogen-containing group of the nitrogen-containing aromatic polycyclic organic compound is selected from nitrogen-containing heterocyclic groups respectively represented by the following formulae.

[Formula 104]

(B7)

[Formula 106]

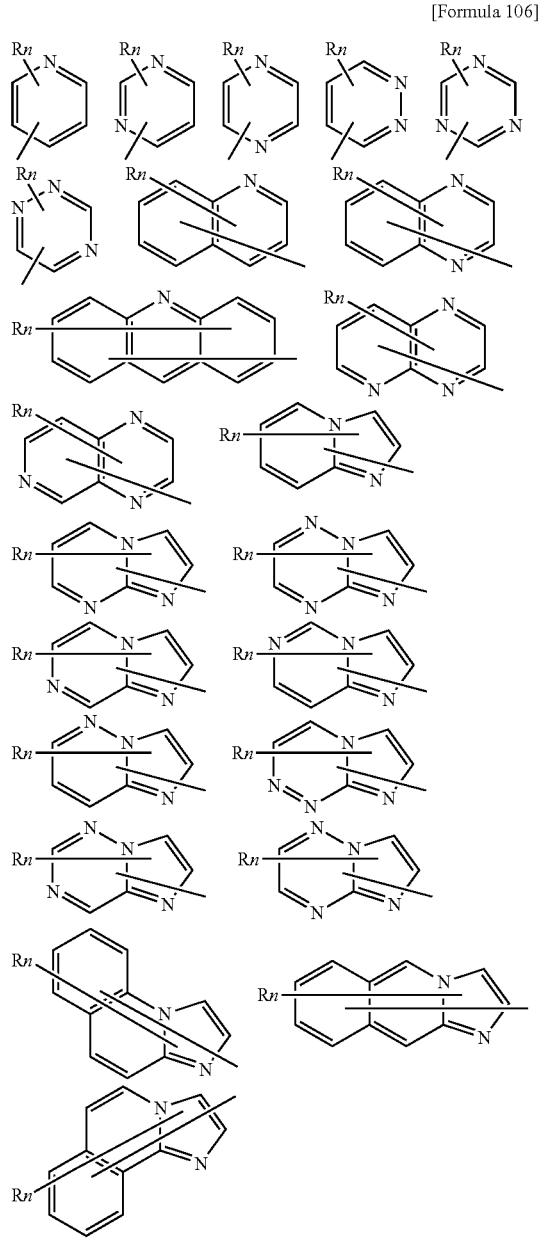

In each of the formulae of the nitrogen-containing heterocyclic groups, R represents an aromatic hydrocarbon group having 6 to 40 ring carbon atoms, an aromatic heterocyclic group having 2 to 40 ring carbon atoms, an alkyl group having 1 to 20 carbon atoms, or an alkoxy group having 1 to 20 carbon atoms.

In each of the formulae of the nitrogen-containing heterocyclic groups, n is an integer of 0 to 5. When n is 2 or more, a plurality of R may be mutually the same or different.

A preferable specific compound is a nitrogen-containing heterocyclic derivative represented by the following formula (B10).

     (B10)

In the formula (B10), HAr represents a nitrogen-containing heterocyclic group having 1 to 40 ring carbon atoms.

In the formula (B10), $L^1$ represents a single bond, an aromatic hydrocarbon group having 6 to 40 ring carbon atoms, or an aromatic heterocyclic group having 2 to 40 ring carbon atoms.

In the formula (B10), $Ar^1$ is a divalent aromatic hydrocarbon group having 6 to 40 ring carbon atoms.

In the formula (B10), $Ar^2$ represents an aromatic hydrocarbon group having 6 to 40 ring carbon atoms, or an aromatic heterocyclic group having 2 to 40 ring carbon atoms.

The nitrogen-containing heterocyclic group, aromatic hydrocarbon group and aromatic heterocyclic group described in relation to HAr, $L^1$, $Ar^1$ and $Ar^2$ in the formula (B10) may have a substituent.

HAr in the formula (B10) is exemplarily selected from the following group.

[Formula 107]

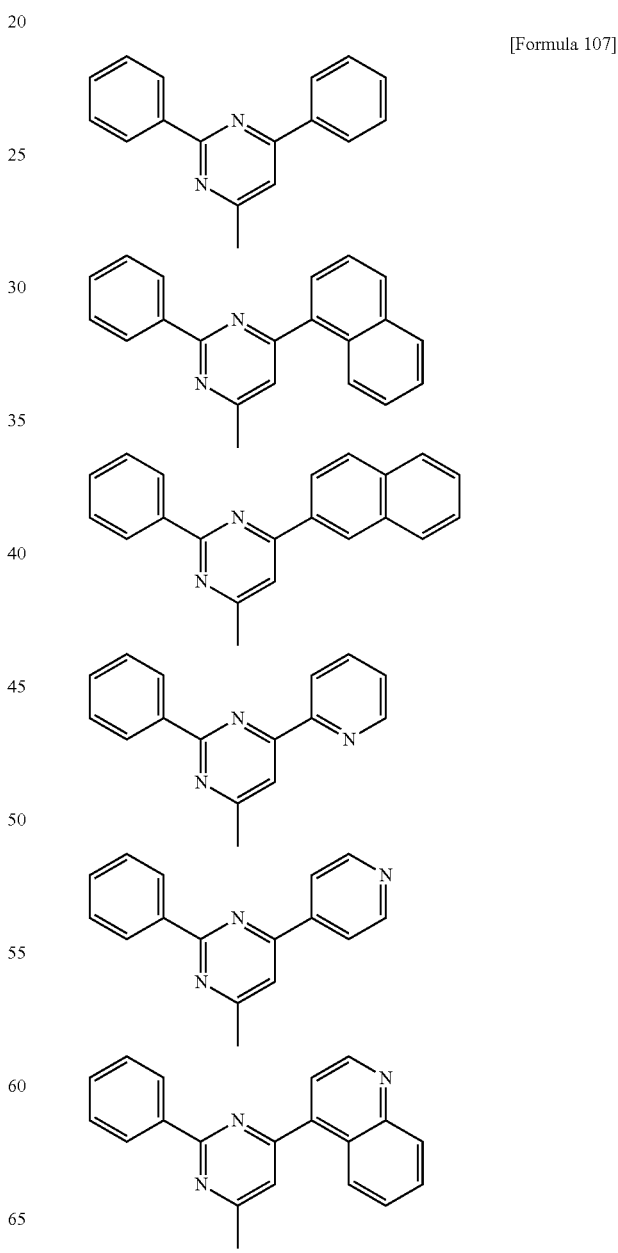

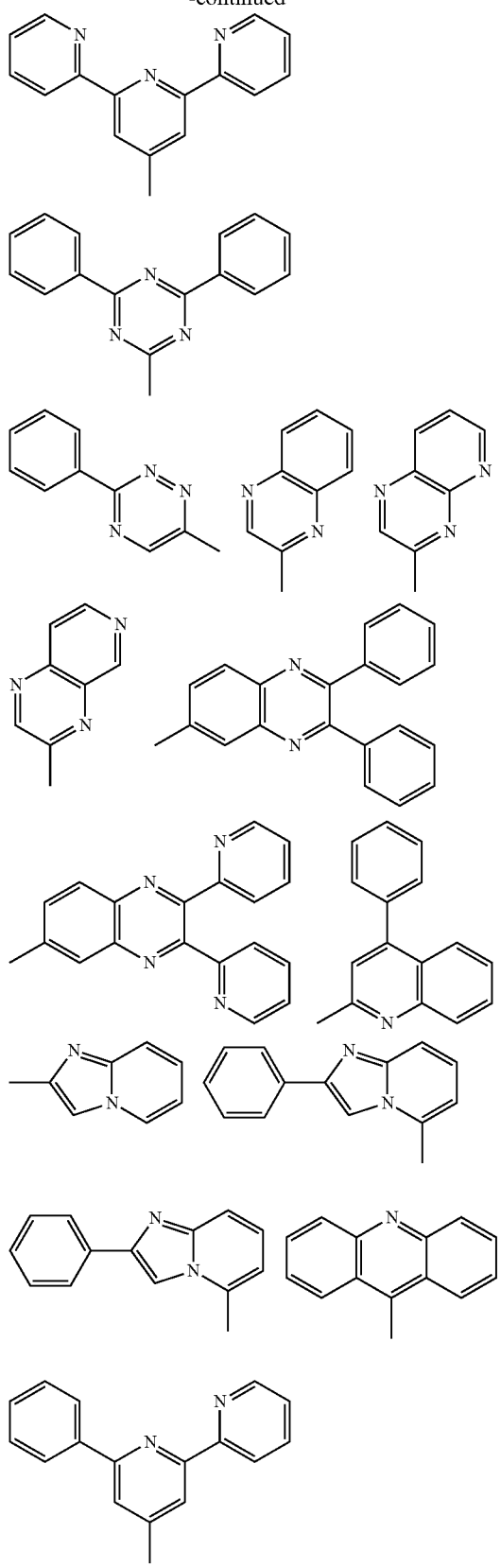

[Formula 108]

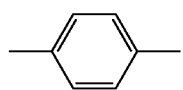 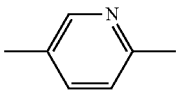

Ar¹ in the formula (B10) is exemplarily selected from the following arylanthranil group.

[Formula 109]

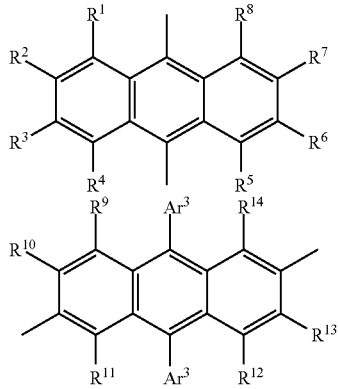

In the formula representing the arylanthranil group, $R^1$ to $R^{14}$ each independently represent a hydrogen atom, a halogen atom, an alkyl group having 1 to 20 carbon atoms, an alkoxy group having 1 to 20 carbon atoms, an aryloxy group having 6 to 40 ring carbon atoms, an aromatic hydrocarbon group having 6 to 40 ring carbon atoms, or an aromatic heterocyclic group having 2 to 40 ring carbon atoms.

In the formula representing the arylanthranil group, $Ar^3$ represents an aromatic hydrocarbon group having 6 to 40 ring carbon atoms, or an aromatic heterocyclic group having 2 to 40 ring carbon atoms.

The aromatic hydrocarbon group and aromatic heterocyclic group described in relation to $R^1$ to $R^{14}$ and $Ar^3$ in the formula of the arylanthranil may have a substituent.

All of $R^1$ to $R^8$ of a nitrogen-containing heterocyclic derivative may be hydrogen atoms.

In the formula of the arylanthranil group, $Ar^2$ is exemplarily selected from the following group.

[Formula 110]

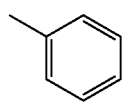 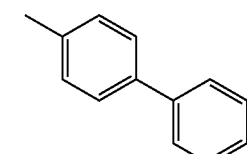

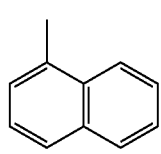 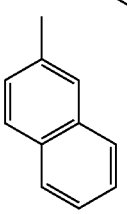

L¹ in the formula (B10) is exemplarily selected from the following group.

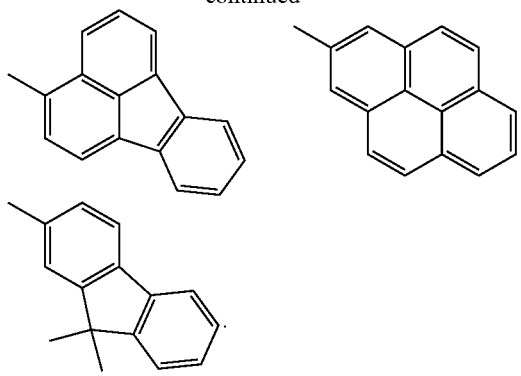

Other than the above, the following compound represented by the following formula (B11) (see JP-A-9-3448) can be favorably used for the nitrogen-containing aromatic polycyclic organic compound as the electron transporting compound.

[Formula 111]

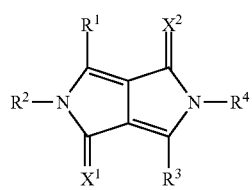

(B11)

In the formula of the nitrogen-containing aromatic polycyclic organic compound, $R^1$ to $R^4$ each independently represent a hydrogen atom, an aliphatic group, an alicyclic group, a carbocyclic aromatic cyclic group, or a heterocyclic group.

Note that the aliphatic group, alicyclic group, carbocyclic aromatic cyclic group and heterocyclic group may have a substituent.

In the formula (B11) of the nitrogen-containing aromatic polycyclic organic compound, $X^1$ and $X^2$ each independently represent an oxygen atom, sulfur atom or dicyanomethylene group.

The following compound represented by the following formula (B12) (see JP-A-2000-173774) can also be favorably used for the electron transporting compound.

[Formula 112]

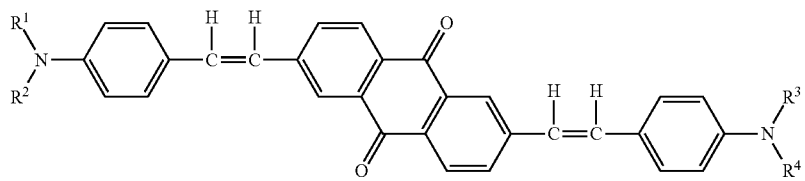

(B12)

In the formula (B12), $R^1$, $R^2$, $R^3$ and $R^4$, which may be mutually the same or different, each represent an aromatic hydrocarbon group or fused aromatic hydrocarbon group represented by the following formula (B12-1).

[Formula 113]

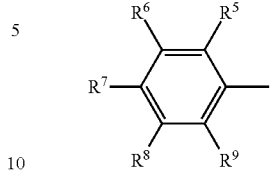

(B12-1)

In the formula (B12-1), $R^5$, $R^6$, $R^7$, $R^8$ and $R^9$, which may be mutually the same or different, each represent a hydrogen atom, a saturated or unsaturated alkoxyl group, alkyl group, amino group or alkylamino group. At least one of $R^5$, $R^6$, $R^7$, $R^8$ and $R^9$ represents a saturated or unsaturated alkoxyl group, alkyl group, amino group or alkylamino group.

A polymer compound containing the nitrogen-containing heterocyclic group or a nitrogen-containing heterocyclic derivative may be used for the electron transporting compound.

Although a film thickness of the electron injecting layer or the electron transporting layer is not specifically limited, the film thickness is preferably in a range of 1 nm to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron capability of the electron injecting layer.

For such an insulator, at least one metal compound selected from a group of alkali metal chalcogenide, alkaline-earth metal chalcogenide, halogenide of alkali metal, and halogenide of alkaline-earth metal may preferably be utilized. A configuration in which the electron injecting layer is formed by these alkali metal chalcogenide and the like is advantageous in that the electron injecting property is further improved. Specifically, preferable examples of the alkali metal chalcogenide are lithium oxide ($Li_2O$), potassium oxide ($K_2O$), sodium sulfide ($Na_2S$), sodium selenide ($Na_2Se$) and sodium oxide ($Na_2O$). Preferable examples of the alkaline-earth metal chalcogenide are calcium oxide (CaO), barium oxide (BaO), strontium oxide (SrO), beryllium oxide (BeO), barium sulfide (BaS) and calcium selenide (CaSe). Preferable examples of the halogenide of the alkali metal are lithium fluoride (LiF), sodium fluoride (NaF), potassium fluoride (KF), lithium chloride (LiCl), potassium chloride (KCl) and sodium chloride (NaCl). Preferable examples of the halogenide of the alkaline-earth metal are fluoride such as calcium fluoride ($CaF_2$), barium fluoride (BaF$_2$), strontium fluoride (SrF$_2$), magnesium fluoride (MgF$_2$) and beryllium fluoride (BeF$_2$) and halogenides other than the fluoride.

Examples of the semiconductor are one of or a combination of two or more of an oxide, a nitride or an oxidized nitride containing at least one element selected from barium (Ba), calcium (Ca), strontium (Sr), ytterbium (Yb), aluminum (Al), gallium (Ga), indium (In), lithium (Li), sodium (Na), cadmium (Cd), magnesium (Mg), silicon (Si), tantalum (Ta), antimony (Sb) and zinc (Zn). An inorganic compound for forming the electron injecting layer is preferably a microcrystalline or amorphous insulative thin-film. When the electron injecting layer is formed of such an insulative thin-film, more uniform thin-film can be formed, thereby reducing pixel defects such as a dark spot. Examples of such an inorganic compound are the above-described alkali metal chalcogenide, alkaline-earth metal chalcogenide, halogenide of the alkali metal and halogenide of the alkaline-earth metal.

When the electron injecting layer contains such an insulator or a semiconductor, a film thickness thereof is preferably in a range of approximately 0.1 nm to 15 nm. The electron injecting layer according to the exemplary embodiment may preferably contain the above-described reductive dopant.

Electron-Donating Dopant and Organic Metal Complex

In the organic EL device according to this exemplary embodiment, at least one of an electron-donating dopant and an organic metal complex is preferably contained in an interfacial region between the cathode and the organic thin-film layer.

With this arrangement, the organic EL device can emit light with enhanced luminance intensity and have a longer lifetime.

The electron-donating dopant may be at least one selected from an alkali metal, an alkali metal compound, an alkaline-earth metal, an alkaline-earth metal compound, a rare-earth metal, a rare-earth metal compound and the like.

The organic metal complex may be at least one compound selected from an organic metal complex including an alkali metal, an organic metal complex including an alkali earth metal, and an organic metal complex including rare-earth metal.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), among which a substance having a work function of 2.9 eV or less is particularly preferable. Among the above, the alkali metal is preferably K, Rb or Cs, more preferably Rb or Cs, the most preferably Cs.

Examples of the alkali earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare-earth metal are scandium (Sc), yttrium (Y), cerium (Ce), terbium (Tb) and ytterbium (Yb), among which a substance having a work function of 2.9 eV or less is particularly preferable.

Since the above preferred metals have particularly high reducibility, addition of a relatively small amount of the metals to an electron injecting zone can enhance luminance intensity and lifetime of the organic EL device.

Examples of the alkali metal compound are an alkali oxide such as lithium oxide (Li$_2$O), cesium oxide (Cs$_2$O) and potassium oxide (K$_2$O), and an alkali halogenide such as sodium fluoride (NaF), cesium fluoride (CsF) and potassium fluoride (KF), among which lithium fluoride (LiF), lithium oxide (Li$_2$O) and sodium fluoride (NaF) are preferable.

Examples of the alkali earth metal compound are barium oxide (BaO), strontium oxide (SrO), calcium oxide (CaO) and a mixture thereof, i.e., Ba$_x$Sr$_{1-x}$O(0<x<1), Ba$_x$Ca$_{1-x}$O (0<x<1), among which BaO, SrO and CaO are preferable.

Examples of the rare-earth metal compound are ytterbium fluoride (YbF$_3$), scandium fluoride (ScF$_3$), scandium oxide (ScO$_3$), yttrium oxide (Y$_2$O$_3$), cerium oxide (Ce$_2$O$_3$), gadolinium fluoride (GdF$_3$) and terbium fluoride (TbF$_3$), among which YbF$_3$, ScF$_3$ and TbF$_3$ are preferable.

The alkali metal complex is not particularly limited, as long as at least one of alkali metal ion, alkali earth metal ion and rare-earth metal ion is contained therein as metal ion. The ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, d-diketones, azomethines, or a derivative thereof, but the ligand is not limited thereto.

The electron-donating dopant and the organic metal complex are added to preferably form a layer or an island pattern in the interfacial region. The layer of the electron-donating dopant or the island pattern of the organic metal complex is preferably formed by evaporating at least one of the electron-donating dopant and the organic metal complex by resistance heating evaporation while an emitting material for forming the interfacial region or an organic substance as an electron-injecting material are simultaneously evaporated, so that at least one of the electron-donating dopant and an organic metal complex reduction-causing dopant is dispersed in the organic substance. Dispersion concentration at which the electron-donating dopant is dispersed in the organic substance is a mole ratio (the organic substance to the electron-donating dopant or the organic metal complex) of 100:1 to 1:100, preferably 5:1 to 1:5.

When at least one of the electron-donating dopant and the organic metal complex forms a layer, the emitting material or the electron injecting material for forming the organic layer of the interfacial region is initially layered, and then, at least one of the electron-donating dopant and the organic metal complex is singularly evaporated thereon by resistance heating evaporation to preferably form a 0.1 nm- to 15 nm-thick layer.

When at least one of the electron-donating dopant and the organic metal complex forms an island pattern, the emitting material or the electron injecting material for forming the organic layer of the interfacial region is initially layered, and then, at least one of the electron-donating dopant is singularly evaporated thereon by resistance heating evaporation to preferably form a 0.05 nm- to 1 nm-thick island pattern. A ratio of the main component to at least one of the electron-donating dopant and the organic metal complex in the organic EL device according to the exemplary embodiment is preferably a mole ratio (the main component to the electron-donating dopant or the organic metal complex) of 5:1 to 1:5, more preferably 2:1 to 1:2.

Manufacturing Method of Each Layer of Organic EL Device

A method of forming each of the layers in the organic EL device according to the exemplary embodiment is not particularly limited. Conventionally-known methods such as vacuum deposition and spin coating may be employed for forming the layers. The organic thin-film layer containing the compound used in the organic EL device according to this exemplary embodiment can be formed by a conventional coating method such as vacuum deposition, molecular beam epitaxy (MBE method) and coating methods using a solution such as a dipping, spin coating, casting, bar coating, and roll coating.

Film Thickness of Each Layer of Organic EL Device

A film thickness of the emitting layer is preferably in a range of 5 nm to 50 nm, more preferably in a range of 7 nm to 50 nm and most preferably in a range of 10 nm to 50 nm. By forming the emitting layer at the film thickness of 5 nm or more, the emitting layer is easily formable and chromaticity is easily adjustable. By forming the emitting layer at the film thickness of 50 nm or less, increase in the drive voltage is suppressible.

A film thickness of the organic thin-film layer other than the emitting layer is not particularly limited, but is preferably in a typical range of several nm to 1 μm. When the film thickness is provided in the above range, defects such as pin holes caused by an excessively thinned film can be avoided while increase in the drive voltage caused by an excessively thickened film can be suppressed to prevent deterioration of the efficiency.

Second Exemplary Embodiment

Next, a second exemplary embodiment is described below.

In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable.

Figure 2:
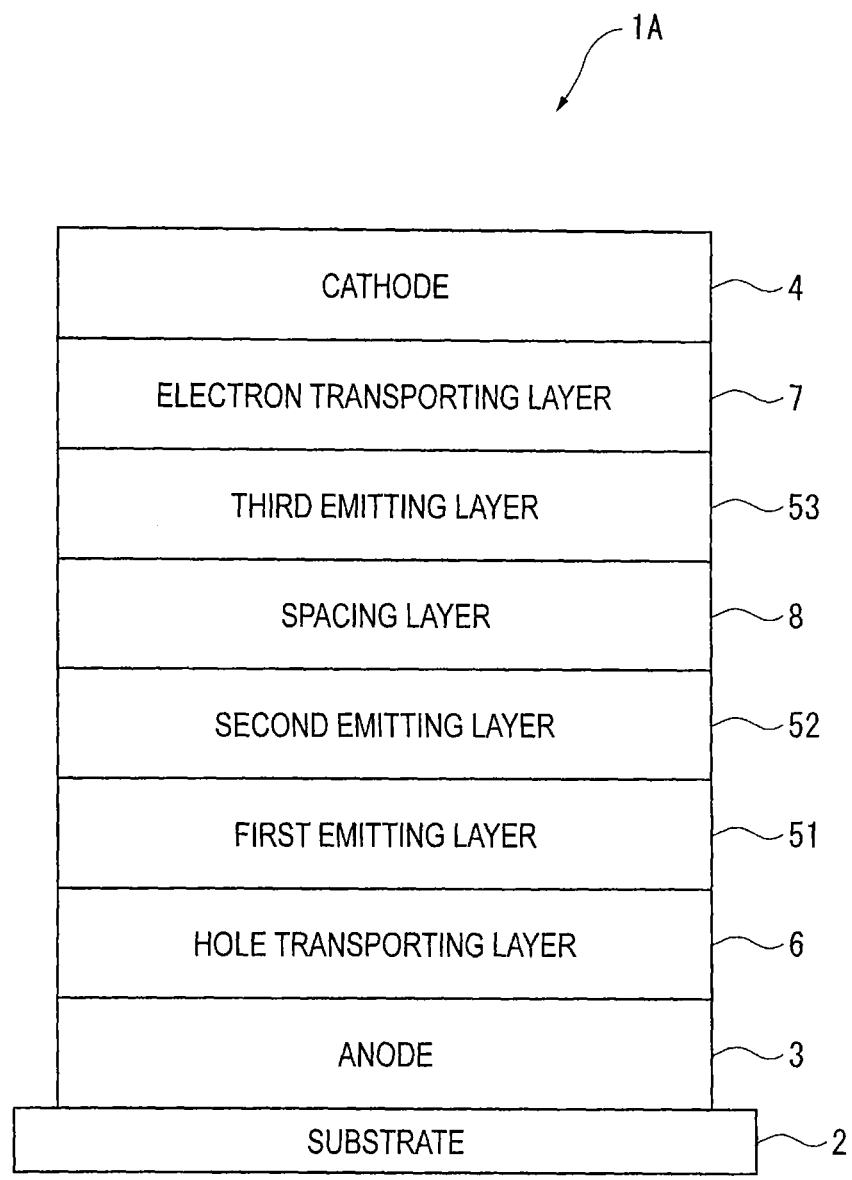
FIG. 2 schematically shows an exemplary arrangement of an organic EL device according to a second exemplary embodiment.

An organic EL device 1A according to the second exemplary embodiment is different from that of the first exemplary embodiment in that a first emitting layer 51, second emitting layer 52 and third emitting layer 53 are provided and a spacing layer 8 is interposed between the first and second emitting layers 51, 52 and the third emitting layer 53. As shown in FIG. 2, the anode, 3, the hole transporting layer 6, the first emitting layer 51, the second emitting layer 52, the spacing layer 8, the third emitting layer 53, the electron transporting layer 7 and the cathode 4 are sequentially laminated on the substrate 2.

The first emitting layer 51 is continuously formed on the hole transporting layer 6. The second emitting layer 52 is continuously formed between the first emitting layer 51 and the spacing layer 8.

The first emitting layer 51 contains a host material and a luminescent material. The host material is preferably an amine derivative such as a monoamine compound, a diamine compound, a triamine compound, a tetramine compound and an amine compound substituted by a carbazole group. The host material may be the same material as the first host material represented by the formula (1) and the second host material represented by the formula (2). The luminescent material preferably exhibits an emission peak of 570 nm or more. The luminescence peak of 570 nm or more is shown by, for instance, red emission.

The second emitting layer 52 is the emitting layer according to the invention. In other words, the second emitting layer 52 functions the same as the emitting layer 5 of the first exemplary embodiment.

By being provided as an energy barrier of a HOMO level or a LUMO level between the second emitting layer 52 and the third emitting layer 53 adjacent thereto, the spacing layer 8 controls injection of charge (holes or electrons) into the second emitting layer 52 and the third emitting layer 53 and controls balance of charge injected thereinto. Moreover, the spacing layer 8 is provided as a barrier of triplet energy, thereby preventing diffusion of triplet energy generated in the second emitting layer 52 to the third emitting layer 53 and providing efficient emission within the second emitting layer 52.

The third emitting layer 53 is, for instance, a blue fluorescent-emitting layer having a peak wavelength of 450 nm to 500 nm. The third emitting layer 53 includes a third host material and a third luminescent material.

Examples of the third host material are a compound having a central anthracene skeleton which is represented by the following formula (41).

[Formula 114]

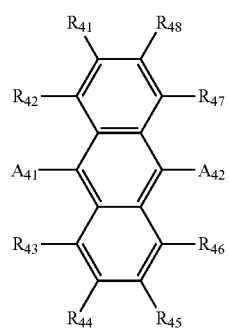

(41)

In the formula (41), $Ar_{41}$ and $Ar_{42}$ each are a group derived from a substituted or unsubstituted aromatic ring having 6 to 20 ring carbon atoms.

$R_{41}$ to $R_{48}$ each are a hydrogen atom, a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of a substituent for the aromatic ring of each of $A_{41}$ and $A_{42}$ are a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of the third luminescent material are an arylamine compound, a styrylamine compound, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumaline, oxadiazole, aldazine, bisbenzoxazoline, bisstyryl, pyrazine, cyclopentadiene, a metal complex of quinoline, a metal complex of aminoquinoline, a metal complex of benzoquinoline, imine, diphenylethylene, vinylanthracene, diaminocarbazole, pyrane, thiopyrane, polymethine, merocyanin, an imidazole chelated oxinoid compound, quinacridone, rubrene and a fluorescent dye.

The third emitting layer 53 is, for instance, a blue fluorescent-emitting layer having a peak wavelength of 450 to 500 nm.

Since the organic EL device 1A includes the first emitting layer 51 exhibiting red emission, the second emitting layer 52 exhibiting green emission and the third emitting layer 53 exhibiting blue emission, the organic EL device 1A can exhibit white emission as a whole.

Accordingly, the organic EL device 1A is suitably applicable as a surface light source for lighting, a backlight and the like.

Third Exemplary Embodiment

Next, a third exemplary embodiment is described below.

In the description of the third exemplary embodiment, the same components as those in the first exemplary embodiment are denoted by the same reference signs and names to simplify or omit an explanation of the components. In the third exemplary embodiment, the same materials and compounds as described in the first exemplary embodiment are usable.

The organic EL device according to the third exemplary embodiment is a so-called tandem-type device including two or more emitting units and an intermediate unit. In addition to charges injected from a pair of electrodes, charges supplied from the intermediate unit are injected into the emitting units. Accordingly, by providing the intermediate unit, luminous efficiency (current efficiency) relative to injected current is improved.

Figure 3:
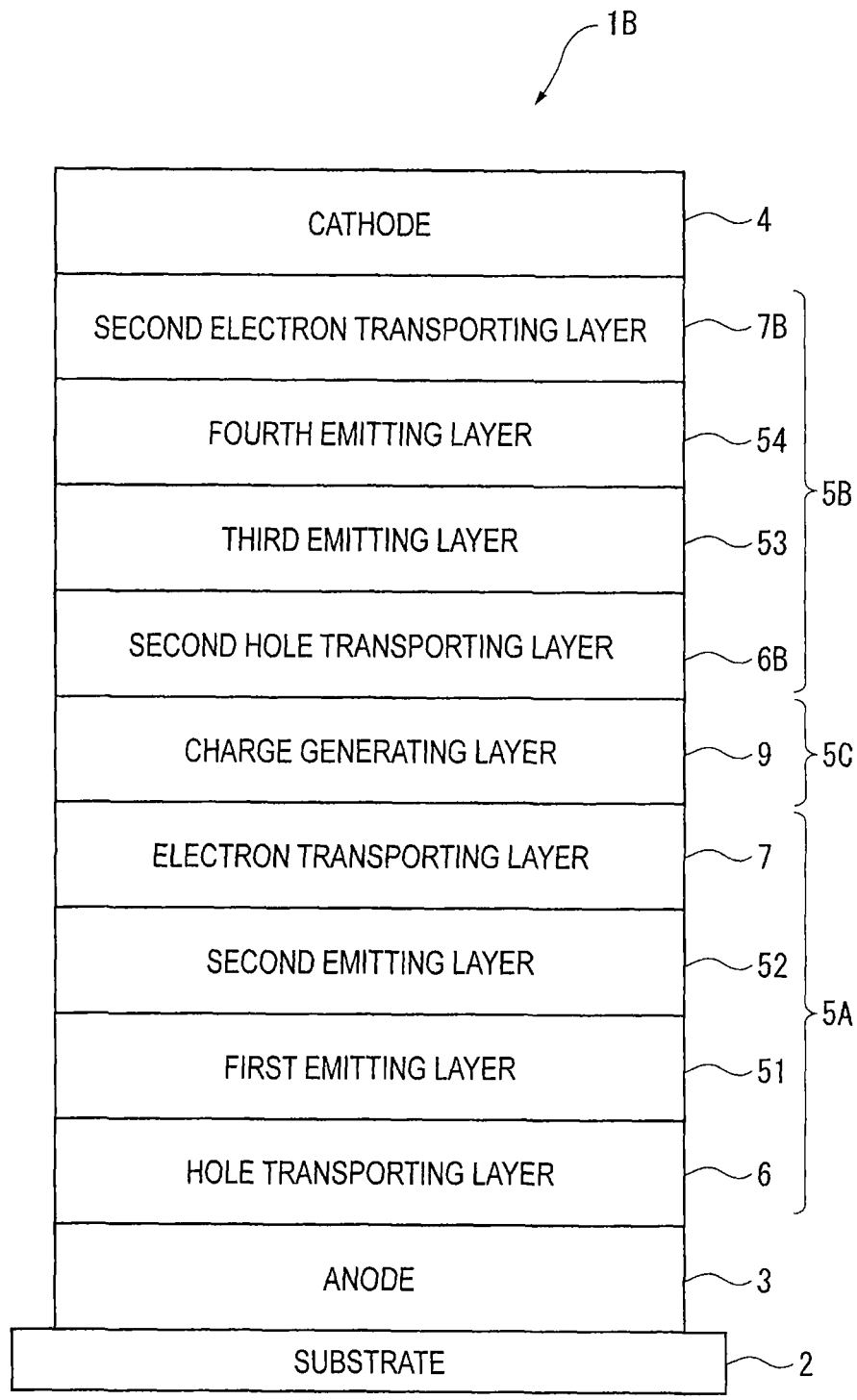
FIG. 3 schematically shows an exemplary arrangement of an organic EL device according to a third exemplary embodiment.

As shown in FIG. 3, an organic EL device 1B according to the third exemplary embodiment is provided by laminating the anode 3, a first emitting unit 5A, an intermediate unit 5C, a second emitting unit 5B and the cathode 4 on the substrate 2 in this sequence.

The first emitting unit 5A includes the hole transporting layer 6, the first emitting layer 51, the second emitting layer 52 and the electron transporting layer 7.

The intermediate unit 5C includes an intermediate conductive layer, charge generating layer and the like. In the third exemplary embodiment, the intermediate unit 5C includes a charge generating layer 9.

The second emitting unit 5B includes a second hole transporting layer 6B, the third emitting layer 53 continuously formed on the second hole transporting layer 6B, a fourth emitting layer 54 continuously formed on the third emitting layer 53, and a second electron transporting layer 7B continuously formed on the continuously formed on the fourth emitting layer 54.

The first emitting layer 51 is the same as the emitting layer 5 of the first exemplary embodiment.

The second emitting layer 52 is the same as the second emitting layer 52 of the second exemplary embodiment.

The third emitting layer 53 is the same as the third emitting layer of the second exemplary embodiment.

The fourth emitting layer 54 is a green fluorescent-emitting layer having a peak wavelength of about 500 nm to 570 nm. The fourth emitting layer 54 contains a fourth host material and a fourth luminescent material.

The charge generating layer 9 in which charges are generated when an electrical field is applied injects electrons into the electron transporting layer 7 and injects holes into the second hole transporting layer 6B.

As a material for the charge generating layer 9, known materials such as the materials described in the specification of U.S. Pat. No. 7,358,661 are usable. Specific examples of the material include oxides, nitrides, iodides and borides of metals such as In, Sn, Zn, Ti, Zr, Hf, V, Mo, Cu, Ga, Sr, La and Ru. The electron transporting layer 7 near an interface with the charge generating layer is preferably doped with a donor (e.g., an alkali metal) in order that the third emitting layer 53 can easily accept electrons from the charge generating layer 9. As the donor, at least one of a donor metal, donor metal compound and donor metal complex can be selected. Examples of the compounds usable for the donor metal, the donor metal compound and the donor metal complex are compounds disclosed in International Publication No. 2010/134352.

The second hole transporting layer 6B and the second electron transporting layer 7B function the same as the hole transporting layer and the electron transporting layer of the first exemplary embodiment.

Since the organic EL device 1B is a so-called tandem-type device, the drive voltage can be reduced and durability can also be improved.

Fourth Exemplary Embodiment

An organic EL device 1C according to a fourth exemplary embodiment is different from that of the second exemplary embodiment in that the first emitting layer 51 is not provided.

In the description of the fourth exemplary embodiment, the same components as those in the second exemplary embodiments are denoted by the same reference signs and names to simplify or omit an explanation of the components. In the fourth exemplary embodiment, the same materials and compounds as described in the second exemplary embodiments are usable.

Figure 4:
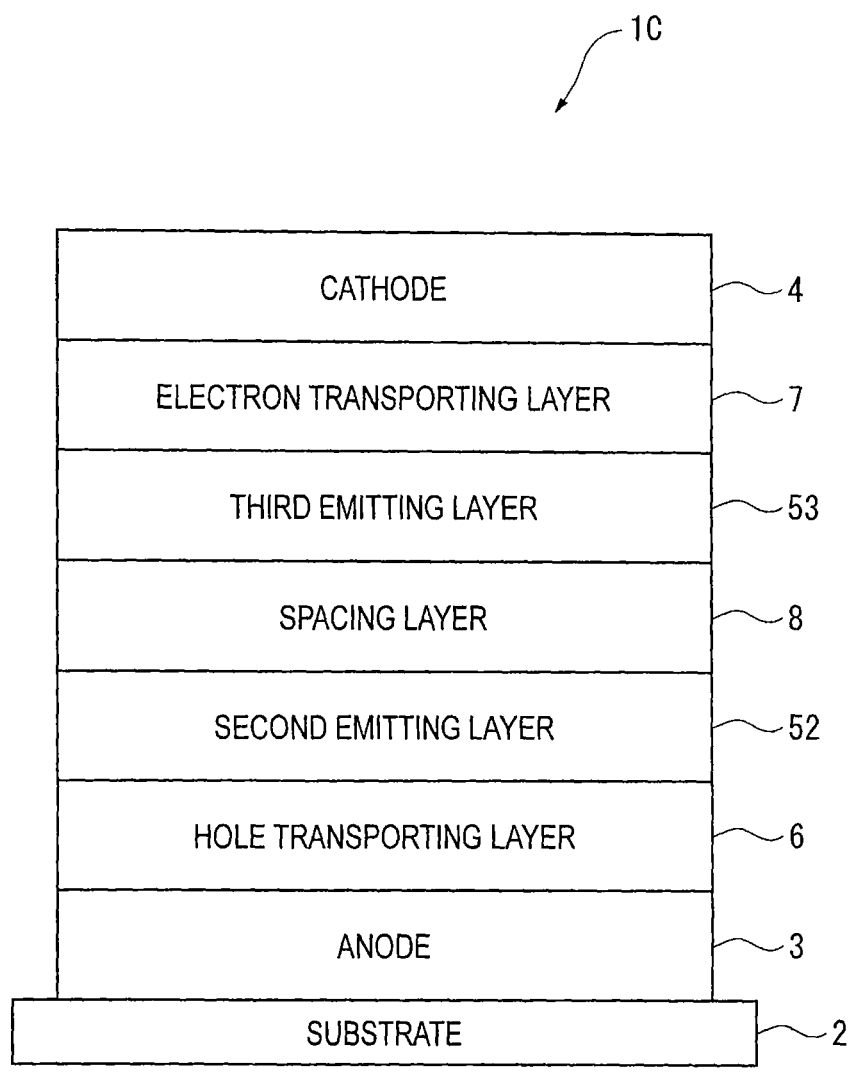
FIG. 4 schematically shows an exemplary arrangement of an organic EL device according to a fourth exemplary embodiment.

As shown in FIG. 4, the organic EL device 1C according to the fourth exemplary embodiment is configured to include the anode 3, the hole transporting layer 6, the second emitting layer 52, the spacing layer 8, the third emitting layer 53, the electron transporting layer 7 and the cathode 4 sequentially laminated on the substrate 2.

The second emitting layer 52 is the emitting layer according to the invention. In other words, the second emitting layer 52 is the same as the emitting layer 5 of the first exemplary embodiment.

The third emitting layer 53 is, for instance, a blue fluorescent-emitting layer having a peak wavelength of 450 nm to 500 nm. The third emitting layer 53 includes a third host material and a third luminescent material.

When a dopant material exhibiting yellow emission is used as the second emitting layer 52 in the organic EL device 1C, since the organic EL device 1C includes the second emitting layer 52 exhibiting yellow emission and the third emitting layer 53 exhibiting blue emission, the organic EL device 1C can exhibit white emission as a whole. Typically, white emission of the entire device requires three layers respectively exhibiting red emission, green emission and blue emission to exhibit emission in good balance. However, in this exemplary embodiment, the layers exhibiting red emission and green emission can be replaced by only the second emitting layer 52 exhibiting yellow emission. Accordingly, the organic EL device IA is suitably applicable as a surface light source for lighting, a backlight and the like.

Fifth Exemplary Embodiment

An organic EL device 1D according to a fifth exemplary embodiment is different from that of the third exemplary embodiment in that the first emitting layer 51 is not provided.

In the description of the fifth exemplary embodiment, the same components as those in the third exemplary embodiments are denoted by the same reference signs and names to simplify or omit an explanation of the components. In the fifth exemplary embodiment, the same materials and compounds as described in the third exemplary embodiments are usable.

Figure 5:
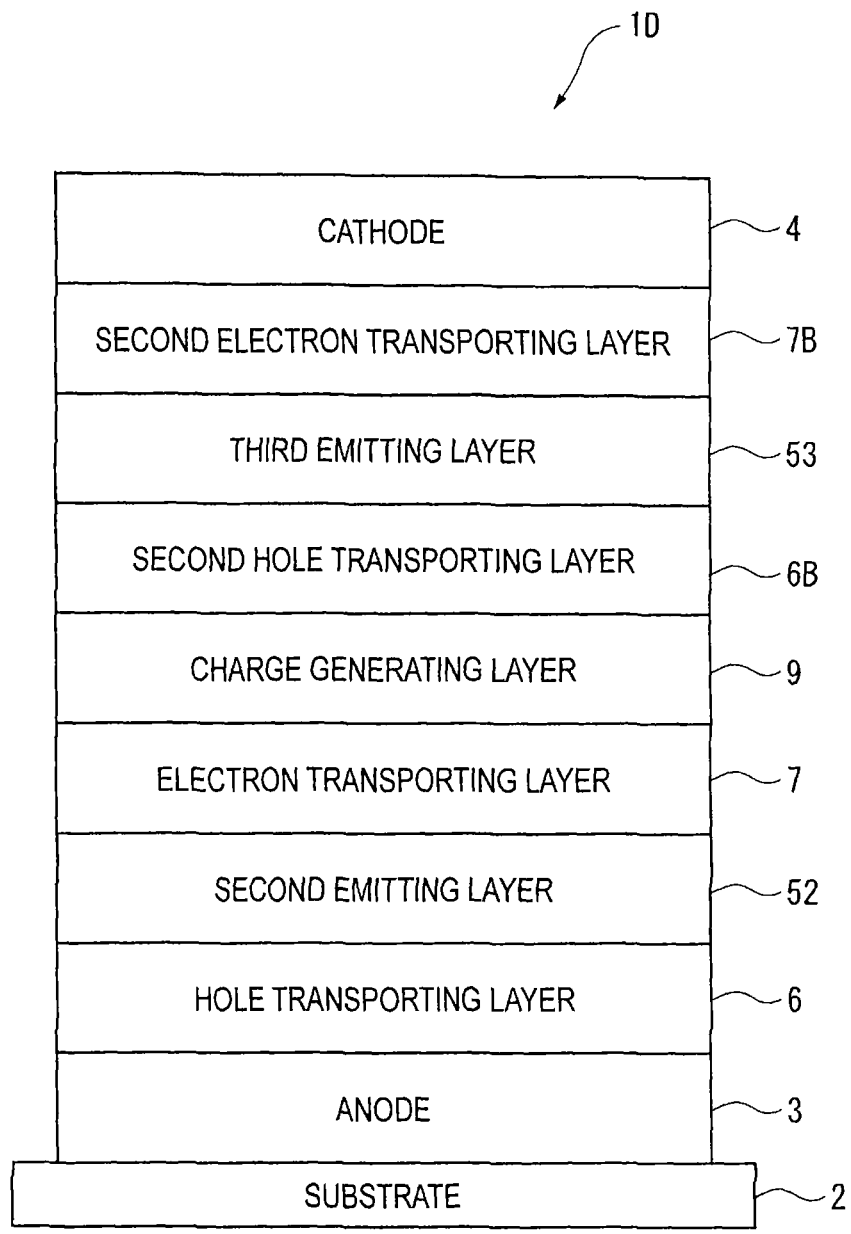
FIG. 5 schematically shows an exemplary arrangement of an organic EL device according to a fifth exemplary embodiment.

As shown in FIG. 5, the organic EL device 1D of the fifth exemplary embodiment is configured to include the anode 3, the hole transporting layer 6, the second emitting layer 52, the electron transporting layer 7, the charge generating layer 9, the second hole transporting layer 6B, the second emitting unit 5B, the second electron transporting layer 7B and the cathode 4 sequentially laminated on the substrate 2.

The second emitting layer 52 is the emitting layer exhibiting yellow emission according to the invention. In other words, the second emitting layer 52 is the same as the emitting layer 5 of the first exemplary embodiment and the second emitting layer of the third exemplary embodiment.

The third emitting layer 53 is the same as the third emitting layer of the second exemplary embodiment.

Since the organic EL device 1D is a so-called tandem-type device, electrical current for driving can be reduced and durability can be improved.

Modification(s) of Embodiment(s)

It should be noted that the invention is not limited to the above description but may include any modification as long as such modification stays within a scope and a spirit of the invention.

In the first and second exemplary embodiments, the hole transporting layer is continuously formed on the anode. However, the hole injecting layer may be further provided between the anode and the hole transporting layer.

Preferable examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

In the first to third exemplary embodiments, the electron transporting layer is continuously formed on the cathode. However, the electron injecting layer may be further formed between the cathode and the electron transporting layer.

Although two emitting units are formed in the third exemplary embodiments, three or more emitting units may be formed.

EXAMPLES

The invention will be described in more detail below by exemplifying examples and comparatives. It should be noted that the invention is not limited to specific description of the examples and the like.

Synthesis Example 1 (Synthesis of Compound H1-1)

Synthesis of Intermediate 1-2

3-bromobenzaldehydro (100 g, 54 mmol) and aniline (50 g, 54 mmol) were added to toluene (1 L) and heated to reflux for eight hours. After the reaction solution was cooled down, a solvent was concentrated under reduced pressure to obtain an intermediate 1-1 (130 g, a yield of 93%).

Subsequently, under an argon gas atmosphere, the intermediate 1-1 (130 g, 50 mmol), benzamidine hydrochloride (152 g, 100 mmol), anhydrous ethanol (1 L), and sodium hydroxide (42 g) were added together in sequential order, and stirred at 80 degrees C. for 16 hours. Subsequently, sodium-t-butoxide (20 g, 208 mmol) were further added and heated at 80 degrees C. for 16 hours with stirring. After the reaction solution was cooled down to the room temperature, a solid was separated by filtration and washed with methanol to obtain an intermediate 1-2 (67 g, a yield of 37%).

Synthesis of Intermediate 1-5

Under a nitrogen atmosphere, 2-nitro-1,4-dibromobenzene (11.2 g, 40 mmol), phenylboronic acid (4.9 g, 40 mmol), tetrakis(triphenylphosphine)palladium (1.39 g, 1.2 mmol), toluene (120 mL) and an aqueous solution of 2M sodium carbonate (60 mL) were added together in sequential order, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 1-3 (6.6 g, a yield of 59%) was obtained.

Subsequently, under an argon gas atmosphere, the intermediate 1-3 (6.6 g, 23.7 mmol), triphenylphosphine (15.6 g, 59.3 mmol), and o-dichlorobenzene (24 mL) were added together in sequential order, and heated to reflux at 180 degrees C. for eight hours.

After cooled down to the room temperature, the reaction solution was refined by silica-gel column chromatography, whereby an intermediate 1-4 (4 g, a yield of 68%) was obtained.

Under a nitrogen atmosphere, the intermediate 1-4 (4 g, 16 mmol), N-phenylcarbazolyl-3-boronic acid (5.1 g, 17.8 mmol), tetrakis(triphenylphosphine)palladium (0.56 g, 0.48 mmol), toluene (50 mL) and an aqueous solution of 2M sodium carbonate (24 mL) were added together in sequential order, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 1-5 (3.2 g, a yield of 49%) was obtained.

Synthesis of Compound H1-1

Under an argon gas atmosphere, the intermediate 1-5 (1.6 g, 3.9 mmol), the intermediate 1-2 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, so that a compound H1-1 (2.3 g, a yield of 82%) was obtained.

As a result of FD-MS (Field Desorption Mass Spectrometry: hereinafter abbreviated to FD-MS) analysis, m/e was equal to 715 while a calculated molecular weight was 715.

Synthesis schemes are shown below.
[Formula 115]
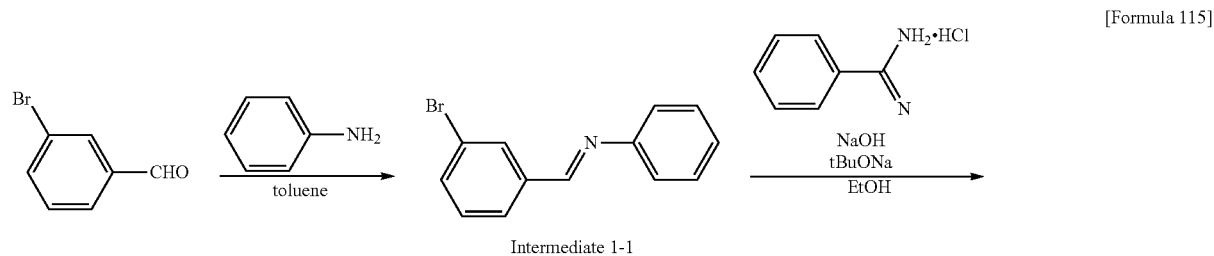
Intermediate 1-1
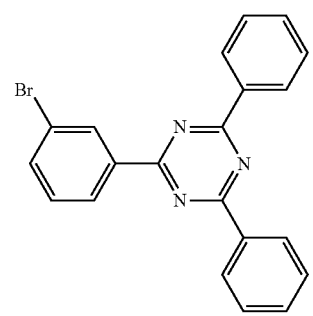
Intermediate 1-2
[Formula 116]
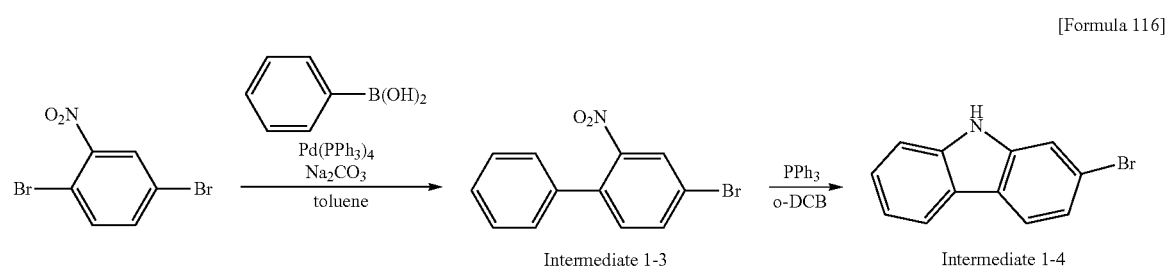
Intermediate 1-3  Intermediate 1-4
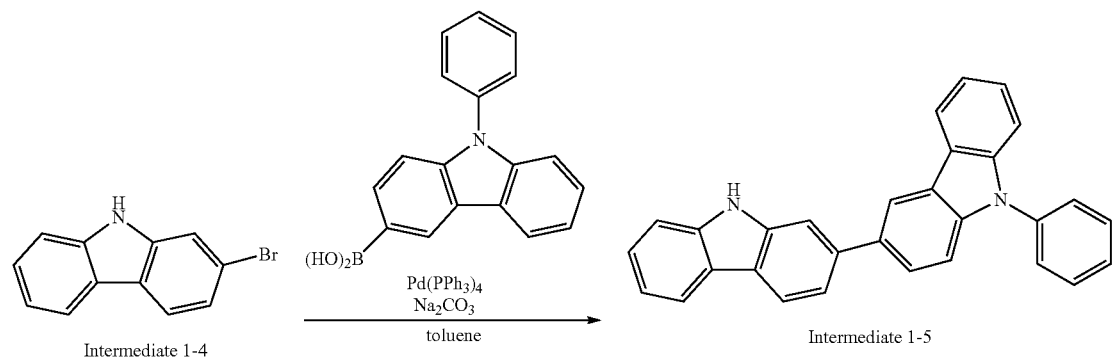
Intermediate 1-4  Intermediate 1-5

-continued

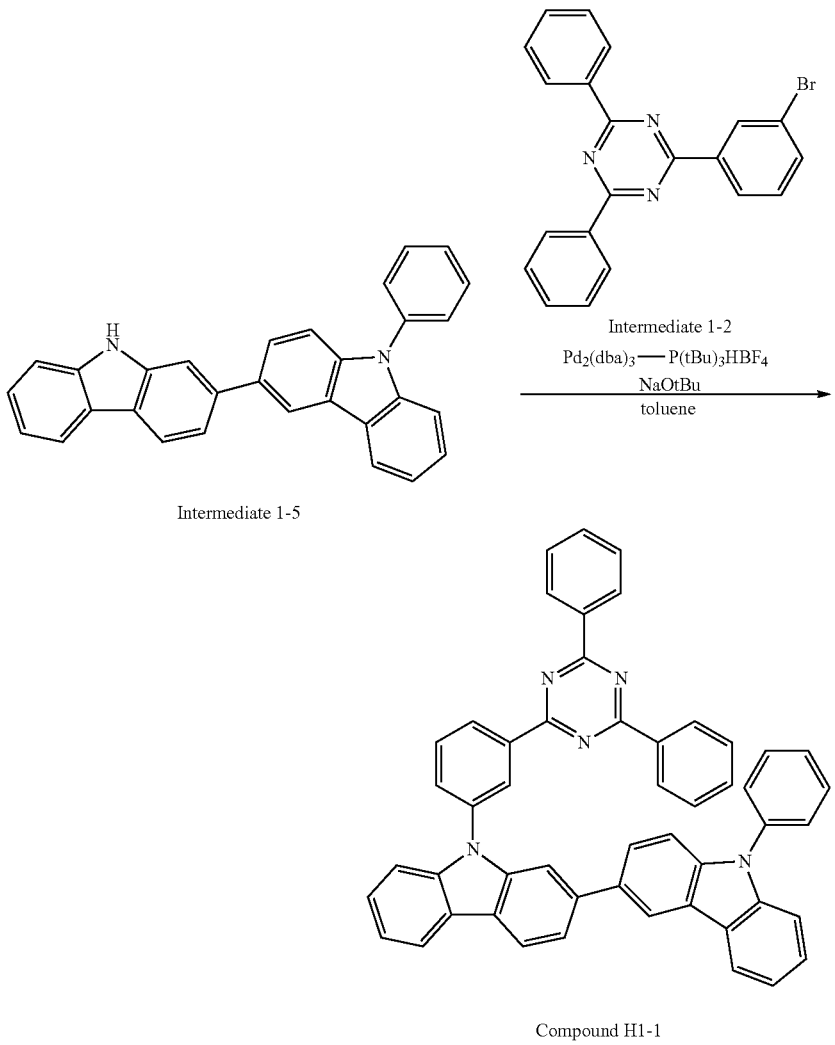

[Formula 117]

Intermediate 1-5

Intermediate 1-2

Pd₂(dba)₃ — P(tBu)₃HBF₄
NaOtBu
toluene

Compound H1-1

Synthesis Example 2 (Synthesis of Compound H1-2)

Synthesis of Intermediate 2-1

Under a nitrogen atmosphere, trichloropyrimidine (8 g, 43.4 mmol), phenylboronic acid (11.6 g, 95.4 mmol), tetrakis(triphenylphosphine)palladium (1.83 g, 1.74 mmol), toluene (300 mL) and an aqueous solution of 2M sodium carbonate (130 mL) were added together in sequential order, and heated to reflux for eight hours. After the reaction solution was cooled down to the room temperature, an organic phase was removed and an organic solvent was distilled away under reduced pressure. The obtained residue was refined by silica-gel column chromatography, whereby an intermediate 2-1 (8.2 g, a yield of 71%) was obtained.

Synthesis of Intermediate 2-2

Under a nitrogen atmosphere, the intermediate 2-1 (8 g, 29.9 mmol), p-chlorophenylboronic acid (5.1 g, 32.9 mmol), tetrakis(triphenylphosphine)palladium (0.63 g, 0.6 mmol), toluene (60 mL) and an aqueous solution of 2M sodium carbonate (30 mL) were added together in sequential order, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 2-2 (7.0 g, a yield of 68%) was obtained.

Under an argon gas atmosphere, the intermediate 1-5 (1.6 g, 3.9 mmol), the intermediate 2-2 (0.05 oz, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, so that a compound H1-2 (2.3 g, a yield of 82%) was obtained.

As a result of the FD-MS analysis, m/e was equal to 715 while a calculated molecular weight was 715.

A synthesis scheme of the compound H1-2 is shown below.
[Formula 118]
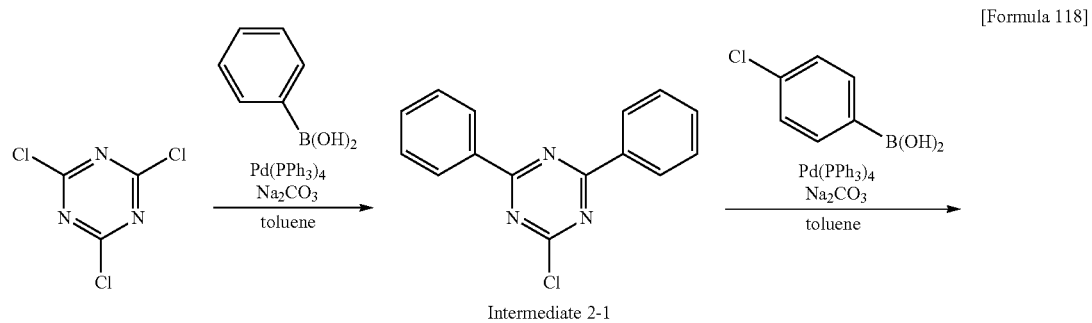
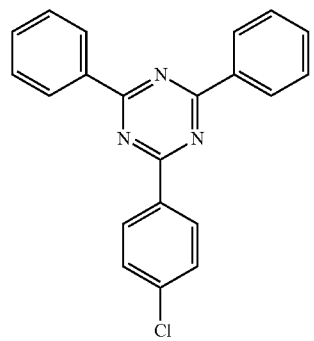
Intermediate 2-2
[Formula 119]
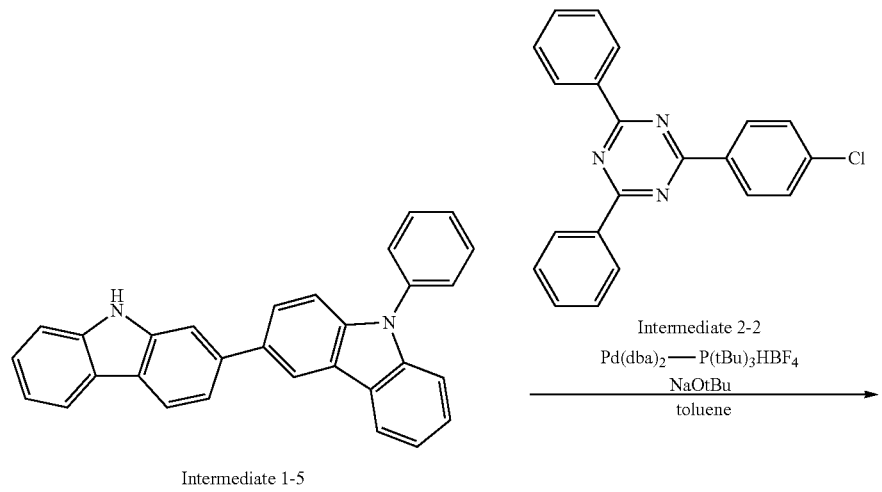

-continued

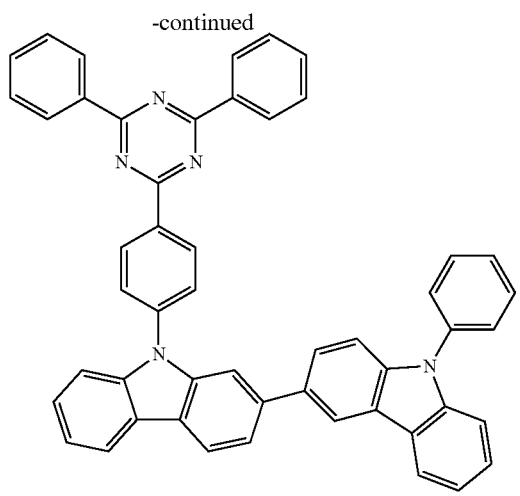

Compound H1-2

Synthesis Example 3 (Synthesis of Compound H1-3)

Synthesis of Intermediate 3-1

Carbazole (15 g, 92.6 mmol) was added to ethanol (70 mL). Sulfuric acid (6 mL), water (3 mL), HIO$_4$.2H$_2$O (8.2 g, 35.9 mmol) and I$_2$ (9.1 g, 35.9 mmol) were added thereto and stirred at room temperature for four hours. Water was added to the reaction solution and a precipitated solid was separated by filtration. Then, the obtained solid was washed with methanol. By dissolving the obtained solid in heated toluene for recrystallization, an intermediate 3-1 (5.1 g, a yield rate 18.8%) was obtained.

Synthesis of Intermediate 3-2

Under an argon gas atmosphere, N-phenylcarbazolyl-3-boronic acid (2.0 g, 7.0 mmol), the intermediate 3-1 (2.05 g, 7.0 mmol), Pd(PPh$_3$)$_4$ (0.15 g, 0.14 mmol), toluene (20 mL) and an aqueous solution of 2M sodium carbonate (10.5 mL) were added together, and stirred at 80 degrees C. for seven hours. Water was added to the reaction solution to precipitate solid. Then, the obtained solid was washed with methanol. By washing the obtained solid by heated toluene, an intermediate 3-2 (2.43 g, a yield rate 84%) was obtained.

Synthesis of Compound H1-3

Under an argon gas atmosphere, the intermediate 1-2 (1.5 g, 3.9 mmol), the intermediate 3-2 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, so that a compound H1-3 (2.3 g, a yield of 82%) was obtained.

As a result of the FD-MS analysis, m/e was equal to 715 while a calculated molecular weight was 715.

A synthesis scheme of the compound H1-3 is shown below.

[Formula 120]

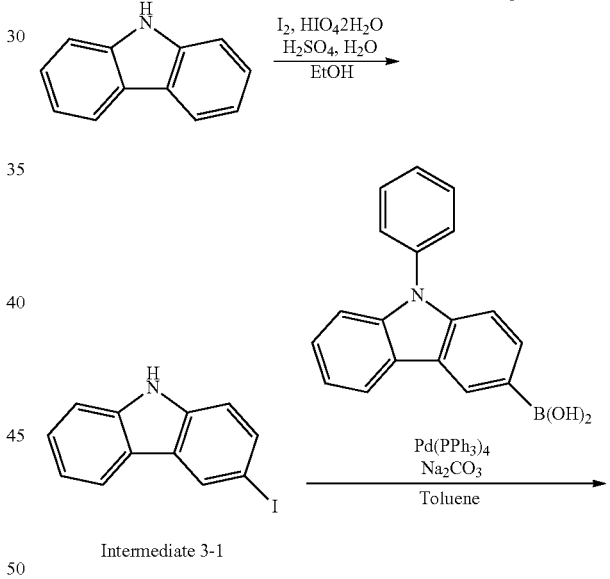

Intermediate 3-1

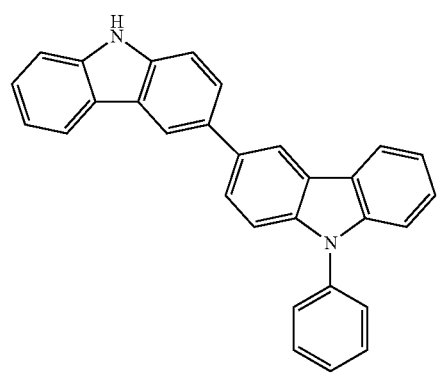

Intermediate 3-2

223 -continued

[Formula 121]

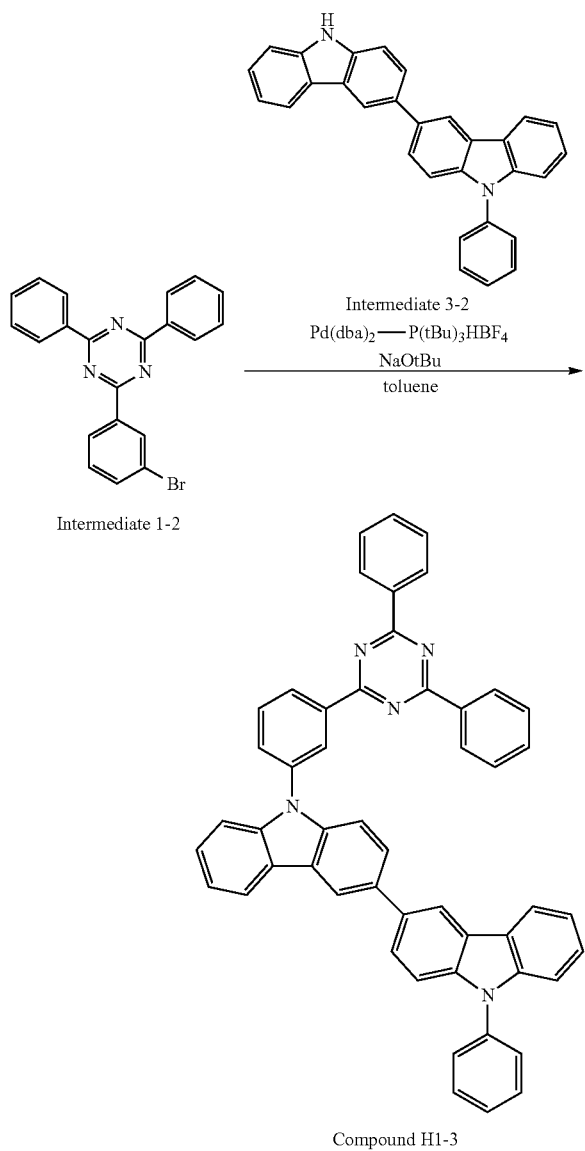

224

Synthesis Example 4 (Synthesis of Compound H1-4)

Synthesis of Intermediate 4-2

4-bromobenzaldehyde (25 g, 135 mmol) and acetophenone (16.2 g, 135 mmol) were added to ethanol (200 mL). An aqueous solution of 3M potassium hydrate (60 mL) was further added thereto and stirred at room temperature for seven hours. A precipitated solid was separated by filtration. Then, the obtained solid was washed with methanol. A white solid intermediate 4-1 (28.3 g, a yield rate 73%) was obtained.

Synthesis of Compound H1-4

The intermediate 4-1 (20 g, 69.7 mmol) and benzamidine hydrochloride (10.8 g, 69.7 mmol) were added to ethanol (300 mL). Sodium hydroxide (5.6 g, 140 mmol) was further added thereto and heated to reflux at room temperature for eight hours. A precipitated solid was separated by filtration. Then, the obtained solid was washed with hexane. A white solid intermediate 4-2 (10.3 g, a yield rate 38%) was obtained.

Under an argon gas atmosphere, the intermediate 1-5 (1.6 g, 3.9 mmol), the intermediate 4-2 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, so that a compound H1-4 (2.2 g, a yield of 80%) was obtained.

As a result of FD-MS analysis, m/e was equal to 714 while a calculated molecular weight was 714.

A synthesis scheme of the compound H1-4 is shown below.

[Formula 122]

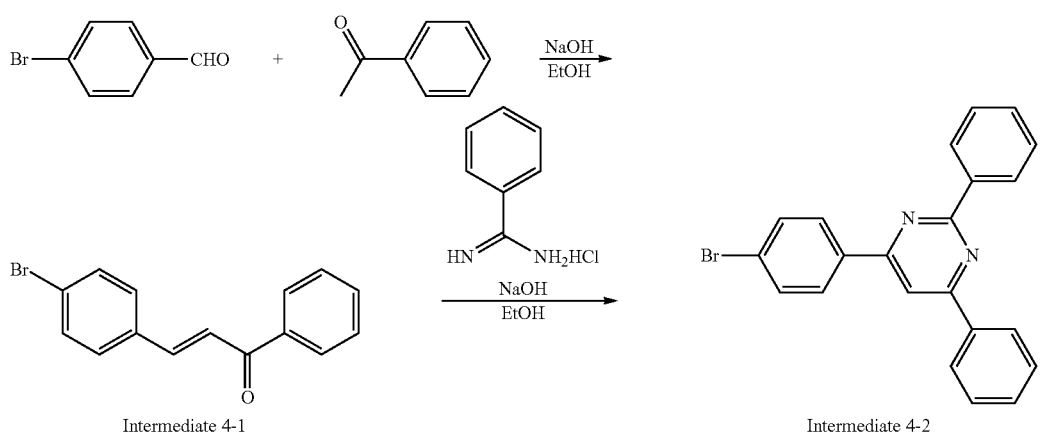

[Formula 123]

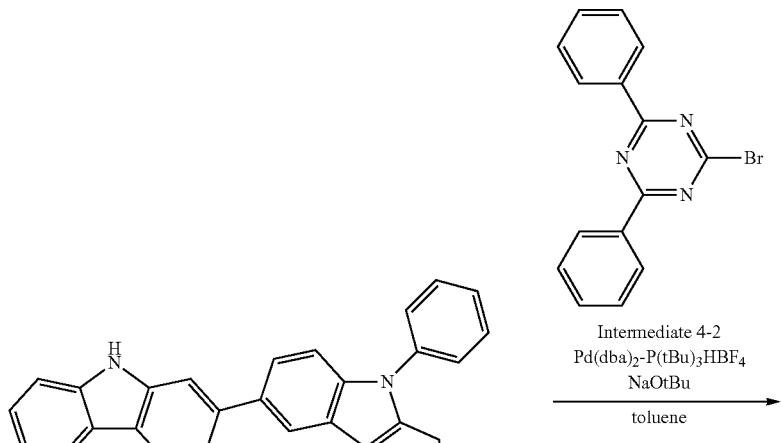

Intermediate 1-5

Intermediate 4-2
Pd(dba)$_2$-P(tBu)$_3$HBF$_4$
NaOtBu
toluene

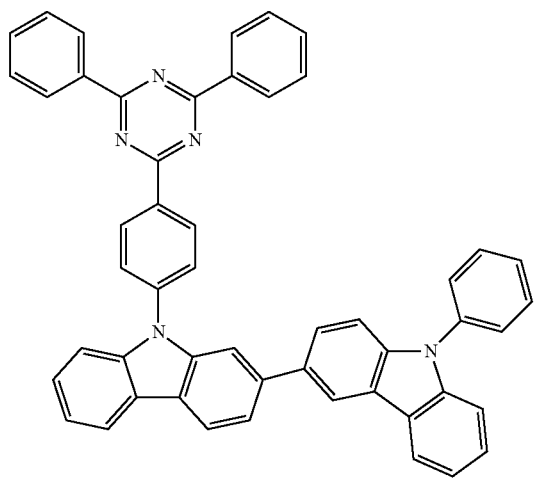

Compound H1-4

Synthesis Example 5 (Synthesis of Compound H2-1)

Synthesis of Intermediate 5-1

Under a nitrogen atmosphere, trichloropyrimidine (10 g, 54.5 mmol), phenylboronic acid (13.3 g, 109 mmol), palladium acetate (0.3 g, 1.37 mmol), triphenylphosphine (0.72 g, 2.73 mmol), dimethoxyethane (150 mL) and an aqueous solution of 2M sodium carbonate (170 mL) were added together in sequential order, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 5-1 (9.2 g, a yield of 63%) was obtained.

Under an argon gas atmosphere, the intermediate 1-3 (1.6 g, 3.9 mmol), the intermediate 5-1 (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, whereby a compound H2-1 (2.4 g, a yield of 95%) was obtained.

As a result of the FD-MS analysis, m/e was equal to 638 while a calculated molecular weight was 638.

A synthesis scheme of the compound H2-1 is shown below.

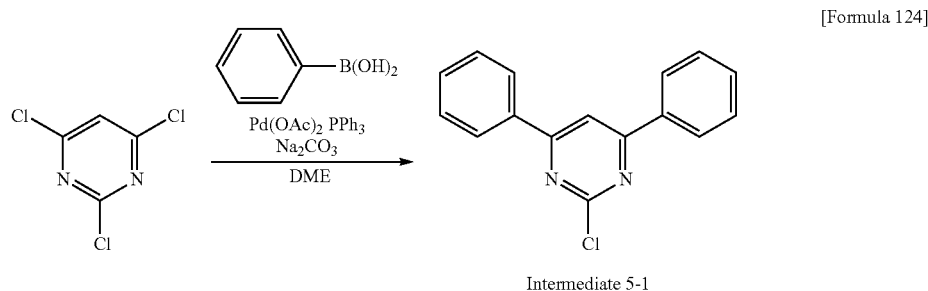

[Formula 124]

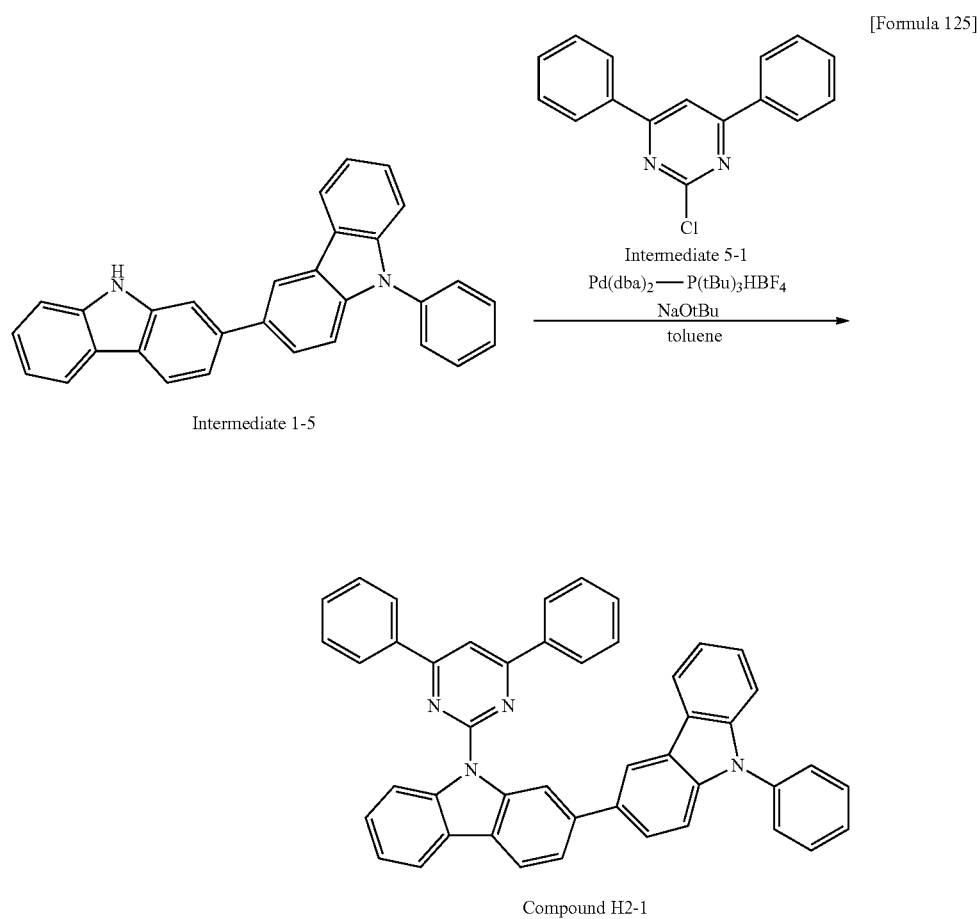

[Formula 125]

Synthesis Example 6 (Synthesis of Compound H2-2)

Under an argon gas atmosphere, the intermediate 1-5 (1.6 g, 3.9 mmol), the intermediate 2-2 (1.5 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, whereby a compound H2-2 (2.2 g, a yield of 80%) was obtained.

As a result of the FD-MS analysis, m/e was equal to 639 while a calculated molecular weight was 639.

A synthesis scheme of the compound H2-2 is shown below.

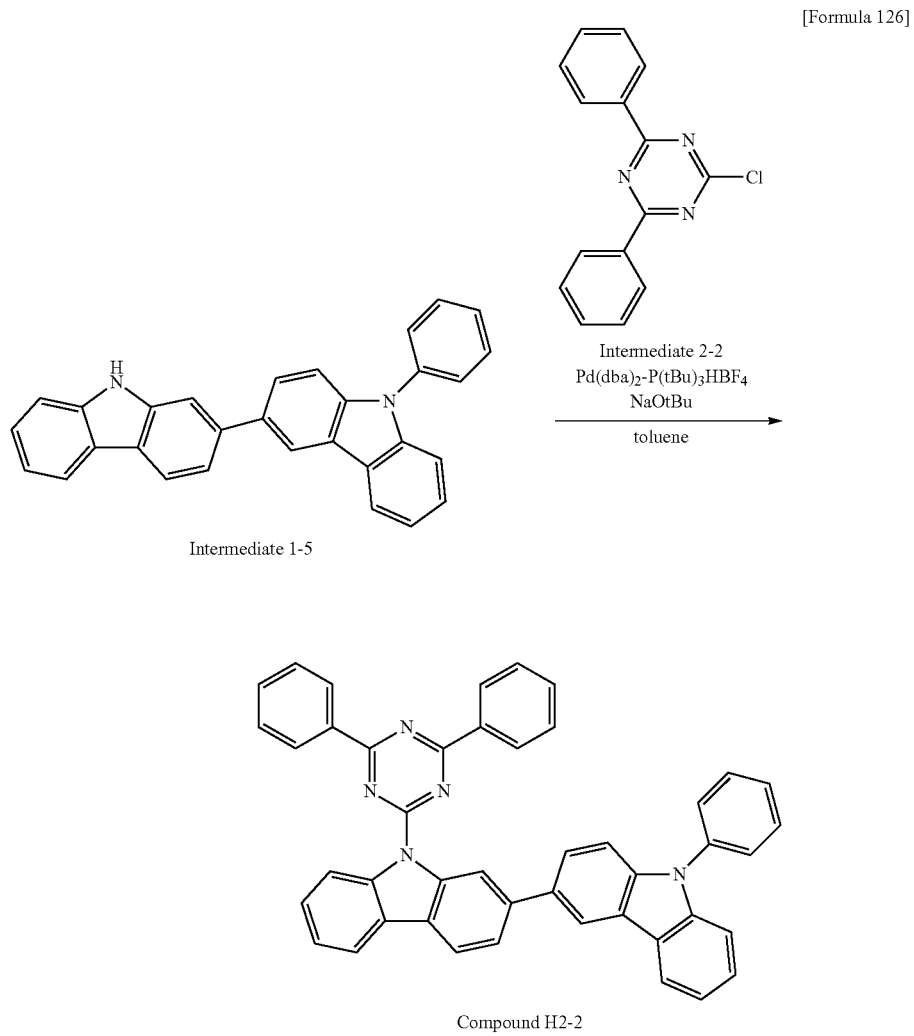

Synthesis Example 7 (Synthesis of Compound H2-3)

Under an argon gas atmosphere, the intermediate 2-2 (1.0 g, 3.9 mmol), the intermediate 3-2 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, whereby a compound H2-3 (1.8 g, a yield of 74%) was obtained.

As a result of the FD-MS analysis, m/e was equal to 639 while a calculated molecular weight was 639.

A synthesis scheme of the compound H2-3 is shown below.

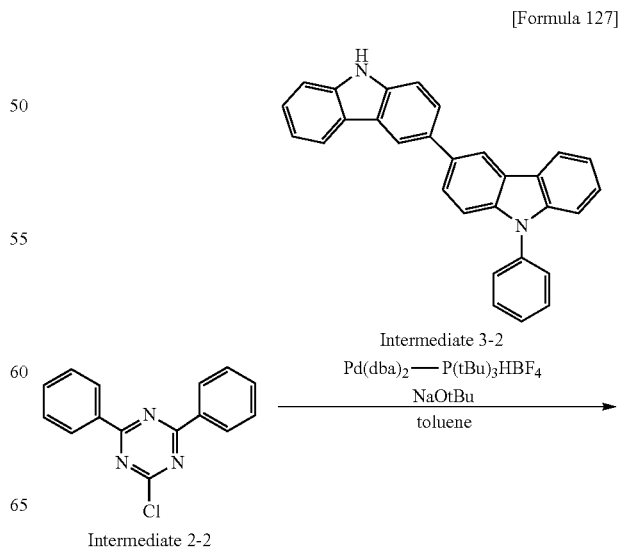

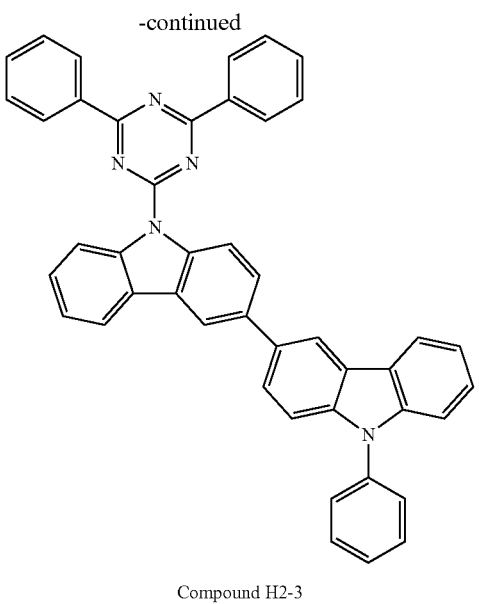

Compound H2-3

Synthesis Example 8 (Synthesis of Compound H1-5)

Synthesis of Intermediate 8-3

Under an argon gas atmosphere, a mixture of o-iodonitrobenzene (25 g, 100 mmol), o-bromophenylboronic acid (21 g, 105 mmol), tetrakis(triphenylphosphine)palladium(0) (2.3 g, 2 mmol), toluene (150 mL), dimethoxyethane (150 mL) and an aqueous solution of 2M sodium carbonate (150 mL) was stirred for eight hours at 80 degrees C. After the organic phase was separated and the solvent was evaporated by an evaporator, the obtained residue was purified by silica-gel column chromatography, so that an intermediate 8-1 (20 g, a yield of 72%) was obtained.

Subsequently, the intermediate 1-2 was synthesized as follows.

Under an argon gas atmosphere, a mixture of the intermediate 8-1 (20 g, 72 mmol), triphenylphosphine (18.9 g, 72 mmol) and o-dichlorobenzene (100 mL) was heated with stirring at 180 degrees C. for eight hours. Water was added to the reaction solution to precipitate solid. Then, the obtained solid was filtrated. The obtained solid was purified by silica-gel column chromatography, so that the intermediate 8-2 (8.4 g, a yield of 47%) was obtained.

Subsequently, the intermediate 1-3 was synthesized as follows.

Under an argon gas atmosphere, a mixture of the intermediate 8-2 (7.4 g, 30 mmol), 9-phenylcarbazole-3-boronic acid (8.7 g, 30 mmol), tetrakis(triphenylphosphine)palladium(0) (0.69 g, 0.6 mmol), toluene (45 mL), dimethoxyethane (45 mL) and an aqueous solution of 2M sodium carbonate (45 mL) was stirred for eight hours at 80 degrees C. After the organic phase was separated and the solvent was evaporated by an evaporator, the obtained residue was purified by silica-gel column chromatography, so that an intermediate 8-3 (9.1 g, a yield of 74%) was obtained.

Synthesis of Compound H1-5

Under an argon gas atmosphere, a mixture of an intermediate A (2.1 g, 5.5 mmol), the intermediate 8-3 (2.0 g, 5 mmol), tris(dibenzylideneacetone)dipalladium (0) (0.09 g, 0.1 mmol), tri-tert-butylphosphonium tetrafluoroborate (0.11 g, 0.4 mmol), sodium t-butoxide (0.67 g, 7 mmol), and xylene (20 mL) was heated to reflux for eight hours. Water was added to the mixture and the obtained mixture was stirred for one hour. After the formed solid was filtrated and washed with water and methanol, the obtained solid was purified by silica-gel column chromatography, so that a compound H1-5 (3.0 g, a yield of 85%) was obtained.

Results of the FD-MS analysis are shown below.

FD-MS: calcd for $C_5H_{33}N_5$=715.27, found m/z=715 (M$^+$, 100)

A synthesis scheme of the compound H1-5 is shown below.

[Formula 128]

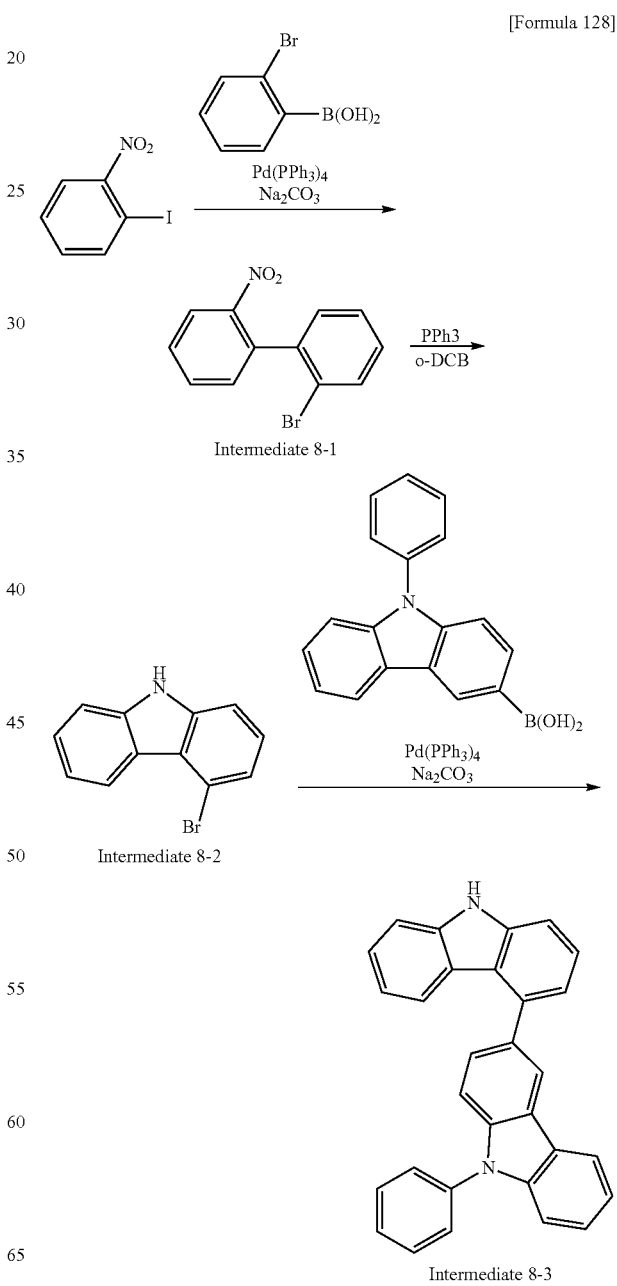

-continued

[Formula 129]

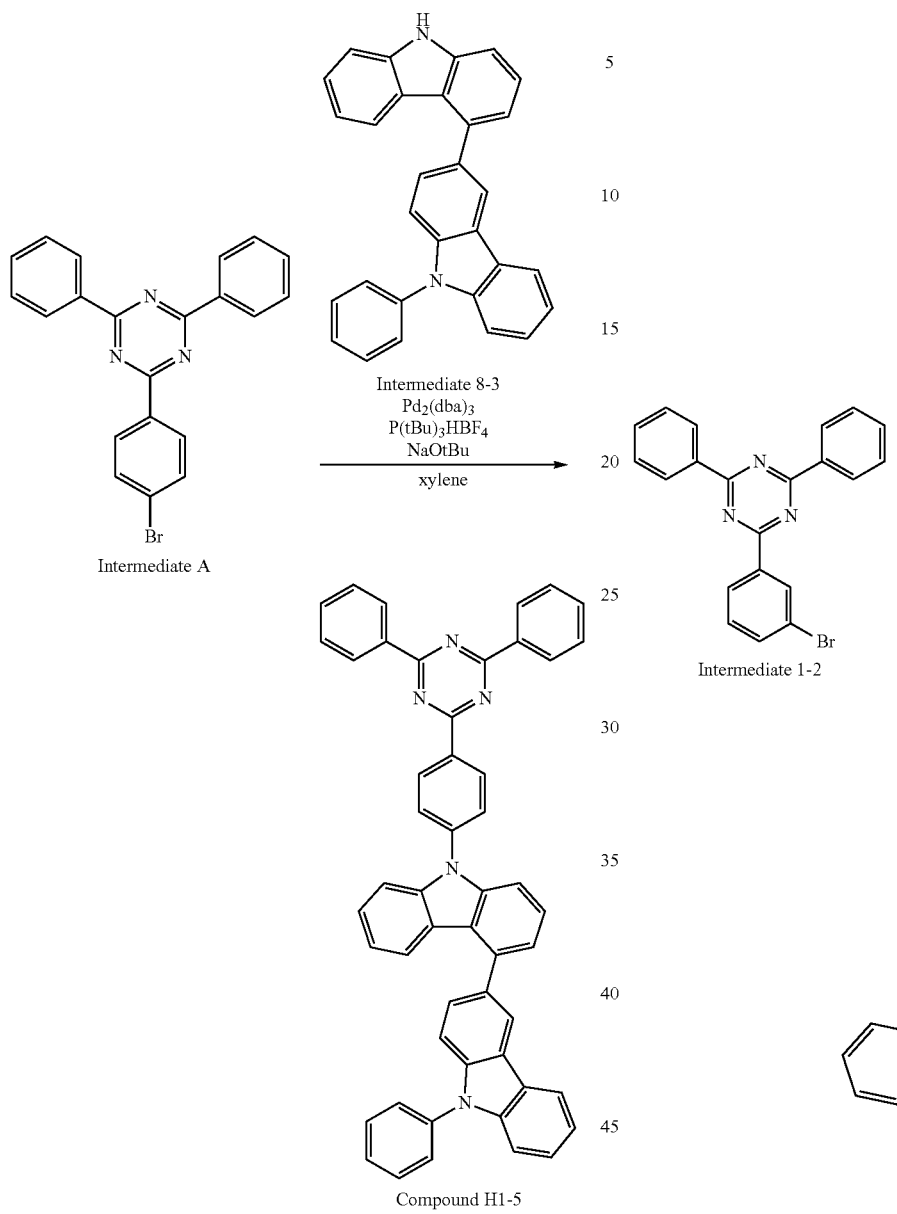

Compound H1-5

A synthesis scheme of the compound H1-5 is shown below.

[Formula 130]

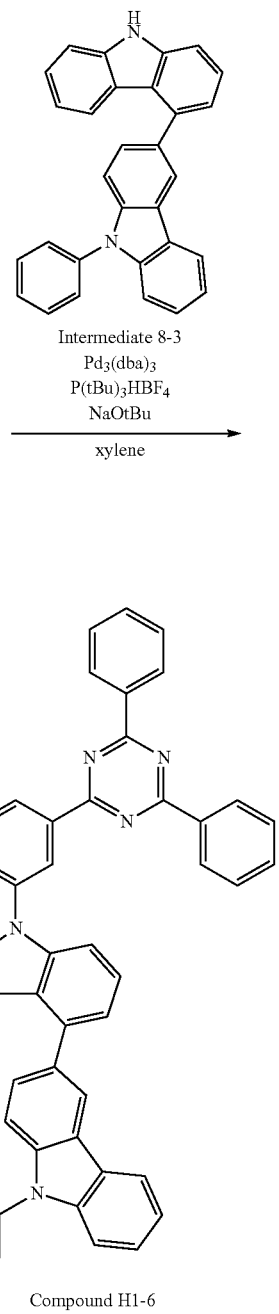

Compound H1-6

Synthesis Example 9 (Synthesis of Compound H1-6)

Under an argon gas atmosphere, a mixture of the intermediate 1-2 (2.1 g, 5.5 mmol), the intermediate 8-3 (2.0 g, 5 mmol), tris(dibenzylideneacetone)dipalladium (0) (0.09 g, 0.1 mmol), tri-tert-butylphosphonium tetrafluoroborate (0.11 g, 0.4 mmol), sodium t-butoxide (0.67 g, 7 mmol), and xylene (20 mL) was heated to reflux for eight hours. Water was added to the mixture and the obtained mixture was stirred for one hour. After the formed solid was filtrated and washed with water and methanol, the obtained solid was purified by silica-gel column chromatography, so that a compound H1-6 (0.07 oz, a yield of 53%) was obtained.

Results of the FD-MS analysis are shown below.

FD-MS: calcd for $C_{51}H_{33}N_5$=715.27,
found m/z=715 (M$^+$,100)

Synthesis Example 10 (Synthesis of Compound H2-4)

Synthesis of Intermediate 10-1

Under an argon gas stream, 4-bromo-1-iodobenzene (11.3 g, 40 mmol), 9-phenylcarbazolyl-3-boronic acid (11.5 g, 40 mmol), tetrakis(triphenylphosphine)palladium (1.39 g, 1.2 mmol), toluene (120 mL) and an aqueous solution of 2M sodium carbonate (60 mL) were added together in sequential order, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 10-1 (11.0 g, a yield of 69%) was obtained. As a result of FD-MS analysis, the reactant was identified as the intermediate 10-1.

Synthesis of Intermediate 10-2

Under an argon gas stream, the intermediate 10-1 (10 g, 25 mmol), bis(pinacolato)diboron (8.3 g, 33 mmol), [1,1'-bis(diphenylphosphino)ferrocene]palladium (II) dichloride dichloromethane adduct (0.62 g, 0.75 mmol), potassium acetate (7.4 g, 75 mmol) and N,N-dimethylformamide (170 mL) were sequentially mixed, and heated to reflux for eight hours.

After the reaction solution was cooled down to the room temperature, an organic phase was removed and an organic solvent was distilled away under reduced pressure. The obtained residue was refined by silica-gel column chromatography, whereby an intermediate 10-2 (10 g, a yield of 91%) was obtained. As a result of FD-MS analysis, the reactant was identified as the intermediate 10-2.

Synthesis of Intermediate 10-3

An intermediate 10-3 was synthesized according to the same method as that for the synthesis of the intermediate 10-1, except for using 3-bromocarbazole in place of 4-bromo-1-iodobenzene and the intermediate 2 in place of 9-phenylcarbazolyl-3-boronic acid. As a result of FD-MS analysis, the reactant was identified as the intermediate 10-3.

Synthesis of Compound H2-4

Under an argon gas stream, the intermediate 10-3 (1.6 g, 3.9 mmol), 2,6-diphenylpyrimidine-4-chloride (1.0 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for eight hours.

After the reaction solution was cooled down to the room temperature, an organic phase was removed and an organic solvent was distilled away under reduced pressure. The obtained residue thereof was refined by silica-gel column chromatography, so that 0.88 g of a white solid was obtained. As a result of FD-MS, the obtained compound was identified as the compound H2-4.

FD-MS:

calcd for $C_{52}H_{34}N_4$=714, found m/z=714 (M+,100)

A synthesis scheme of the compound H2-4 is shown below.

[Formula 131]

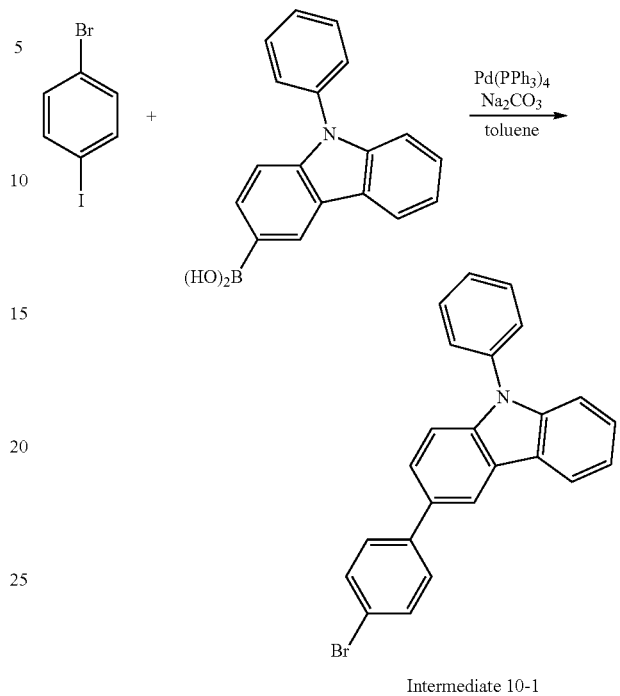

Intermediate 10-1

[Formula 132]

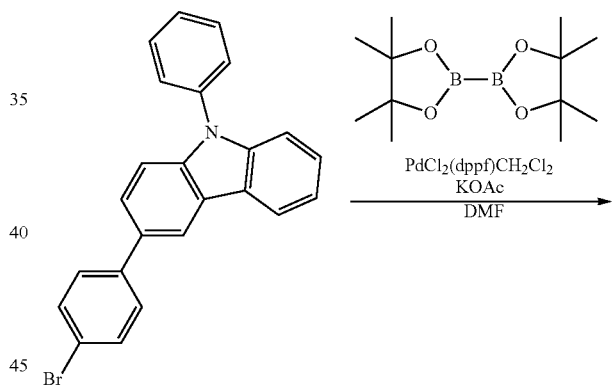

Intermediate 10-1

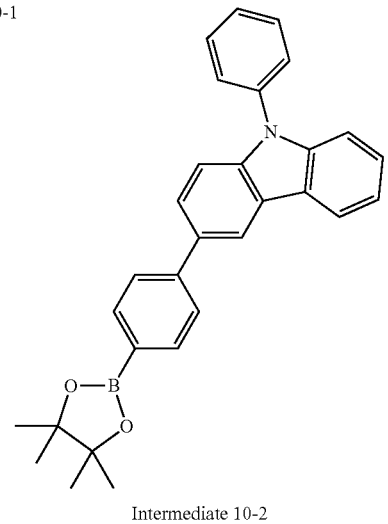

Intermediate 10-2

[Formula 133]

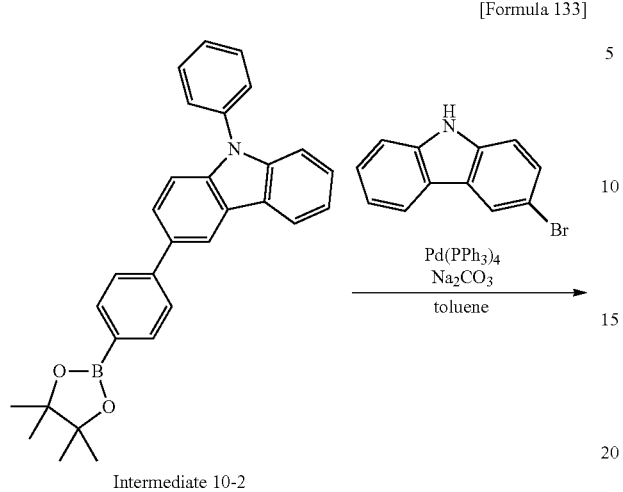

Intermediate 10-2

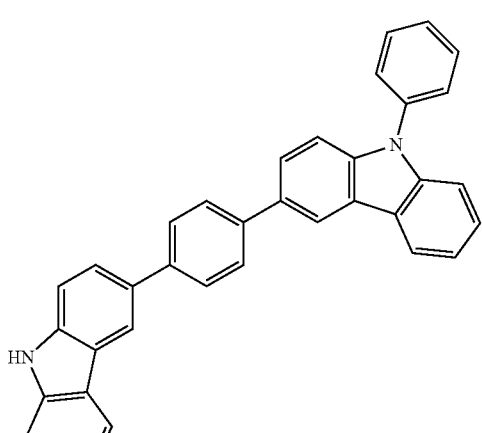

Intermediate 10-3

[Formula 134]

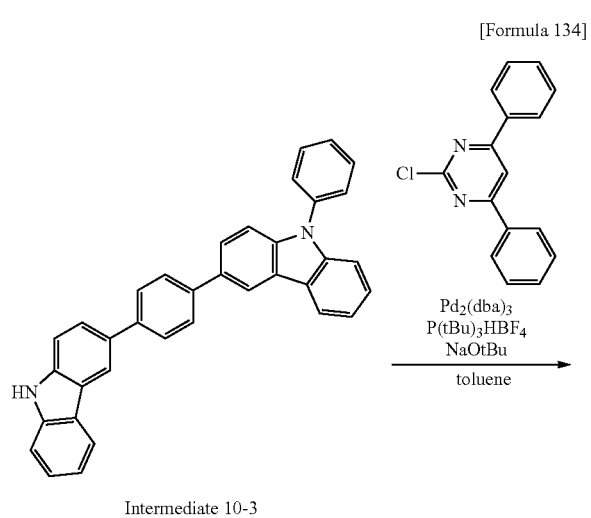

Intermediate 10-3

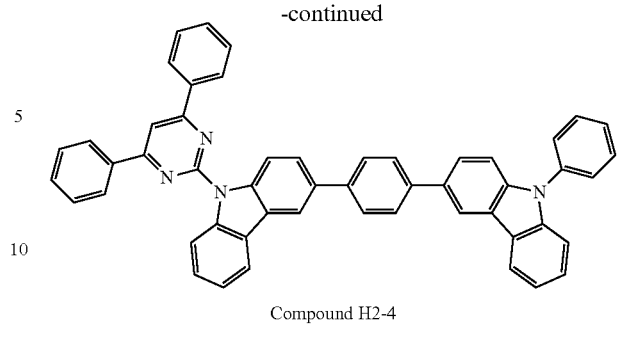

Compound H2-4

Example 1

An organic EL device according to Example 1 was manufactured as follows.

A glass substrate (size: 25 mm×75 mm×1.1 mm thick) having an ITO transparent electrode (anode) (manufactured by Geomatec Co., Ltd.) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum deposition apparatus. A compound HA-1 was deposited on a surface of the glass substrate where the transparent electrode line was provided in a manner to cover the transparent electrode, thereby forming a 5-nm thick HA-1 film. The HA-1 film serves as a hole injecting layer.

A compound HT-1 was deposited on the HA-1 film to form a 65-nm thick HT-1 film. The HT-1 film serves as a hole transporting layer.

The compound H1-1 (the first host material), the compound H2-1 (the second host material) and Ir(bzq)$_3$ (the phosphorescent dopant material) were co-deposited on the HA-1 film. Thus, a 25-nm thick emitting layer exhibiting yellow emission was formed. The concentration of the phosphorescent dopant material was set at 10 mass %, the concentration of the first host material was set at 45 mass %, and the concentration of the second host material was at 45 mass %.

A compound ET-1 was deposited on the emitting layer to form a 35-nm electron transporting layer.

LiF was further evaporated at a rate of 1 Å/min on the electron transporting layer to form a 1-nm electron injecting layer. A metal Al was further deposited on the electron injecting layer to form an 80-nm thick cathode.

Comparative 1

In Comparative 1, an organic EL device was manufactured in the same manner as in Example 1 except for using the compound H1-3 as the first host material and not using the second host material.

Table 1 shows the device arrangement of Example 1 and Comparative 1. The numerals without a unit in parentheses in Table 1 indicate a thickness of each layer (unit: nm). The numerals with % indicate a mass % concentration of the compound.

Evaluation of Organic EL Device

The prepared organic EL devices were evaluated in terms of drive voltage, external quantum efficiency EQE and lifetime. The results are shown in Table 2.

Drive Voltage

Electrical current was applied between ITO and Al such that a current density was 10 mA/cm², where voltage (unit: V) was measured.

External Quantum Efficiency EQE

Voltage was applied on each of the organic EL devices at the room temperature such that a current density was 10 mA/cm², where EL emission spectrum was measured by a spectroradiometer (CS-1000 manufactured by Konica Minolta, Inc.). The external quantum efficiency EQE (unit: %) was calculated based on the obtained spectral-radiance spectra, assuming that the spectra was provided under a Lambertian radiation.

Lifetime

Time (LT80) elapsed until the luminance intensity when driven at a predetermined current (50 mA/cm²) was decreased to 80% was obtained.

Examples 2 to 9

In Examples 2 to 9, organic EL devices were manufactured in the same manner as in Example 1 except that the materials used in Example 1 were replaced as shown in Table 2.

Comparatives 2 to 5

In Comparatives 2 to 4, organic EL devices were manufactured in the same manner as in Example 1 except for using the material shown in Table 2 as the first host material and not using the second host material.

In Comparative 5, an organic EL device was manufactured in the same manner as in Example 1 except for not using the first host material but using the second host material shown in Table 2.

The first host material and the second host material used in Examples 1 to 9 and Comparatives 1 to 5 are shown below. In Examples 1 to 9, the compounds H1-1 to H1-6 contained in the emitting layer are the first host material of the invention and the compounds H2-1 to H2-4 are the second host material of the invention.

These organic EL devices were evaluated in the same manner as in Example 1. The results are shown in Table 2.

[Formula 135]

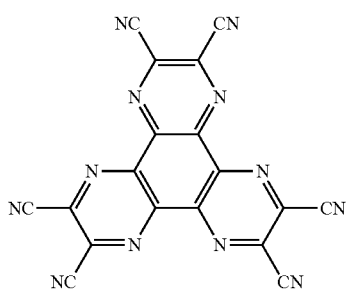

HA-1

-continued

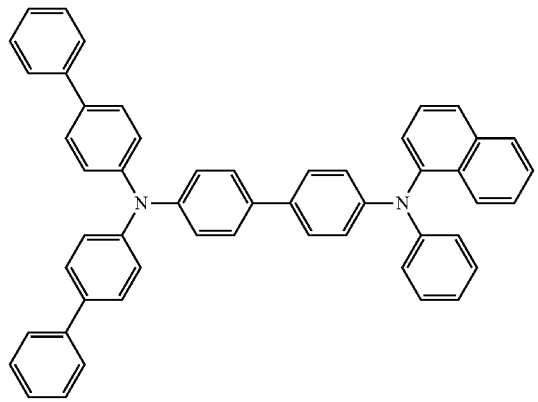

HT-1

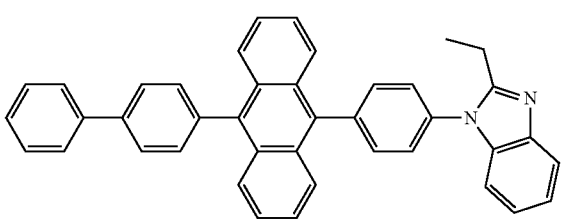

ET-1

[Formula 136]

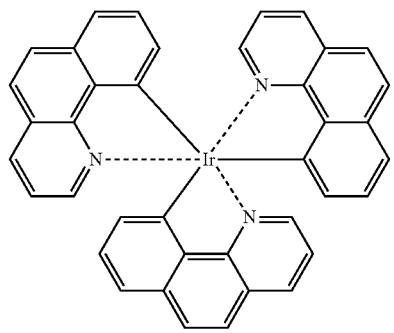

Ir(bzq)₃

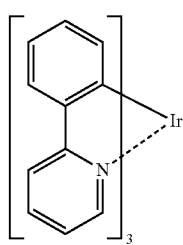

Ir(ppy)₃

TABLE 1

| | Device Arrangement |
|---|---|
| Example 1 | ITO(75)/HA-1(5)/HT-1(65)/<br>H1-1:H2-1:Ir(bzq)₃(25,45%:45%:10%)/<br>ET-1(35)/LiF(1)/Al(80) |
| Comparative 1 | ITO(75)/HA-1(5)HT-1(65)/<br>H1-3:Ir(bzq)₃(25,90%:10%)/ ET-1(35)/<br>LiF(1)/Al(80) |

TABLE 2

|  | First Host Material | Second Host Material | Dopant Material | Current Density (mA/cm$^2$) | Voltage (V) | EQE (%) | LT80 (hrs) |
|---|---|---|---|---|---|---|---|
| Example 1 | H1-1 | H2-1 | Ir(bzq)$_3$ | 10 | 3.1 | 20.9 | 431 |
| Example 2 | H1-2 | H2-1 | Ir(bzq)$_3$ | 10 | 3.1 | 20.4 | 347 |
| Example 3 | H1-3 | H2-1 | Ir(bzq)$_3$ | 10 | 3.2 | 20.2 | 344 |
| Example 4 | H1-4 | H2-1 | Ir(ppy)$_3$ | 10 | 3.0 | 16.1 | 80 |
| Example 5 | H1-1 | H2-2 | Ir(bzq)$_3$ | 10 | 3.6 | 20.9 | 285 |
| Example 6 | H1-1 | H2-3 | Ir(bzq)$_3$ | 10 | 3.2 | 21.3 | 210 |
| Example 7 | H1-5 | H2-1 | Ir(bzq)$_3$ | 10 | 3.2 | 14.4 | 52 |
| Example 8 | H1-6 | H2-1 | Ir(bzq)$_3$ | 10 | 3.2 | 15.2 | 53 |
| Example 9 | H1-1 | H2-4 | Ir(bzq)$_3$ | 10 | 3.3 | 17.3 | 485 |
| Comparative 1 | H1-3 | — | Ir(bzq)$_3$ | 10 | 3.1 | 21.4 | 50 |
| Comparative 2 | H1-5 | — | Ir(bzq)$_3$ | 10 | 3.2 | 9.9 | 18 |
| Comparative 3 | H1-6 | — | Ir(bzq)$_3$ | 10 | 3.1 | 10.6 | 16 |
| Comparative 4 | H1-1 | — | Ir(bzq)$_3$ | 10 | 3.1 | 16.8 | 330 |
| Comparative 5 | — | H2-4 | Ir(bzq)$_3$ | 10 | 3.2 | 17.4 | 80 |

It is understood from Table 2 that the organic EL device of each of Examples has a longer lifetime than a lifetime of the organic EL device of Comparative Example while keeping a high efficiency. Particularly, the material used for the first host material is the same in the organic EL devices in Example 3 and Comparative 1, in the organic EL devices in Example 7 and Comparative 2 and in the organic EL devices in Example 8 and Comparative 3. It is understood that the organic EL devices in Examples 3, 7 and 8 in which the second host material was used have a significantly longer lifetime than the organic EL devices in Comparatives in which the second host material was not used. It is also understood that, in comparison between Example 9 and Comparatives 4 and 5, the organic EL device in Example 9 of the invention has a longer lifetime with a high efficiency.

INDUSTRIAL APPLICABILITY

An organic EL device of the invention is applicable to a display and an illuminator.

EXPLANATION OF CODES 1, 1A, 1B, 1C, 1D organic EL device (organic electroluminescence device)
2 substrate
3 anode
4 cathode
5 emitting layer
6 hole transporting layer
7 electron transporting layer

The invention claimed is:

1. An organic electroluminescence device comprising:
a cathode;
an anode; and
an organic thin-film layer disposed between the cathode and the anode, the organic thin-film layer having one or more layers comprising an emitting layer,
the emitting layer comprising:
a first host material;
a second host material; and
a phosphorescent dopant material, wherein
the first host material is a compound represented by a formula (1A), and
the second host material is represented by a formula (2A),

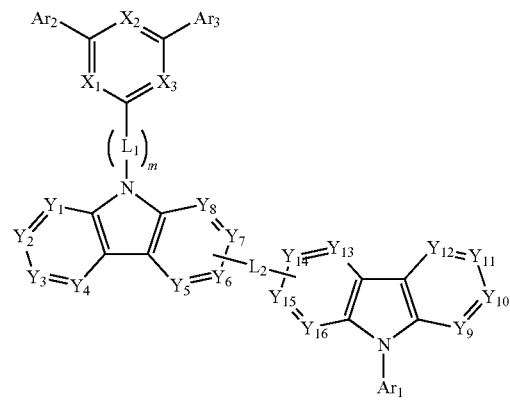

(1A)

where: $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen- containing six-membered heterocyclic group;
$L_1$ is a substituted or unsubstituted arylene group having 6 to 30 ring carbon atoms;
$L_2$ represents a single bond, a substituted or unsubstituted arylene group having 6 to 30 ring carbon atoms, or substituted or unsubstituted divalent heterocyclic group having 5 to 30 ring atoms;
$X_1$ to $X_3$ each independently represent CR or a nitrogen atom and at least one of $X_1$ to $X_3$ is a nitrogen atom;
$Y_1$ to $Y_{16}$ each independently represent CR or a nitrogen atom, but one of $Y_5$ to $Y_8$ is a carbon atom to be bonded to $L_2$ and one of $Y_{13}$ to $Y_{16}$ is a carbon atom to be bonded to $L_2$;
R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms;
a plurality of R are optionally the same or different and adjacent plural R groups are optionally bonded to form a ring structure;
m is an integer of 1 to 4; and
when m is 2 or more, $L_1$ is optionally the same or different,

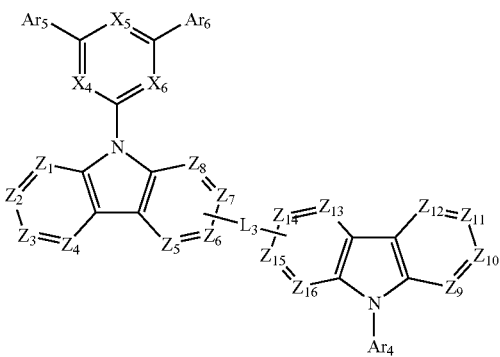

(2A)

where $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group;
$L_3$ represents a single bond, a substituted or unsubstituted arylene group having 6 to 30 ring carbon atoms, or substituted or unsubstituted divalent heterocyclic group having 5 to 30 ring atoms;
$X_4$ to $X_6$ each independently represent CR or a nitrogen atom and at least one of $X_4$ to $X_6$ is a nitrogen atom;
$Z_1$ to $Z_{16}$ represent CR or a nitrogen atom, but one of $Z_5$ to $Z_8$ is a carbon atom to be bonded to $L_3$ and one of $Z_{13}$ to $Z_{16}$ is a carbon atom to be bonded to $L_3$;
R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms;
a plurality of R are optionally the same or different and adjacent plural R groups are optionally bonded to form a ring structure; and
when $Y_6$ is directly bonded to $Y_{14}$ in (1A) and $Z_6$ is bonded to $Z_{14}$ through $L_3$ in (2A), $L_3$ is a substituted or unsubstituted arylene group having 6 to 30 ring carbon atoms, or a substituted or unsubstituted divalent heterocyclic group having 5 to 30 ring atoms.

2. The organic electroluminescence device according to claim 1, wherein
$L_2$ is a single bond.
3. The organic electroluminescence device according to claim 1, wherein
$L_3$ is a single bond.
4. The organic electroluminescence device according to claim 1, wherein
$L_2$ is a substituted or unsubstituted arylene group having 6 to 30 ring carbon atoms, or a substituted or unsubstituted divalent heterocyclic group having 5 to 30 ring atoms.
5. The organic electroluminescence device according to claim 1, wherein
$L_3$ is a substituted or unsubstituted arylene group having 6 to 30 ring carbon atoms, or a substituted or unsubstituted divalent heterocyclic group having 5 to 30 ring atoms.
6. The organic electroluminescence device according to claim 1, wherein
when $Y_6$ is directly bonded to $Y_{14}$ in (1A) and $Z_7$ is bonded to $Z_{14}$ through $L_3$ in (2A), $L_3$ is a substituted or unsubstituted arylene group having 6 to 30 ring carbon atoms, or a substituted or unsubstituted divalent heterocyclic group having 5 to 30 ring atoms.
7. The organic electroluminescence device according to claim 1, wherein
the first host material is a compound represented by a formula (1), and
the second host material is represented by a formula (2),

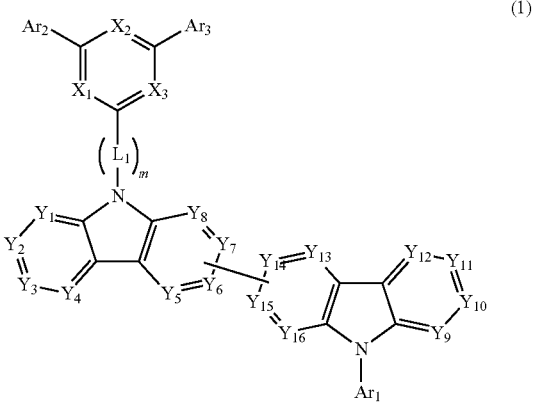

(1)

where $Ar_1$ to $Ar_3$ each independently represent a substituted or unsubstituted aryl group having 6 to 30 ring carbon atoms, or substituted or unsubstituted heterocyclic group having 5 to 30 ring atoms, with a proviso that $Ar_1$ is not a nitrogen-containing six-membered heterocyclic group;
$L_1$ is a substituted or unsubstituted arylene group having 6 to 30 ring carbon atoms;
$X_1$ to $X_3$ each independently represent CR or a nitrogen atom and at least one of $X_1$ to $X_3$ is a nitrogen atom;
$Y_1$ to $Y_{16}$ each independently represent CR, but one of $Y_6$ and $Y_7$ is a carbon atom to be bonded to $Y_{14}$ or $Y_{15}$ and one of $Y_{14}$ and $Y_{15}$ is a carbon atom to be bonded to $Y_6$ or $Y_7$;

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 7 to 30 ring carbon atoms, or a substituted or unsubstituted aryloxy group having 6 to 30 ring carbon atoms;

a plurality of R are optionally the same or different and adjacent plural R groups are optionally bonded to form a ring structure;

m is an integer of 1 to 4; and when m is 2 or more, $L_1$ is optionally the same or different,

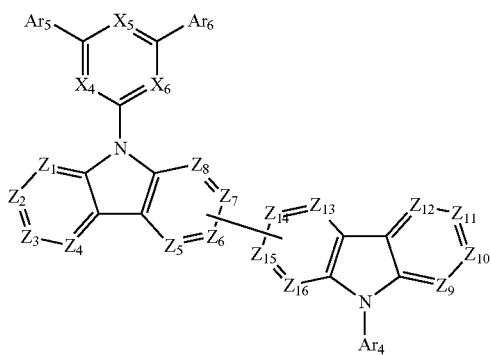

(2)

where $Ar_4$ to $Ar_6$ each independently represent a substituted or unsubstituted aryl group having 6 to 30 ring carbon atoms, or a substituted or unsubstituted heterocyclic group having 5 to 30 ring atoms, with a proviso that $Ar_4$ is not a nitrogen-containing six-membered heterocyclic group;

$X_4$ to $X_6$ each independently represent CR or a nitrogen atom and at least one of $X_4$ to $X_6$ is a nitrogen atom;

$Z_1$ to $Z_{16}$ each independently represent CR, but one of $Z_6$ and $Z_7$ is a carbon atom to be bonded to $Z_{14}$ or $Z_{15}$ and one of $Z_{14}$ and $Z_{15}$ is a carbon atom to be bonded to $Z_6$ or $Z_7$;

R independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms; and a plurality of R are optionally the same or different and adjacent plural R groups are optionally bonded to form a ring structure.

8. The organic electroluminescence device according to claim 7, wherein in the formula (1), $Y_7$ is bonded to $Y_{14}$ or $Y_6$ is bonded to $Y_{15}$.

9. The organic electroluminescence device according to claim 7, wherein in the formula (2), $Z_7$ is bonded to $Z_{14}$ or $Z_6$ is bonded to $Z_{15}$.

10. The organic electroluminescence device according to claim 1, wherein two or more of $X_1$ to $X_3$ are nitrogen atoms; and two or more of $X_4$ to $X_6$ are nitrogen atoms.

11. The organic electroluminescence device according to claim 1, wherein the number of nitrogen atoms of $X_1$ to $X_3$ is different from the number of nitrogen atoms of $X_4$ to $X_6$.

12. The organic electroluminescence device according to claim 1, wherein $L_1$ is a substituted or unsubstituted phenylene group, substituted or unsubstituted naphthylene group, substituted or unsubstituted fluorenylene group, substituted or unsubstituted phenanthrenediyl group, or substituted or unsubstituted triphenylenediyl group.

* * * * *